US011345950B2

(12) United States Patent
Wright et al.

(10) Patent No.: US 11,345,950 B2
(45) Date of Patent: May 31, 2022

(54) PROBE FOR SELECTIVELY CHARACTERIZING ENZYMES INVOLVED IN XENOBIOTIC METABOLISM AND METHOD OF MAKING AND USING THE SAME

(71) Applicant: Battelle Memorial Institute, Richland, WA (US)

(72) Inventors: Aaron T. Wright, Richland, WA (US); Susan Ramos-Hunter, Kennewick, WA (US); Christopher Whidbey, Seattle, WA (US)

(73) Assignee: Battelle Memorial Institute, Richland, WA (US)

( * ) Notice: Subject to any disclaimer, the term of this patent is extended or adjusted under 35 U.S.C. 154(b) by 269 days.

(21) Appl. No.: 16/151,170

(22) Filed: Oct. 3, 2018

(65) Prior Publication Data
US 2019/0100792 A1    Apr. 4, 2019

Related U.S. Application Data

(60) Provisional application No. 62/591,697, filed on Nov. 28, 2017, provisional application No. 62/568,151, filed on Oct. 4, 2017.

(51) Int. Cl.
| | |
|---|---|
| *C12Q 1/68* | (2018.01) |
| *C12Q 1/6837* | (2018.01) |
| *C07K 1/13* | (2006.01) |
| *C12Q 1/6841* | (2018.01) |
| *C12Q 1/48* | (2006.01) |
| *C07D 311/16* | (2006.01) |
| *C07D 405/04* | (2006.01) |
| *C07C 233/33* | (2006.01) |
| *C07C 233/20* | (2006.01) |
| *C07C 247/00* | (2006.01) |
| *G01N 33/58* | (2006.01) |
| *C07C 305/22* | (2006.01) |
| *C07D 203/26* | (2006.01) |
| *C07C 247/12* | (2006.01) |
| *C07C 203/04* | (2006.01) |
| *C07C 271/28* | (2006.01) |
| *C07D 405/12* | (2006.01) |
| *C07H 19/067* | (2006.01) |
| *C07H 15/203* | (2006.01) |
| *C12Q 1/34* | (2006.01) |
| *C07C 317/40* | (2006.01) |

(52) U.S. Cl.
CPC .......... *C12Q 1/6837* (2013.01); *C07C 203/04* (2013.01); *C07C 233/20* (2013.01); *C07C 233/33* (2013.01); *C07C 247/00* (2013.01); *C07C 247/12* (2013.01); *C07C 271/28* (2013.01); *C07C 305/22* (2013.01); *C07C 317/40* (2013.01); *C07D 203/26* (2013.01); *C07D 311/16* (2013.01); *C07D 405/04* (2013.01); *C07D 405/12* (2013.01); *C07H 15/203* (2013.01); *C07H 19/067* (2013.01); *C07K 1/13* (2013.01); *C12Q 1/34* (2013.01); *C12Q 1/48* (2013.01); *C12Q 1/6841* (2013.01); *G01N 33/582* (2013.01); *G01N 33/583* (2013.01); *C12Q 2565/514* (2013.01); *C12Q 2600/106* (2013.01); *G01N 2333/91177* (2013.01)

(58) Field of Classification Search
CPC ... C12Q 1/54; C12Q 1/34; C12Q 1/48; C12Q 1/6837; C12Q 1/6841
See application file for complete search history.

(56) References Cited

U.S. PATENT DOCUMENTS

| 7,736,911 B2 | 6/2010 | Zhang et al. |
| 2011/0020837 A1 | 1/2011 | Kant et al. |

FOREIGN PATENT DOCUMENTS

| EP | 2 482 077 | 8/2012 |
| WO | WO 2001/77684 | 10/2001 |
| WO | WO 2004/033397 | 4/2004 |
| WO | WO 2014/031498 | 2/2014 |
| WO | WO 2017/221270 | 12/2017 |

OTHER PUBLICATIONS

Su et al. Molecular Cancer Therapeutics (2014), 13(12), 2852-2863 (Year: 2014).*
Invitation to Pay Additional Fees issued by International Searching Authority dated Jan. 16, 2019, for International Application No. PCT/US2018/054242.
Sadler et al., "Activity-based protein profiling of microbes," *Current Opinion in Chemical Biology*, vol. 24, pp. 139-144, Dec. 19, 2014.
Bottcher et al., "β-Lactams and β-lactones as activity-based probes in chemical biology," *MedChemComm*, No. 3, pp. 408-417, Jan. 4, 2012.
Lockhart et al., "Screening-based discovery of *Aspergillus fumigatus* plant-type chitinase inhibitors," *FEBS Letters*, No. 588, pp. 3282-3290, Jul. 22, 2014.
Hirose et al., "Review: Recent development of two chitinase inhibitors, Argifin and Argadin, produced by soil microorganisms," *Proc. Jpn. Acad. Ser. B*, 86(2): 85-102, Feb. 2010.
Invitation to Pay Additional Fees issued by International Searching Authority dated Feb. 12, 2019, for International Application No. PCT/US2018/051230.

(Continued)

*Primary Examiner* — Jezia Riley
(74) *Attorney, Agent, or Firm* — Klarquist Sparkman, LLP

(57) ABSTRACT

Activity-based probes that can be used to selectively identify and characterize enzymes that are involved in different phases of xenobiotic metabolism in a host and its microbiota population(s) are described. The activity-based probes described specifically label only their target active enzymes involved in xenobiotic metabolism and therefore provide a measurement of true protein functional activity rather than transcript or protein abundance. The activity-based probes also provide multimodal profiling of these active enzymes. Methods for preparing the activity based probes and exemplary methods for their use also are disclosed.

22 Claims, 31 Drawing Sheets

Specification includes a Sequence Listing.

(56) References Cited

OTHER PUBLICATIONS

Wright et al., "A Suite of Activity-Based Probes for Human Cytochrome P450 Enzymes," *J. Am. Chem. Soc.*, 131(30): 10692-10700, Aug. 5, 2009.

Lumba et al., "A β-galactosidase probe for the detection of cellular senescence by mass cytometry," *Org. Biomol. Chem.*, 15(30): 6388-6392, May 19, 2017.

Hsu et al., "Development of Activity-Based Probes for Imaging Human α-L-Fucosidases in Cells," *J. Org. Chem.*, vol. 80, pp. 8458-8463, Aug. 4, 2015.

Chauvigne-Hines et al., "Suite of Activity-Based Probes for Cellulose-Degrading Enzymes," *J. Am. Chem. Soc.*, 134(50): 20521-20532, Nov. 24, 2012.

Lu et al., "Design of a Mechanism-Based Probe for Neuraminidase To Capture Influenza Viruses," *Angew. Chem. Int. Ed.*, vol. 44, pp. 6888-6892, 2005.

Wright et al., "Chemical Proteomic Probes for Profiling Cytochrome P450 Activities and Drug Interactions in Vivo," *Chemistry & Biology*, vol. 14., pp. 1043-1051, Sep. 2007.

Dai et al., "A practical strategy to design and develop an isoform-specific fluorescent probe for a target enzyme: CYP1A1 as a case study," *Chem. Sci.*, vol. 8, pp. 2795-2803, Sep. 5, 2016.

International Search Report and Written Opinion issued for International Application No. PCT/IB2018/059536 dated Apr. 9, 2019.

WU et al., "Activity-based probes for functional interrogation of retaining β-glucuonidases," *Nat. Chem. Biol.*, 13(8): 867-873, Jun. 5, 2017.

Verhelst et al., "Probing Functional Tyrosines," *Chemistry & Biology*, 20(4): 541-548, Apr. 18, 2013.

Stoddard et al., "Activity-based probes for isoenzyme- and site-specific functional characterization of glutathione S-transferases," *J. Am. Chem. Soc.*, 139(45): 16032-16035, Oct. 25, 2017.

Davis et al., "Nuclear magnetic resonance identification of the taurine conjugate of 3α,6β,7β-trihydroxy-5β,22-cholen-24-oic acid (tauro-$\Delta^{22}$β-muricholate) in the serum of female rats treated with a-naphthylisothiocyanate," *Journal of Lipid Research*, vol. 34, pp. 651-662, May 1993.

Examination Report issued for European Application No. 18826838.7 dated Mar. 25, 2021.

Examination Report dated Apr. 30, 2021, for European Application No. 18800783.5.

Hong et al., "Live-cell stimulated raman scattering imaging of alkyne-tagged biomolecules," *Angew. Chem. Int. Ed.*, 53(23): 5827-5831, 2014.

International Search Report and Written Opinion issued for International Application No. PCT/IB2018/058935 dated Jun. 27, 2019.

Invitation to Pay Additional fees issued by International Searching Authority dated Feb. 8, 2019, for International Application No. PCT/US2018/055666.

Kirby et al., "Continuous Spectrophotometric Assay of Conjugated Bile Acid Hydrolase," *Lipids*, 30(9): 863-867, Sep. 1995.

Kumar et al., "Design, synthesis, and physico-chemical interactions of bile acid derived dimeric phospholipid amphiphiles with model membranes," *Journal of Colloid and Interface Science*, vol. 448, pp. 398-406, Feb. 7, 2015.

Liu et al., "Exploring the binding proteins of glycolipids with bifunctional chemical probes," *Angew. Chem. Int. Ed.*, 55(46): 14330-14334, Nov. 7, 2016.

Sun et al., "Biological deoxycholic acid-coumarin conjugates: photo-switchable structures and self-assembly morphology," *Tetrahedron Letters*, vol. 57, pp. 2125-2128, Apr. 7, 2016.

Heckendorn et al., "Synthesis and binding properties of 2-Amino-5-phosphono-3-pentenoic acid photoaffinity ligands as probes for the glutamate recognition site of the NMDA receptor," *J. Med. Chem.*, 36(23): 3721-3726, Nov. 1, 1993.

Esaki N. et al., "Deamination and γ-addition reactions of vinylglycine by Lmethionine γ-lyase." *FEBS Letters*, Dec. 15, 1977, vol. 84, No. 2, pp. 309-312.

Written Opinion and Search Report dated Sep. 14, 2021, for corresponding Singapore Application No. 11202002913Q.

\* cited by examiner

FIG. 8A              FIG. 8B

PROBE FOR SELECTIVELY CHARACTERIZING ENZYMES INVOLVED IN XENOBIOTIC METABOLISM AND METHOD OF MAKING AND USING THE SAME

CROSS REFERENCE TO RELATED APPLICATIONS

This application claims the benefit of the earlier filing dates of U.S. Provisional Application No. 62/568,151, filed on Oct. 4, 2017, and U.S. Provisional Application No. 62/591,697, filed on Nov. 28, 2017; each of these prior applications is incorporated herein by reference in its entirety.

ACKNOWLEDGMENT OF GOVERNMENT SUPPORT

This invention was made with government support under Contract No. DE-AC05-76RL01830 awarded by the Department of Energy. The government has certain rights in the invention.

FIELD

The present disclosure concerns enzymes of xenobiotic metabolism of both human host and microbiota origin.

BACKGROUND

There is a growing research interest in avoiding characterizing microbial communities by genomes or transcriptomes alone. However, current techniques using fluorescence in situ hybridization (FISH) for sorting microbes from microbiomes based upon gene content still almost universally fail to provide a sorting mechanism based solely upon function. This technique, and many others, are based upon labeling of genes or amino acids; however, the presence of a gene or an amino acid does not necessarily equal function. New techniques are needed that identify, separate, and quantify analyte species (for example, microbes, enzymes, toxins, and the like) present in biological environments so that such species and their functions can be determined.

SUMMARY

The present disclosure concerns activity-based probes capable of detecting, measuring and affecting enzyme activity for enzymes involved in xenobiotic metabolism in real time. Probe formulas and structures are described herein. Also disclosed herein are embodiments of a method for using the probes, which can comprise exposing a subject or a sample to a probe embodiment described herein for a time sufficient to allow the probe to bind to an enzyme involved in xenobiotic metabolism such that a probe-enzyme conjugate is formed; and analyzing the probe-enzyme conjugate using a fluorescent detection technique, a colorimetric detection technique, a mass spectrometry technique, or a combination thereof. Other method embodiments also are described.

Devices and kits comprising the probe embodiments of the present disclosure also are described, along with methods of using such devices and kits. In some embodiments, an assay platform is described, which can comprise a substrate and a probe embodiment as described herein.

The foregoing and other objects and features of the present disclosure will become more apparent from the following detailed description, which proceeds with reference to the accompanying figures.

BRIEF DESCRIPTION OF THE DRAWINGS

FIG. 8A illustrates results from active, WT b-glucuronidase from E. coli as labeled with a representative probe embodiment described herein, wherein "+" represents a sample with 10 µM of probe and "−" represents a control with no probe and wherein the E413A/E505A active site mutant is not labeled.

FIG. 8B shows protein isolated from the mouse large intestine microbiome, which is labeled by a GlcA-ABP (M: MW marker).

FIG. 16A shows a volcano plot of GSH-ABP enrichment, wherein black dots represent all GSTs that did not demonstrate competitive inhibition of probe labeling, green dots represent GSTs whose probe labeling was competitively inhibited by 2.5× excess 2,3-dichloro-1,4-napthoquinone (Dichlon) over probe, and blue dots represent GSTs whose probe labeling was competitively inhibited by 2.5× excess Dichlon and 2.5× excess S-hexylglutathione.

FIG. 16B shows a volcano plot of GST-ABP enrichment, wherein black dots represent all GSTs whose probe labeling was not competitively inhibited, blue dots represent GSTs whose probe labeling was competitively inhibited by 20× S-hexylglutathione, and red dots represent GSTs whose probe labeling was competitively inhibited by 10× N-ethylmaleimide.

SEQUENCE LISTING

Figure 1:
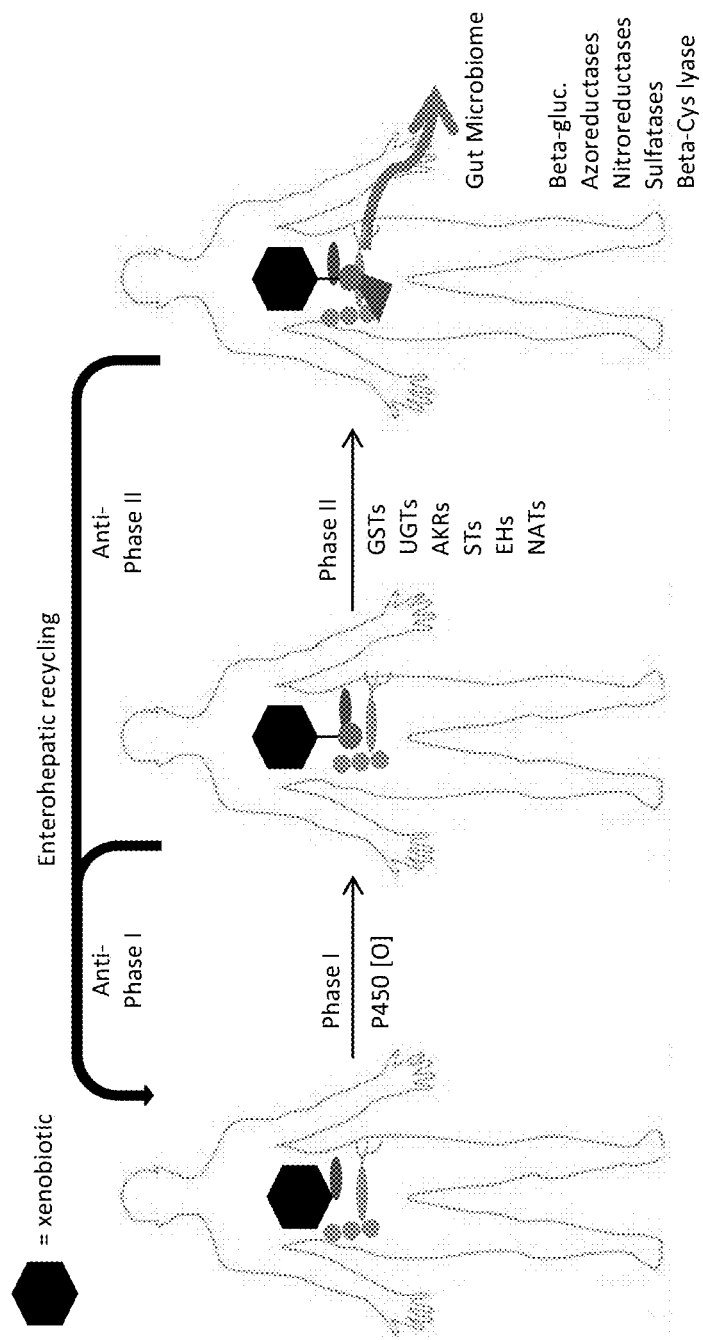
FIG. 1 is a schematic illustration showing the different stages of xenobiotic metabolism, including Phase I and Phase II metabolism, and metabolic events that occur in the gut microbiome.

The nucleic acid sequences listed in the accompanying sequence listing are shown using standard letter abbreviations for nucleotide bases, as defined in 37 C.F.R. § 1.822. Only one strand of each nucleic acid sequence is shown, but the complementary strand is understood as included by any reference to the displayed strand. The sequence listing submitted herewith, generated on Oct. 2, 2018, 2 Kb, is herein incorporated by reference in its entirety. In the accompanying sequence listing:

SEQ ID NO: 1 is the sequence for primer uidA_F.
SEQ ID NO: 2 is the sequence for primer uidA_R.
SEQ ID NO: 3 is the sequence for primer pET_F.
SEQ ID NO: 4 is the sequence for primer pET_R.

DETAILED DESCRIPTION

I. Explanation and Overview of Terms

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

Compounds disclosed herein may contain one or more asymmetric elements such as stereogenic centers, chiral axes and the like, e.g., asymmetric carbon atoms, so that the chemical conjugates can exist in different stereoisomeric forms. These compounds can be, for example, racemates or optically active forms. For compounds with two or more asymmetric elements, these compounds can additionally be mixtures of diastereomers. For compounds having asymmetric centers, all optical isomers in pure form and mixtures thereof are encompassed. In these situations, the single enantiomers, i.e., optically active forms, can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column. All forms are contemplated herein regardless of the methods used to obtain them.

Stereochemical definitions and conventions used herein generally follow S. P. Parker, Ed., McGraw-Hill *Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory All forms (for example solvates, optical isomers, enantiomeric forms, polymorphs, free compound and salts) of a probe may be employed either alone or in combination.

To facilitate review of the various embodiments of the disclosure, the following explanations of specific terms are provided. Certain functional group terms include a "–" symbol at the beginning of the functional group formula; this symbol is not a part of the functional group, but instead denotes how the functional group connects to the formulas described herein. For example, a functional group with a formula "—OC(O)$R^b$" is attached to an atom of the functionalized compound by the oxygen atom of the functional group that is next to the "–" symbol.

Acyloxy: —OC(O)$R^b$, wherein $R^b$ is selected from hydrogen, aliphatic, aryl, heteroaliphatic, aliphatic-aryl, heteroaryl, aliphatic-heteroaryl, heteroaliphatic-aryl, heteroaliphatic-heteroaryl, and any combination thereof.

Aldehyde: —C(O)H.

Aliphatic: A hydrocarbon group having at least one carbon atom to 50 carbon atoms ($C_{1-50}$), such as one to 25 carbon atoms ($C_{1-25}$), or one to ten carbon atoms ($C_{1-10}$), and which includes alkanes (or alkyl), alkenes (or alkenyl), alkynes (or alkynyl), including cyclic versions thereof, and further including straight- and branched-chain arrangements, and all stereo and position isomers as well.

Aliphatic-aromatic: An aromatic group that is or can be coupled to a probe disclosed herein, wherein the aromatic group is or becomes coupled through an aliphatic group.

Aliphatic-aryl: An aryl group that is or can be coupled to a probe disclosed herein, wherein the aryl group is or becomes coupled through an aliphatic group.

Aliphatic-heteroaromatic: A heteroaromatic group that is or can be coupled to a probe disclosed herein, wherein the heteroaromatic group is or becomes coupled through an aliphatic group.

Aliphatic-heteroaryl: A heteroaryl group that is or can be coupled to a probe disclosed herein, wherein the heteroaryl group is or becomes coupled through an aliphatic group.

Alkenyl: An unsaturated monovalent hydrocarbon having at least two carbon atoms to 50 carbon atoms ($C_{2-50}$), such as two to 25 carbon atoms ($C_{2-25}$), or two to ten carbon atoms ($C_{2-10}$), and at least one carbon-carbon double bond, wherein the unsaturated monovalent hydrocarbon can be derived from removing one hydrogen atom from one carbon atom of a parent alkene. An alkenyl group can be branched, straight-chain, cyclic (e.g., cycloalkenyl), cis, or trans (e.g., E or Z).

Alkoxy: —O-aliphatic, such as —O-alkyl, —O-alkenyl, or —O-alkynyl, with exemplary embodiments including, but not limited to, methoxy, ethoxy, n-propoxy, isopropoxy, n-butoxy, t-butoxy, sec-butoxy, n-pentoxy.

Alkyl: A saturated monovalent hydrocarbon having at least one carbon atom to 50 carbon atoms ($C_{1-50}$), such as one to 25 carbon atoms ($C_{1-25}$), or one to ten carbon atoms ($C_{1-10}$), wherein the saturated monovalent hydrocarbon can be derived from removing one hydrogen atom from one carbon atom of a parent compound (e.g., alkane). An alkyl group can be branched, straight-chain, or cyclic (e.g., cycloalkyl).

Alkynyl: An unsaturated monovalent hydrocarbon having at least two carbon atoms to 50 carbon atoms ($C_{2-50}$), such as two to 25 carbon atoms ($C_{2-25}$), or two to ten carbon atoms ($C_{2-10}$), and at least one carbon-carbon triple bond, wherein the unsaturated monovalent hydrocarbon can be derived from removing one hydrogen atom from one carbon atom of a parent alkyne. An alkynyl group can be branched, straight-chain, or cyclic (e.g., cycloalkynyl).

Alkylaryl/Alkenylaryl/Alkynylaryl: An aryl group that is or can be coupled to a probe disclosed herein, wherein the aryl group is or becomes coupled through an alkyl, alkenyl, or alkynyl group, respectively.

Alkylheteroaryl/Alkenylheteroaryl/Alkynylheteroaryl: A heteroaryl group that is or can be coupled to a probe disclosed herein, wherein the heteroaryl group is or becomes coupled through an alkyl, alkenyl, or alkynyl group, respectively.

Amide: —C(O)NR$^b$R$^c$ wherein each of R$^b$ and R$^c$ independently is selected from hydrogen, aliphatic, aryl, heteroaliphatic, aliphatic-aryl, heteroaryl, aliphatic-heteroaryl, heteroaliphatic-aryl, heteroaliphatic-heteroaryl, and any combination thereof.

Amine: —NR$^b$R$^c$, wherein each of R$^b$ and R$^c$ independently is selected from hydrogen, aliphatic, aryl, heteroaliphatic, aliphatic-aryl, heteroaryl, aliphatic-heteroaryl, heteroaliphatic-aryl, heteroaliphatic-heteroaryl, and any combination thereof.

Aromatic: A cyclic, conjugated group or moiety of, unless specified otherwise, from 5 to 15 ring atoms having a single ring (e.g., phenyl, pyridinyl, or pyrazolyl) or multiple condensed rings in which at least one ring is aromatic (e.g., naphthyl, indolyl, or pyrazolopyridinyl); that is, at least one ring, and optionally multiple condensed rings, have a continuous, delocalized π-electron system. Typically, the number of out of plane π-electrons corresponds to the Hückel rule (4n+2). The point of attachment to the parent structure typically is through an aromatic portion of the condensed ring system. For example,

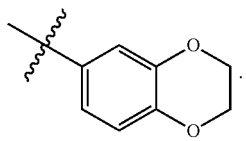 [SMILES: *c1ccc2c(c1)OCCO2]

However, in certain examples, context or express disclosure may indicate that the point of attachment is through a non-aromatic portion of the condensed ring system. For example,

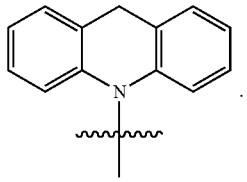 [SMILES: *N1c2ccccc2Cc2ccccc21]

An aromatic group or moiety may comprise only carbon atoms in the ring, such as in an aryl group or moiety, or it may comprise one or more ring carbon atoms and one or more ring heteroatoms comprising a lone pair of electrons (e.g. S, O, N, P, or Si), such as in a heteroaryl group or moiety.

Aryl: An aromatic carbocyclic group comprising at least five carbon atoms to 15 carbon atoms ($C_5$-$C_{15}$), such as five to ten carbon atoms ($C_5$-$C_{10}$), having a single ring or multiple condensed rings, which condensed rings can or may not be aromatic provided that the point of attachment to a remaining position of the compounds disclosed herein is through an atom of the aromatic carbocyclic group. Aryl groups may be substituted with one or more groups other than hydrogen, such as aliphatic, heteroaliphatic, aryl, heteroaryl, other functional groups, or any combination thereof. In some embodiments, the aryl ring is selected from, but not limited to, phenyl, naphthyl, anthracenyl, indenyl, azulenyl, fluorenyl, tetracyanoanthaquinodimethyl, and the like.

Azo Compound: A compound that contains an R$^1$—N=N—R$^2$ group, where R$^1$ and R$^2$ typically are aromatic groups. Azo compounds, for example, are widely used as colorants in food, cosmetics, pharmaceuticals and other industries.

Azoreductase: A group of diverse enzymes found in bacterial and eukaryotic enzymes that are Flavin-dependent (typically Flavin mononucleotide) enzymes able to reductively cleave compounds containing an azo bond by means of electron donation by NADH and FMN as a cofactor. Several species of gut bacteria have been identified to have azoreductase activity, as described in Ryan, A. *Br. J. Pharmacol.* (2017) 174: 2161-73.

Benzyl carbonyl: —C(O)Ph.

Binding: Binding, and its other grammatical forms, means a lasting attraction between chemical substances.

Binding specificity: Binding specificity involves both binding to a specific partner and not binding to other molecules. Functionally important binding may occur at a range of affinities from low to high, and design elements may suppress undesired cross-interactions. Post-translational modifications also can alter the chemistry and structure of interactions. "Promiscuous binding" may involve degrees of structural plasticity, which may result in different subsets of residues being important for binding to different partners. "Relative binding specificity" is a characteristic whereby in a biochemical system a molecule interacts with its targets or partners differentially, thereby impacting them distinctively depending on the identity of individual targets or partners.

Carboxyl: —C(O)OR$^b$, wherein R$^b$ is aliphatic, aryl, heteroaliphatic, aliphatic-aryl, heteroaryl, aliphatic-heteroaryl, heteroaliphatic-aryl, heteroaliphatic-heteroaryl, hydrogen, and any combination thereof.

Chemical Bond: An attractive force between atoms strong enough to permit the combined aggregate to function as a unit. The different principal types of bonds include metallic, covalent, ionic and bridge. "Metallic bonding" is the attraction of all of the atomic nuclei in a crystal for the outer shell electrons which are shared in a delocalized manner among all available orbitals. "Covalent bonding" results most commonly when electrons are shared by two atomic nuclei. A conventional single covalent bond involves the sharing of two elections. There also may be double bonds with four shared electrons, triple bonded with six shared elections, and bonds of intermediate multiplicity. Covalent bonds may range from nonpolar, involving electrons evenly shared by the two atoms, to extremely polar, where the bonding electrons are very unevenly shared. The limit of uneven sharing occurs when the bonding electron spends full time with one of the atoms, making the atom into a negative ion and leaving the other atom in the form of a positive ion. "Electrostatic (or ionic) bonding" is the electrostatic attraction between oppositely charged ions. "Bridge or hydrogen bonds" involve compounds of hydrogen in which the hydrogen bears either a + or a − charge.

Click Chemistry: Chemical synthetic methods for making compounds using reagents that can be joined together using efficient reagent conditions and that can be performed in benign solvents or solvents that can be removed or extracted using facile methods, such as evaporation, extraction, or distillation. Several types of reactions that fulfill these criteria have been identified, including nucleophilic ring opening reactions of epoxides and aziridines, non-aldol type carbonyl reactions, such as formation of hydrazones and heterocycles, additions to carbon-carbon multiple bonds, such as oxidative formation of epoxides and Michael Additions, and cycloaddition reactions. A representative example of click chemistry is a reaction that couples an azide and an alkyne to form a triazole. The copper-catalyzed azide-alkyne cycloaddition (CuAAC) features an enormous rate acceleration of $10^7$ to $10^8$ compared to the uncatalyzed 1,3-dipolar cycloaddition. It succeeds over a broad temperature range, is insensitive to aqueous conditions and pH range over 4 to 12, and tolerates a broad range of functional groups. Pure products can be isolated by simple filtration or extraction without the need for chromatography or recrystallization.

Clickable Functional Group: A functional group that can be used in click chemistry to form a product. In some embodiments, the clickable functional group is an azide or an alkyne.

Contact: The state or condition of touching or being in immediate proximity. In some examples, contacting occurs in vitro or ex vivo, for example, by adding a reagent to a sample (such as one containing cells or proteins).

Control: A sample without an activity-based probe.

Dichloro Dione: A group having a structure wherein at least a portion of the structure has a

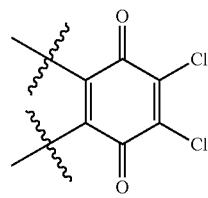 [SMILES: *C1=C(*)C(=O)C(Cl)=C(Cl)C1=O]

group.

Differential Label: A stain, dye, marker, or activity probe used to characterize or contrast structures, components or proteins of a single cell or organism.

Ester: —C(O)OR$^b$, wherein R$^b$ is selected from hydrogen, aliphatic, aryl, heteroaliphatic, aliphatic-aryl, heteroaryl, aliphatic-heteroaryl, heteroaliphatic-aryl, heteroaliphatic-heteroaryl, or any combination thereof.

Enzyme Binding Group (or EBG): A molecule, or a functional group, or a combination thereof that is part of a probe described herein that becomes covalently bound to an enzyme. In some embodiments, the EBG can become activated for reaction with the enzyme by removing an enzyme reactive group from the probe and/or by chemically modifying the EBG, such as by reducing the EBG, oxidizing the EBG, or a combination thereof. In some additional embodiments, the EBG can be photochemically activated to promote binding with the enzyme.

Enzyme Reactive Group (or ERG): A molecule, or a functional group, or a combination thereof that is attached to a probe described herein and that is capable of being removed from the probe by an enzyme, such as through enzymatic cleavage and/or chemical displacement. In particular disclosed embodiments, the enzyme that removes the ERG is an enzyme involved in xenobiotic metabolism. Representative examples of ERGs that are capable of being enzymatically cleaved by an enzyme include sugars (such as glucuronic acid), sulfates, and phosphates. Representative examples of ERGs that are capable of being displaced by an enzyme include, but are not limited to halides, phenol-containing molecules, and the like.

Enzyme specificity: Enzymes are highly specific in the reaction catalyzed and in their substrates. In general, there are four distinct types of enzyme specificity: (1) Absolute specificity—the enzyme will catalyze only one reaction; (2) Group specificity—the enzyme will act only on molecules that have specific functional groups, such as amino, phosphate and methyl groups; (3) Linkage specificity—the enzyme will act on a particular type of chemical bond regardless of the rest of the molecular structure; and (4) Stereochemical specificity—the enzyme will act on a particular steric or optical isomer. Though enzymes exhibit great degrees of specificity, cofactors may serve many apoenzymes. For example, nicotinamide adenine dinucleotide (NAD) is a coenzyme for a great number of dehydrogenase reactions in which it acts as a hydrogen acceptor.

Fluorescence: The result of a three-state process that occurs in certain molecules, generally referred to as "fluorophores" or "fluorescent dyes," when a molecule or nanostructure relaxes to its ground state after being electrically excited. Stage 1 involves the excitation of a fluorophore through the absorption of light energy; Stage 2 involves a transient excited lifetime with some loss of energy; and Stage 3 involves the return of the fluorophore to its ground state accompanied by the emission of light.

Fluorescent dye, Fluorochrome or Fluorophore: A component of a molecule which causes the molecule to be fluorescent. The component is a functional group in the molecule that absorbs energy of a specific wavelength and re-emits energy at a different (but equally specific) wavelength. The amount and wavelength of the emitted energy depend on both the dye and the chemical environment of the dye. Many dyes are known, including, but not limited to, fluorescein isothiocyanate (FITC), R-phycoerythrin (PE), PE-Texas Red Tandem, PE-Cy5 Tandem, propidium iodem, EGFP, EYGP, ECF, DsRed, allophycocyanin (APC), PerCp, SYTOX Green, courmarin, Alexa Fluors (350, 430, 488, 532, 546, 555, 568, 594, 633, 647, 660, 680, 700, 750), Cy2, Cy3, Cy3.5, Cy5, Cy5.5, Cy7, Hoechst 33342, DAPI, Hoechst 33258, SYTOX Blue, chromomycin A3, mithramycin, YOYO-1, SYTOX Orange, ethidium bromide, 7-AAD, acridine orange, TOTO-1, TO-PRO-1, thiazole orange, TOTO-3, TO-PRO-3, thiazole orange, propidium iodide (PI), LDS 751, Indo-1, Fluo-3, DCFH, DHR, SNARF, Y66F, Y66H, EBFP, GFPuv, ECFP, GFP, AmCyanI, Y77W, S65A, S65C, S65L, 565T, ZsGreenI, ZsYellowI, DsRed2, DsRed monomer, AsRed2, mRFP1, HcRedI, monochlorobimane, calcein, the DyLight Fluors, cyanine, hydroxycoumarin, aminocoumarin, methoxycoumarin, Cascade Blue, Lucifer Yellow, NBD, PE-Cy5 conjugates, PE-Cy7 conjugates, APC-Cy7 conjugates, Red 613, fluorescein, FluorX, BODIDY-FL, TRITC, X¬rhodamine, Lissamine Rhodamine B, Texas Red, TruRed, and derivatives thereof.

Halogen: An atom selected from fluoro, chloro, bromo, or iodo.

Heteroaliphatic: An aliphatic group comprising at least one heteroatom to 20 heteroatoms, such as one to 15 heteroatoms, or one to 5 heteroatoms, which can be selected from, but not limited to oxygen, nitrogen, sulfur, selenium, phosphorous, and oxidized forms thereof within the group. Exemplary heteroaliphatic groups include, but are not limited to, aliphatic groups comprising an ether, a thioether, an ester, an amine, a carboxy, a carbonyl, or an amide.

Heteroaliphatic-aromatic: An aromatic group that is or can be coupled to a probe disclosed herein, wherein the aromatic group is or becomes coupled through a heteroaliphatic group.

Heteroaliphatic-aryl: An aryl group that is or can be coupled to a probe disclosed herein, wherein the aryl group is or becomes coupled through a heteroaliphatic group.

Heteroalkyl/Heteroalkenyl/Heteroalkynyl: An alkyl, alkenyl, or alkynyl group (which can be branched, straight-chain, or cyclic) comprising at least one heteroatom to 20 heteroatoms, such as one to 15 heteroatoms, or one to 5 heteroatoms, which can be selected from, but not limited to oxygen, nitrogen, sulfur, selenium, phosphorous, and oxidized forms thereof within the group.

Heteroaromatic: An aromatic group comprising at least one heteroatom to 20 heteroatoms, such as one to 15 heteroatoms, or one to 5 heteroatoms, which can be selected from, but not limited to oxygen, nitrogen, sulfur, selenium, phosphorous, and oxidized forms thereof within the group.

Heteroaryl: An aryl group comprising at least one heteroatom to six heteroatoms, such as one to four heteroatoms, which can be selected from, but not limited to oxygen, nitrogen, sulfur, selenium, phosphorous, and oxidized forms thereof within the ring. Such heteroaryl groups can have a single ring or two or more fused rings, which fused rings may or may not be aromatic and/or contain a heteroatom, provided that the point of attachment is through an atom of the aromatic heteroaryl group. In some embodiments, the heteroaryl ring is selected from, but not limited to, pyridinyl, quinolinyl, quinazolinyl, quinoxalinyl, benzoquinolinyl, benzoquinoxalinyl, benzoquinazolinyl, indolyl, indolinyl, benzofuranyl, benzothiophenyl, benzimidizolyl, purinyl, carbazolyl, acridinyl, phenazinyl, and the like.

Heteroaliphatic-heteroaromatic: A heteroaromatic group that is or can be coupled to a probe disclosed herein, wherein the heteroaromatic group is or becomes coupled through a heteroaliphatic group.

Ketone: —C(O)$R^b$, wherein $R^b$ is selected from aliphatic, aryl, heteroaliphatic, aliphatic-aryl, heteroaryl, aliphatic-heteroaryl, heteroaliphatic-aryl, heteroaliphatic-heteroaryl and any combination thereof.

Label: A traceable constituent incorporated onto a molecule in order to spatially locate the molecule or follow it through a reaction or purification scheme. As a verb, to add such a group or atom that can be detected or measured.

Lyase: An enzyme that breaks C—C or C—X bonds (where X=O, N, S, P or halides) without relying on oxidation or the addition of water. Microbial polysaccharide lyases (PLs) modify polysaccharides that contain a glycosidic bond at the β position relative to a carboxylic acid (e.g., alginate, pectin, chondroitin, and heparan). Microbial C—S β-lyases cleave C—S bonds found in both dietary compounds and cysteine-S-conjugates of xenobiotics, which are formed by liver enzymes. These enzymes generate an aldimine linkage between pyridoxal 5-phosphate (PLP) and the α-amino group of the cysteine-derived substituent, acidifying the adjacent proton. β-elimination releases a thiol-containing metabolite and aminoacrylate, the latter of which spontaneously breaks down to form ammonia and pyruvate. Microbes can further metabolize these thiols, altering their physical properties and localization within the body. For example, gut bacterial C—S β-lyases cleave cysteine-S-conjugates of polychlorinated biphenyls to produce thiol metabolites that are further methylated and accumulate in lipophilic host tissues.

Modulate: To regulate, alter, adapt, or adjust to a certain measure or proportion.

NADPH-cytochrome P450 oxidoreductase (POR): A flavoprotein involved in electron transfer to microsomal cytochromes P450 (P450), cytochrome b5, squalene mono-oxygenase, and heme oxygenase. Electron transfer from POR to cytochrome b5, a small microsomal hemoprotein, is important in fatty acid metabolism since it supports fatty acid desaturase and elongase activities. Cytochrome b5 also plays a role in electron transfer to the microsomal P450s. Squalene mono-oxygenase utilizes electrons donated by POR to support sterol biosynthesis. An additional electron acceptor is heme oxygenase, the enzyme that degrades heme to biliverdin, iron, and carbon monoxide. POR also can directly catalyze the one-electron reductive bioactivation of prodrugs such as the antineoplastic agents mitomycin C and tirapazamine. Riddick, D S et al, *Drug Metabolism and Disposition* (2013) 41 (1): 12-23.

Nitroreductase: An enzyme (e.g., xanthine oxidase, aldehyde oxidase in the cytosolic fraction; and NADPH-cytochrome P-450 reductase in the microsomal fraction) that reduces nitro compounds to primary amine metabolites requiring a total of six electrons, e.g., $RNO_2 \rightarrow RNO \rightarrow RNHOH \rightarrow RNH_2$. Each reductive step requires two electrons. Zbaida, S., in *Enzyme Systems that Metabolise Drugs and Other Xenobiotics* (2002), John Wiley & Sons Ltd., chapter 16, pages 555-66.

Normal Healthy Control: A subject having no symptoms or other clinical evidence of a disease.

Phosphate: A functional group having a structure —P(O)(O$^-$)$_2$ or —P(O)(OH)$_2$ when attached to a probe embodiment described herein and having a structure P(O)(O$^-$)$_3$ or P(O)(OH)$_3$ when not attached to a probe embodiment. Any anionic phosphate groups can comprise a suitable counterion that balances the negative charge on the corresponding oxygen atom, such as an alkali metal ion like K$^+$, Na$^+$, Li$^+$, or the like; an ammonium ion, or other positively charged ionized organic compounds.

Photo-activate: Causing to function or act (activate) or control using an energy source capable of producing irradiation, such as light.

Reporting Moiety: A functional group or a molecule that is capable of producing a signal that can be visually and/or instrumentally detected. In particular disclosed embodiments, the reporting moiety provides the ability to visualize or detect, using an appropriate detection method, an enzyme because the reporting moiety becomes covalently attached to the enzyme.

Sample: Biological specimens containing biomolecules, for example nucleic acid molecules (e.g., genomic DNA, cDNA, RNA, and/or mRNA), proteins, and/or cells. Example samples are those containing cells or cell lysates from a subject (and which may contain one or more pathogens, such as bacteria), such as peripheral blood (or a fraction thereof such as plasma or serum), urine, saliva, sputum, tissue biopsy, cheek swabs, fecal specimen (e.g., stool sample), respiratory specimen, surgical specimen, fine needle aspirates, amniocentesis samples and autopsy material. In one example, the sample is obtained from the gut of a subject, such as the stomach, small intestine, large intestine, or rectum of the subject. Samples can be used directly, but can also be concentrated, filtered, lysed, washed, and/or diluted before analysis with the disclosed methods.

Subject: An organism, such as a vertebrate, such as a mammal, for example a human. Mammals include, but are not limited to, murines, simians, humans, farm animals, sport animals, and pets. In one example, the subject is a non-human mammalian subject, such as a monkey or other non-human primate, mouse, rat, rabbit, pig, goat, sheep, dog, cat, horse, or cow. In some examples the subject is a reptile, amphibian, fish or bird. Subjects can serve as a source of samples analyzed using the disclosed methods and devices.

Sulfate: A functional group having a structure —SO$_2$O$^-$ or —SO$_2$OH when attached to a probe embodiment described herein and having a structure SO$_2$(O$^-$)$_2$ or SO$_2$(OH)$_2$ when not attached to a probe embodiment. Any anionic sulfate groups can comprise a suitable counterion that balances the negative charge on the corresponding oxygen atom, such as an alkali metal ion like K$^+$, Na$^+$, Li$^+$, or the like; an ammonium ion, or other positively charged ionized organic compounds.

Toxicant: A poison made by humans or that is put into the environment by human activities, e.g., a pesticide.

Xenobiotic: A pharmacologically, endocrinologically, or toxicologically active chemical substance that is not a natural component of the organism exposed to it. Examples of xenobiotics include, without limitation, foods, dietary supplements, carcinogens, toxins and drugs.

The description of terms provided above are not intended to include impermissible substitution patterns (e.g., methyl substituted with 5 different groups, and the like). Such impermissible substitution patterns are easily recognized by a person of ordinary skill in the art. In formulas and specific compounds disclosed herein, a hydrogen atom is present and completes any formal valency requirements (but may not necessarily be illustrated) wherever a functional group or other atom is not illustrated. For example, a phenyl ring that is drawn as

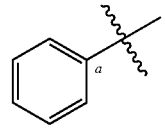 [SMILES: *c1ccccc1]

comprises a hydrogen atom attached to each carbon atom of the phenyl ring other than the "a" carbon, even though such hydrogen atoms are not illustrated.

Any functional group disclosed herein and/or defined above can be substituted or unsubstituted, unless otherwise indicated herein. The publications discussed herein are provided solely for their disclosure prior to the filing date of the present application and each is incorporated by reference in its entirety. Nothing herein is to be construed as an admission that the present disclosure is not entitled to antedate such publication by virtue of prior invention. Further, the dates of publication provided may be different from the actual publication dates which may need to be independently confirmed.

II. Introduction

A. Drug Metabolism

The lipophilic characteristics of drugs that promote their passage through biological membranes and subsequent access to their site of action hinder their excretion from the body. Renal excretion of unchanged drug plays only a modest role in the overall elimination of most therapeutic agents, since lipophilic compounds filtered through the glomerulus are largely reabsorbed back into the systemic circulation during passage through the renal tubules. The metabolism of drugs and other xenobiotics into more hydrophilic metabolites is therefore essential for the elimination of these compounds from the body and termination of their biological activity. Many of the metabolic biotransformation reactions apply as well to endogenous compounds, including steroids, vitamins and fatty acids. Although in general, biotransformation reactions generate more polar, inactive metabolites that are readily excreted, in some cases, metabolites with potent biological activity or toxic properties are generated. Many of the metabolic biotransformation reactions leading to inactive metabolites of drugs also generate biologically active metabolites of endogenous compounds. (*Goodman & Gilman's The Pharmacological Basis of Therapeutics*, Hardman, J G and Limbird, L. Eds, 10th Ed. McGraw-Hill Companies, Inc., Intl Edn (2001) at 12-15).

A hallmark of drug metabolism is a large inter-individual variability that often results in marked differences and, as a result, a drug's rate of elimination and other characteristics of its plasma concentration-time profile. Such variability is a major reason why patients differ in their response to a standard dose of a drug and must be considered in optimizing a dosage regimen for a particular individual. A combination of genetic, environmental, and disease-state factors affect drug metabolism, with the relative contribution of each depending on the specific drug.

B. Phase I and Phase II Metabolism.

The metabolism of xenobiotics usually involves two distinct stages. Phase I metabolism involves an initial oxidation, reduction or dealkylation of the xenobiotic by microsomal cytochrome P-450 monooxygenases (Guengerich, F. P. *Chem. Res. Toxicol.* 4: 391-407 (1991)); this step often is needed to provide hydroxyl- or amino groups, which are essential for phase II reactions. Oxidation is the most common phase I reaction.

Phase II metabolism involves conjugation, i.e., the attachment of ionized groups to the drug. These groups include glutathione, methyl or acetyl groups, which generally make a xenobiotic more water soluble and less biologically active. Frequently involved phase II conjugation reactions are catalyzed by glutathione S-transferases (Beckett, G. J. & Hayes, J. D., *Adv. Clin. Chem.* 30: 281-380 (1993)), epoxide hydrolases, sulfotransferases (Falany, C N, *Trends Pharmacol. Sci.* 12: 255-59 (1991)), and UDP-glucuronyl-transferases (Bock, K W, *Crit. Rev. Biochem. Mol. Biol.* 26:129-50 (1991)).

C. Site of Biotransformation

The metabolic conversion of xenobiotics generally is enzymatic in nature. The enzyme systems involved in the biotransformation of drugs are localized in the liver, although every tissue examined has some metabolic activity. Other organs with significant metabolic capacity include the gastrointestinal tract, kidneys and lungs. Following nonparenteral administration of a drug, a significant portion of the dose may be metabolically inactivated in either the intestinal epithelium or the liver before it reaches the systemic circulation. This "first pass" metabolism, significantly limits the oral availability of highly metabolized drugs. (*Goodman & Gilman's The Pharmacological Basis of Therapeutics*, Hardman, J G and Limbird, L. Eds, 10th Ed. McGraw-Hill Companies, Inc., Intl Edn (2001) at 12-15).

Within a given cell, most drug-metabolizing activity is found in the endoplasmic reticulum and the cytosol, although drug biotransformations also can occur in the mitochondria, nuclear envelope and plasma membrane. The enzyme systems involved in phase I reactions are located primarily in the endoplasmic reticulum, while the phase II conjugation enzyme systems are mainly cytosolic. Often drugs biotransformed through a phase I reaction in the endoplasmic reticulum are conjugated at this same site or in the cytosolic fraction of the same cell.

D. Cytochrome P450 Monooxygenase System

The cytochrome P450 enzymes are a superfamily of heme-thiolate proteins widely distributed across all living organisms. The enzymes are involved in the metabolism of a plethora of chemically diverse, endogenous and exogenous compounds, including xenobiotics. Usually they function as a terminal oxidase in a multicomponent electron-transfer chain that introduces a single atom of molecular oxygen into the substrate with the other atom being incorporated into water. In microsomes, the electrons are supplied from NADPH via cytochrome P450 reductase, which is closely associated with cytochrome P450 in the lipid membrane of the smooth endoplasmic reticulum. Cytochrome P450 catalyzes many oxidative reactions, including aromatic and side-chain hydroxylation; N-, O- and S-dealkylation; N-oxidation; N-hydroxylation; sulfoxidation; deamination; dehalogenation; and desulfuration. A number of reductive reactions also are catalyzed by these enzymes, generally under conditions of low oxygen tension.

Approximately 57 cytochrome P450s are functionally active in humans, of which ~40 are involved in xenobiotic metabolism. These are categorized into 17 families and many subfamilies. About 8 to 10 isoforms in the CYP1, CYP2, and CYP3 families primarily are involved in the majority of all drug metabolism reactions in humans. CYP3A4 and CYP3A5 together are involved in the metabolism of about 50% of drugs. Members of the other families are important in the biosynthesis and degradation of steroids, fatty acids, vitamins and other endogenous compounds. Each individual CYP isoform appears to have a characteristic substrate specificity based on structural features of the substrate, although considerable overlap often is present.

Besides the CYP enzyme system, an alternate enzyme for chemical oxidation is prostaglandin H synthase (PGHS) also known as cyclooxygenase (COX), which is the initial enzyme in arachidonate metabolism and formation of prostanoids such as prostaglandins, prostacyclins and thromboxanes. During the reduction of the endogenous substrate, hydroperoxy-endoperoxide (PGG2) to hydroxy-endoperoxide (PGH2), the PGHS enzyme is capable of co-oxidizing xenobiotics. In this reaction, a broad spectrum of chemicals can serve as electron donors such as phenolic compounds, aromatic amines, and polycyclic aromatic hydrocarbons. In contrast to numerous CYP enzymes in liver, the PGHS is an alternate enzyme for xenobiotic metabolism in extrahepatic tissues. Vogel, C., *Curr. Drug Metab.* (2000) 1(4): 391-404.

E. Hydrolytic Enzymes

A number of nonspecific esterases and amidases have been identified in the endoplasmic reticulum of human liver, intestine, and other tissues. The alcohol and amine groups exposed following hydrolysis of esters and amides are suitable substrates for conjugation reactions. *Goodman & Gilman's The Pharmacological Basis of Therapeutics*, Hardman, J G and Limbird, L. Eds, 10th Ed. McGraw-Hill Companies, Inc., Intl Edn (2001) at 12-15.

Microsomal epoxide hydrolase is found in the endoplasmic reticulum of essentially all tissues, and is in close proximity to the cytochrome P450 enzymes. Epoxide hydrolase generally is considered a detoxification enzymes, hydrolyzing highly reactive arene oxides generated from cytochrome P450 oxidation reactions to inactive, water-soluble transdihydrodiol metabolites.

Glycosidases and sulfatases are further hydrolases of importance for drug metabolism. They primarily metabolize endogenous substrates including glycosaminoglycans and steroids, but they also accept some xenobiotic substrates; this is particularly true for the beta-glucuronidases. The gut flora can deconjugate compounds that are excreted via the bile as glucuronides or sulfates; the deconjugation products are often reabsorbed from the gut leading to enterohepatic circulation. Glycosidases are toxifying in many cases; frequently, the toxicity and mutagenicity of natural products is masked by sugar moieties in glycosides and deglycosylation leads to their toxic effects. Oesch-Bertlomowicz, F. Oesch, *Comprehensive Medicinal Chemistry II* (2007) 5: 193-214. Organosulfate ester cleavage is catalyzed by sulfatase enzymes, resulting in the formation of the corresponding alcohol and inorganic sulfate. Sulfatases catalyze the hydrolysis of the sulfate esters formed by the action of the SULTs. Three classes of sulfatase enzymes have been discovered and are differentiated by the types of cofactors utilized for catalysis. Group I enzymes, termed arylsulfatases, are found in archaea, bacteria, and eukaryotes and require either a calcium or a magnesium ion and a formylglycine (FGly) cofactor. FGly is a catalytically essential residue found almost exclusively in the active sites of type I sulfatases formed by post-translational oxidation of cysteine or serine side chains. Appel, M J, Bertozzi, C. R., *ACS Chem. Biol.* (2015) 10(1): 72-84. Eukaryotic sulfatase enzymes are involved in a multitude of processes, such as hydrolysis of sulfate ester linkages in steroids, lipids, and glycosaminoglycans. Schepart, E. M., Broderick, J B, in *Comprehensive Natural Products II* (2010) 8: 625-661.

Protease and peptidase enzymes are widely distributed and are involved in the botransformation of polypeptide drugs.

F. Conjugation Reactions.

Both an activated form of an endogenous compound and an appropriate transferase enzyme are necessary for the formation of a conjugated metabolite.

G. Glucuronidation

Glucuronidation involves the reaction of uridine 5' diphosphoglucuronic acid with one of a number of possible functional groups, such as R—OH, R—NH$_2$, R—COOH, and others. The reaction is metabolized by UGTs (also called glucuronyltransferases), which are present in many tissues. Together with cytochrome P450 enzymes, UGTs represent more than 80% of the metabolic pathways. The site of glucuronidation is generally an electron-rich nucleophilic heteroatom (oxygen, nitrogen, or sulfur). DeGroot, M J et al, *Comprehensive Medicinal Chemistry II* (2007) 5: 809-25. UGTs are classified into two distinct gene families: UGT1 and UGT2, the latter showing genetic polymorphisms. In humans, up to 16 different functional UGT isoforms belonging to subfamilies 1A and 2B have been characterized. (https://www.pharmacogenomics.pha.ulaval.ca/ugt-alleles-nomenclature/), which have distinct but overlapping substrate specificities. Extensive glucuronidation of phenolics, for example, can be a barrier to their oral bioavailability as the first-pass glucuronidation (or premature clearance by UGTs) of orally administered agents usually results in the poor oral bioavailability and lack of efficacy. Wu, B. et al, *J. Pharm. Sci* (2011) 100(9): 3655-81. The glucuronides of ezetimibe and morphine are equivalent or more potent than the parent compounds. The glucuronides of some natural isoflavone phenolics found in soybeans and other legumes (e.g., daidzein and genistein) retain the weaker biological activities of their unconjugated parent, including estrogen receptor binding and natural killer cell activation.

H. Sulfonation

The sulfonation of xenobiotics and small endogenous substrates, such as steroids and neurotransmitters is widely distributed in nature, and occurs in organisms ranging from microbes to man. The process of sulfonation involves the transfer of a sulfo ($SO_3^-$) moiety, generally to a hydroxyl on an acceptor molecule, which is catalyzed by sulfotransferases (SULTs). The universal sulfonate donor for these reactions is 3'-phosphoadenosine 5-phosphosulfonate (PAPS). In the case of most xenobiotics (e.g., acetaminophen) and small endogenous substrates (e.g. dopamine), sulfonation has generally been considered a detoxification pathway leading to more water-soluble products, thereby aiding their excretion via the kidneys or bile, and less biological activity. For, some xenobiotics, e.g., hydroxyl heterocyclic amines and hydroxymethyl polycyclic aromatic hydrocarbons, sulfonation leads to highly reactive electrophiles that are both mutagenic and carcinogenic. Sulfonation of the hair growth stimulant minoxidil and the neuroendocrine peptide cholecystokinin elicits their biological effects, increases its water solubility and decreases its biological activity. Gamage, N. et al, *Toxicological Sci.* (2006) 90(1): 5-22. In humans three SULT families, SULT1, SULT2, and SULT4, have been identified that contain at least thirteen distinct members with distinct but overlapping substrate specificities. The broad substrate specificity of SULTS is due to the fact that multiple forms of these enzymes exist, and the binding sites of some isoforms is plastic, allowing the enzyme to adopt varying architectures so that it can interact with small aromatics, L-shaped aromatics, and fused ring compounds.

I. Acetylation

Two N-acetyltransferases (NAT1 and NAT2) are involved the acetylation of amines, hydrazines and sulfonamides. In contrast to most drug conjugates, acetylated metabolites often are less-water soluble than the parent drug. *Goodman & Gilman's The Pharmacological Basis of Therapeutics*, Hardman, J G and Limbird, L. Eds, 10th Ed. McGraw-Hill Companies, Inc., Intl Edn (2001) at 12-15.

J. Glutathione S-Transferase

Glutathione S-transferases catalyze the addition of aliphatic, aromatic, or heterocyclic radicals as well as epoxides and arene oxides to glutathione (GSH). These glutathione conjugates then are cleaved to cysteine derivatives primarily by renal enzymes and then acetylated, thus forming N-acetylcysteine derivatives. Examples of compounds transformed to reactive intermediates and then bound to GSH include, but are not limited to, bromobenzene, chloroform, and acetaminophen. Such toxicants may deplete GSH. Depletion of GSH can diminish the body's ability to defend against lipid peroxidation. Glutathione peroxidase (GPx), an enzyme of the oxidoreductase class, catalyzes the detoxifying reduction of hydrogen peroxide and organic peroxides via oxidation of glutathione. GSH is oxidized to the disulfide linked dimer (GSSG), which is actively pumped out of cells and becomes largely unavailable for reconversion to reduced glutathione.

GSH also is a cofactor for glutathione peroxidase. Thus, unless glutathione is resynthesized through other pathways, utilization of oxidized glutathione is associated with a reduction in the amount of glutathione available.

Glutathione reductase (NADPH), a flavoprotein enzyme of the oxidoreductase class, is essential for the maintenance of cellular glutathione in its reduced form (Carlberg & Mannervick, *J. Biol. Chem.* 250: 5475-80 (1975)). It catalyzes the reduction of oxidized glutathione (GSSG) to reduced glutathione (GSH) in the presence of NADPH and maintains a high intracellular GSH/GSSG ratio of about 500:1 in red blood cells.

Synthesis of GSH requires cysteine, a conditionally essential amino acid that must be obtained from dietary sources or by conversion of dietary methionine via the cystathionase pathway. If the supply of cysteine is adequate, normal GSH levels are maintained. GSH depletion occurs if supplies of cysteine are inadequate to maintain GSH homeostasis in the face of increased GSH consumption. Acute GSH depletion causes severe—often fatal—oxidative and/or alkylation injury, and chronic or slow arising GSH deficiency due to administration of GSH-depleting drugs, such as acetaminophen, or to diseases and conditions that deplete GSH, can be similarly debilitating.

K. Reductases

The aldo-keto reductases (AKRs) and short chain dehydrogenases/reductases (SDRs) are the main enzymes that catalyze oxidation-reduction reactions involving a xenobiotic carbonyl. The AKRs are involved in redox transformations of carbonyls introduced by metabolic transformations by CYPs or other enzyme systems, or present on the parent xenobiotic. The major impetus driving research on AKR1B, for example, has been the potential involvement of this enzyme in hyperglycemic injury and promise of specific AKR1B1 inhibitors for the treatment of diabetic complications. Barski, O. A. et al, *Drug Metab. Rev.* (2008) 40(4): 553-624.

L. Metabolite Formation by Gut Microbiota

Microbial metabolism of xenobiotics must be understood in the context of the concurrent and often competing metabolic processes occurring in the human host. Orally ingested compounds pass through the upper GI tract to the small intestine where they can be modified by digestive enzymes and absorbed by host tissues. Readily absorbed xenobiotics pass between or through intestinal epithelial cells, where they may be processed by host enzymes before transport to the liver via the portal vein. Following exposure to the liver's rich collection of metabolic enzymes, xenobiotics and their metabolites enter systemic circulation, distributing into tissues and potentially affecting distal organs. By contrast, intravenously administered compounds circumvent this "first-pass" metabolism and are immediately introduced into systemic circulation. Compounds in the circulatory system are eventually further metabolized and/or excreted, which generally occurs either via the biliary duct back into the gut lumen (biliary excretion) or through the kidneys into the urine. Metabolites returned to the gut lumen can either continue on to the large intestine, where they will eventually be excreted in the feces, or they can potentially be reabsorbed by host cells in the small intestine through a process known as enterohepatic circulation. Koppel, N. et al., *Science* (2017) 356 (6344): 1246 DOI: 10.1126/science.aag2770.

Xenobiotics can therefore encounter gut microbes via multiple routes. In contrast to compounds that are absorbed in the small intestine, poorly absorbed xenobiotics continue through the small intestine into the large intestine and may be transformed by gut microbes. Readily absorbed compounds and compounds administered via other routes (e.g., intravenous injection) can also reach gut microbes through biliary excretion. The products of gut microbial metabolism can be absorbed by the host and circulated systemically or interact locally with the epithelial cells lining the GI tract. Ultimately, these microbial metabolites are excreted in feces or filtered by the kidneys and eliminated in the urine. Overall, human and microbial transformations generate a complex intertwined metabolic network that affects both the host and the members of the microbiota.

In contrast to the oxidative and conjugative metabolism favored following systemic absorption, metabolism by gut bacteria is mostly reductive and hydrolytic (Klaassen C D and Cui J Y, (2015) *Drug Metab. Dispos.* 43:1505-1521). Many of the enzyme classes associated with xenobiotic metabolism (hydrolases, lyases, oxidoreductases, and transferases) and highlighted here are widely distributed among sequenced gut microorganisms. It is therefore likely that many important transformations of xenobiotics may be performed by multiple different phylogenetic groups of gut microbes. However, it is critical to note that broad annotations are not predictive of substrate specificity, as enzymes with high sequence similarity can catalyze distinct chemical reactions. Metabolic activities can also be discontinuously distributed across closely related strains and acquired via horizontal gene transfer, making it problematic to infer gut microbial metabolic capabilities from phylogenetic analyses alone. Koppel, N. et al., *Science* (2017) 356 (6344): 1246; DOI: 10.1126/science.aag2770.

Because the expression and activity of drug- and xenobiotic-metabolizing Phase I enzymes (which include enzymes that oxidize drugs/xenobiotics) and Phase II enzymes (which include enzymes that promote conjugation/modification of the drugs/xenobiotics to conjugated species) are major determinants of the overall pharmacokinetic profiles of mammals, such as humans, nearly every pharmaceutical drug needs to be assessed for its metabolic profile—that is, how the drug is metabolized by Phase I and Phase II enzymes. Such enzymes typically include enzymes in the liver and gut microbiome. Likewise, potentially toxic xenobiotics (e.g., pesticides and other chemical contaminants in the environment) need to be assessed for their human metabolism.

The human gut lacks a well-defined core set of organisms that spans all human populations, yet microbiota across healthy individuals have common functional capacities for xenobiotic metabolism that arise from disparate combinations of >1,000 microbial taxa. Even within an individual, xenometabolism in the microbiota is largely maintained despite composition shifts during a lifetime. This suggests that understanding the molecular basis for gut microbiota-enabled susceptibility to environmental- or pharmacological-induced toxicity and disease can not readily be inferred from metagenomes alone. It also suggests that interindividual differences in phylogenetic composition may not produce varied xenometabolic function. A more accurate model of microbiota-xenobiotic interaction considers xenometabolism at three structural levels: community xenometabolism, taxa-level xenometabolism, and enzyme-level xenometabolism. Complex xenometabolic pathways often emerge through interactions within and across these hierarchical scales. At the community level, the spatial and compositional structure influences proliferation, activity, and survival of specific taxa. At the species level, the expression of enzymes for xenometabolism is controlled by various regulatory mechanisms. Finally, at the enzyme level the actual biotransformations are performed.

At present, xenobiotic metabolism is largely determined by treating a liver microsome extract with the xenobiotic, then determining what metabolites of the xenobiotic are present after some incubation period. After the metabolites are determined then assumptions can be made about the types of metabolism the xenobiotic goes through. As for what exists, there has long been antibodies for determining protein expression levels for these enzyme families. There are also colorimetric and fluorescent activity assays that provide readout for an enzyme family's activity, but not the individual enzyme contributions. Furthermore, RNA or protein abundances rarely correlate to functional activity levels. As such, current methods for evaluating xenobiotic metabolism do not provide sufficient information regarding the activity contribution of individual enzymes. Additionally, current approaches for evaluating xenobiotics in the gut microbiome, such as metagenomics and metatranscriptomics, can address the first two levels of the three structural levels discussed above, but are intrinsically unable to address the third. These techniques are not sufficient to identify the organisms or enzymes responsible for the activity. For example, a common approach to parsing function in the microbiome is to use a general assay that measures the total activity in the community, and to use metagenomes and metatranscriptomes taken from the community to identify the highest abundance taxa and enzymes; these are then inferred to be the dominant drivers of the observed cumulative activity (FIG. 1).

Figure 2:
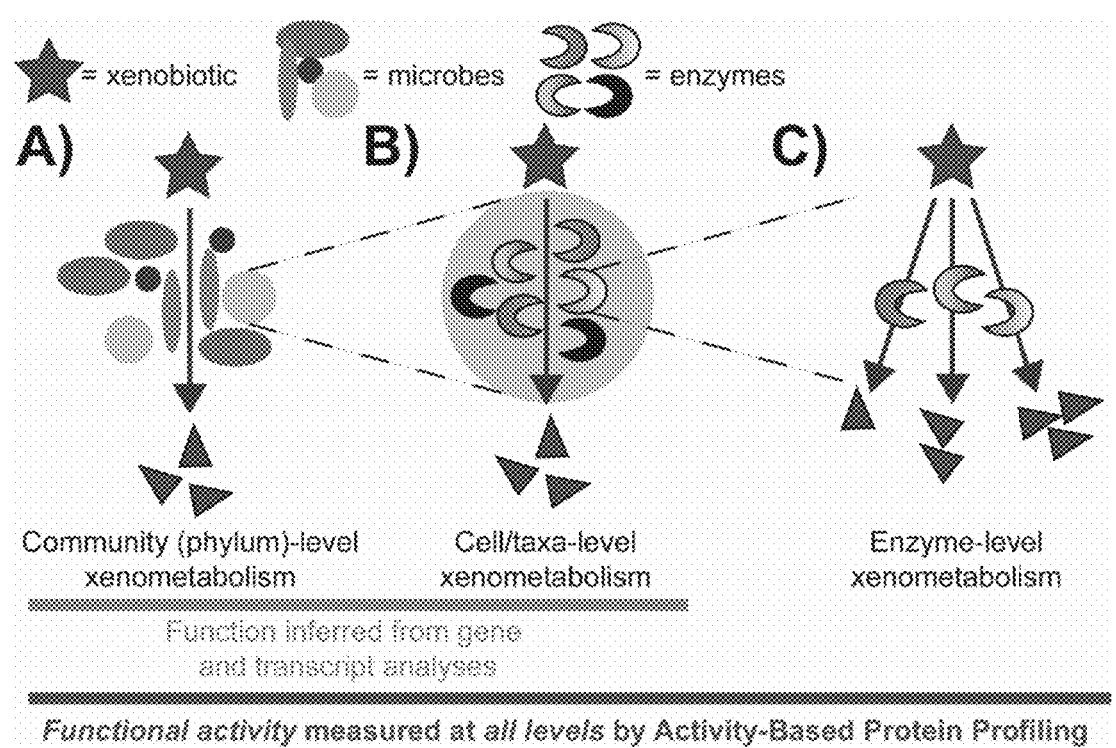
FIG. 2 is a schematic diagram showing how disclosed activity-based probe ("ABP") embodiments can be used to measure all levels of protein functional activity during xenometabolism, including at the community (phylum)-level of xenometabolism, the cell/taxa-level of xenometabolism, and the enzyme-level of xenometabolism.

Many factors impede a direct correlation of gene or transcript abundance to enzyme function, including RNA processing and stability, requisite posttranslational modifications, small molecule or oxidative inhibition of enzymes, or requisite protein-protein and cofactor enzyme interactions. The correlation of transcript abundance to enzyme abundance is as low as 40%. Therefore, transcript to enzyme function correlation is even lower. To accurately assign function to specific taxa and enzymes in the microbiome, new approaches are needed, particularly methods that can measure functional activity at all levels, such as illustrated in FIG. 2.

Perturbations to gut microbial xenometabolism via inhibition, antibiotic usage, host diet, dysbiosis, persistent organic pollutants, or other mechanisms can result in changes to host health, particularly in early life where gut colonization is impaired. What constitutes an ideal microbiome composition for good health is not clear, but there is a growing consensus that the microbiome should be able to perform a set of metabolic functions together with the host. Enzyme families that are known to be involved in xenometabolism include β-glucuronidases, azoreductases, nitroreductases, sulfatases, and b-cysteine lyases. Importantly, xenobiotic exposure can change the composition of the gut microbiota, potentially changing xenometabolic activity. This can lead to complicated feedback loops. For example, aryl hydrocarbon receptor (AhR) agonists, including the organic pollutant 2,3,7,8-tetrachlorodibenzodioxin (TCDD), can alter host metabolism and immunity. Recent evidence indicates that AhR can also modulate the composition of the gut microbiome, and C57BL6/J Ahr−/− mice have varied gut composition and metabolic activities. Thus, xenobiotic activation of AhR alters host metabolism and immunity, altering the gut microbiota. This can lead to altered xenometabolism by the gut microbiota, potentially disrupting physiological homeostasis and playing a role in xenobiotic-induced diseases. Developing strategies to track all levels of xenometabolism throughout perturbation are needed to define the functional and molecular basis for microbiota-mediated toxicity and disease susceptibility, to improve exposure risk assessment, and to identify functional biomarkers for toxicity and susceptibility. The present inventors have developed such a strategy.

While microbiota-xenobiotic interactions play an important role in overall metabolism, knowledge gaps exist in understanding the molecular mechanisms responsible. Indeed, much of this understanding to date has been derived from experiments using antibiotic treatment, gnotobiotic animals, or in vitro systems to identify metabolite fate with and without the entire microbiota. Such studies are incapable of providing molecular-scale resolution by identifying active enzymes and microbes. Metagenomic and metatranscriptomic studies can provide this resolution; however, presence or expression of a gene does not necessarily indicate that a protein is produced or that the protein is active. For example, given differences in activity of purified β-glucuronidases, it is unlikely that even successfully translated glucuronidases have the same impact on glucuronidated metabolites. These differences cannot be identified using sequencing technologies alone, but coupling to activity-based strategies clarifies the functionally-active population of microbiota. The present inventors have developed a powerful activity-based strategy, which directly addresses the need to move beyond inference to molecular-scale measurement of functional activity in situ, and highlights the utility of chemical biology tools to provide an avenue for a more complete understanding of how host, microbiota, and xenobiotics interact.

III. Probe Embodiments

The present disclosure provides an Activity-Based Probe (also referred to herein as an "ABP" or a "probe") that is effective to define the functional and molecular basis for microbiota-mediated toxicity and disease susceptibility. The disclosed ABP embodiments are small molecule substrates that, upon activation by a catalytically active target enzyme, form a covalent bond with that enzyme. Because the probe only binds when an active enzyme is present, the ABP can be used to demonstrate a specific enzyme activity in lysate, live cells, or tissue. For example, it is contemplated that a patient sample containing a target enzyme can be reacted with a probe before adding the target enzyme-probe complexes to a solid phase support, so that clickable functional groups on the probe are available for reaction with clickable functional group containing-reporter molecules for direct detection of the target enzyme-probe complex. Alternatively, it is contemplated that the probe can first be immobilized by reaction of a clickable functional group of the probe with a clickable functional group-derivatized solid phase support surface to attach the probe to the solid phase support before reacting it with a patient sample containing a target enzyme, and that a second reporter can then be used for indirect detection of target enzyme-probe binding. The disclosure therefore includes probes comprising moieties that facilitate adhering the probe to a resin or support, or labeling the probe such that the enzyme to which it is bound can be enriched and measured by proteomics, and/or labeling the probe such that it and the enzyme to which it is bound can undergo further analysis (e.g., imaging, SDS-PAGE, or fluorescence-activated cell sorting (or "FACS")).

The ABP described herein have a structure comprising an enzyme-binding group and a Tag moiety (or a precursor thereof) that can be used to adhere the probe to a support or resin or to label the probe (and the enzyme to which it becomes attached) as described above. According to some embodiments, the ABP can have a structure satisfying general Formula I, illustrated below.

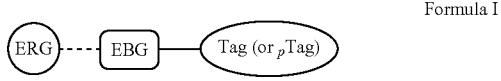

Formula I

Exemplary scenarios for binding of a probe to a target enzyme involved in xenobiotic metabolism comprising both human and gut microbiota targets, include, without limitation: (1) the enzyme cleaving the ERG from the EBG of the probe, which produces an activated EBG that can be bound to the enzyme; (2) selective binding of the EBG to the target enzyme, where the probe contains a group that is chemically modified by the enzyme to form another group that then activates the EBG so that the probe can bind to the enzyme; and (3) the ERG group being displaced by the enzyme such that the EBG of the probe is bound to the enzyme.

With reference to Formula I, "EBG" represents an enzyme-binding group, "Tag" represents a labeling moiety that can be used to visualize the probe; and "$_p$Tag" represents a precursor moiety that can be converted to a Tag moiety or that can be used to attach the probe to a support or resin. As illustrated in Formula I, some ABP embodiments can further comprise an enzyme-reactive group (or "ERG"), but this group need not be present in all embodiments. The optional presence of the ERG is illustrated by a dashed line in Formula I. In embodiments where the ERG is present, it can be a functional group or a molecule that is attached, either directly or indirectly, to the EBG and that is capable of being cleaved from the EBG by an enzyme or that can be displaced from the probe by an enzyme. In some embodiments, the ERG, if present, can be directly or indirectly coupled to the EBG. In some embodiments, the EBG can be directly or indirectly coupled to the Tag or, alternatively, the $_p$Tag. The phrase "directly coupled" means that the referenced groups are chemically coupled to one another with nothing in between. The phrase "indirectly coupled" means that the referenced groups are chemically coupled to one another through another moiety (e.g., a functional group, a linker, or a combination thereof).

According to some embodiments, the EBG of Formula I can be a group capable of binding to an enzyme upon chemical modification. Representative embodiments of EBGs are described herein. In exemplary disclosed embodiments, the EBG can be a group capable of binding to the same enzyme that chemically modifies the ERG. In some embodiments, the EBG becomes covalently bound to the enzyme after the enzyme has cleaved an ERG of a probe embodiment. Exemplary enzymes that can cleave an ERG or displace an ERG include, but are not limited to, enzymes capable of NAD(P)H quinone oxidoreductase activity (e.g., NAD(P)H quinone oxidoreductase), enzymes capable of aldoketoreductase activity (e.g., aldoketoreductase), glucuronidase transferases, sulfatases, phosphatases, and prostaglandin H synthases (PGHSs).

According to some additional embodiments, the EBG becomes covalently bound to the enzyme after the enzyme has chemically modified a functional group of the EBG (e.g., such as by reducing or oxidizing a functional group of the EBG). Exemplary enzymes that can activate the EBG group by chemically modifying a functional group of EBG include, but are not limited to, azoreductases, including, without limitation, Flavin-dependent NADH preferred azoreductases, Flavin-dependent NADPH preferred azoreductases, Flavin-free NADPH preferred azoreductases, that reduce azo-functional groups to amines, or nitroreductases that reduce nitro groups to amines.

According to some additional embodiments, the EBG can become covalently bound to the enzyme by simply combining the enzyme and the probe. Exemplary enzymes that can react with the EBG in this manner include enzymes capable of β-cysteine lyase activity, such as β-cysteine lyases).

According to yet additional embodiments, the EBG can become covalently bound to the enzyme after being exposed to a light source that induces a photochemical reaction within the EBG such that it can form a covalent bond with a functional group of the enzyme. Exemplary enzymes that can be bound to the EBG in such embodiments include, but are not limited to, glutathione S transferases, glucuronosyltransferases, and sulfotransferases.

The Tag (or $_p$Tag) moiety provides a handle for further modification of the probe before or after the probe has been bound to the enzyme. In embodiments comprising a Tag moiety, the Tag moiety can be a reporting moiety that is capable of being detected using a detection technique suited for use with biological samples. Suitable Tag moieties include functional groups and/or molecules that can generate a detectable signal, which can be detected using fluorescence detection techniques, colorimetric detection techniques, binding assay techniques, and the like. According to exemplary disclosed embodiments, the Tag moiety can be, for example, a fluorophore, a binding partner of an affinity-based binding pair, a quantum dot, a dye, and the like. For example, the Tag moiety can be a biotin moiety, an avidin or streptavidin moiety, a fluorescein moiety, a rhodamine moiety, a coumarin moiety, a quinine moiety, or a combination thereof.

According to embodiments wherein the probe comprises a $_p$Tag moiety, the $_p$Tag moiety can be further modified to provide a Tag moiety and/or that can be used to fix the probe to a support or resin. According to such embodiments, the $_p$Tag moiety typically is a functional group that can be chemically coupled with a chemical coupling partner that itself comprises a Tag moiety or that is bound to a support or resin. For example, the $_p$Tag moiety can comprise a clickable functional group that can be chemically coupled to a separate compound comprising a Tag moiety and a clickable functional group (referred to as a Tag-containing compound) or comprising a support- or resin-bound clickable functional group (referred to as a support-containing compound). Exemplary clickable functional groups that can be selected for the $_p$Tag moiety, the Tag-containing compound, and/or the support-containing compound include, but are not limited to alkyne groups and azide groups. The Tag-containing compound can comprise at least one Tag moiety, such as a fluorophore, a binding partner of an affinity-based binding pair, a quantum dot, a dye, and the like. The support-containing compound can comprise a support or resin, e.g., one that typically is used in biological analysis, wherein the support or a functional group of the resin is bound directly or indirectly (e.g., covalently) to the clickable functional group. Solely by way of example, some probe embodiments can comprise a $_p$Tag moiety that comprises an alkyne. This probe embodiment can be coupled with a Tag-containing compound that comprises a Tag moiety and an azide or a support-containing compound that comprises a support and an azide, respectively. The alkyne and the azide can be chemically coupled via click chemistry so as to provide the Tag moiety illustrated in Formula I. According to some such embodiments, the clickable functional group of the Tag precursor and the Tag-containing compound are different; that is, if one comprises an alkyne, then the other comprises an azide (or vice versa) so that click chemistry can be used to join the two components and form the probe. According to some embodiments, click chemistry can be used to combine the $_p$Tag moiety and a corresponding Tag-containing compound or a support-containing compound before or after the probe has been bound to an enzyme.

According to some embodiments, the ABP can comprise a plurality of Tag moieties and/or $_p$Tag moieties, such as two or more Tag moieties and/or $_p$Tag moieties. According to some such embodiments, the two or more Tag moieties and/or $_p$Tag moieties are attached (directly or indirectly) to the EBG. According to some embodiments, the probe can comprise two Tag moieties attached (directly or indirectly) to the EBG. According to some such embodiments, each Tag moiety can be the same moiety or a moiety different from the other. According to yet other embodiments, the probe can comprise two $_p$Tag moieties attached (directly or indirectly) to the EBG. According to some such embodiments, each $_p$Tag moiety can be the same moiety or a moiety different from the other. Solely by way of example, one $_p$Tag moiety can comprise an alkyne group and the other $_p$Tag moiety can comprise an azide group; each of the two $_p$Tag moieties can comprise an alkyne group; or each of the two $_p$Tag moieties can comprise an azide group. According to yet other embodiments, the probe can comprise one Tag moiety and one $_p$Tag moiety.

According to some embodiments, the probe can have a structure satisfying Formula II below.

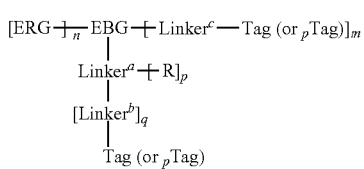

Formula II

With reference to Formula II, the ERG (when present) is a functional group or a molecule that can be cleaved or displaced from the EBG by an enzyme; the EBG is a functional group that is capable of covalently bonding with an enzyme involved in Phase II metabolism or that is present in the gut microbiome; $Linker^a$ comprises an aliphatic group, a heteroaliphatic group, an aromatic group, an aliphatic-aromatic group, a heteroaliphatic-aromatic group, a heteroaromatic group, an aliphatic-heteroaromatic group, or a heteroaliphatic-heteroaromatic group; $Linker^b$ and $Linker^c$ (when present) each independently can comprise an aliphatic group, a heteroaliphatic group, an aromatic group, an aliphatic-aromatic group, a heteroaliphatic-aromatic group, a heteroaromatic group, an aliphatic-heteroaromatic group, or a heteroaliphatic-heteroaromatic group; each Tag moiety (if present) independently is a functional group (or a molecule) capable of generating a detectable signal; each $_p$Tag moiety (if present, such as when a Tag is not present) comprises a clickable functional group; each of n, m, p, and q independently can be 0 or 1. In embodiments where any one or more of n, m, p, and q are 0, then the group qualified with n, m, p, or q is not present and the groups formerly indirectly coupled together may now be directly coupled (e.g., EBG-Tag (or $_p$Tag)). In embodiments where q is 0, $Linker^a$ is directly attached to the illustrated Tag moiety or $_p$Tag moiety.

In exemplary embodiments where n is 1, the ERG is present and is bound to the EBG. According to some such embodiments, the ERG is a functional group or molecule that can be cleaved or displaced from the EBG group, such as by an enzyme. ERGs that can be enzymatically cleaved include, but are not limited to, glucuronic acid moieties, glucuronic acid derivatives (e.g., aziridine-functionalized glucuronic acid groups, such as

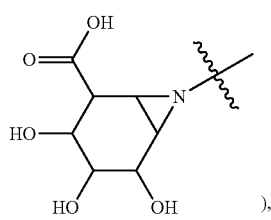

sulfate (or sulfonic acid) moieties, phosphate (or phosphoric acid) moieties, or the like. Representative ERGs that can be displaced by an enzyme include, but are not limited to, a halogen (e.g., I, Cl, F, or Br) or a phenol-containing group of formula —OPh, wherein the Ph group optionally comprises one or more substituents other than hydrogen. In exemplary disclosed embodiments, the ERG is selected from glucuronic acid

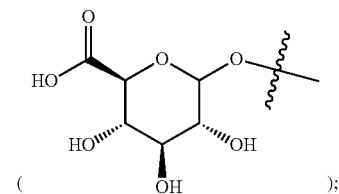 [SMILES: *OC1O[C@H](C(=O)O)[C@@H](O)[C@H](O)[C@H]1O]

a glucuronic acid derivative that, prior to being enzymatically cleaved, is attached to an ERG that comprises a nitrogen atom that forms an aziridine ring with the glucuronic acid moiety; a sulfate (or a protonated version thereof); a phosphate (or a protonated version thereof); iodo, or —OPh optionally comprising a —CH$_2$ONO$_2$ group in the ortho, meta, or para position of the phenyl ring relative to the oxygen atom of the —OPh group.

In exemplary disclosed embodiments, the EBG comprises a functional group that (a) is capable of being chemically modified by an enzyme to which it ultimately becomes covalently bound; or (b) is capable of becoming activated for reaction with an enzyme after the same enzyme cleaves an ERG attached to the EBG; or (c) is capable of becoming bound to an enzyme after the enzyme displaces an ERG attached to the EBG; or (d) is capable of becoming activated for reaction with an enzyme after being exposed to a light source; or (e) is capable of becoming bound to an enzyme upon being exposed to the enzyme. In exemplary disclosed embodiments, the EBG can comprise an azo group, a nitro group, an ortho- or para-substituted phenol group capable of forming an ortho- or para-quinone methide, an olefin, an amide, a dichloro dione group, or a benzyl carbonyl group.

According to some embodiments, the EBG has a structure satisfying one or more of Formulas $IIA_{EBG}$-$IIJ_{EBG}$ illustrated below. Solely for exemplary purposes, additional components of the probe (e.g., $Linker^a$, $Linker^c$, and/or ERG) are illustrated to show connectivity.

Formula $IIA_{EBG}$

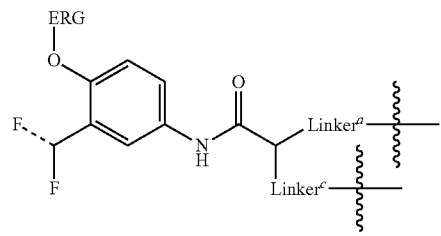

Formula $IIB_{EBG}$

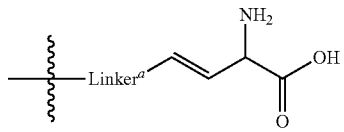

Formula $IIC_{EBG}$

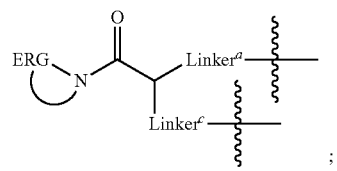

-continued

Formula IID$_{EBG}$

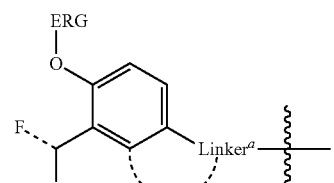

Formula IIE$_{EBG}$

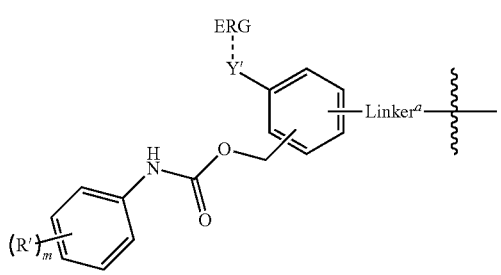

Formula IIF$_{EBG}$

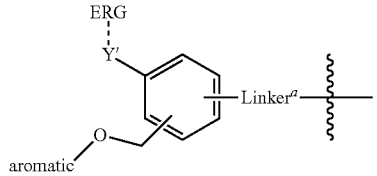

wherein Y' is O (in which case an ERG is present), —N=NR''' (wherein R''' is a dye or other reporting moiety), or nitro; m is an integer selected from 0 to 5; and each R' independently is selected from aldehyde, ketone, ester, carboxylic acid, acyl, acyl halide, cyano, sulfonate, nitro, nitroso, quaternary amine, CF$_3$, alkyl halide, or combinations thereof;

Formula IIG$_{EBG}$

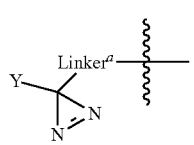

wherein Y is —CH$_3$ or —CF$_3$;

Formula IIH$_{EBG}$

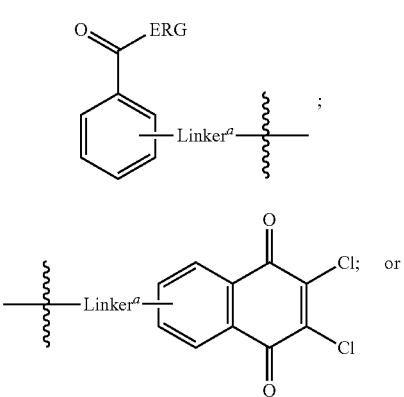

Formula III$_{EBG}$

-continued

Formula IIJ$_{EBG}$

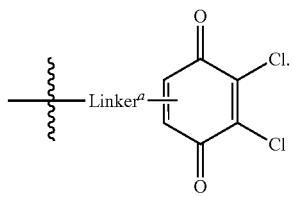

According to some embodiments, Linker$^a$ can comprise an alkylene oxide, an amine, an amide, an ester, a —(CH$_2$)$_{n'}$— group (wherein n' is an integer ranging from 1 to 50, such as 1 to 25, or 1 to 10, or 1 to 5, or 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50), or any combination thereof. In exemplary disclosed embodiments, Linker$^a$ can have a structure satisfying any one or more of Formulas IIA$_{Linkera}$-IIG$_{Linkera}$. Solely for exemplary purposes, additional components of the probe (e.g., EBG, R, Tag (or $_p$Tag), and/or Linker$^b$) are illustrated to show connectivity.

Formula IIA$_{linkera}$

 

wherein n' is an integer ranging from 1 to 50, such as 1 to 25, or 1 to 10, or 1 to 5; or 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50;

Formula IIB$_{linkera}$

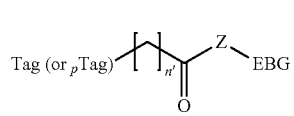

wherein n' is an integer ranging from 0 to 50, such as 1 to 25, or 1 to 10, or 1 to 5, or 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, and Z is oxygen or NR''', wherein R''' is hydrogen, aliphatic, or aromatic;

Formula IIC$_{linkera}$

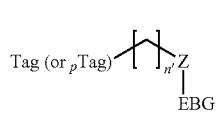

wherein n' is an integer ranging from 1 to 50, such as 1 to 25, or 1 to 10, or 1 to 5, or 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, and Z is oxygen or NR''', wherein R''' is hydrogen, aliphatic, or aromatic;

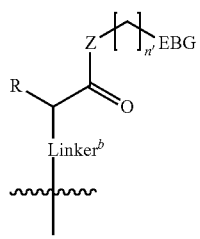

Formula IID$_{linkera}$ wherein n' is an integer ranging from 1 to 50, such as 1 to 25, or 1 to 10, or 1 to 5, or 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, and Z is oxygen or NR''', wherein R''' is hydrogen, aliphatic, or aromatic;

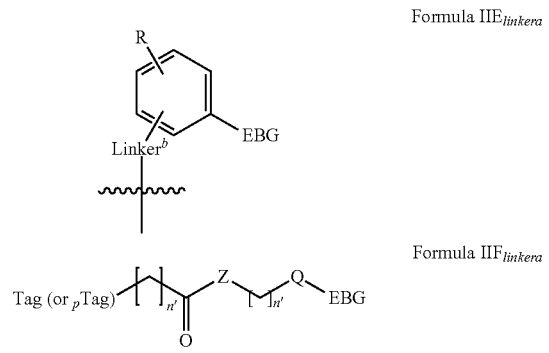

Formula IIE$_{linkera}$

Formula IIF$_{linkera}$ wherein each n' independently is an integer ranging from 1 to 50, such as 1 to 25, or 1 to 10, or 1 to 5, or 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, and Q is $CH_2$, O, or NR''', wherein R''' is hydrogen, aliphatic, or aromatic; or Formula IIG$_{linkera}$

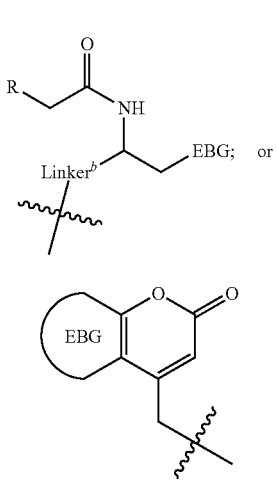

Formula IIH$_{linkera}$

In embodiments comprising a Linker$^b$, this moiety can comprise a —$(CH_2)_{n'}$— group (wherein n' is an integer ranging from 1 to 50, such as 1 to 25, or 1 to 10, or 1 to 5, or 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50); an amide group; or any combination thereof. In exemplary disclosed embodiments, the Linker$^b$ group can be a —$(CH_2)_{n'}$— group wherein n' is 1 to 5 (1, 2, 3, 4, or 5), or —C(O)NR'''$CH_2$—, wherein the carbonyl portion is attached to Linker$^a$ and the methylene portion is attached to the Tag (or $_p$Tag) and wherein R''' is hydrogen, aliphatic, or aromatic.

In embodiments comprising a Linker$^c$, this moiety can comprise an amide, an aliphatic group, an alkylene oxide group, or any combination thereof. In exemplary disclosed embodiments, Linker$^c$ can have a structure satisfying Formula IIA$_{Linkerc}$ or Formula IIB$_{Linkerc}$ illustrated below. Solely for exemplary purposes, additional components of the probe (e.g., EBG, R, Tag (or $_p$Tag), and/or Linker$^a$) are illustrated to show connectivity.

Formula IIA$_{Linkerc}$

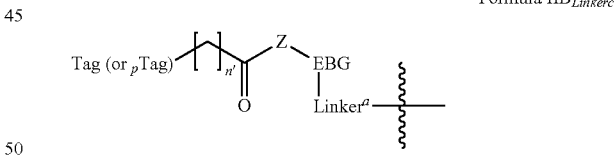

wherein n' is an integer ranging from 0 to 50, such as 1 to 25, or 1 to 10, or 1 to 5, or 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, and Z is oxygen or NR''', wherein R''' is hydrogen, aliphatic, or aromatic; or Formula IIB$_{Linkerc}$ wherein n' is an integer ranging from 0 to 50, such as 1 to 25, or 1 to 10, or 1 to 5, or 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, and Z is oxygen or NR''', wherein R''' is hydrogen, aliphatic, or aromatic.

In embodiments where the probe comprises an R group, the R group can be a group comprising a carbamate or a carbonate that links the R group to Linker$^a$. In exemplary disclosed embodiments, the R group can have a structure satisfying any one or more of Formulas IIA$_R$-IIC$_R$. Solely for exemplary purposes, additional components of the probe (e.g., EBG, Linker$^a$ and/or Linker$^b$) are illustrated to show connectivity.

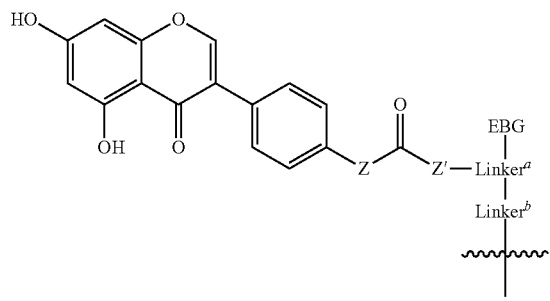

Formula IIA$_R$ wherein Z and Z' independently are oxygen or NR''', wherein R''' is hydrogen, aliphatic, or aromatic;

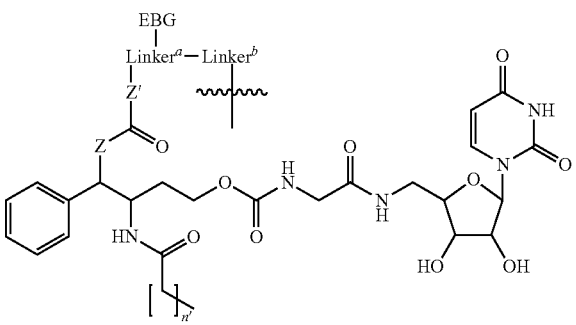

Formula IIC$_R$ wherein Z and Z' independently are oxygen or NR''', wherein R''' is hydrogen, aliphatic, or aromatic, and n' is an integer ranging from 0 to 50, such as 1 to 25, or 1 to 10, or 1 to 5; or

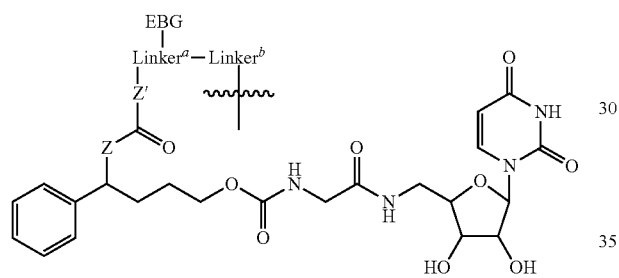

Formula IIB$_R$ wherein Z and Z' independently are oxygen or NR''', wherein R''' is hydrogen, aliphatic, or aromatic;

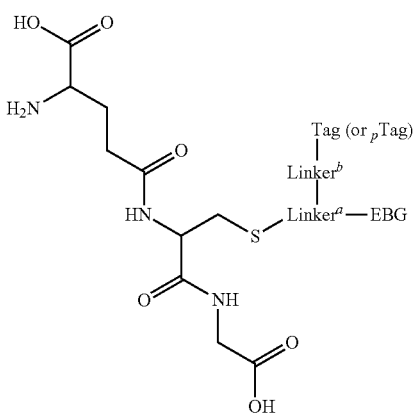

Formula IID$_R$

In exemplary disclosed embodiments, the probe can have a structure selected from any of the structures illustrated below.

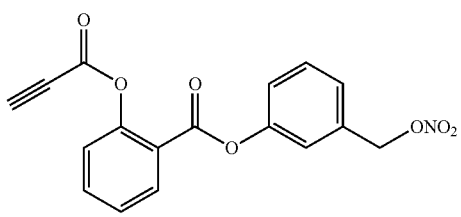
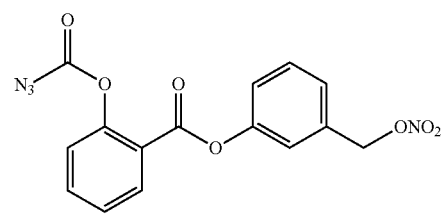
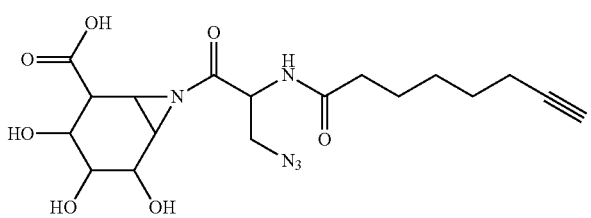
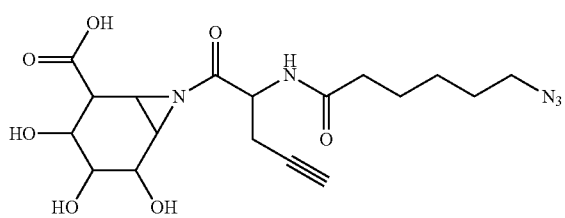

33 34
-continued
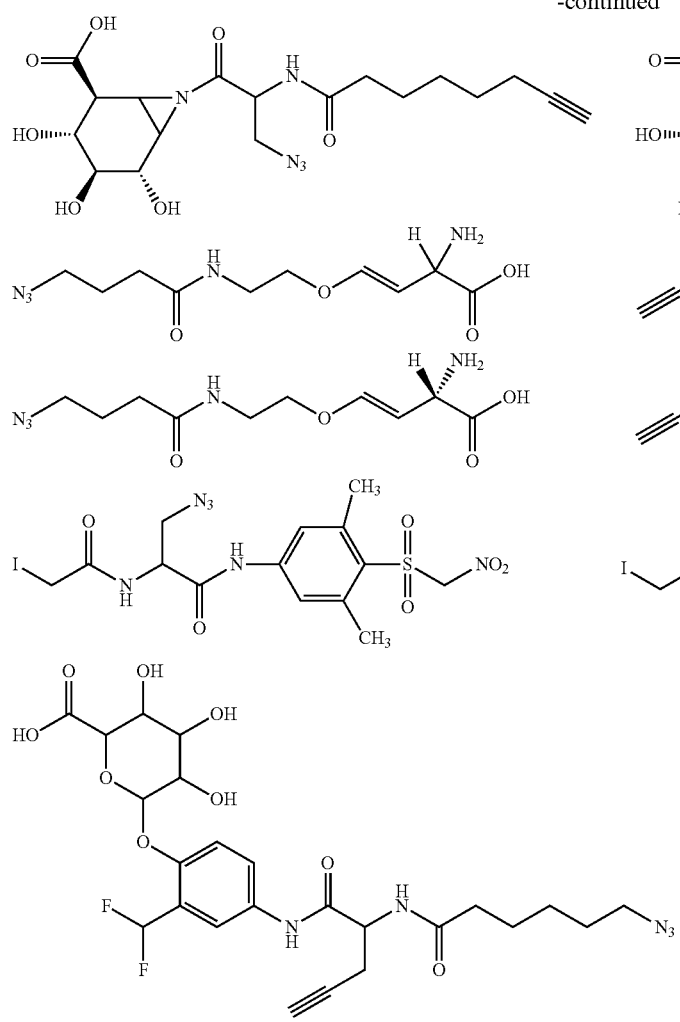
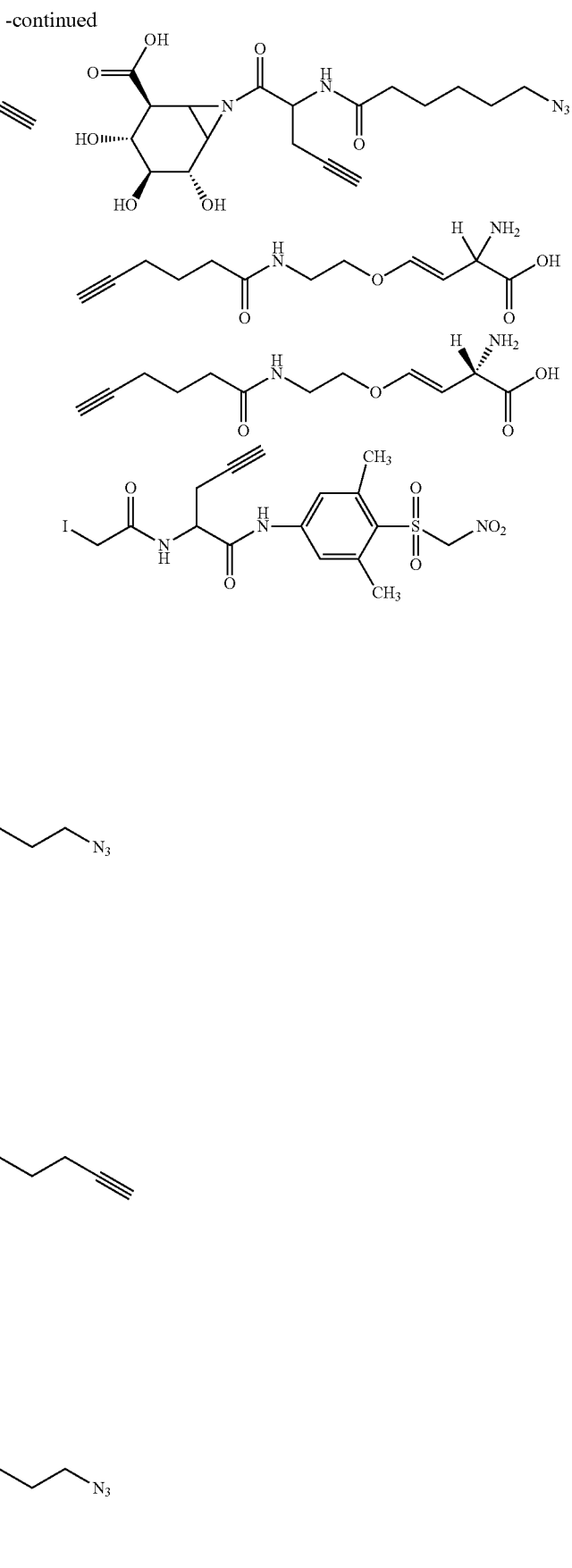

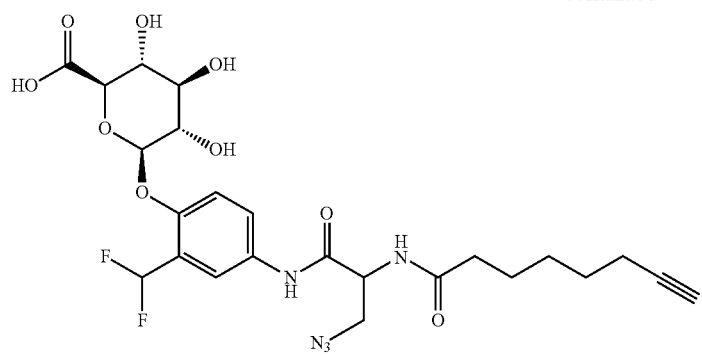
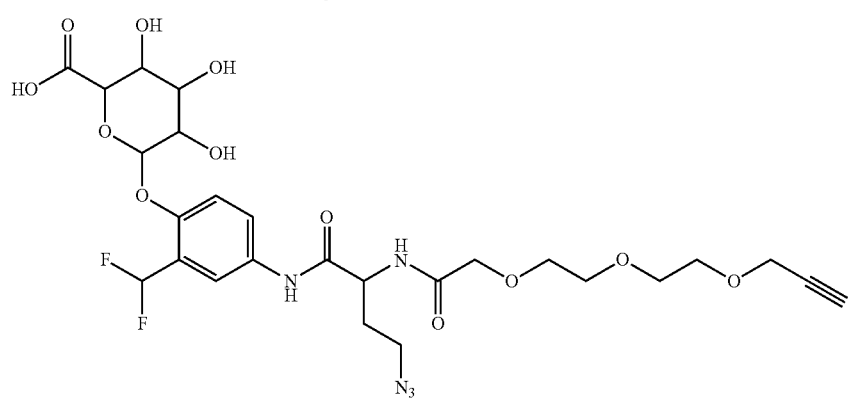
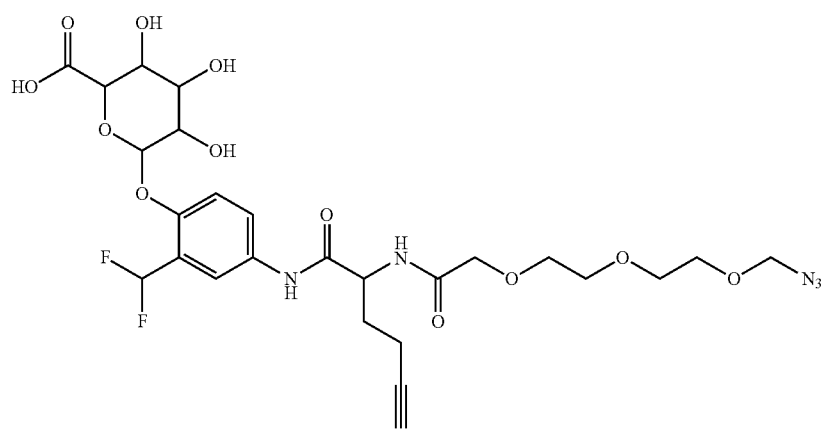
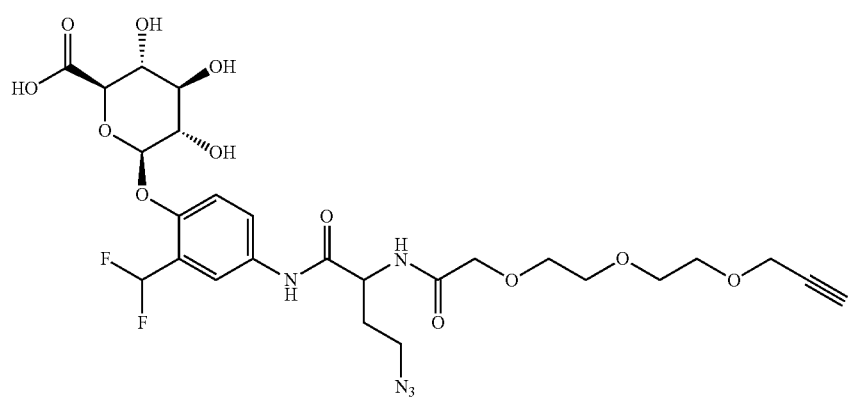

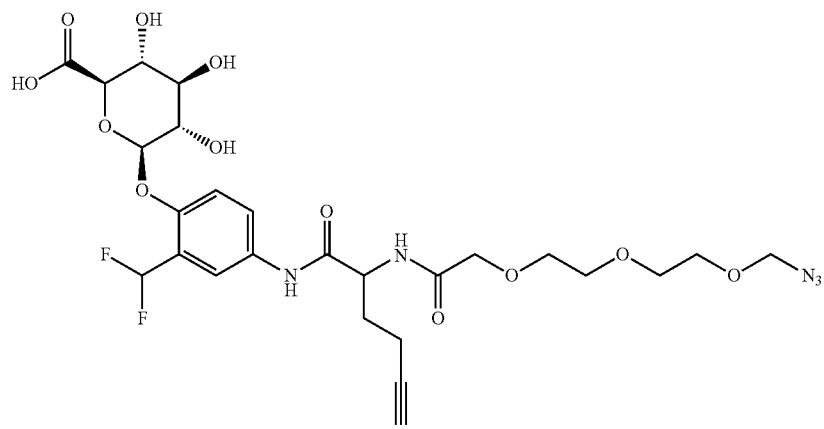
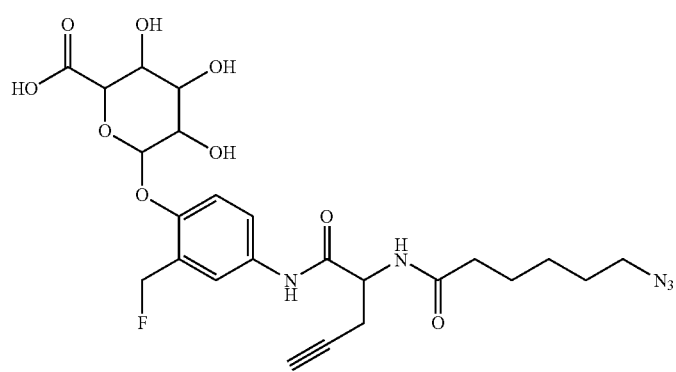
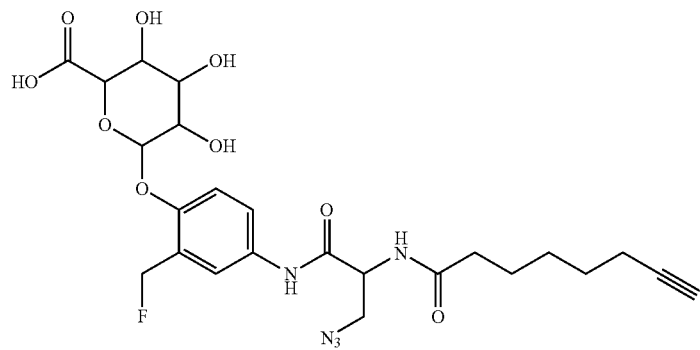
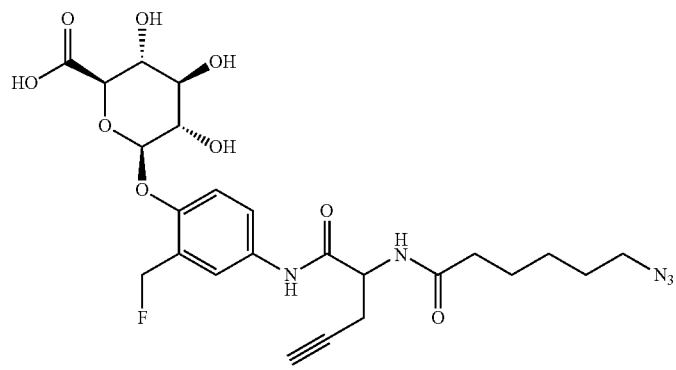

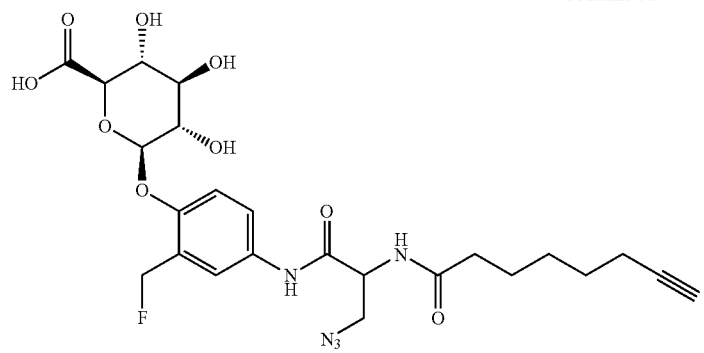
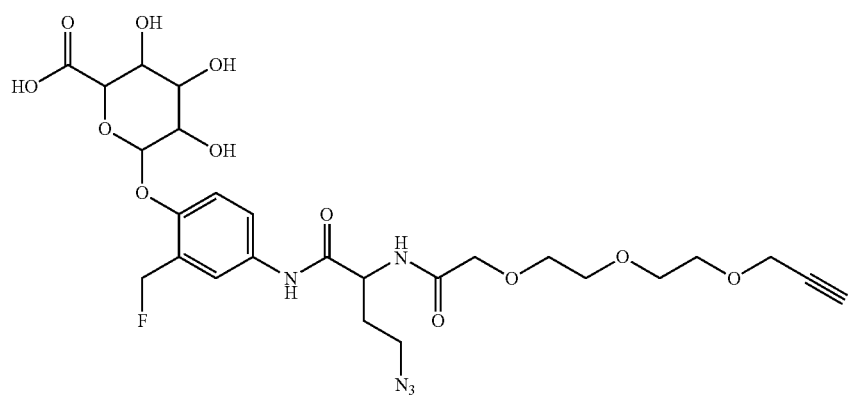
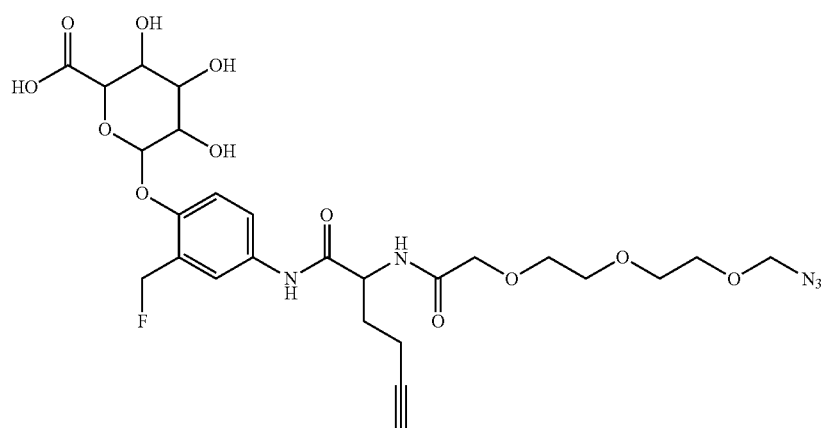
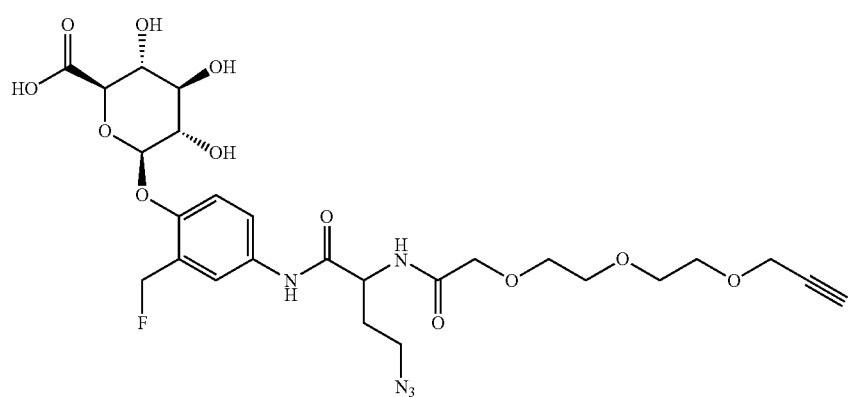

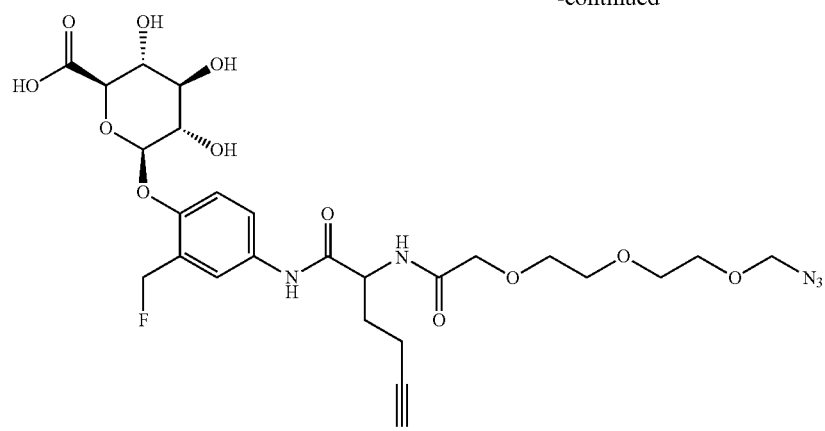
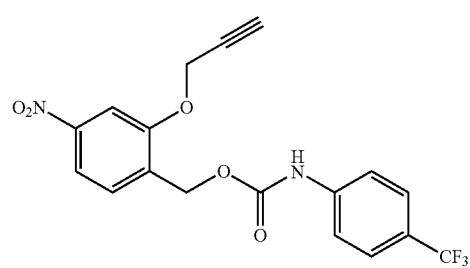
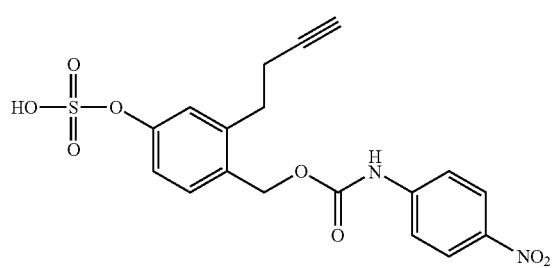
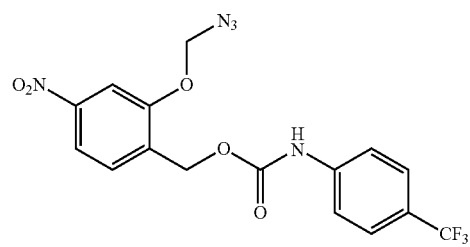
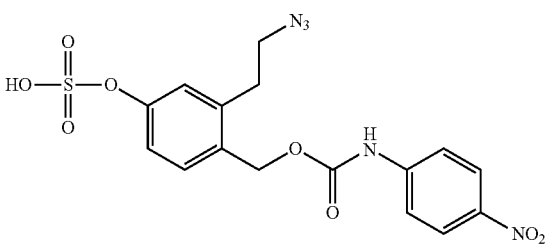
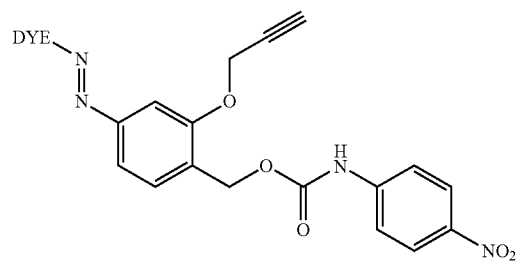
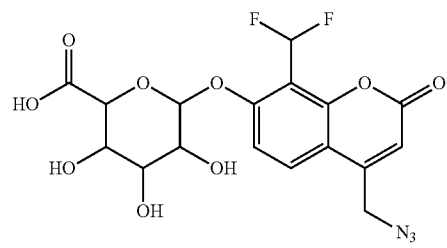
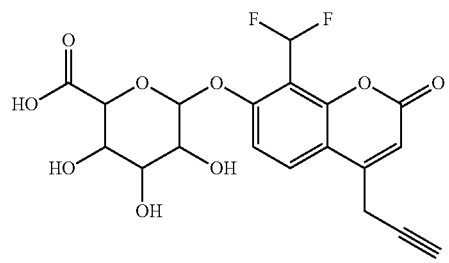
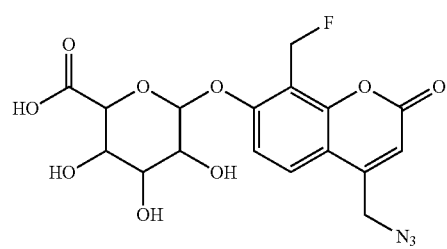
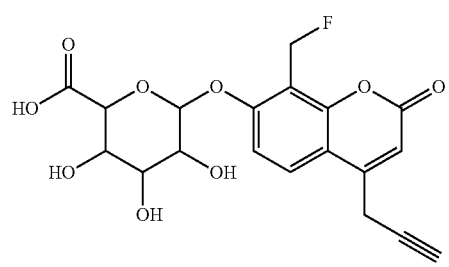

43
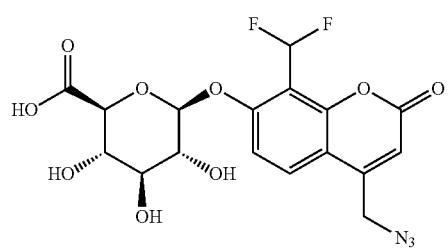
44
-continued
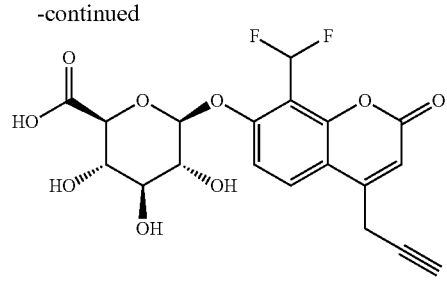
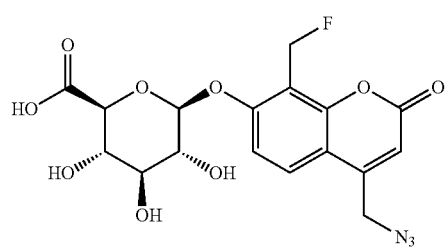
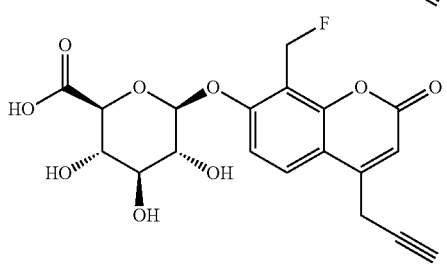
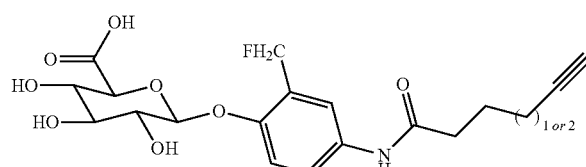
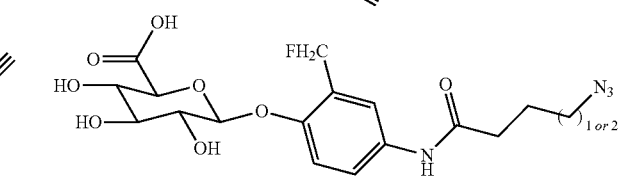
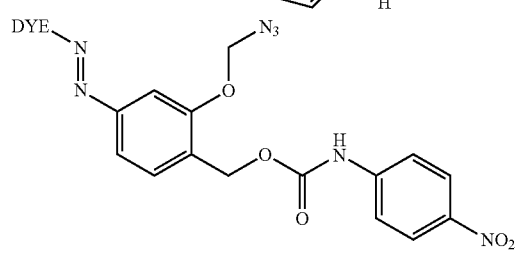
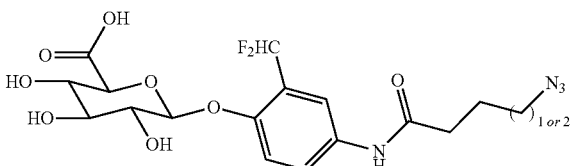
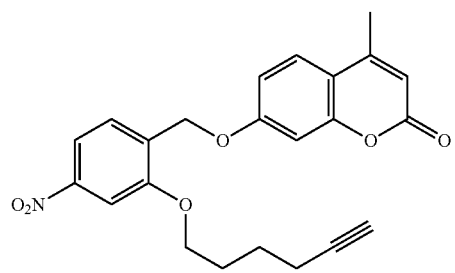
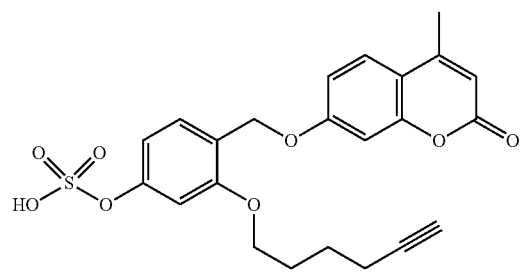
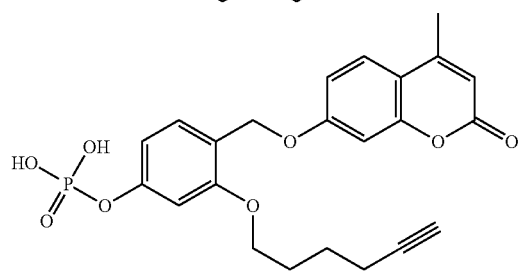
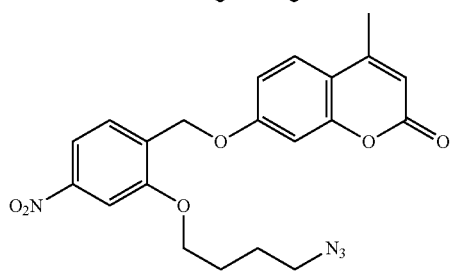
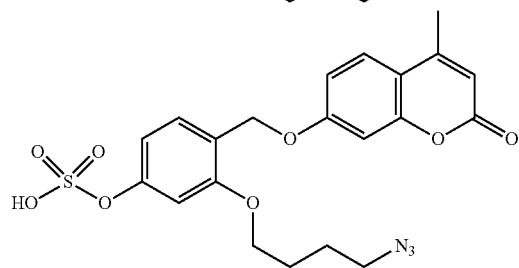
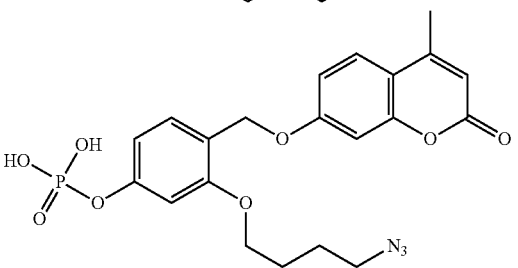

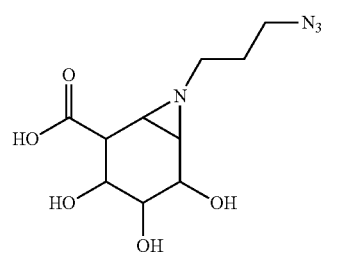
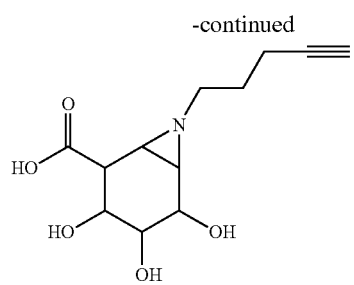
-continued
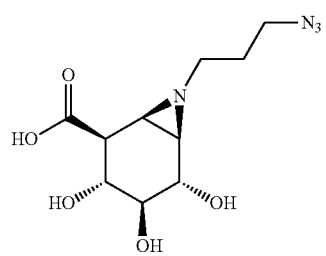
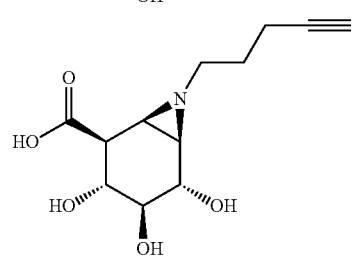
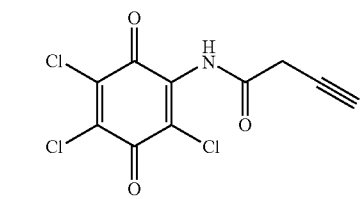
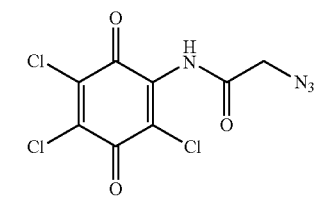
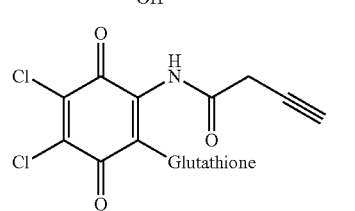
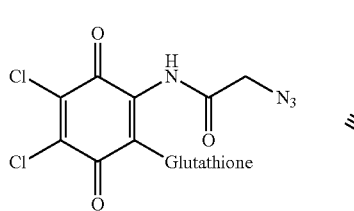
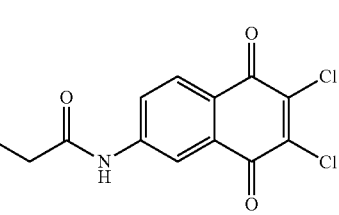
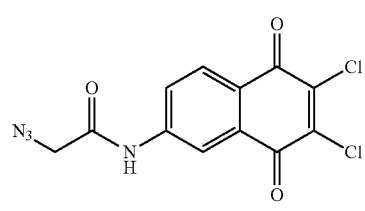
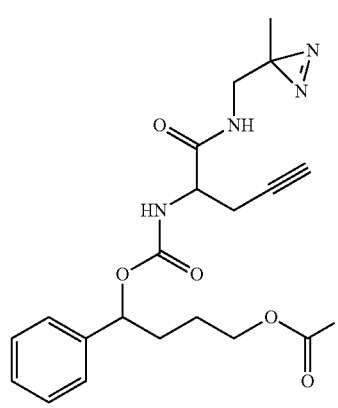
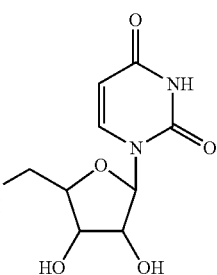
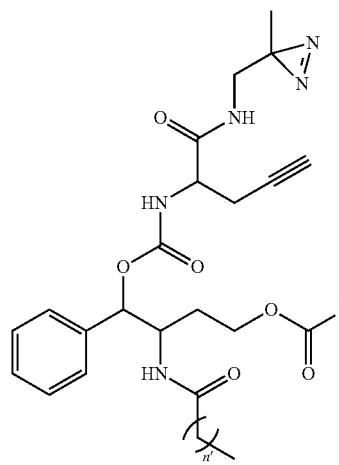
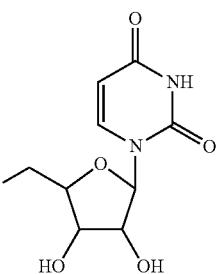
(wherein n′ is as recited above)

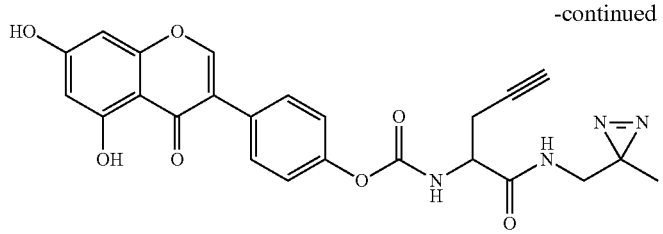

According to some embodiments, the probe can have a structure satisfying Formula IIIA.

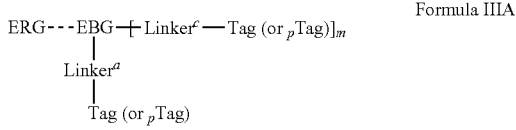

Formula IIIA

With reference to Formula IIIA, the following substituent recitations can apply:

the ERG, if present, can be a halogen, a phenol, a sulfate, a phosphate, glucuronic acid, or a glucuronic acid group wherein two hydroxyl groups have been displaced by a nitrogen atom of the EBG to form an aziridine;

the EBG can be a moiety that comprises a dichloro dione group, a phenol group, an olefin, an azo group, an amide group, a carbonyl group, a nitro group, or a carbon atom;

each of Linker$^a$ and Linker$^c$ can be as recited above for Formula II;

each Tag, if present, independently can be a functional group or molecule that generates a detectable signal; alternatively, if the probe comprises a $_p$Tag (an "Tag precursor") group, then each $_p$Tag independently can be a Tag precursor comprising a clickable functional group; and m can be 0 or 1.

In exemplary disclosed embodiments of Formula IIIA, the following can apply:

the ERG is present and is selected from iodo, —OPh, wherein the Ph group optionally can comprise one or more substituents other than hydrogen, such as a —CH$_2$ONO$_2$ group, or a glucuronic acid group wherein two hydroxyl groups have been displaced by a nitrogen atom of the EBG to form an aziridine;

the EBG is selected from Formula IIA$_{EBG}$, IIB$_{EBG}$, IIC$_{EBG}$, IID$_{EBG}$, IIE$_{EBG}$, IIG$_{EBG}$, IIH$_{EBG}$, III$_{EBG}$, or IIJ$_{EBG}$;

Linker$^a$ is an ester group, a —(CH$_2$)$_{n'}$— group, an —O(CH$_2$)$_n$NR'''C(O)(CH$_2$)$_{n'}$— group, wherein each n' independently is an integer ranging from 1 to 20, such as 1 to 10, or 1 to 5, or 1, 2, 3, 4, 5, 6, 7, 8, 9, 10, 11, 12, 13, 14, 15, 16, 17, 18, 19, or 20, and wherein R''' is hydrogen, aliphatic, or aromatic;

Linker$^c$ is an —NR'''C(O)(CH$_2$)$_{n'}$— group or an —NR'''C(O)CH$_2$[O(CH$_2$)$_2$]$_n$CH$_2$— group, wherein each n' independently is an integer ranging from 1 to 20, such as 1 to 10, or 1 to 5, or 1, 2, 3, 4, 5, 6, 7, 8, 9, 10, 11, 12, 13, 14, 15, 16, 17, 18, 19, or 20, and wherein R''' is hydrogen, aliphatic, or aromatic;

each Tag, if present, can be a fluorophore, a binding partner of an affinity-based binding pair, a quantum dot, or a dye; alternatively, if a $_p$Tag group is present, then each $_p$Tag independently is an alkyne or an azide; and m is 1.

In exemplary disclosed embodiments, compounds satisfying Formula IIIA can be selected from the azide- and alkyne-containing compounds illustrated below.

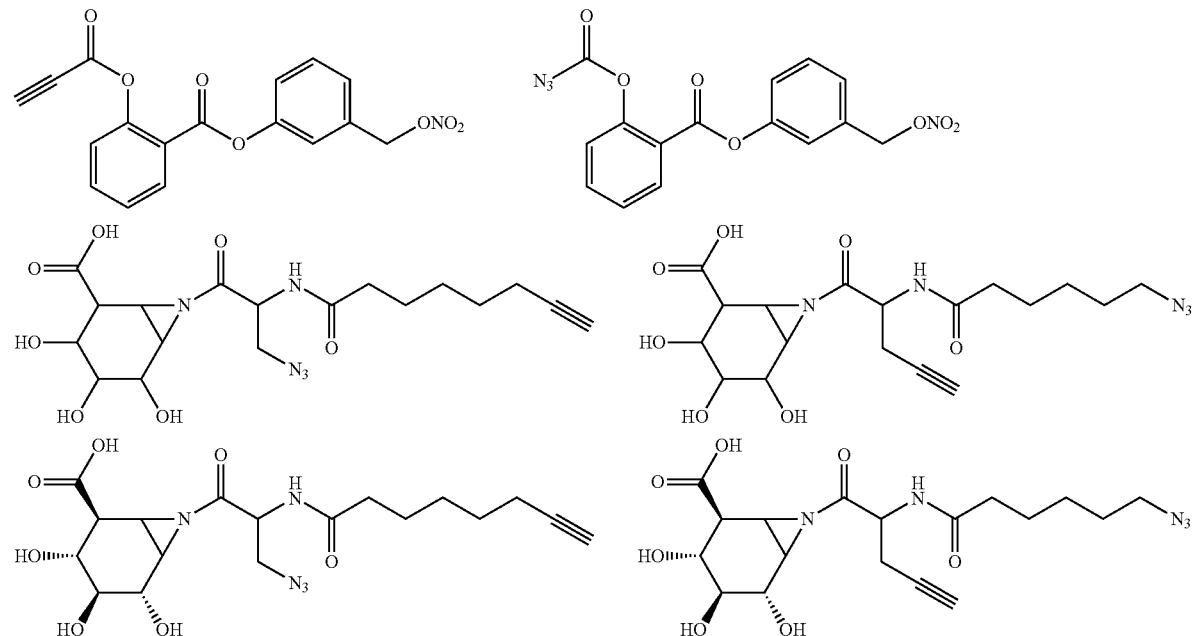

49 50
-continued
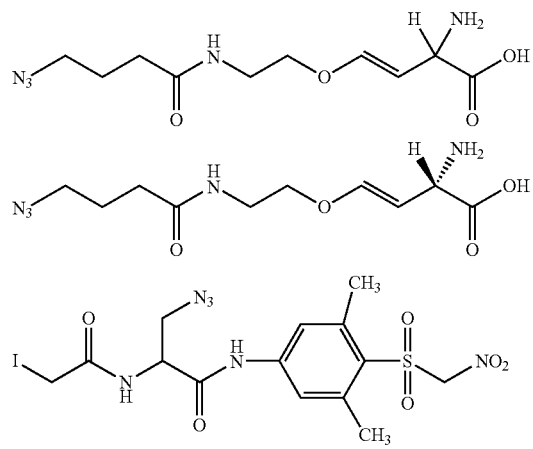
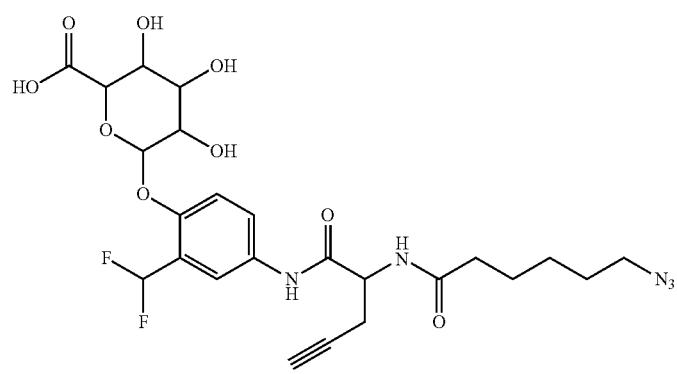
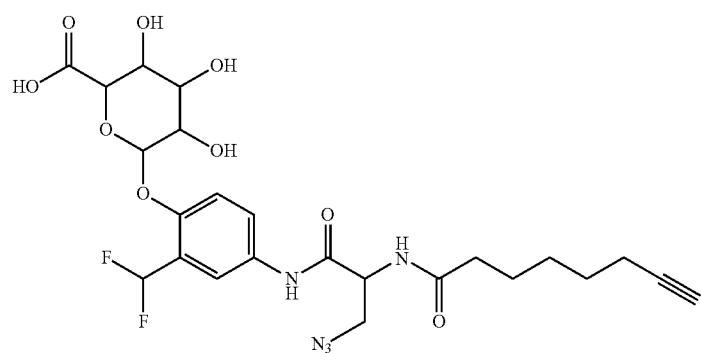
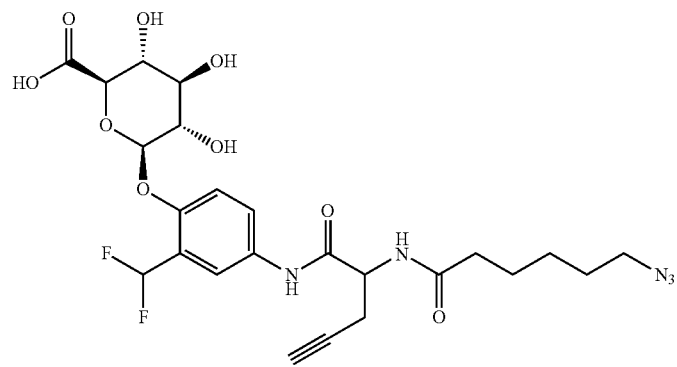

-continued
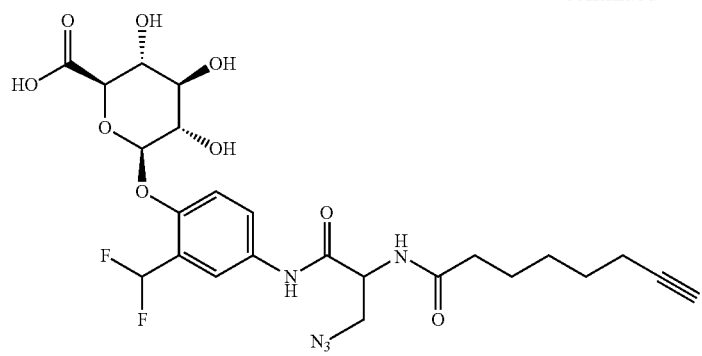
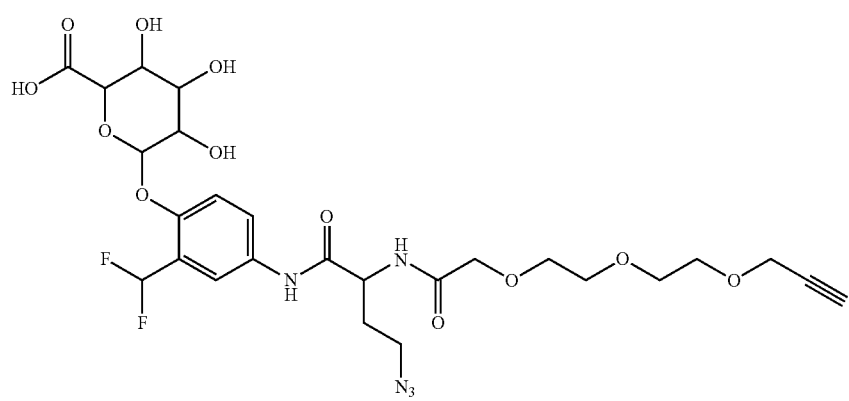
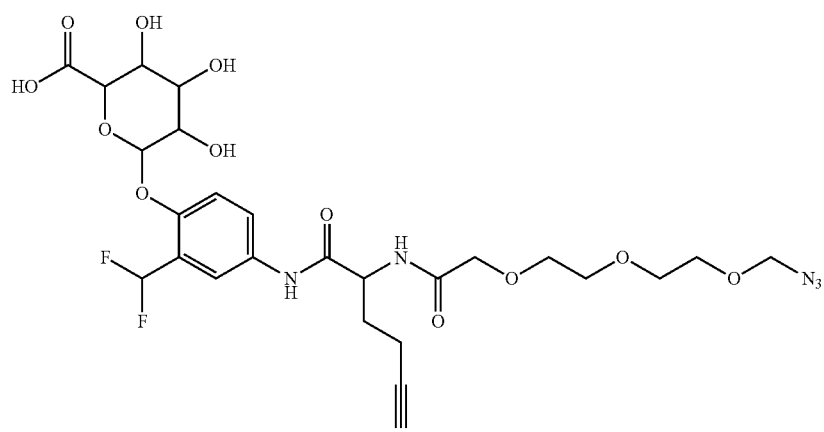
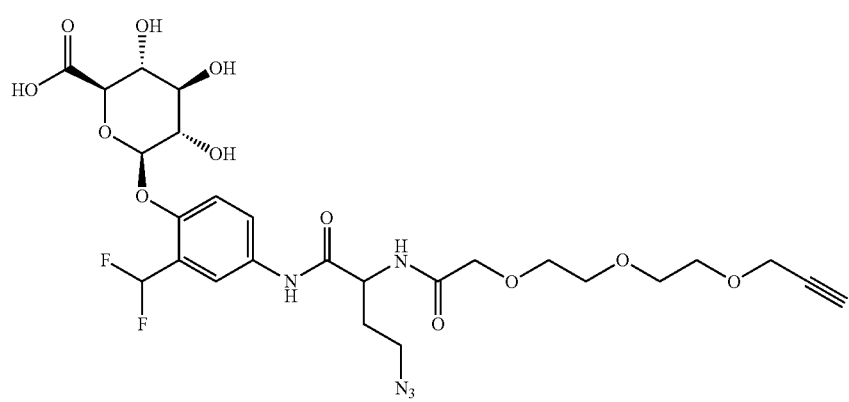

-continued
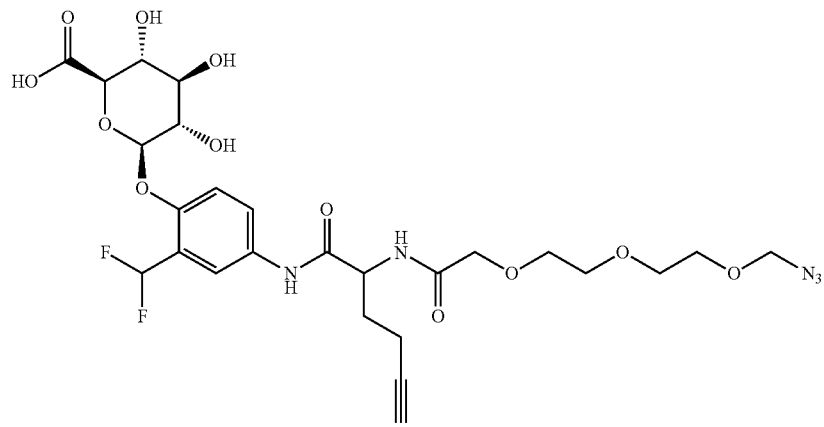
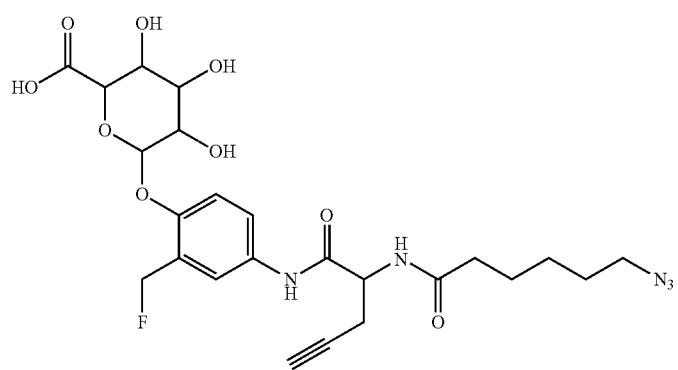
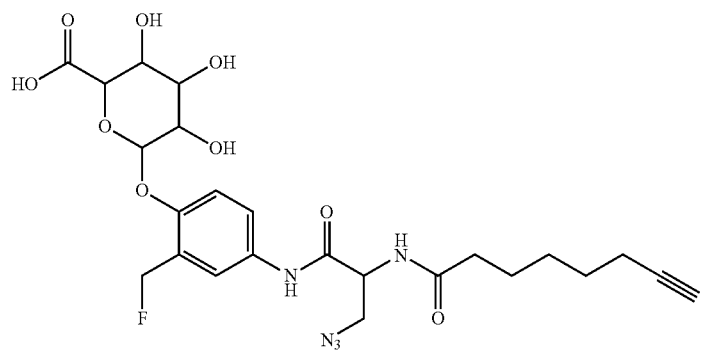
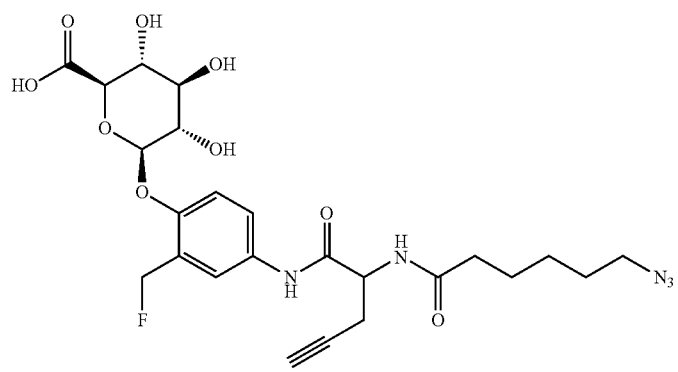

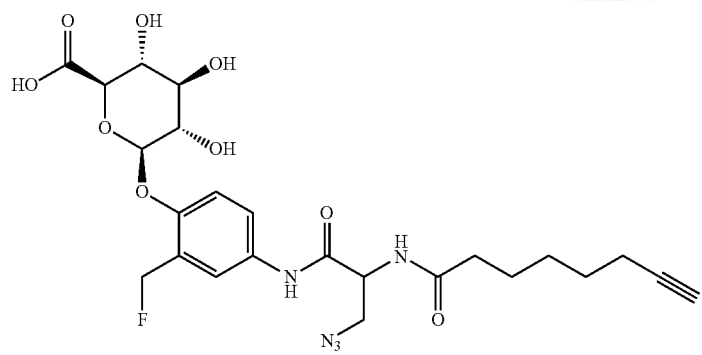
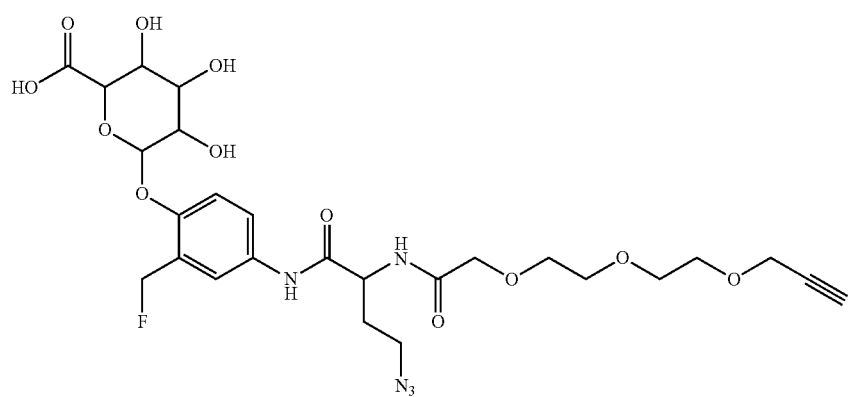
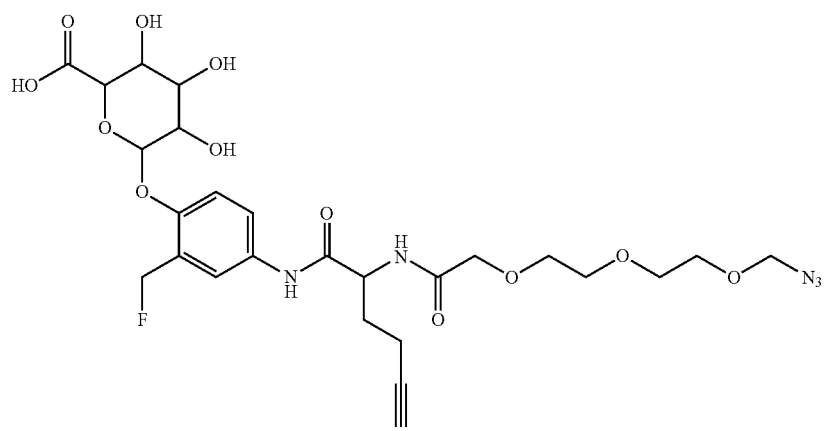
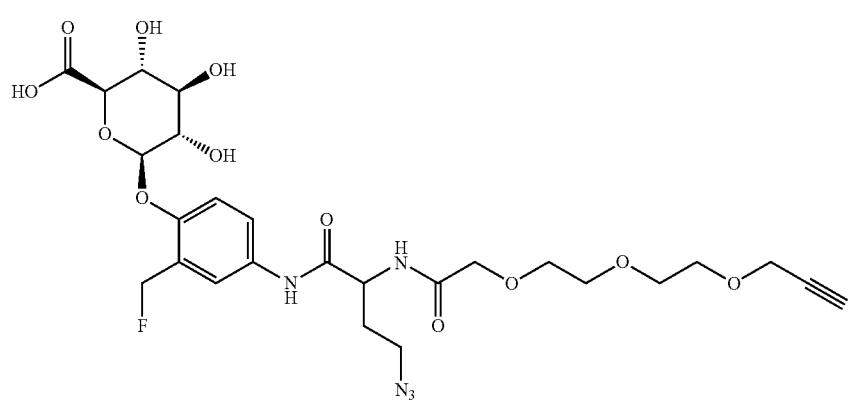

-continued
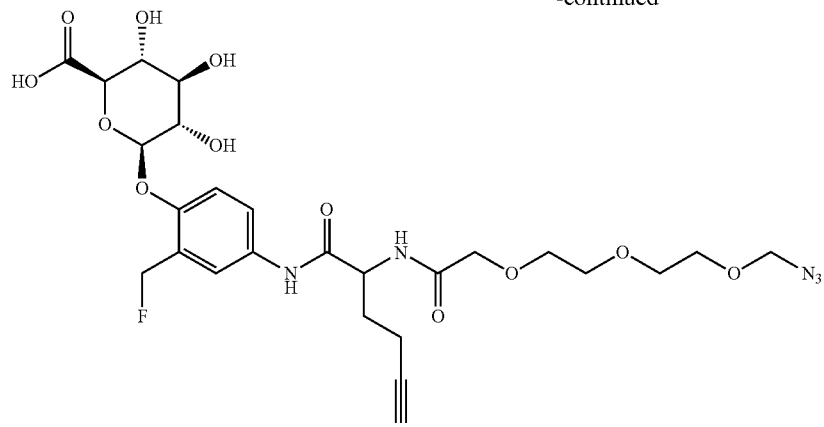
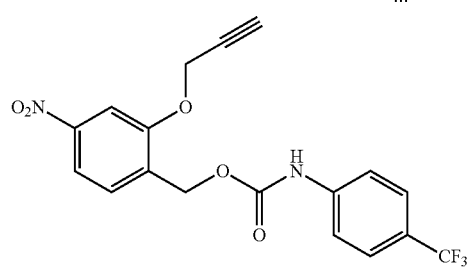
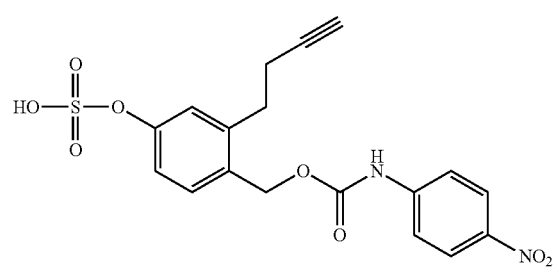
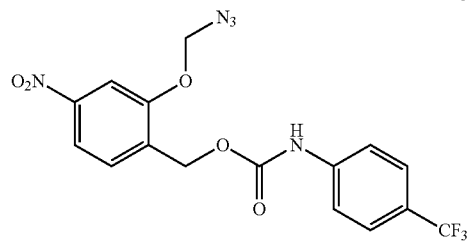
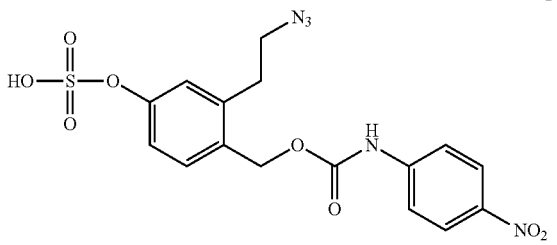
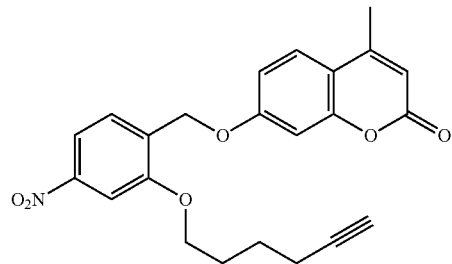
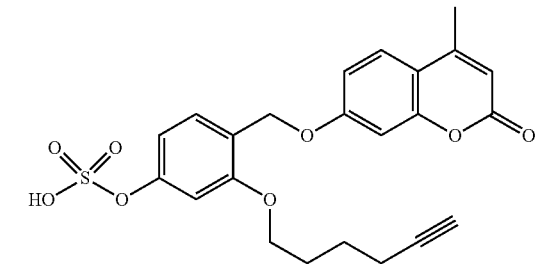
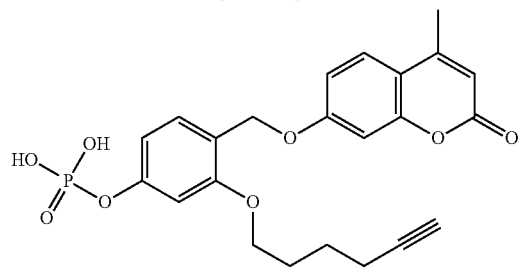
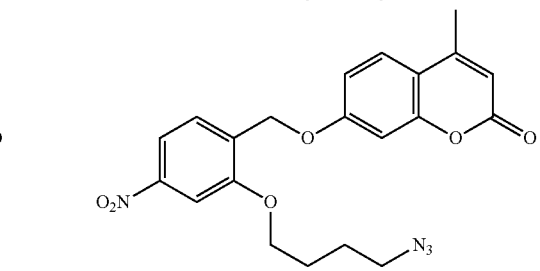
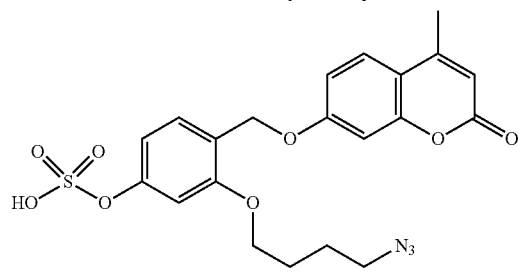
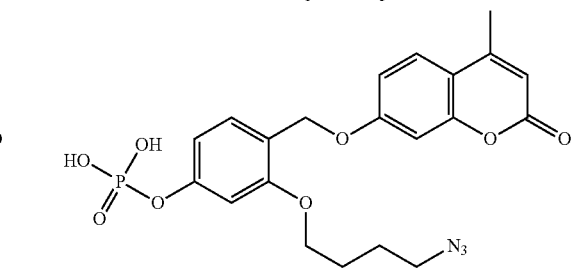

-continued
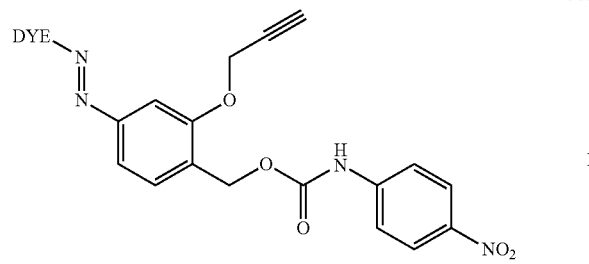
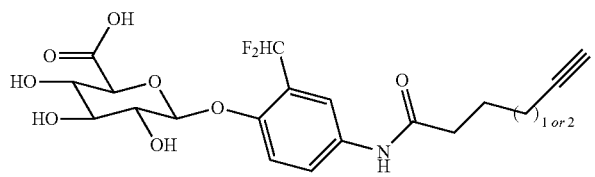
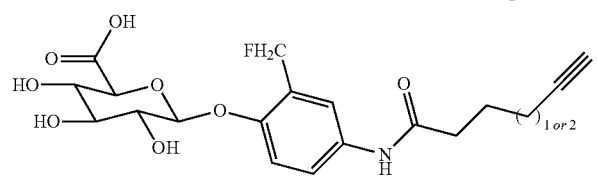
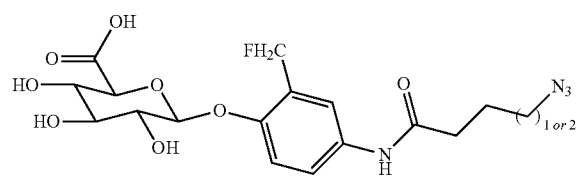
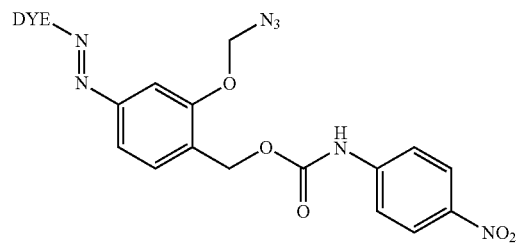
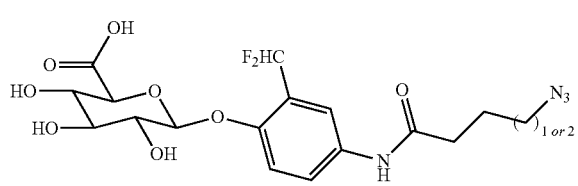
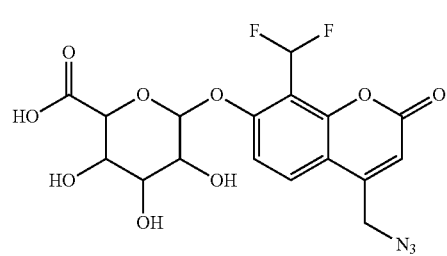
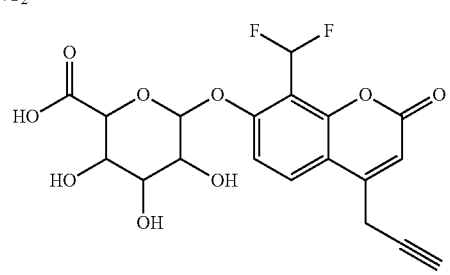
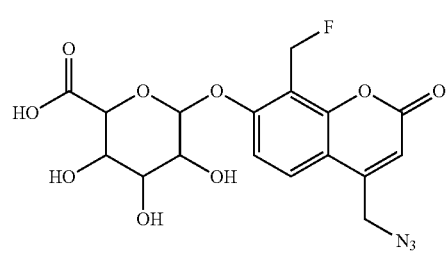
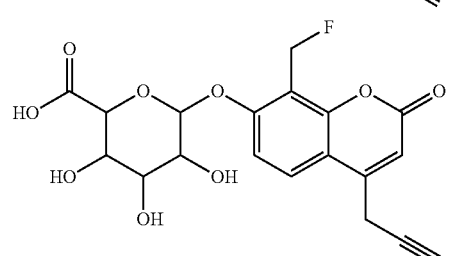
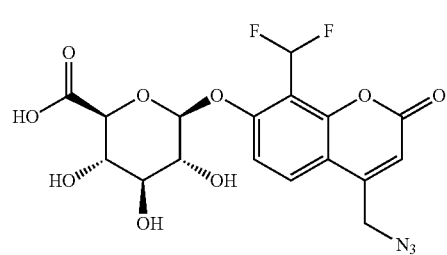
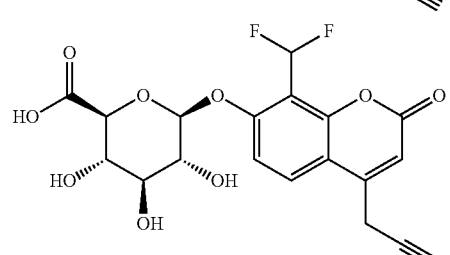
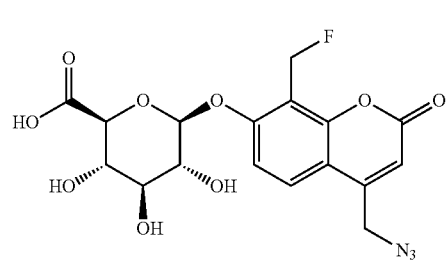
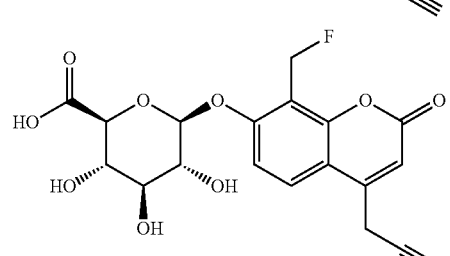

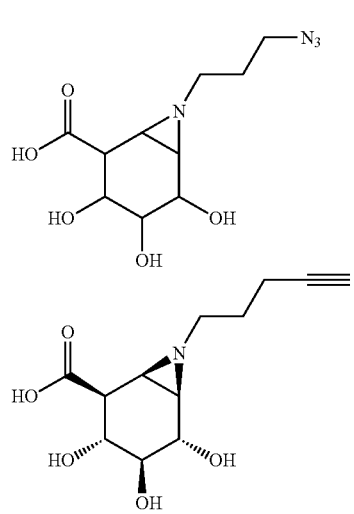
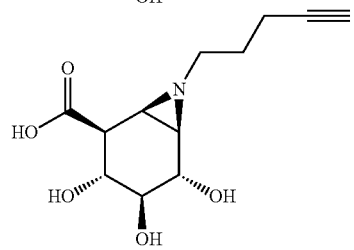
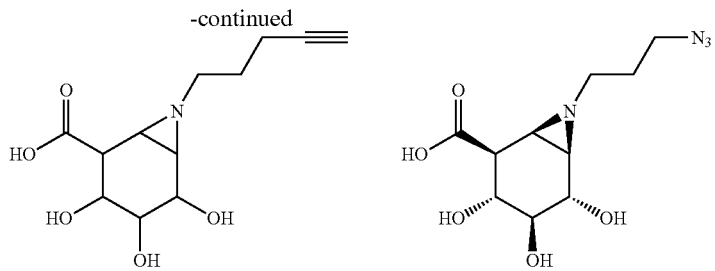

In some embodiments, the probe can have a structure satisfying Formula IIIB.

$$\begin{array}{c} \text{EBG} \\ | \\ \text{Linker}^a\text{-R} \\ | \\ \text{Linker}^b \\ | \\ \text{Tag (or }_p\text{Tag)} \end{array} \quad \text{Formula IIIB}$$

With reference to Formula IIIB, the following substituent recitations can apply:

the EBG can be a photo-activatable enzyme binding group that becomes bound to the enzyme after exposing the EBG to a light source as described herein;

Linker$^a$ can be a phenyl group or can have a structure satisfying Formula IID$_{Linkera}$;

Linker$^b$ is —(CH$_2$)$_{n'}$—, wherein n' is an integer ranging from 1 to 5;

the Tag, if present, can be a functional group or molecule that generates a detectable signal; alternatively, if the probe comprises a $_p$Tag (an "Tag precursor") group, then the $_p$Tag can be a Tag precursor comprising a clickable functional group; and R can have a structure satisfying Formula IIA$_R$, Formula IIB$_R$, or Formula IIC$_R$ In some exemplary embodiments of Formula IIIB, the following substituent recitations can apply:

the EBG can be an diaziridine, such as

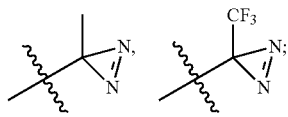

or a benzophenone

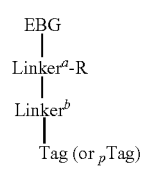

Linker$^a$ can be a phenyl group or

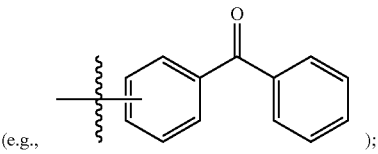

Linker$^b$ can be —(CH$_2$)$_{n'}$— or —(CH$_2$)$_m$[O(CH$_2$)$_2$]$_{n'}$OCH$_2$—, wherein each m independently is 0 or 1 and each n' independently is 1 to 50, such as 1 to 25, or 1 to 10, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50;

the Tag, if present, can be a fluorophore, a binding partner of an affinity-based binding pair, a quantum dot, or a dye; alternatively, if a $_p$Tag group is present, then the $_p$Tag is an alkyne or an azide; and R can be selected from the following structures:

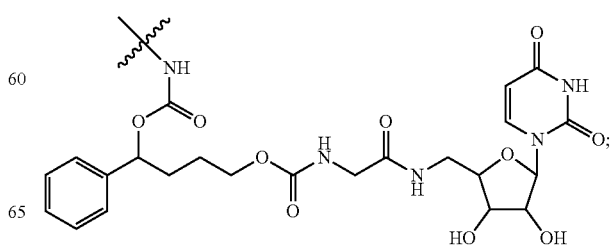

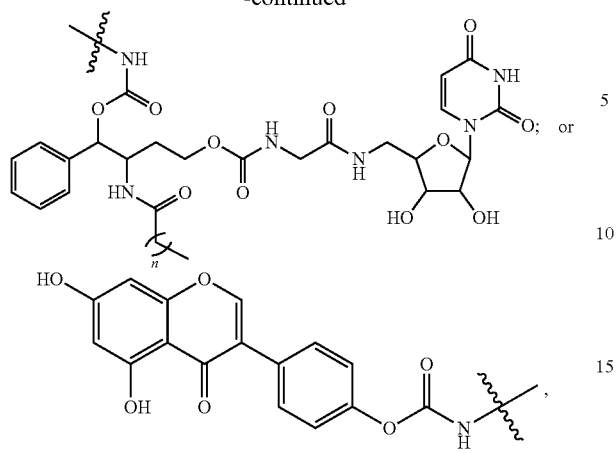
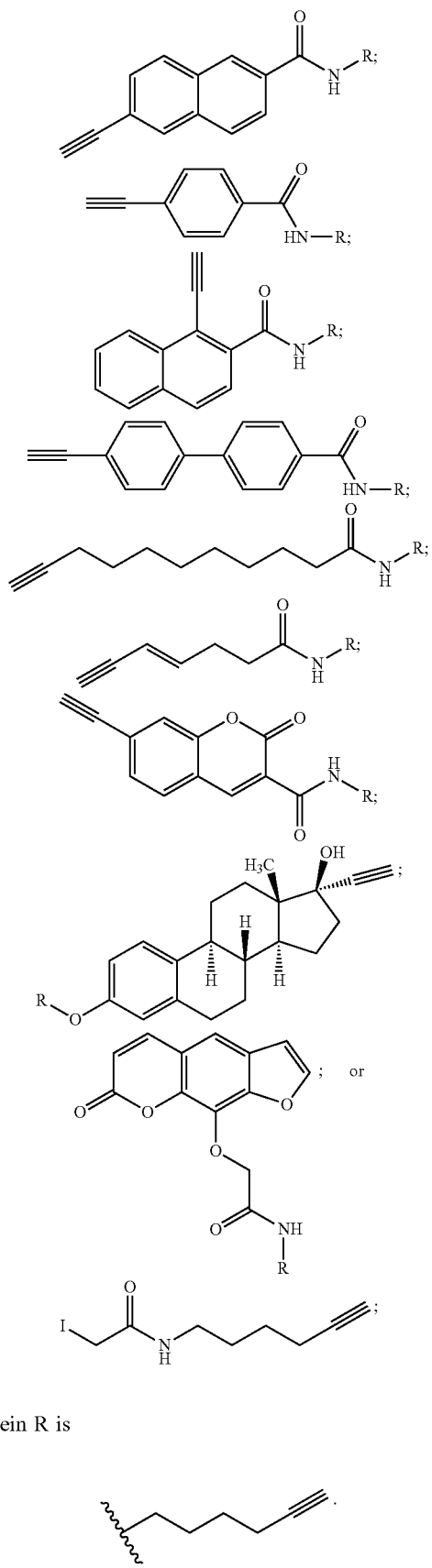
wherein n' is an integer ranging from 0 to 50, such as 1 to 25, or 1 to 10, or 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.
In exemplary disclosed embodiments, compounds satisfying Formula IIIB can be selected from the compounds illustrated below.
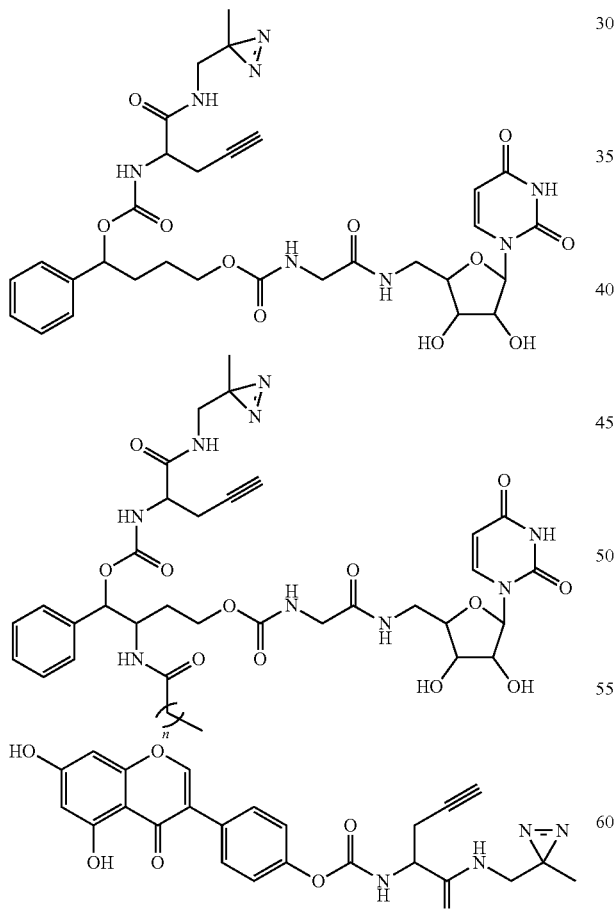
wherein R is
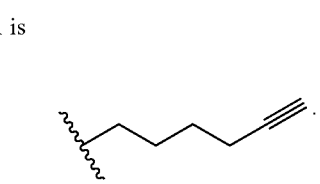
Independently, the probe is not selected from any of the compounds illustrated below.

It is nevertheless possible that such compounds can be used in the methods described herein.

A. β-Glucuronidase and Glucuronosyl Transferase Probe Embodiments

One pathway modulated by the gut microbiome is glucuronidation. Glucuronidation facilitates mammalian Phase II metabolism and clearance of xenobiotics, mediated by the conjugation of a glucuronic acid to xenobiotics and endogenous metabolites to increase their solubility. Microbial β-glucuronidases present in the gut can hydrolyze this conjugate back to the parent compound, leading to altered pharmacodynamics, failure of therapeutics, or severe side effects. Recent work has identified conserved motifs to improve annotation (in bioinformatics, meaning the elucidation and description of biologically relevant features; text fields of information about a biosequence which are added to a sequence database by way of explanation or commentary) of β-glucuronidases; however, these genes are widespread amongst members of the gut microbiota, making prediction of the specific taxa active in deglucuronidation extremely difficult.

To address the challenge of characterizing functional activity in Phase II metabolism and the gut microbiome, the inventors have developed ABP embodiments specific for β-glucuronidases. According to some embodiments, these ABP embodiments can have a structure satisfying Formula II or Formula IIA as described above; in exemplary disclosed embodiments, these ABPs have structures that also satisfy Formula IVA, IVB, or IVC below. In embodiments satisfying Formula IVA, when an active glucuronidase reacts with the probe, an electrophilic o-quinone methide forms and is attacked by a nearby nucleophilic residue of the enzyme, creating a covalent bond between the reactive group and the enzyme. In embodiments satisfying Formula IVC, binding of an enzyme to the probe produces a fluorescent turn-on response. The alkyne handle of the probe enables Tag attachment and/or support or resin attachment via click chemistry as described above.

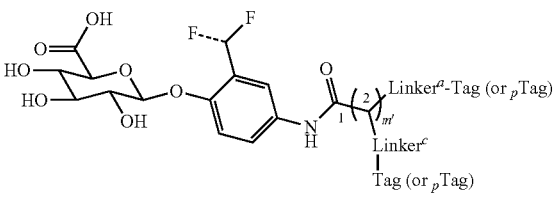

Formula IVA

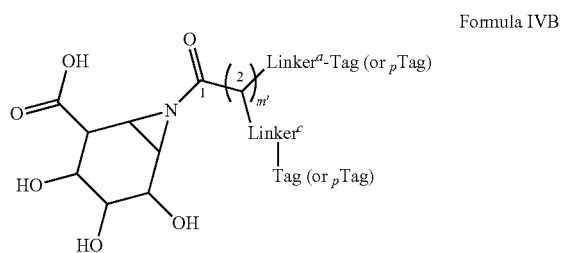

Formula IVB

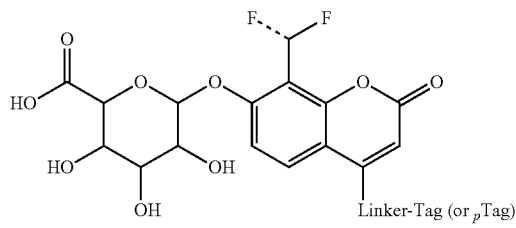

Formula IVC

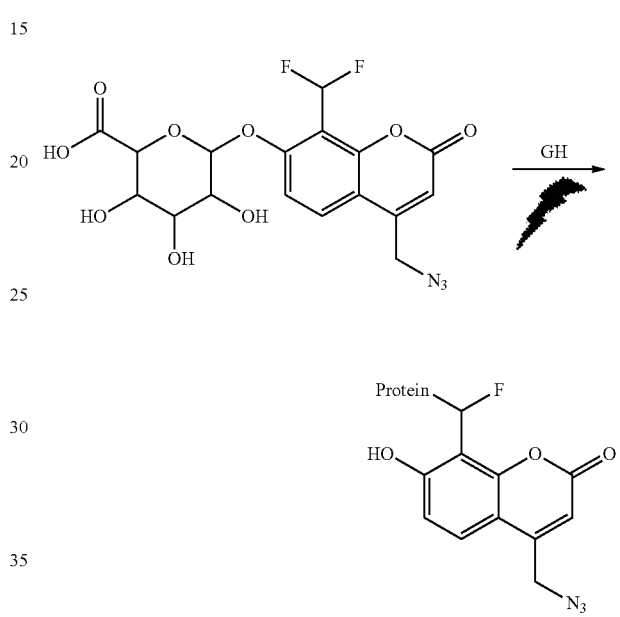

Activation and Fluorescent "Turn-On" Response

Figure 3:
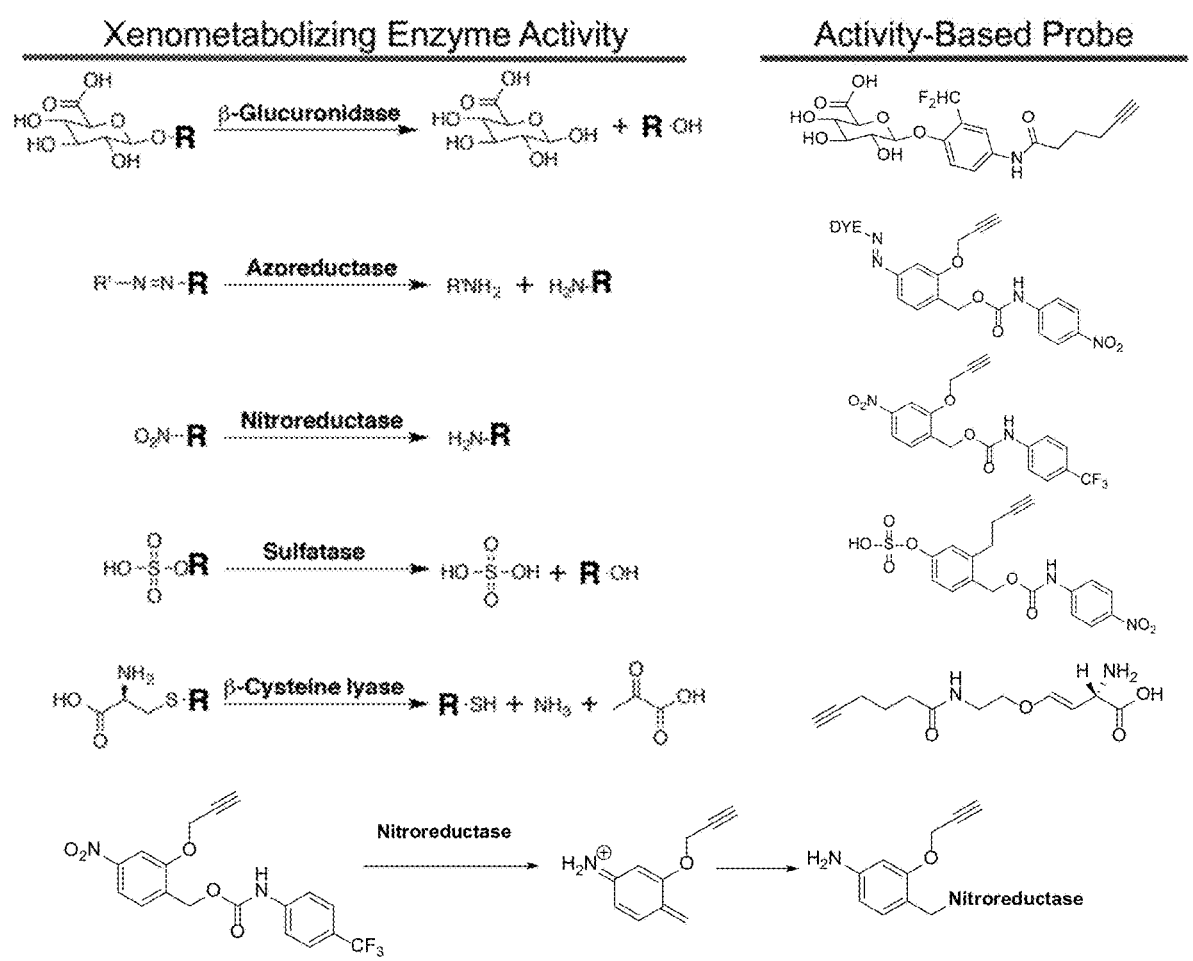
FIG. 3 provides a summary of xenometabolizing enzyme activity for certain ABP embodiments described herein, including the structure of at least one representative probe embodiment for measuring that activity.

With reference to these formulas, each Tag moiety, if present, and/or each $_p$Tag moiety, if present, independently can be as recited above for any of the formulas above and each of Linker$^a$ and Linker$^c$ can be as recited for any of the formulas above. According to some embodiments, each of Linker$^a$ and Linker$^c$ independently can be selected from —CH$_2$[O(CH$_2$)$_2$]$_{n'}$OCH$_2$—, —(CH$_2$)$_{n'}$—, or —(CH$_2$)$_{n'}$Ph-, wherein each n' independently can be an integer ranging from 1 to 50, such as one to 25, or one to ten, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. Variable m' can be 1 or zero. In embodiments where m is zero, carbon 2 is not present and carbon 1 is attached to the Linker$^a$ group. Representative embodiments of such probes are illustrated below and, without being limited to a particular theory, an exemplary mechanism for how such probe embodiments can be activated for enzyme coupling are illustrated in FIG. 3. Where a dashed bond (i.e., "----") is used in the structures below, this indicates that the fluorine atom attached with the dashed bond is optionally present (and when it is not, a hydrogen atom is present).

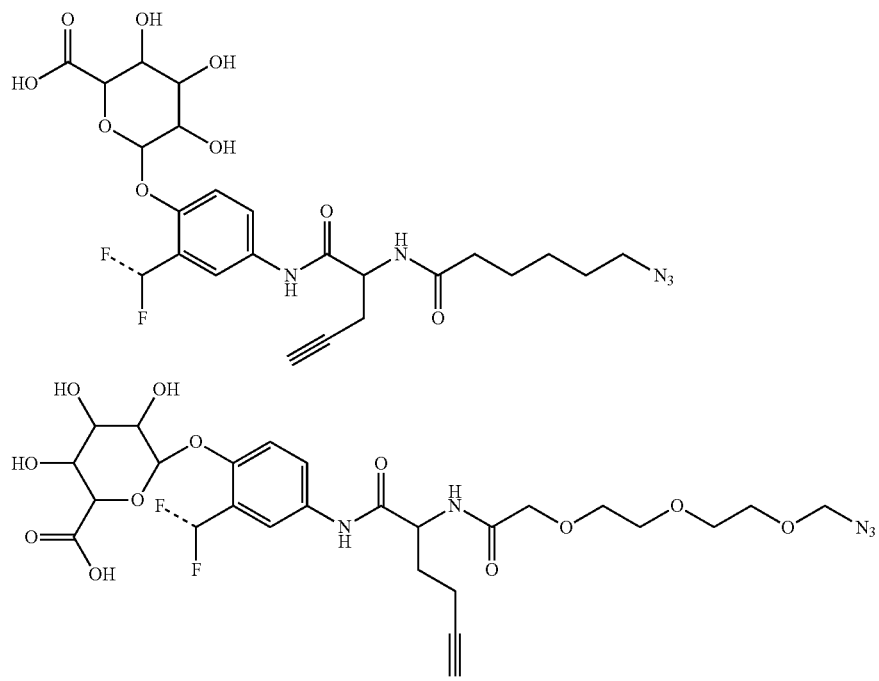
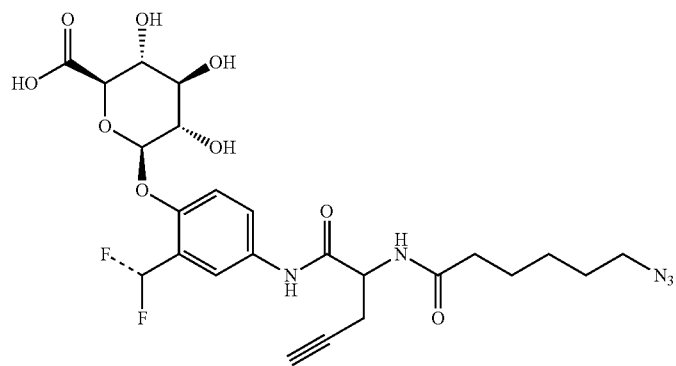
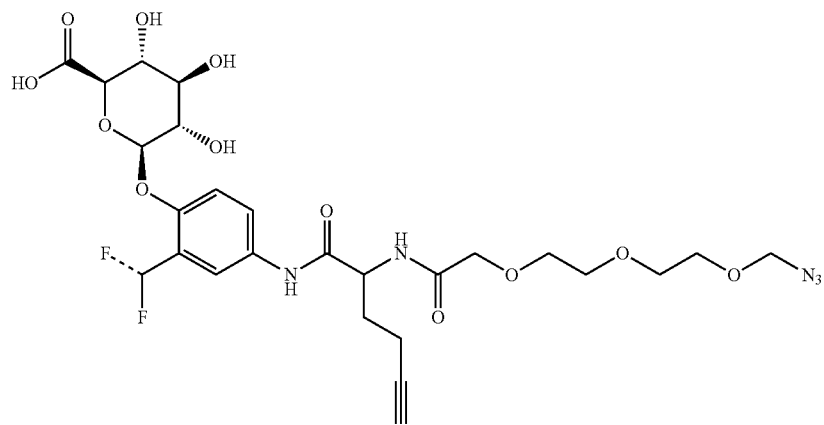

-continued
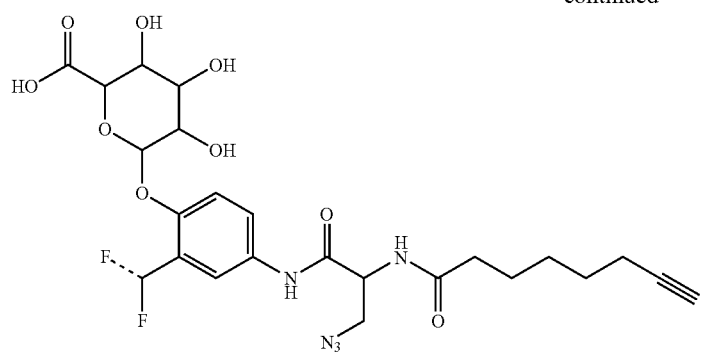
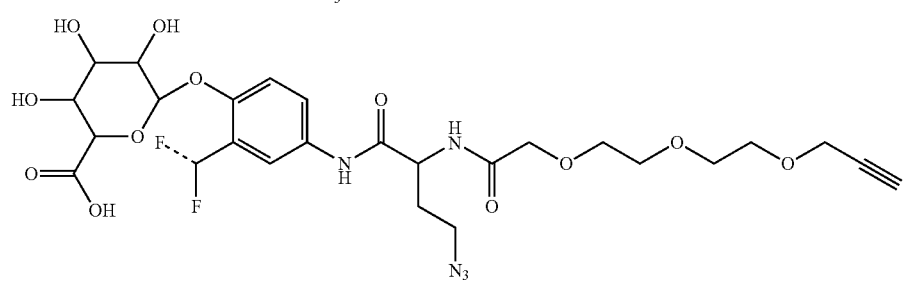
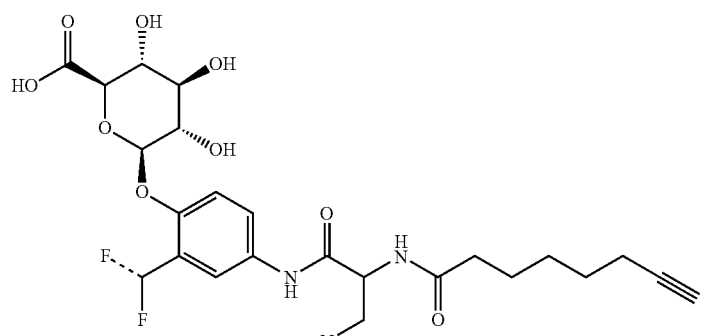
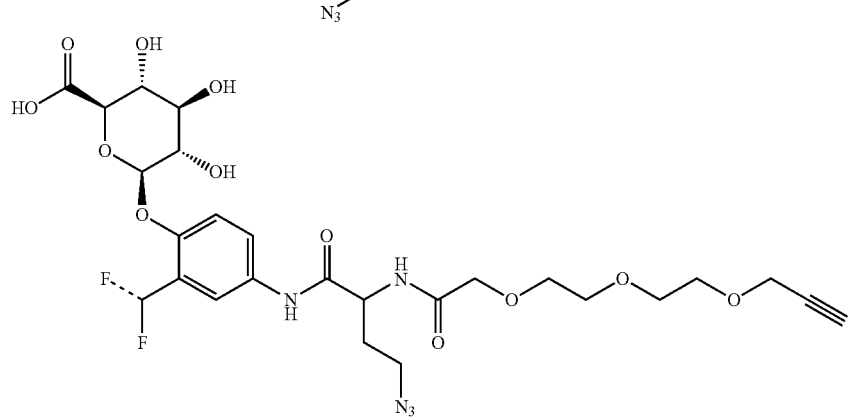
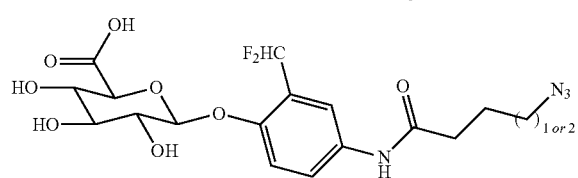
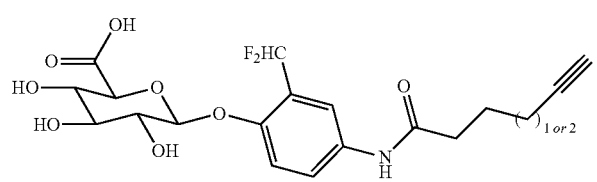
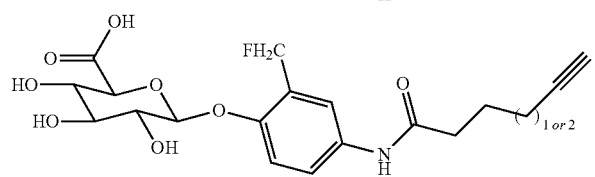
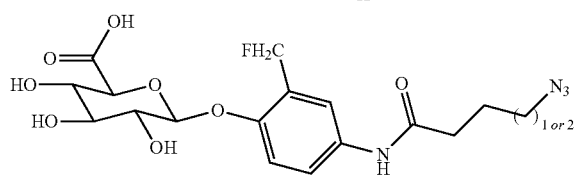

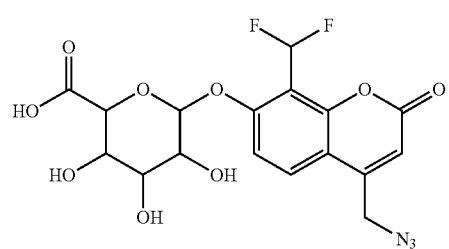
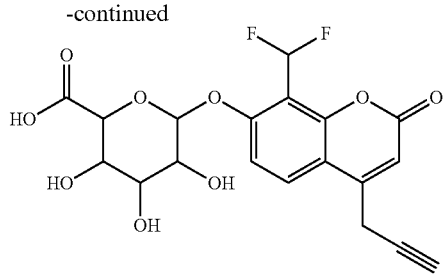
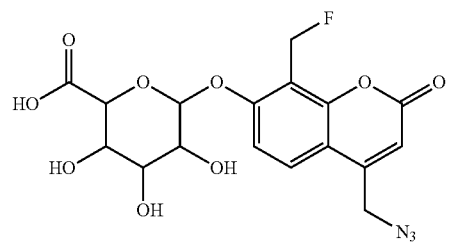
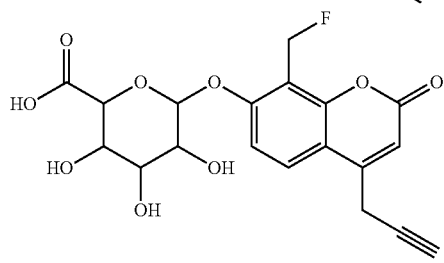
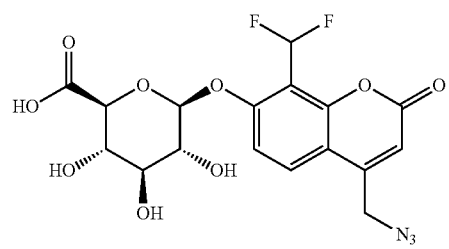
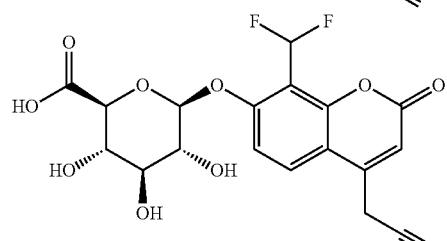
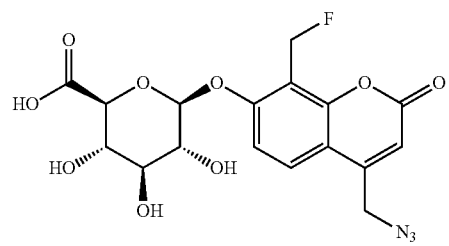
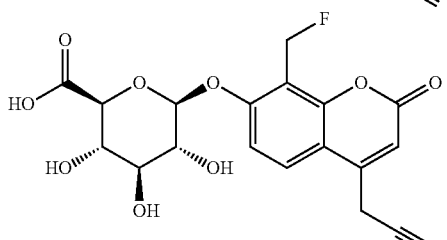
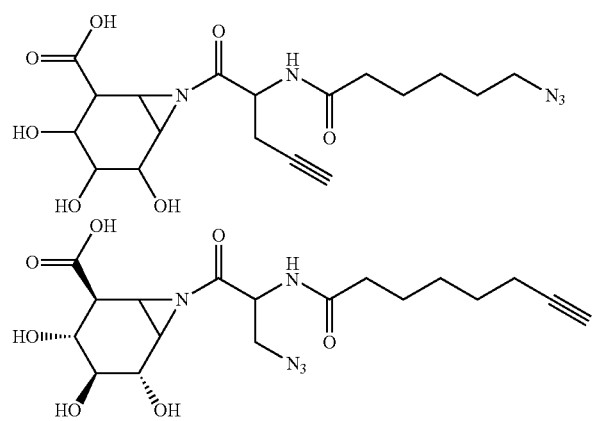
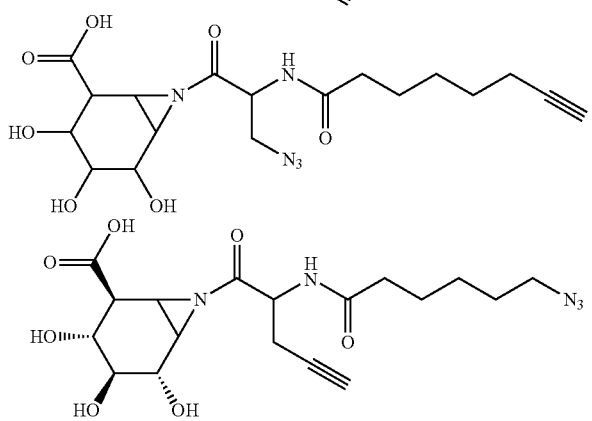

The inventors also have developed ABP embodiments that can be used to specifically bind to glucuronosyl transferases, which are enzymes for which no irreversible inhibitors currently exist. Glucuronosyl transferases are enzymes involved in Phase II metabolism of drug substances and other xenobiotics. By targeting and forming irreversible bonds with one of these particular enzymes, probe embodiments described herein can be used to determine or affect the activity of these Phase II enzymes. Probes capable of binding glucuronosyl transferases can have a structure satisfying Formula II or Formula IIIB as described above. In exemplary disclosed embodiments, these probes also can have structures satisfying any one or more of Formulas VA-VC illustrated below. These probes comprise an ERG that can be photo-activated to then bind with the enzyme. Groups that can be photo-activated include, but are not limited to, benzophenone groups and diazirine groups (e.g., aliphatic diazirines and trifluoromethylphenyl diazirines).

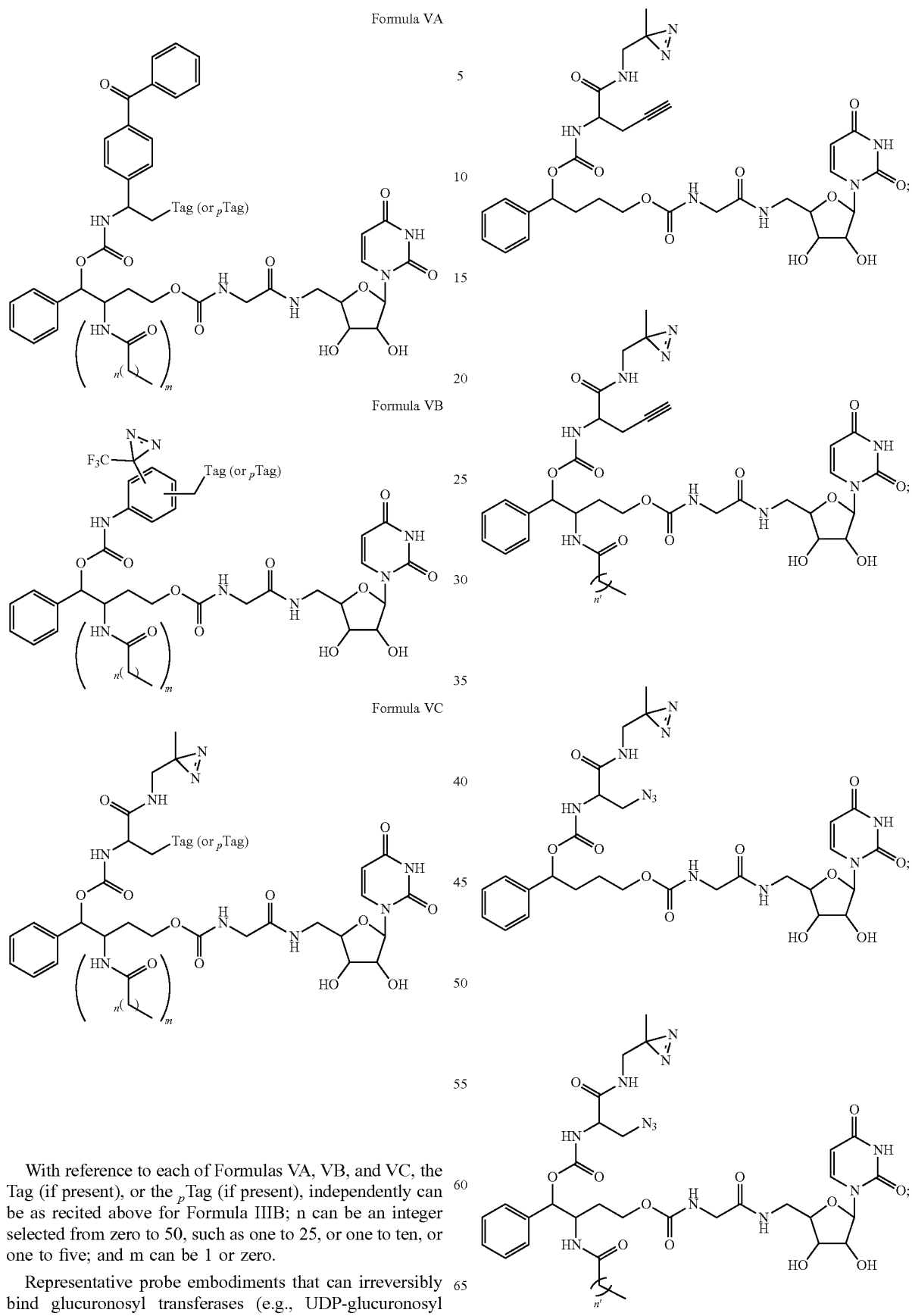

With reference to each of Formulas VA, VB, and VC, the Tag (if present), or the $_p$Tag (if present), independently can be as recited above for Formula IIIB; n can be an integer selected from zero to 50, such as one to 25, or one to ten, or one to five; and m can be 1 or zero.

Representative probe embodiments that can irreversibly bind glucuronosyl transferases (e.g., UDP-glucuronosyl transferases) are illustrated below.

75
-continued

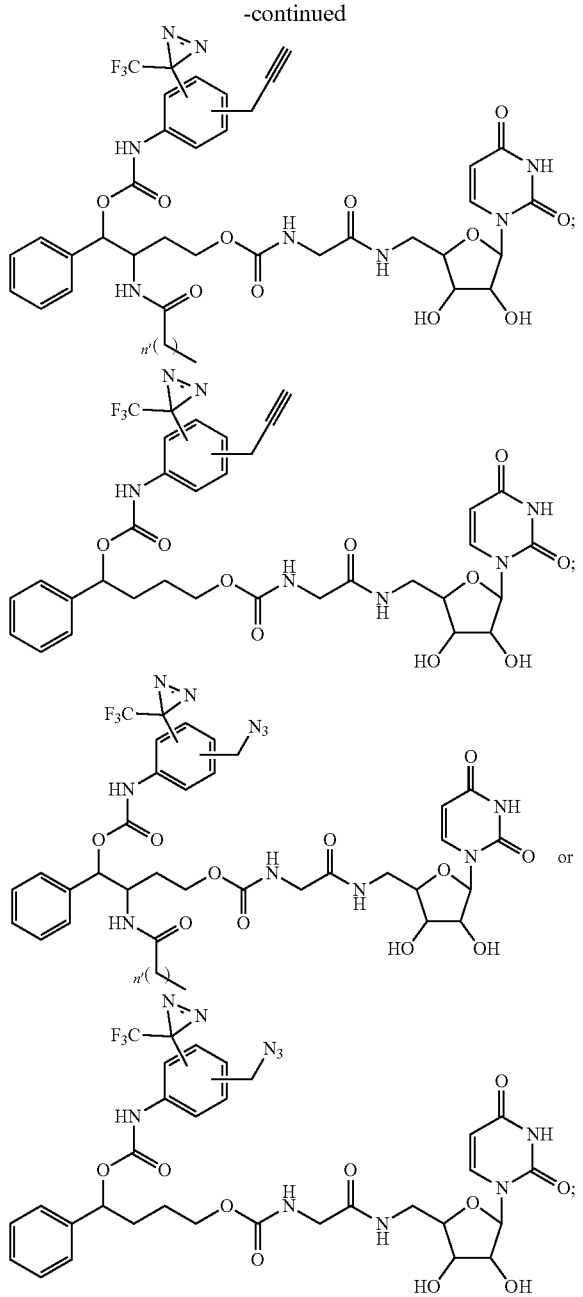

wherein each n' independently ranges from zero to 50, or 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

B. Glutathione S-Transferase Probe Embodiments

Glutathione S-transferases (GSTs) are categorized by their subcellular location into cytosolic, mitochondrial, and microsomal superfamilies, which are further divided into classes based on sequence homology. GSTs contain a GSH binding "G" site and a substrate-binding "H" site. Expression of GSTs, measured by transcriptomics and/or global proteomics, often does not correlate with their detoxifying GSH transferase activity. This discrepancy between expression and activity can be attributed to known post-translational modifications, alternative enzyme-specific non-transferase activities, and activity altering protein-protein interactions.

76

Figure 4:
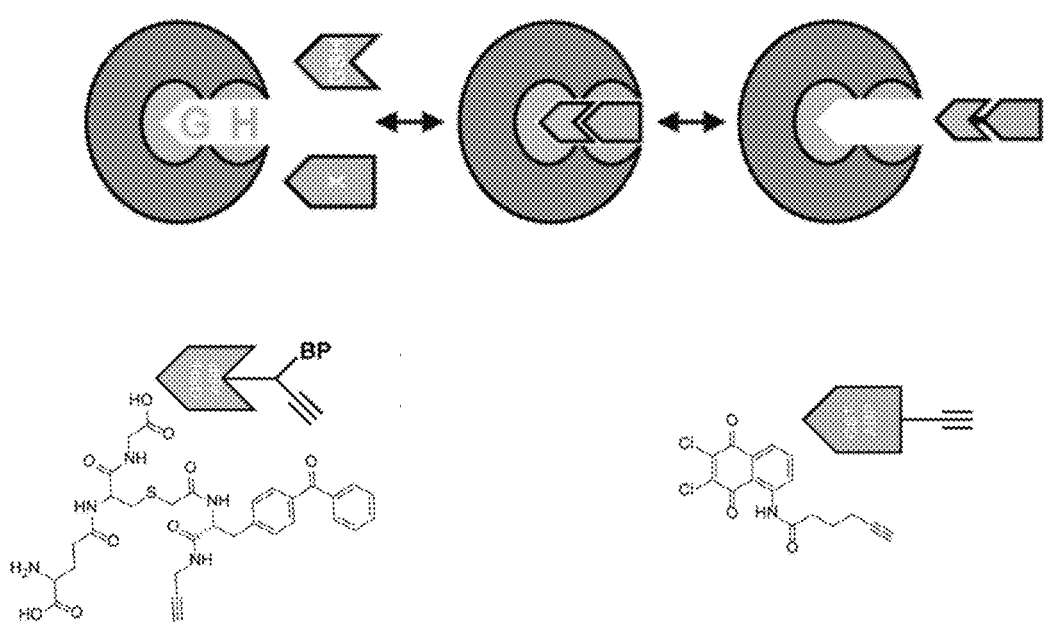
FIG. 4 is a schematic illustration of the function of active glutathione transferases ("GSTs"), which shows the mechanism of conjugating reduced glutathione (GSH) to a xenobiotic (X) stabilized by "G" and "H" site binding by representative probe embodiments described herein.

The GSH transferase activity of GSTs relies on the activities of both the GSH-binding G site and the substrate binding H site (see FIG. 4). Certain probe embodiments described herein can target each site and measure the activity of GSTs, with representative examples being illustrated in FIG. 4. Exemplary probe embodiments have a structure satisfying any one of Formulas VIA or VIB below.

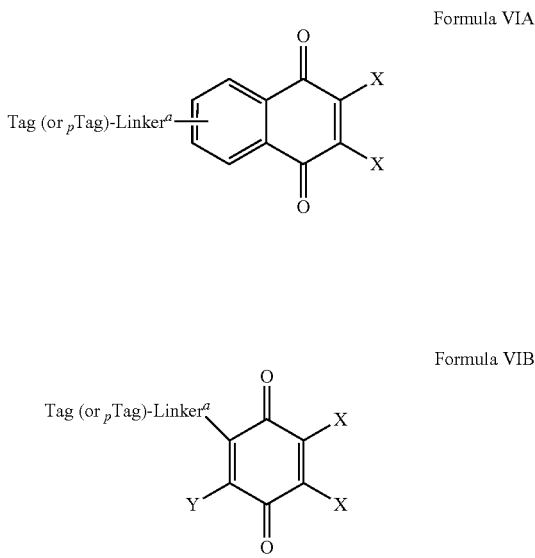

With reference to Formulas VIA and VIB, the following substituent recitations can apply:

each X independently can be a halogen;

Linker$^a$ can comprise an aliphatic group, a heteroaliphatic group, an aromatic group, an aliphatic-aromatic group, a heteroaliphatic-aromatic group, a heteroaromatic group, an aliphatic-heteroaromatic group, or a heteroaliphatic-heteroaromatic group;

the Tag, if present, can be a functional group or molecule that generates a detectable signal; alternatively, if the probe comprises a $_p$Tag (an "Tag precursor") group, then the $_p$Tag can be a Tag precursor comprising a clickable functional group; and with reference to Formula IIIE, Y can be a halogen or a glutathione moiety.

In exemplary disclosed embodiments, the following substituent recitations can apply:

each X is chloro;

Linker$^a$ is —NR'''C(O)(CH$_2$)$_{n'}$—, or —NR'''C(O)CH$_2$[O(CH$_2$)$_2$]$_{n'}$OCH$_2$—, wherein each n' independently is an integer ranging from 1 to 20, such as 1 to 10, or 1 to 5, or 1, 2, 3, 4, 5, 6, 7, 8, 9, 10, 11, 12, 13, 14, 15, 16, 17, 18, 19, or 20, and wherein R''' is hydrogen, aliphatic, or aromatic;

the Tag, if present, can be a fluorophore, a binding partner of an affinity-based binding pair, a quantum dot, or a dye; alternatively, if a $_p$Tag group is present, then the $_p$Tag is an alkyne or an azide; and with reference to Formula VIB, Y can be chloro or glutathione.

In exemplary disclosed embodiments, the probe can have a structure according to Formula VIC illustrated below.

Formula VIC

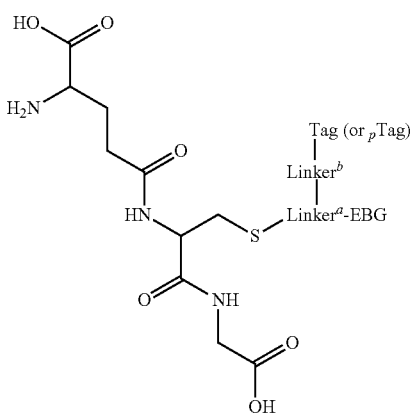

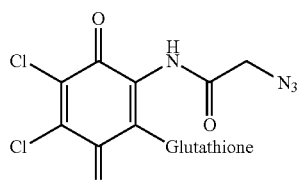

With reference to Formula VIC, Linker$^a$ can be as illustrated for Formula IIG$_{Linker a}$ above; the EBG can be a photo-activatable group, such as a diaziridine or a benzophenone; and Linker$^b$ can comprise an amide. The Tag (if present), or the $_p$Tag (if present), independently can be as recited above.

Exemplary azide- or alkyne-containing probe embodiments that can irreversibly bind a glutathione transferase are illustrated below.

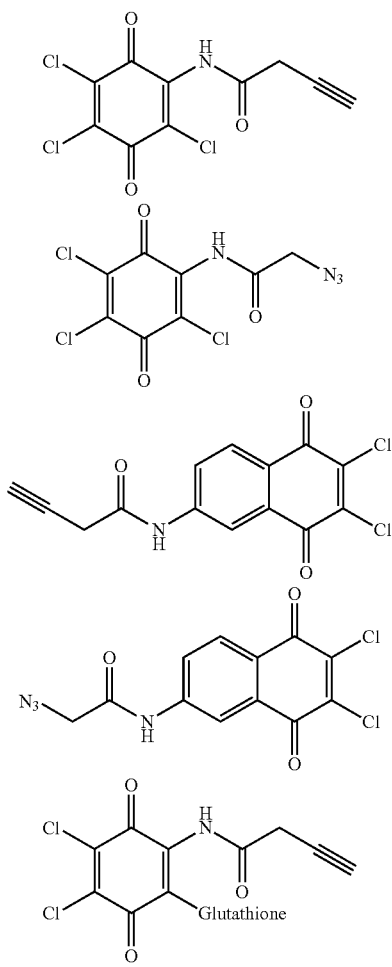

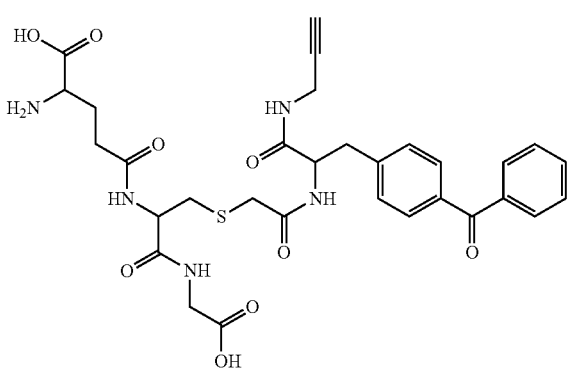

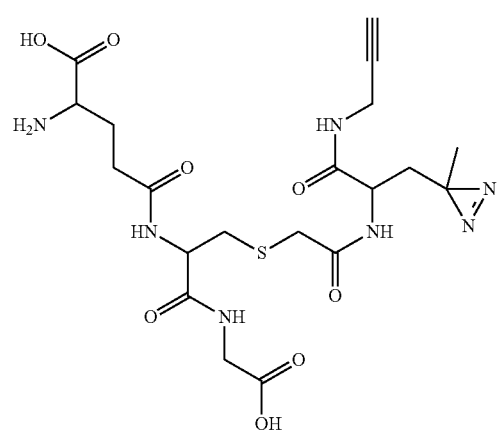

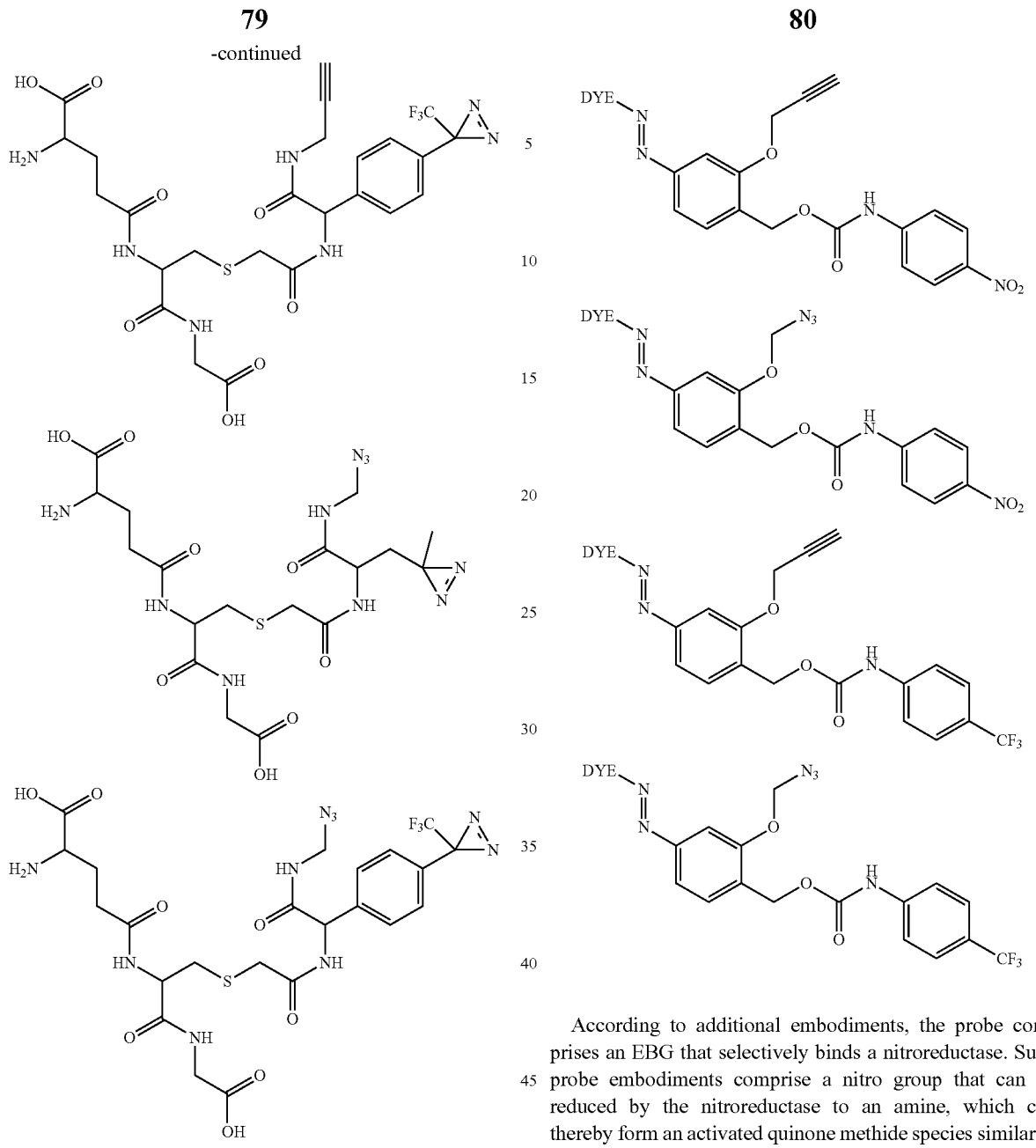

C. Reductase Probe Embodiments

According to some embodiments, the ABP can be a probe that selectively binds to a reductase enzyme, such as an azoreductase, a nitroreductase, an NAD(P)H quinone oxidoreductase, or an aldoketoreductase (AKR). Such probe embodiments can have a structure satisfying one or more of the Formulas described above, such as Formula II or Formula IIIA.

According to some embodiments, the probe comprises an EBG that selectively binds an azoreductase. Such probe embodiments comprise an azo group that is first chemically modified by the azoreductase to form an amine, which thereby activates the EBG (e.g., such as by forming an activated quinone methide species) so that the azoreductase can bind to the probe. Exemplary probe embodiments that can bind azoreductases are illustrated below. Without being limited to any particular theory, an exemplary mechanism for activation of such probe embodiments for enzyme coupling is illustrated in FIG. 3.

According to additional embodiments, the probe comprises an EBG that selectively binds a nitroreductase. Such probe embodiments comprise a nitro group that can be reduced by the nitroreductase to an amine, which can thereby form an activated quinone methide species similar to the azoreductase probe embodiments described above. Exemplary embodiments of a probe effective for targeting a nitroreductase are illustrated below. Without being limited to a particular theory, an exemplary mechanism for activating such probe embodiments for enzyme coupling is illustrated in FIG. 3.

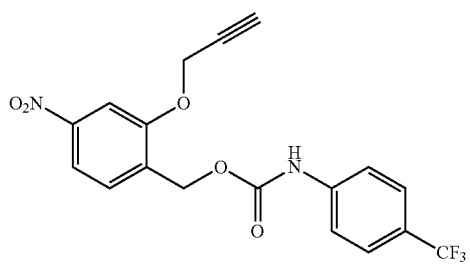

-continued

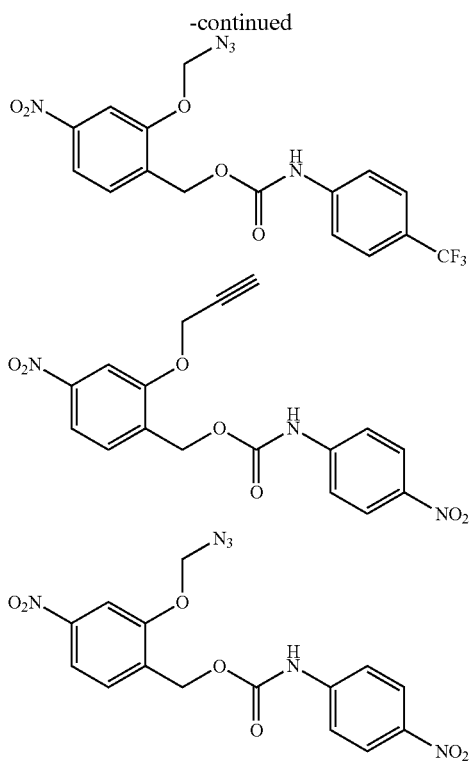

According to some embodiments, the probe comprises an EBG that selectively binds to an NAD(P)H quinone oxidoreductase. Such probe embodiments also comprise an ERG group that is displaced by the NAD(P)H quinone oxidoreductase. According to some embodiments, the ERG can be a phenolic group that is bound to the EBG through an ester bond. The phenolic ERG can be displaced by the NAD(P)H quinone oxidoreductase such that the EBG is bound to the NAD(P)H quinone oxidoreductase. An exemplary embodiment of such a probe is illustrated below.

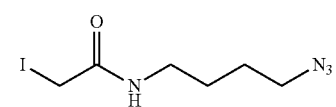 [SMILES: [N-]=[N+]=NCCCCNC(=O)CI]

According to some embodiments, the probe illustrated below also can be used to bind to the NAD(P)H quinone oxidoreductase, in combination with one or more of the other probes described herein.

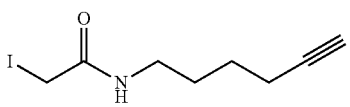

According to some embodiments, the probe comprises an EBG that selectively binds the active site cysteine residues of an aldoketoreductase (AKR). Such probe embodiments also comprise an ERG group that is cleaved by the aldoketoreductase. According to some embodiments, the ERG group can be a reactive iodo group that is displaced by a cysteine group of the aldoketoreductase. Exemplary embodiments of such a probe are illustrated below.

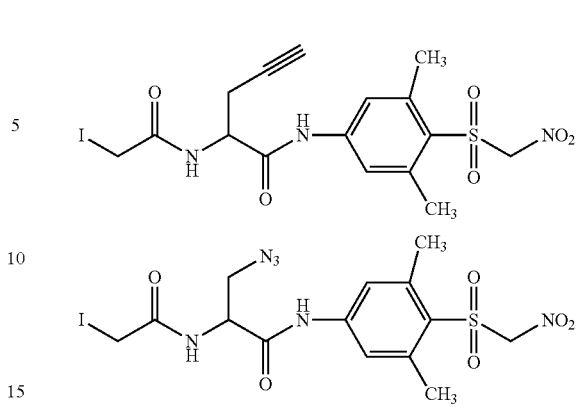

D. Sulfatase and Sulfotransferase Probe Embodiments

Also described herein are probe embodiments that can selectively and irreversibly bind sulfatase enzymes and sulfotransferase enzymes. Probe embodiments that can bind to sulfatase enzymes comprise an ERG that is first cleaved from the EBG of the probe by the sulfatase. This produces an activated ERG (e.g., a quinone methide group) that can be bound to the sulfatase. Suitable probes can have structures satisfying Formula II and/or Formula IIIA as described above. Exemplary probe embodiments that target sulfatases include those illustrated below. Without being limited by any particular theory, an exemplary mechanism for how such probe embodiments can be activated for enzyme coupling is illustrated in FIG. 3.

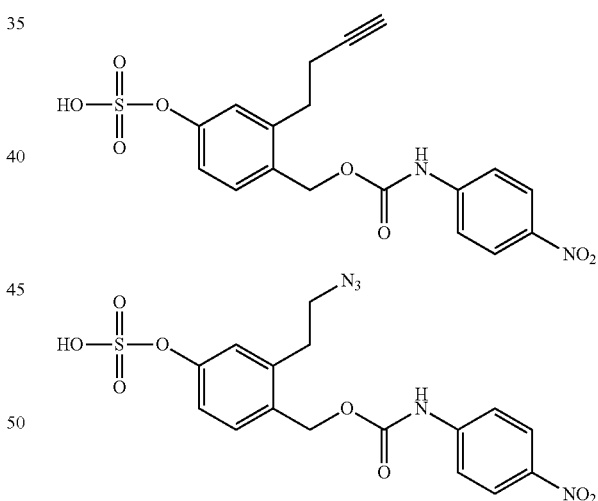

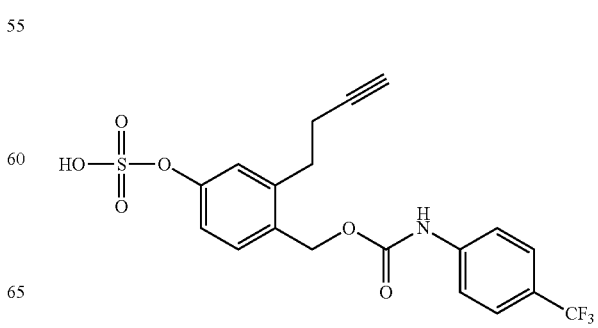

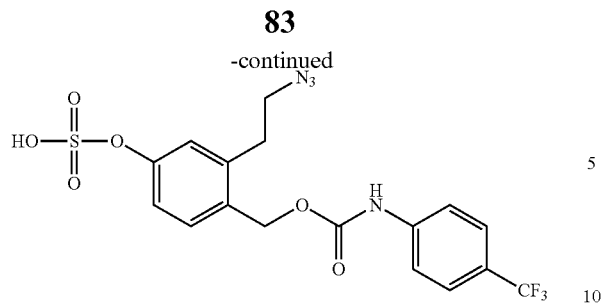

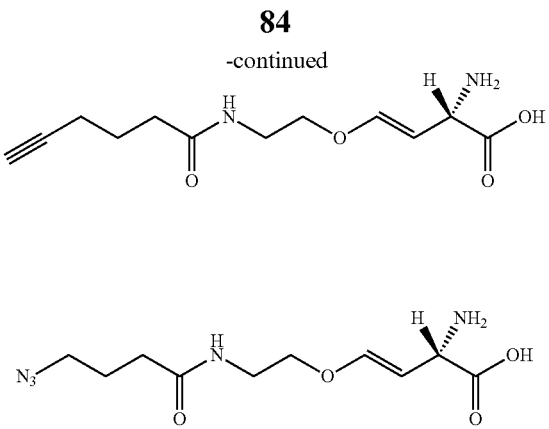

According to some additional embodiments, the probe can selectively bind to sulfotransferases. In such embodiments, the probe comprises a photo-reactive EBG that can be photo-activated to then bind to the enzyme. As described above, the photo-reactive EBG can comprise a benzophenone moiety or a diazirane moiety. Suitable probes can have structures satisfying Formula IIIC as described above. Exemplary probe embodiments that can be used to bind to sulfotransferases are illustrated below.

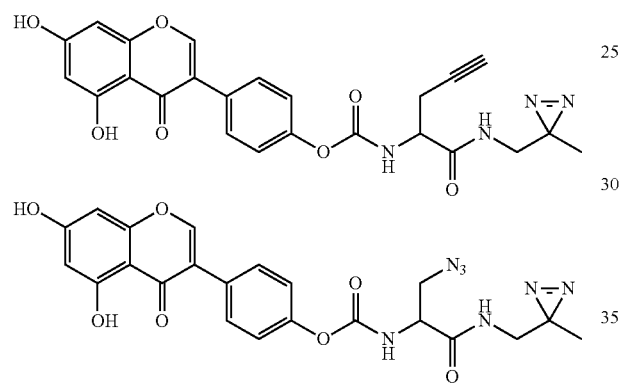

E. Cysteine Lyase Probe Embodiments

According to some embodiments, the probe can selectively bind to cysteine lyase, which is an enzyme that is active in the gut microbiome. Such probe embodiments comprise an olefin-containing EBG that forms a covalent bond with a cysteine moiety of the cysteine lyase. In exemplary disclosed embodiments, the EBG comprises an olefin that covalently binds with the sulfur atom of the cysteine moiety of the lyase. Suitable probes can have structures satisfying Formula II or Formula IIA as described above. Exemplary cysteine lyase probe embodiments are provided below. Without being limited by any particular theory, an exemplary mechanism for how such probe embodiments can be activated for enzyme coupling is illustrated in FIG. 3.

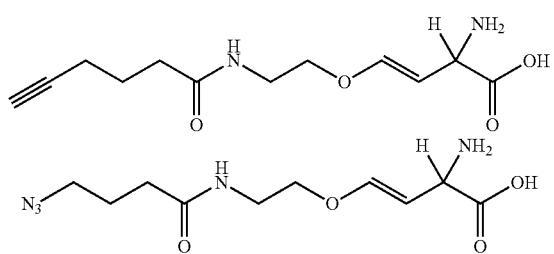

F. Prostaglandin H Synthase (PGHS) Probe Embodiments

According to some embodiments, the probe can selectively bind to PGHS, an enzyme that is active in Phase II metabolism. Such probe embodiments comprise an ERG that is displaced by a PGHS enzyme, thereby coupling, through an EBG, the probe to the enzyme. Suitable probes can have structures satisfying Formula II or Formula IIIA as described above. Exemplary PGHS probe embodiments are provided below.

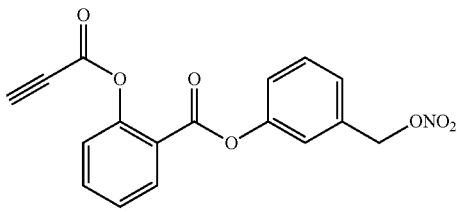

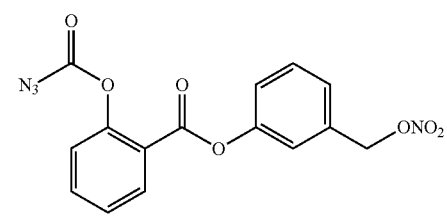

IV. Method of Making Probe Embodiments

Exemplary embodiments of a method for making an activity-based probe of the present disclosure are provided below. It is understood that suitable reagents appropriate for certain embodiments can be used even if such reagents are not expressly recited.

In an exemplary embodiment, a method for making an activity-based probe can include the steps illustrated below in Scheme 1.

Scheme 1
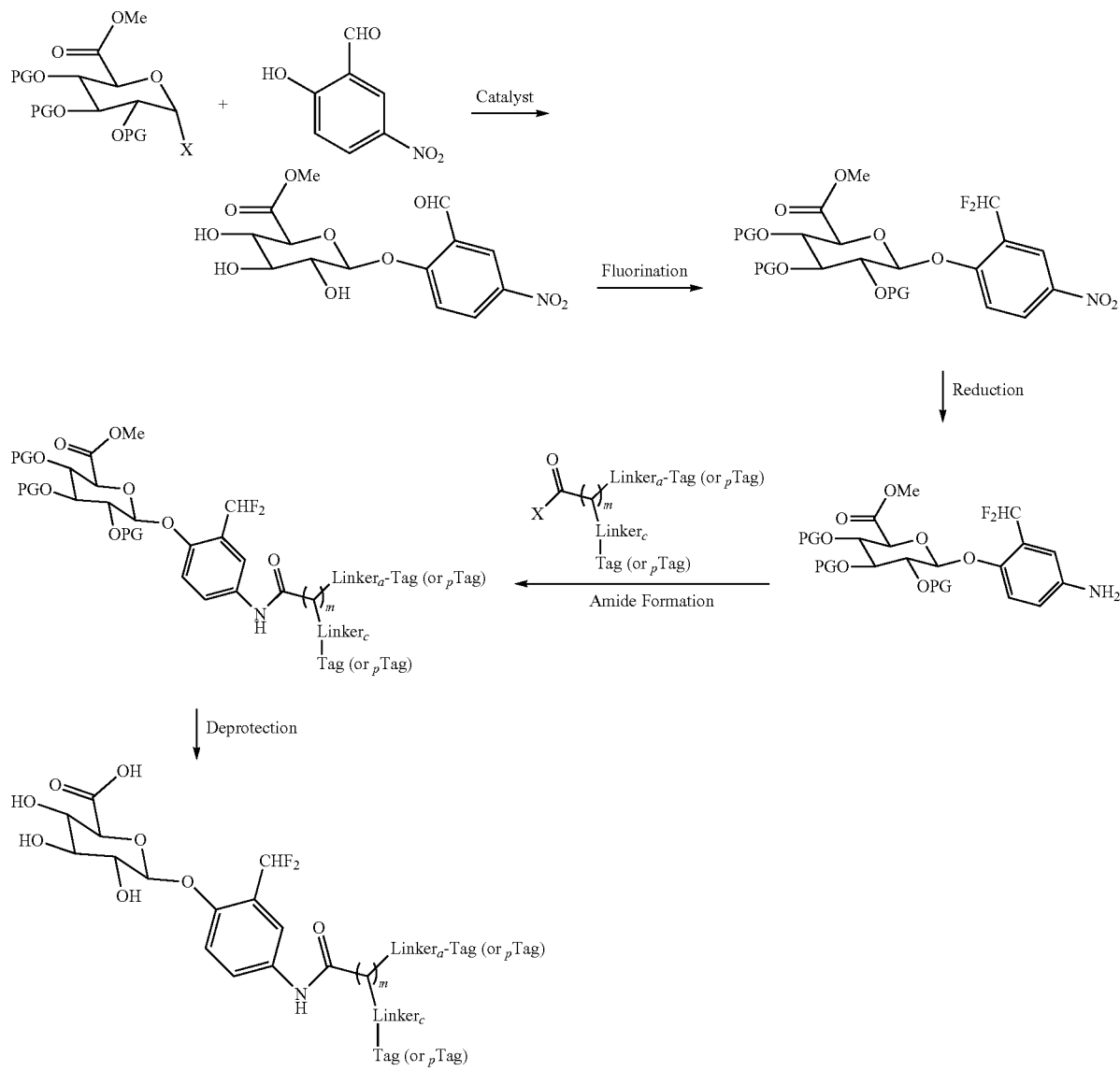
Exemplary embodiments of the method illustrated above in Scheme 1 are shown below in Scheme 2 and Schemes 3A and 3B.
Scheme 2
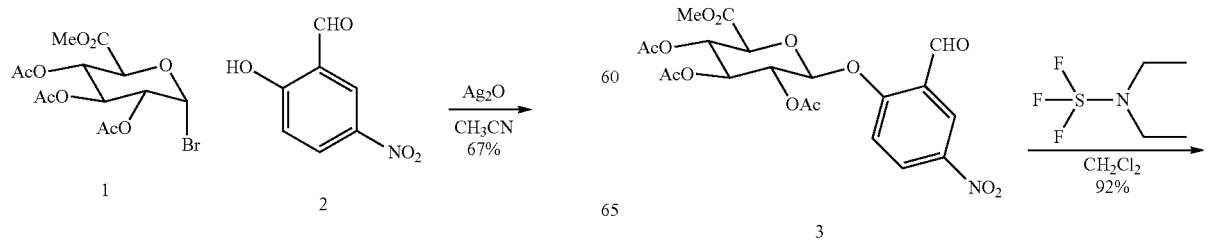

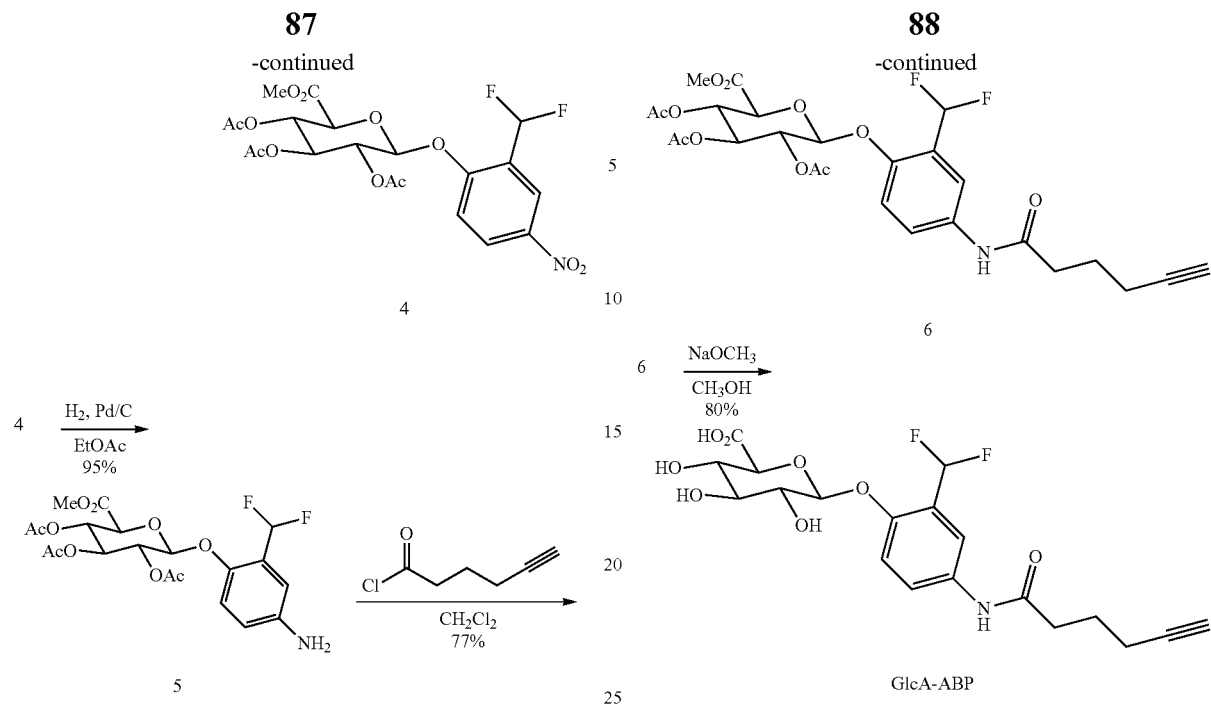
Scheme 3A
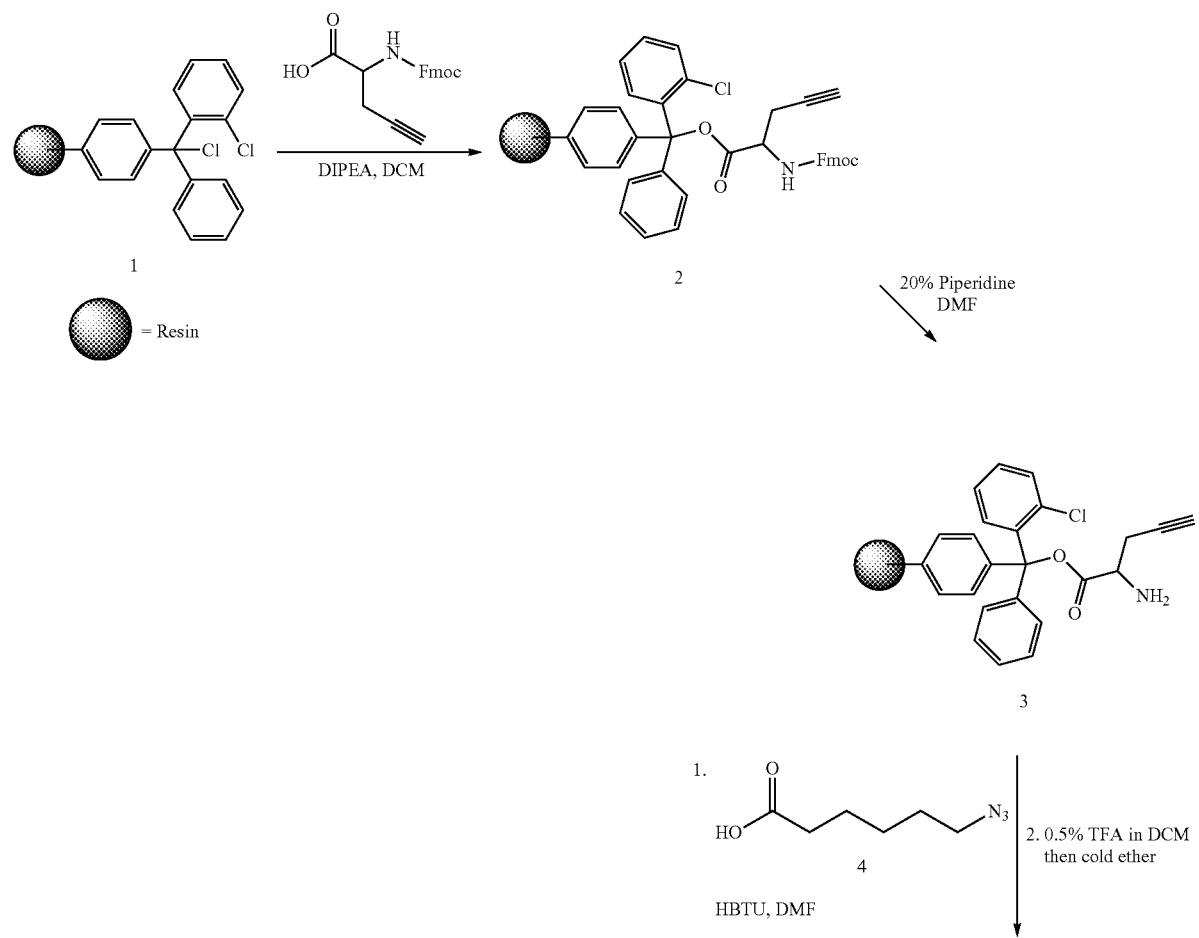

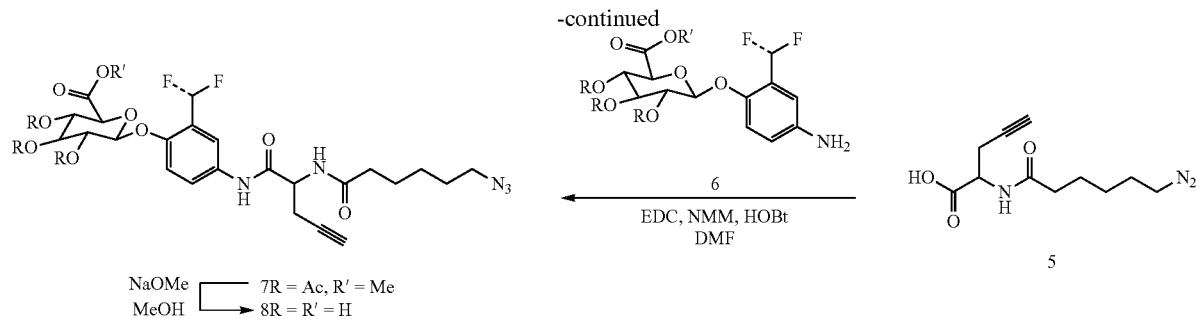

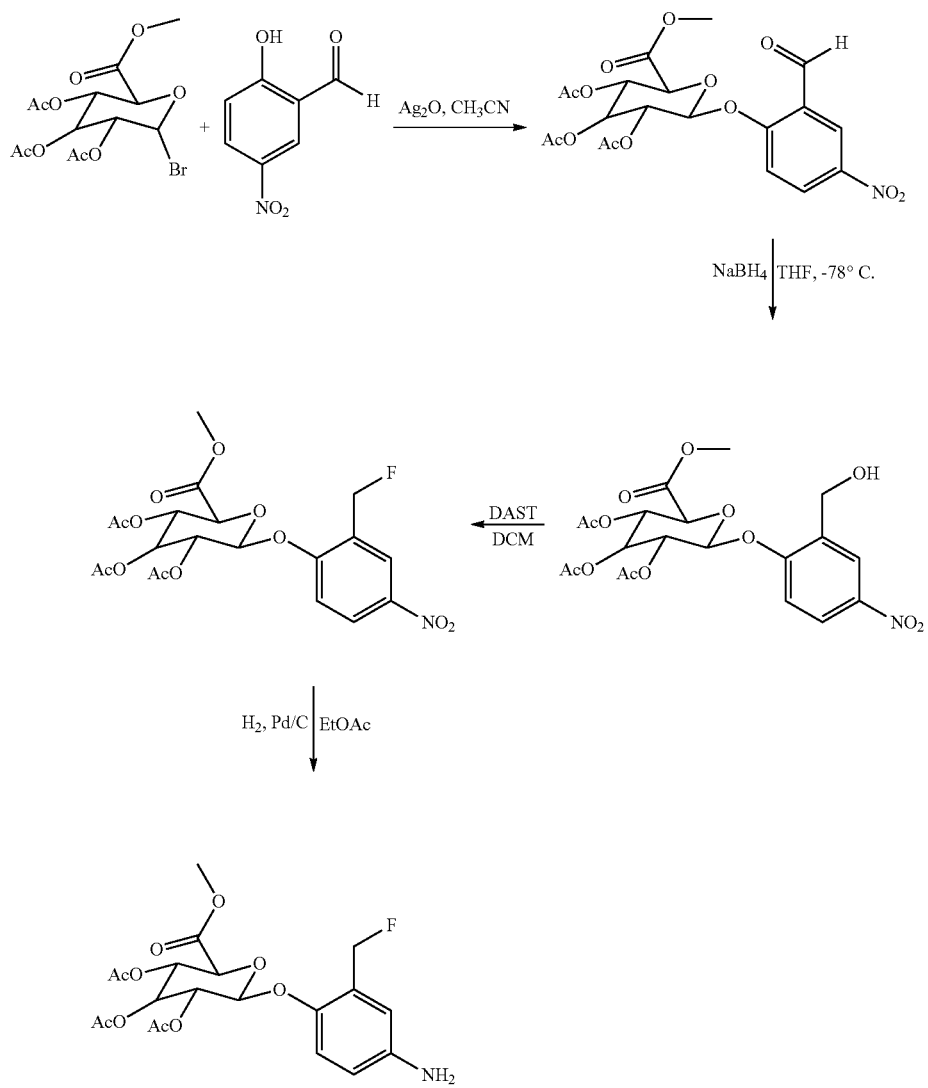

Scheme 3B

In some exemplary embodiments, the method can comprise the steps illustrated below in Scheme 4. With reference to Scheme 4, "PG" represents a protecting group that can be used to protect the phenol group of the nitro-containing starting material. With the benefit of the present disclosure, suitable reducing agents for converting the aldehyde of the protected phenol and coupling conditions for coupling the resulting primary alcohol with an amide-containing coupling partner will be recognized by a person of ordinary skill in the art.

Scheme 4
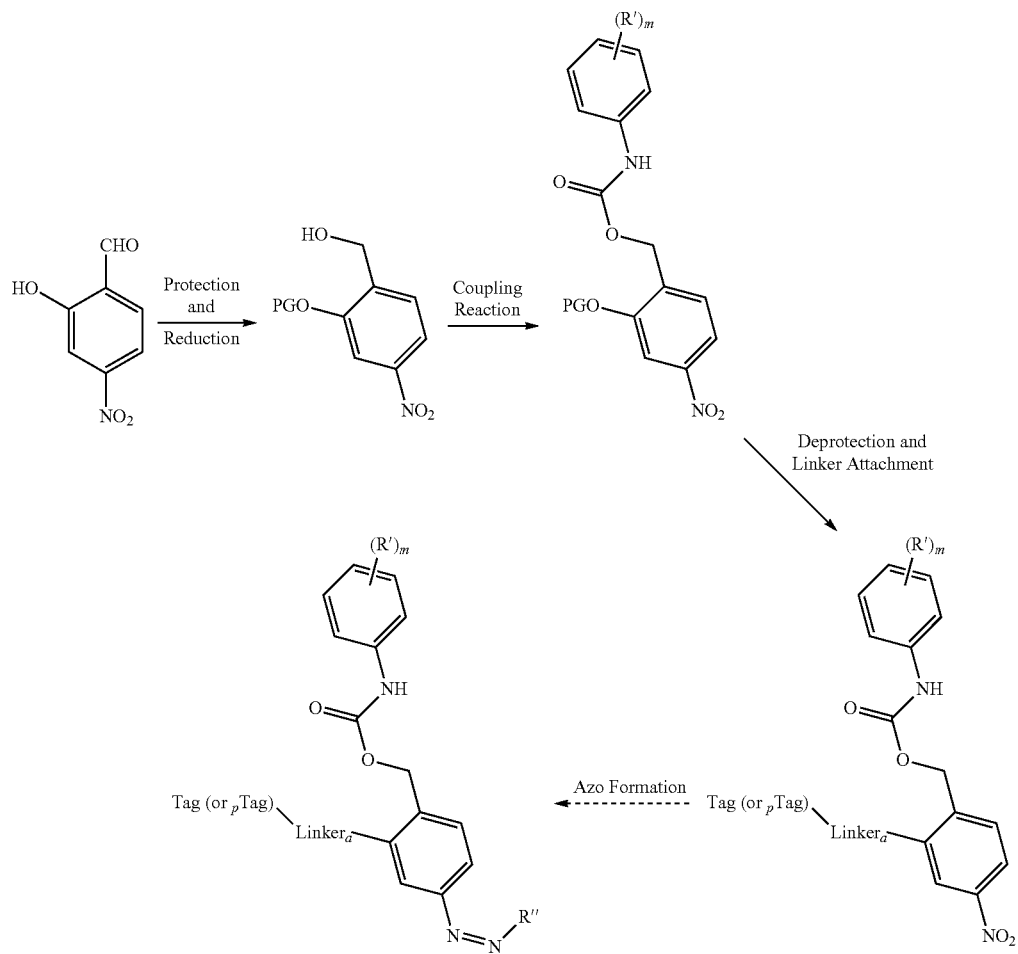
An exemplary embodiment of the method illustrated above in Scheme 4 is shown below in Scheme 5.
Scheme 5
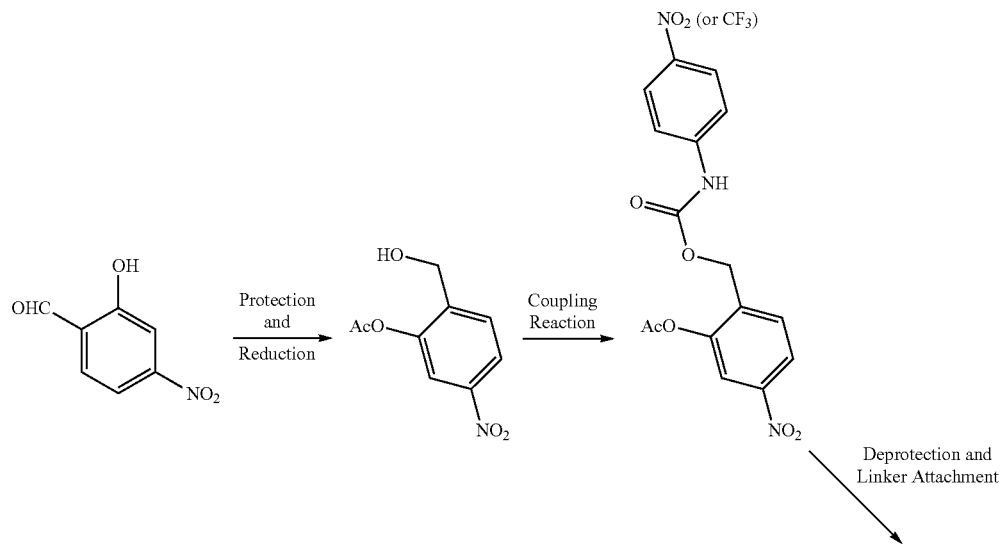

-continued
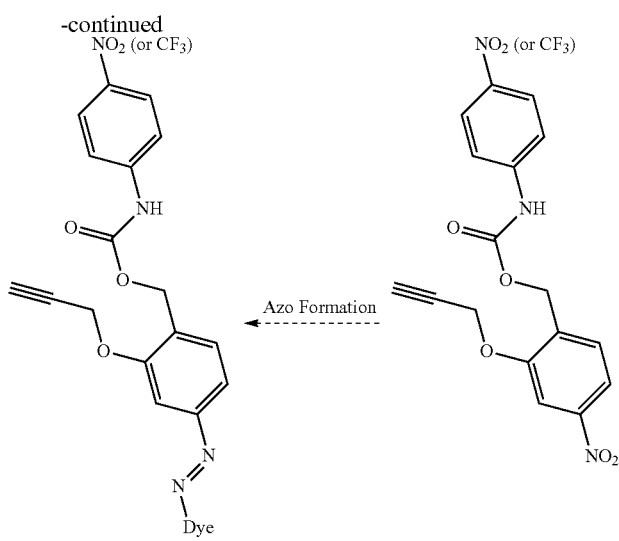
Additional exemplary embodiments are shown below in Schemes 6-8.
Scheme 6
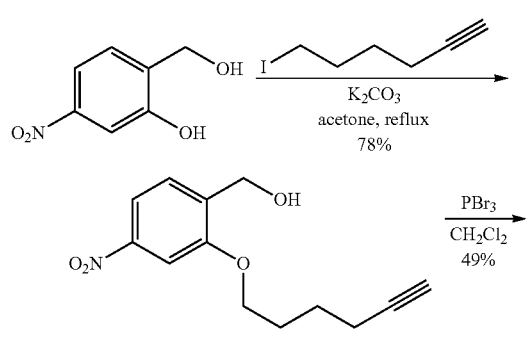
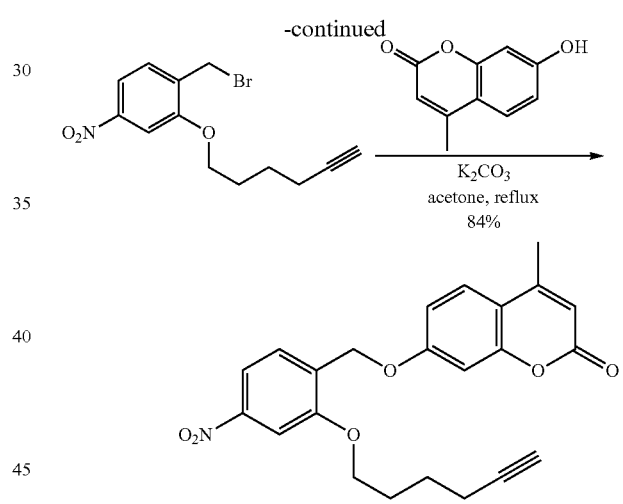
Scheme 7
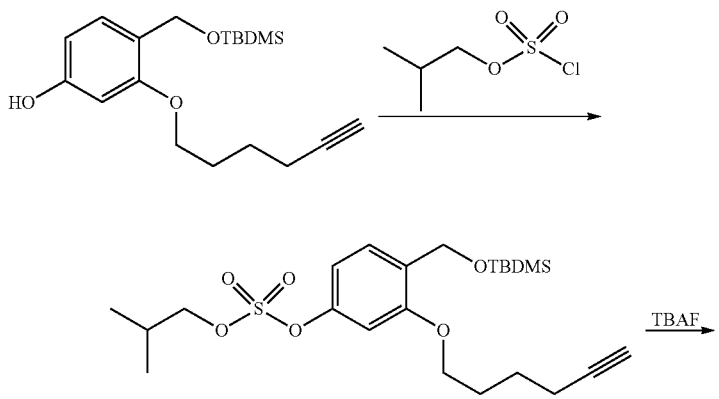

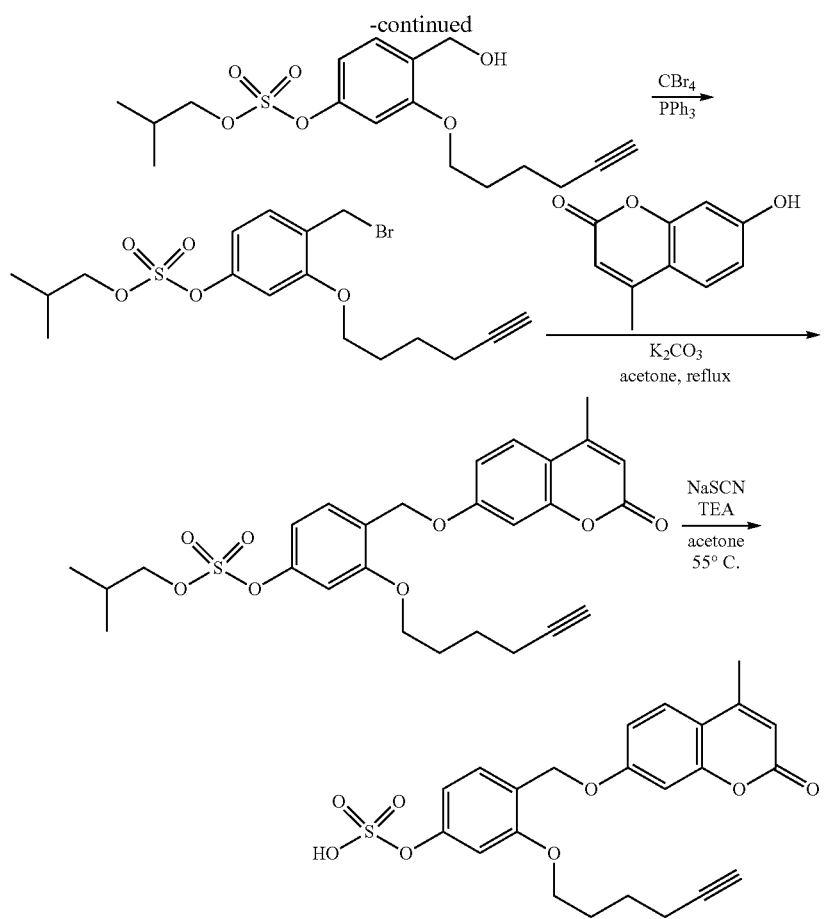

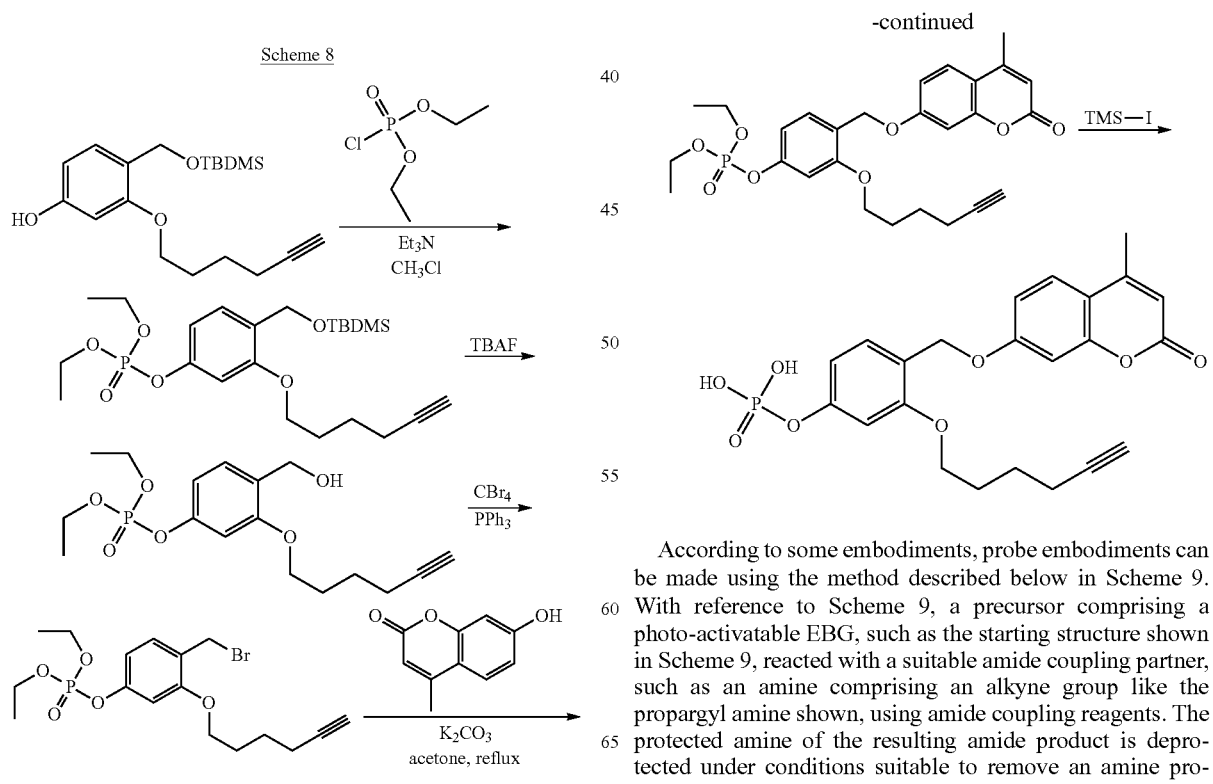

According to some embodiments, probe embodiments can be made using the method described below in Scheme 9. With reference to Scheme 9, a precursor comprising a photo-activatable EBG, such as the starting structure shown in Scheme 9, reacted with a suitable amide coupling partner, such as an amine comprising an alkyne group like the propargyl amine shown, using amide coupling reagents. The protected amine of the resulting amide product is deprotected under conditions suitable to remove an amine protecting group (e.g., Fmoc), such as by using a base (e.g., piperidine). The resulting primary amine product is coupled to iodoacetic anhydride to form an iodoacetamide product (e.g., compound 5). The iodoacetamide product cis then coupled with a reduced glutathione moiety to form the probe (e.g., probe GSH-ABP-G).

Scheme 9

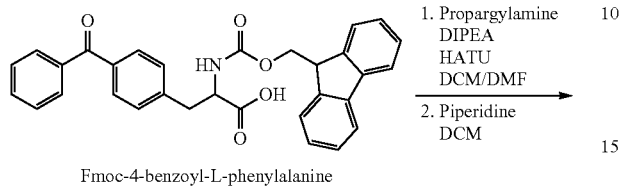

Fmoc-4-benzoyl-L-phenylalanine

1. Propargylamine
DIPEA
HATU
DCM/DMF
2. Piperidine
DCM

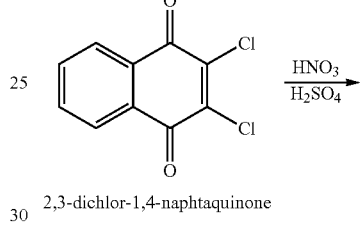

4, 34%

Iodoacetic anhydride
DCM

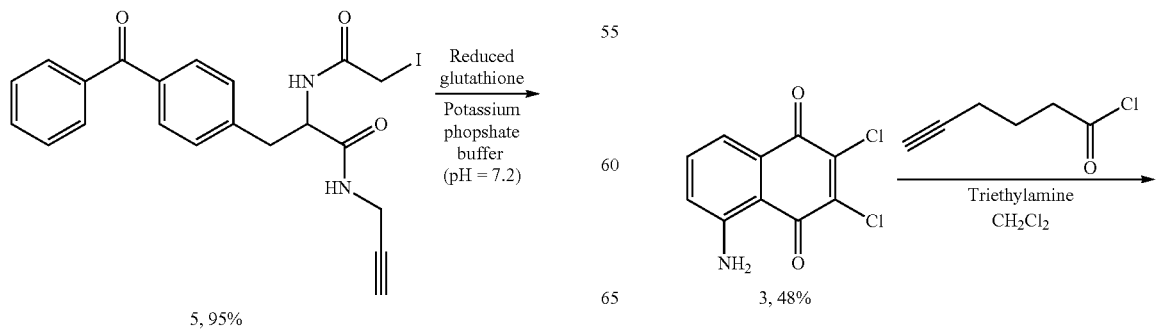

5, 95%

Reduced glutathione
Potassium phopshate buffer
(pH = 7.2)

5, 95%

-continued

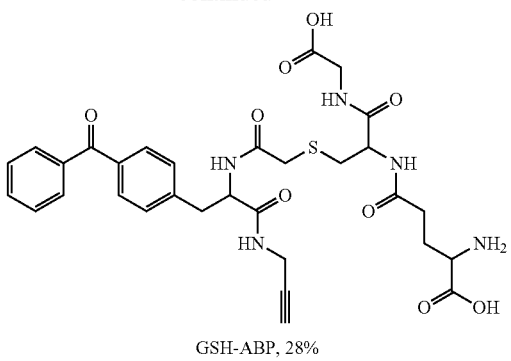

GSH-ABP, 28%

Another exemplary method is shown in Scheme 10.

Scheme 10

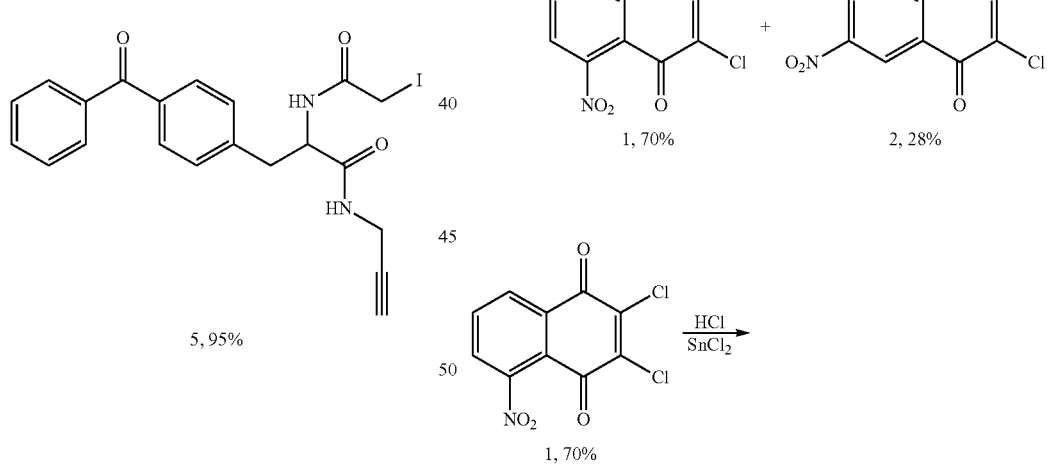

2,3-dichlor-1,4-naphtaquinone

HNO$_3$
H$_2$SO$_4$ 1, 70%    2, 28%

HCl
SnCl$_2$ 1, 70%

Triethylamine
CH$_2$Cl$_2$ 3, 48%

-continued

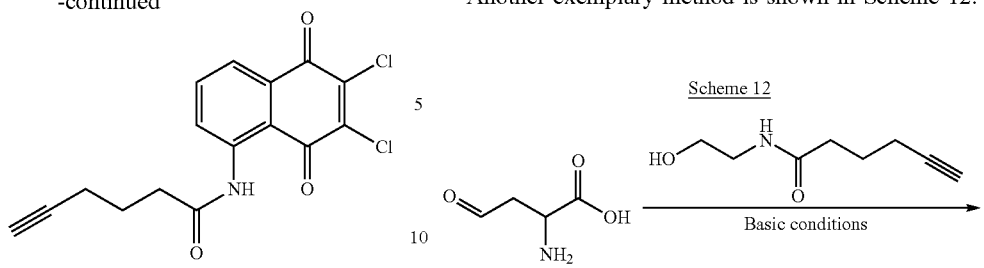

Another exemplary method is shown in Scheme 11.

Another exemplary method is shown in Scheme 12.

Scheme 12

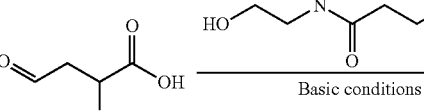

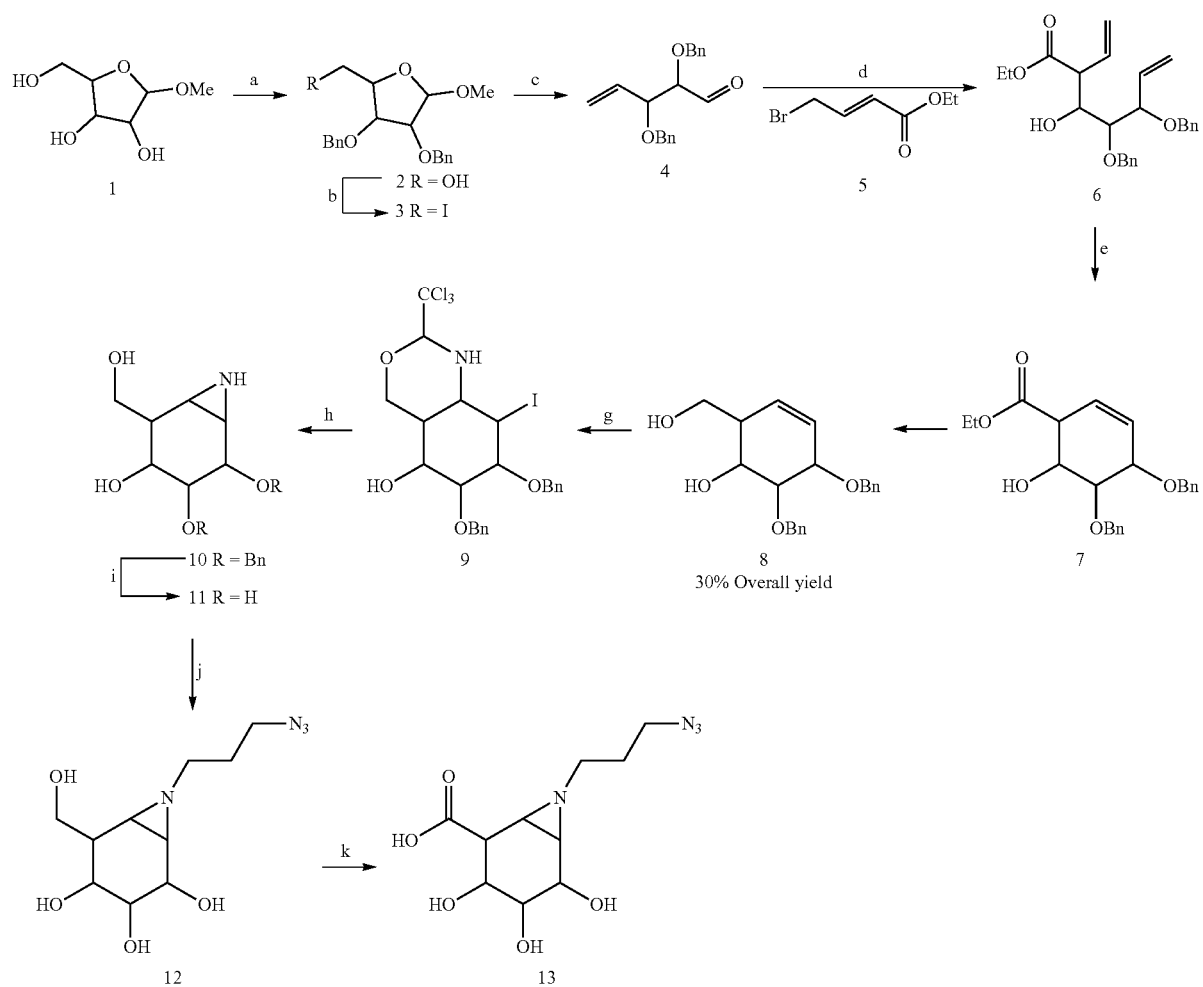

With reference to Scheme 11, the conditions that can be used include the following: a) (i) TrCl, Et₃N, DMAP, DMF, (ii) NaH, BnBr, TBAI, DMF 0° C. to room temperature (iii) p-TsOH, MeOH, CH₂Cl₂; b) I₂, PPh₃, imidazole, THF, 70° C.; c) zinc dust, THF/H₂O (9:1), sonication, 40° C.; d) 5, indium powder, La(OTf)₃, H₂O, sonication; e) second-generation Grubbs catalyst, CH₂Cl₂, 40° C.; f)(i) DIBAL-H, THF, 0° C. to RT, (ii) NaBH₄, H₂O, EtOAc; g) (i) Cl₃CN, DBU, CH₂Cl₂, 0° C. (ii) I₂, NaHCO₃, H₂O; h) (i) 37% HCl, dioxane, 60° C., (ii) NaHCO₃, MeOH, 60%, i) Li, NH₃, THF, −60° C.; j) K₂CO₃, DMF, any azide- or alkyne-containing group further comprising a halogen, 80° C.; and k) TEMPO, NaClO, NaBr, NaOH, H₂O.

-continued

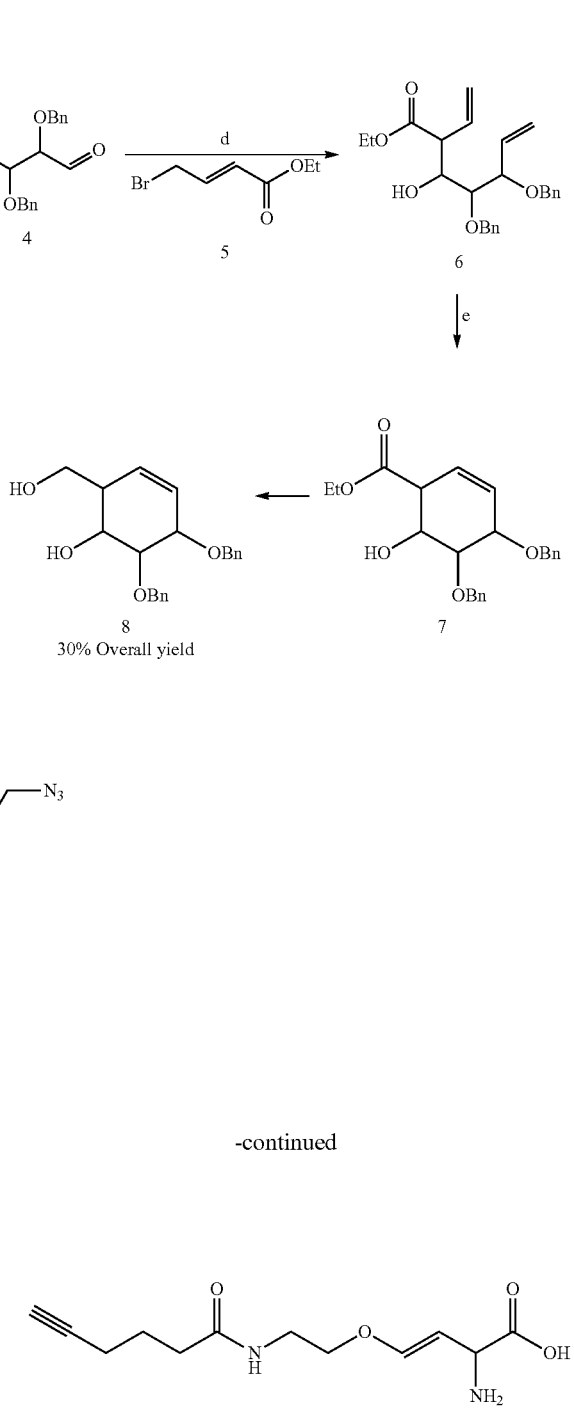

Another exemplary method is shown in Scheme 13.
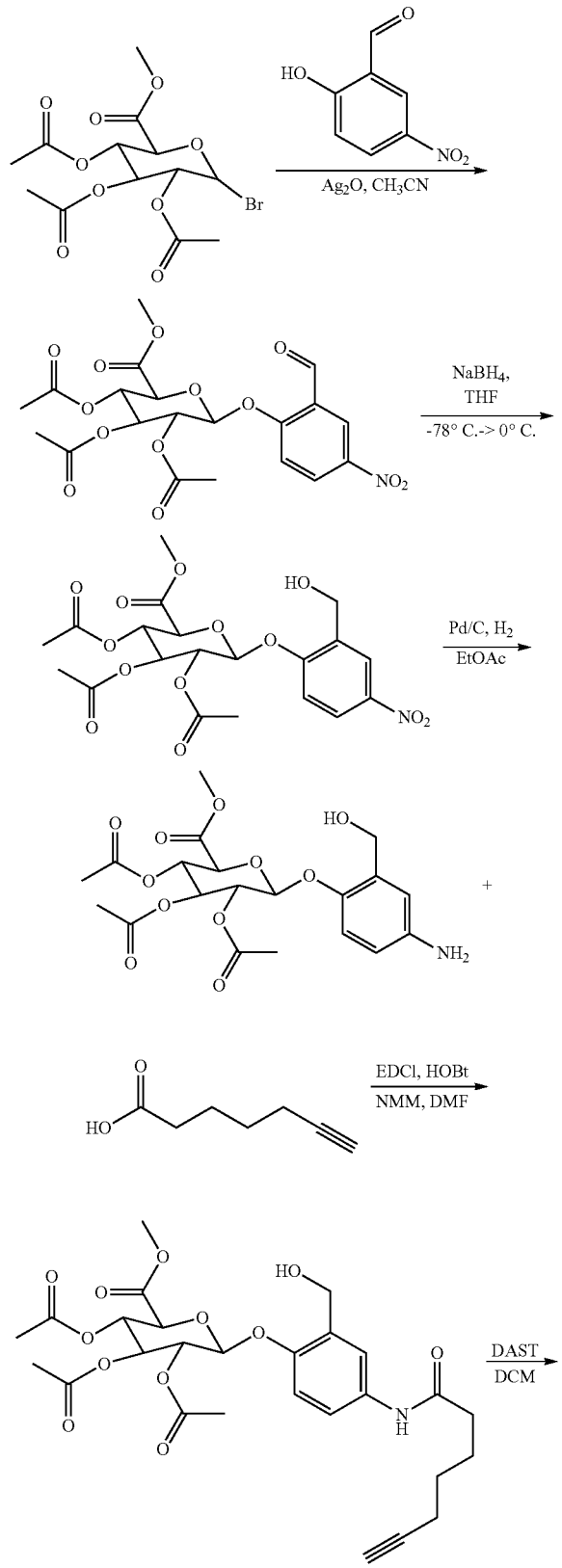
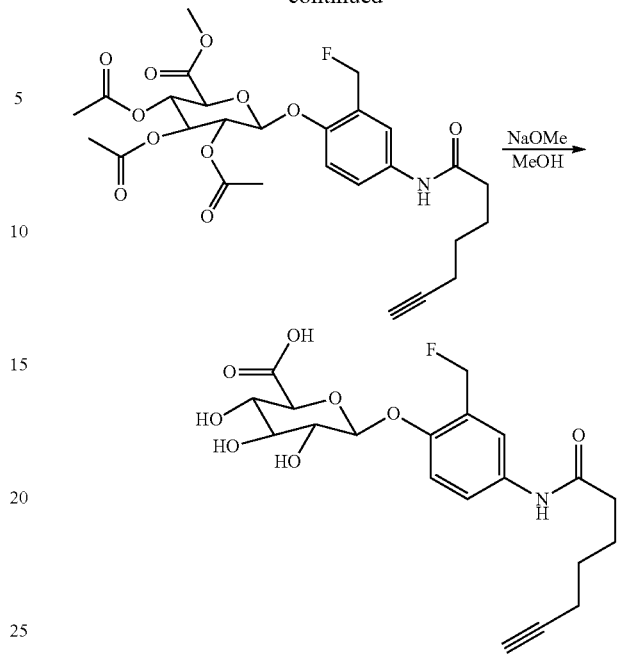
Yet another exemplary method for making a probe embodiment of the present disclosure is shown below in Scheme 14.
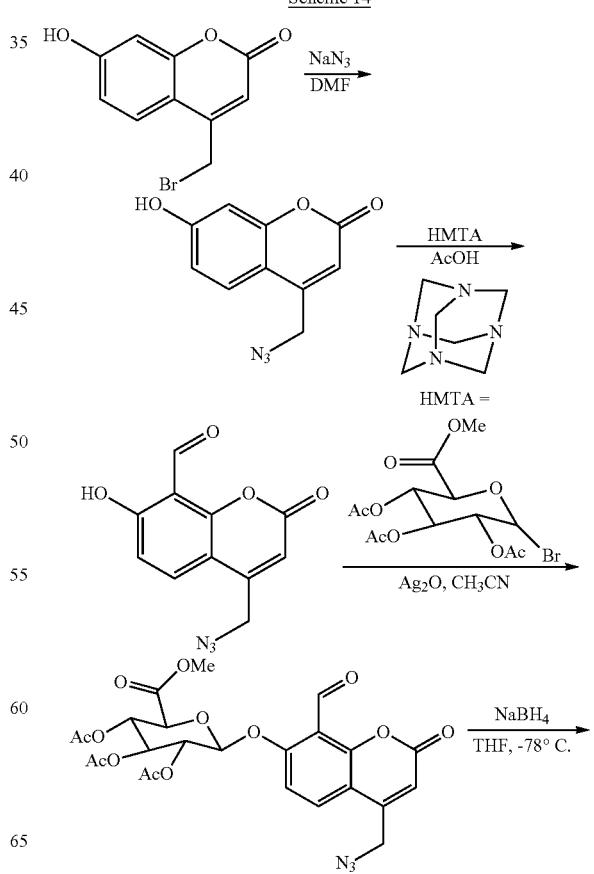

-continued

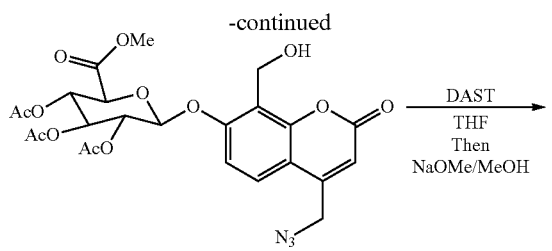

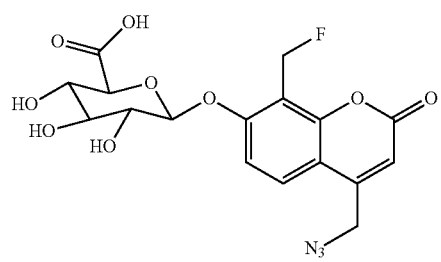

V. Exemplary Methods

The activity-based probes can be used in the following exemplary methods. For example, according to one aspect, the present disclosure provides a method of detecting and measuring activity of one or more target enzymes of xenobiotic metabolism in a sample obtained from a subject. Such a method can include: (a) obtaining the sample from the subject; and (b) detecting activity of the target enzyme in the sample by (i) contacting the sample with an activity probe activated by click chemistry that is effective to specifically and irreversibly bind the target enzyme; and (ii) measuring binding between the activity probe and the target enzyme.

For example, according to another aspect, the present disclosure provides a method for determining individual enzyme contribution to metabolism of a xenobiotic by gut microbiota of a subject. Such a method can include: (a) contacting a xenobiotic to a sample obtained from the subject; (b) incubating the sample with the xenobiotic for an incubation period; (c) exposing the sample to one or more differentially labeled enzyme activity probes, each of which is effective to specifically and irreversibly bind its target enzyme by contacting the sample with each enzyme activity probe activated by click chemistry; (d) detecting binding, measuring binding, or both between each activity probe and its target enzyme compared to a control; and (e) determining contribution of the individual target enzymes to metabolism of the xenobiotic.

For example, according to another aspect, the present disclosure provides a method of diagnosing and treating a microbiota-mediated toxicity due to metabolism of a xenobiotic in a subject in need thereof. Such a method can include: (a) contacting a xenobiotic with a sample obtained from the subject; (b) incubating the sample with the xenobiotic for an incubation period; (c) exposing the sample to one or more differentially labeled enzyme activity probes, each of which is effective to specifically and irreversibly bind its target enzyme by contacting the sample with each enzyme activity probe activated by click chemistry; (d) detecting and measuring binding of each activity probe to its target host enzyme and target microbiota enzyme compared to a control; (e) diagnosing the subject with a microbiota-induced toxicity; and (f) treating the subject with an antibacterial agent effective (i) to modulate the microbiota population and (ii) to reduce the toxicity.

According to some embodiments, the term "antibacterial agent" is meant to refer to any of a group of chemical substances having the capacity to inhibit the growth of, or to destroy bacteria, and other microorganisms, used chiefly in the treatment of infectious diseases. Antibacterial agents include, without limitation, penicillins, cephalosporins, carbacephems, cephamycins, carbapenems, monobactams, aminoglycosides, glycopeptides, quinolones, tetracyclines, macrolides, and fluoroquinolones. Examples include, without limitation, Penicillin G; Methicillin; Nafcillin; Oxacillin; Cloxacillin; Dicloxacillin; Ampicillin; Amoxicillin; Ticarcillin; Carbenicillin; Mezlocillin; Azlocillin; Piperacillin; Imipenem; Aztreonam; Cephalothin; Cefaclor; Cefoxitin; Cefuroxime; Cefonicid; Cefmetazole; Cefotetan; Cefprozil; Loracarbef; Cefetamet; Cefoperazone; Cefotaxime; Ceftizoxime; Ceftriaxone; Ceftazidime; Cefepime; Cefixime; Cefpodoxime; Cefsulodin; Fleroxacin; Nalidixic acid; Norfloxacin; Ciprofloxacin; Ofloxacin; Enoxacin; Lomefloxacin; Cinoxacin; Doxycycline; Minocycline; Tetracycline; Amikacin; Gentamicin; Kanamycin; Netilmicin; Tobramycin; Streptomycin; Azithromycin; Clarithromycin; Erythromycin; Erythromycin estolate; Erythromycin ethyl succinate; Erythromycin glucoheptonate; Erythromycin lactobionate; Erythromycin stearate; Vancomycin; Teicoplanin; Chloramphenicol; Clindamycin; Trimethoprim; Sulfamethoxazole; Nitrofurantoin; Rifampin; Mupirocin; Metronidazole; Cephalexin; Roxithromycin; Co-amoxiclavuanate; combinations of Piperacillin and Tazobactam; and their various salts, acids, bases, and other derivatives.

According to some embodiments, the methods can be used to determine how drugs and other xenobiotics are metabolized by Phase I and Phase II enzymes and enzymes in the gut microbiome, how drugs and xenobiotics inhibit (or activate) such enzymes, and how subject perturbations (e.g., obesity, chemical exposure, developmental life stages, etc.) are effective to impact Phase I and Phase II metabolism and/or the gut microbiome.

According to some embodiments, the target enzyme is an enzyme active in Phase I xenobiotic metabolism. According to some embodiments, the target enzyme is an enzyme active in Phase II xenobiotic metabolism. According to some embodiments, the target enzyme is one or more selected from a β-glucuronidase and a glucuronosyl transferase, a glutathione S transferase, a reductase enzyme, e.g., an azoreductase, a nitroreductase, an NAD(P)H quinone oxidoreductase, or an aldoketoreductase (AKR), a sulfatase and sulfotransferase; a cysteine lyase, and a prostaglandin H synthase. According to some embodiments the target enzyme is of mammalian origin, of microbiome origin, or both. According to some embodiments, for an enzyme that requires activation before it can exhibit catalytic activity, the method further comprises exposing the sample to a compound that serves as an enzyme activator (e.g., NADPH) in order to facilitate conjugation of a probe with the enzyme.

According to some embodiments, the enzyme of xenobiotic metabolism is a β-glucuronidase and the probe is a β-glucuronidase-specific probe of Formula IVA, IVB, or IVC:

Formula IVA
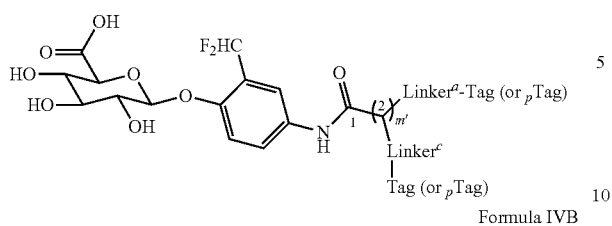
Formula IVB
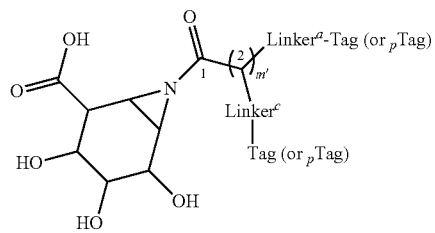
Formula IVC
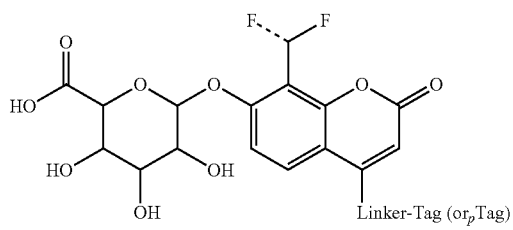
According to some embodiments, the β-glucuronidase-specific probe of Formula IVA or IVB is selected from:
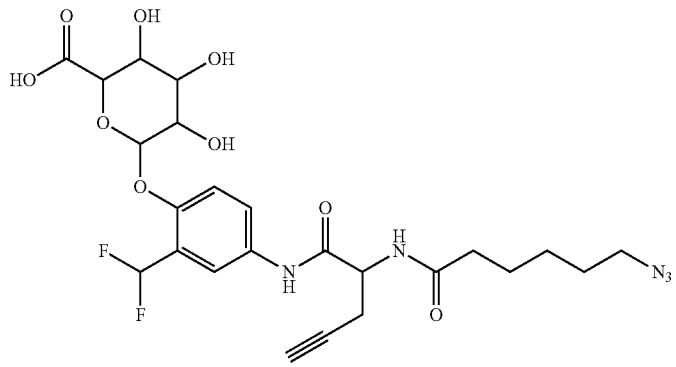
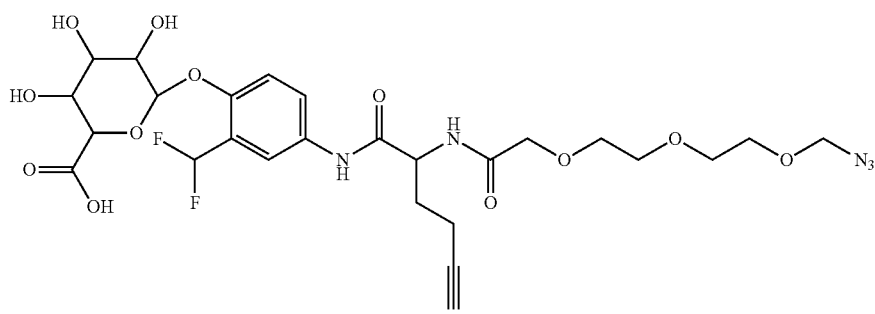
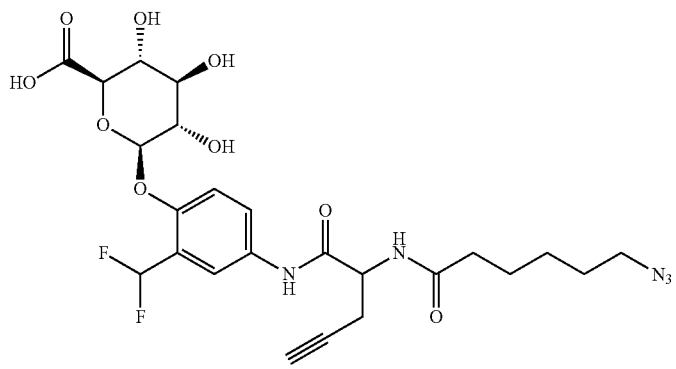

-continued
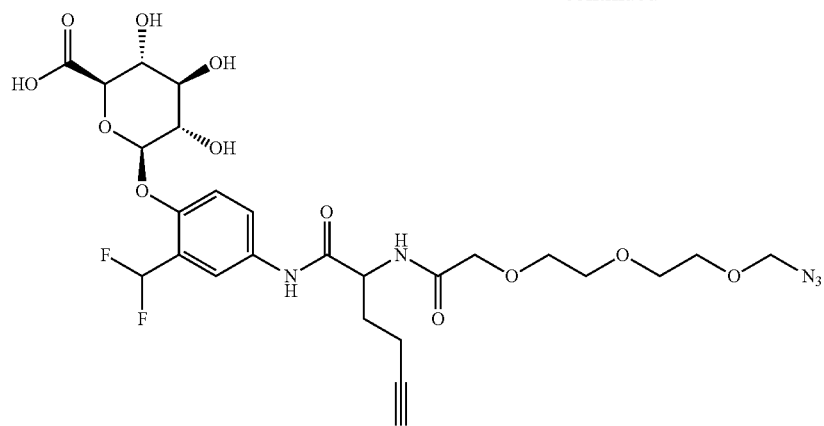
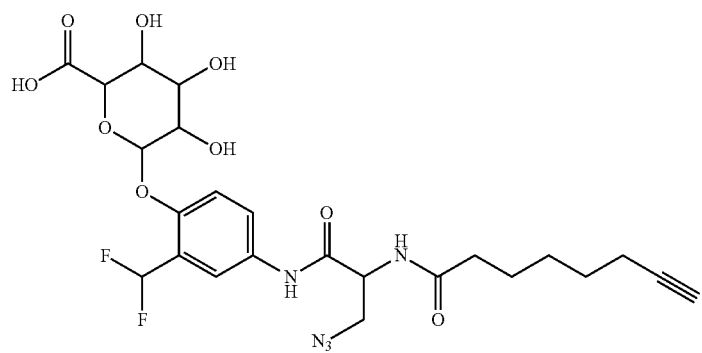
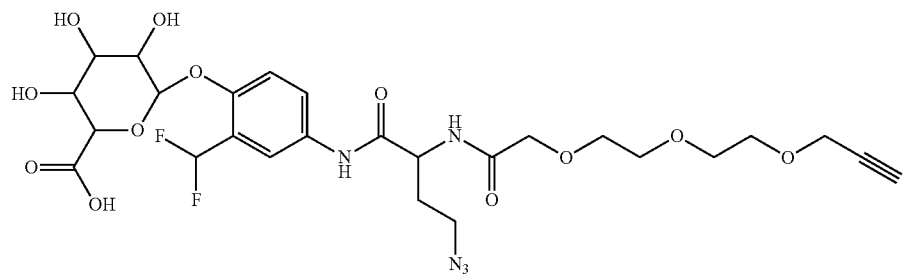
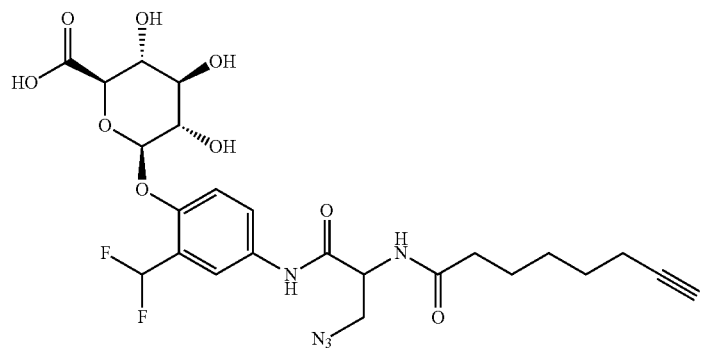

-continued
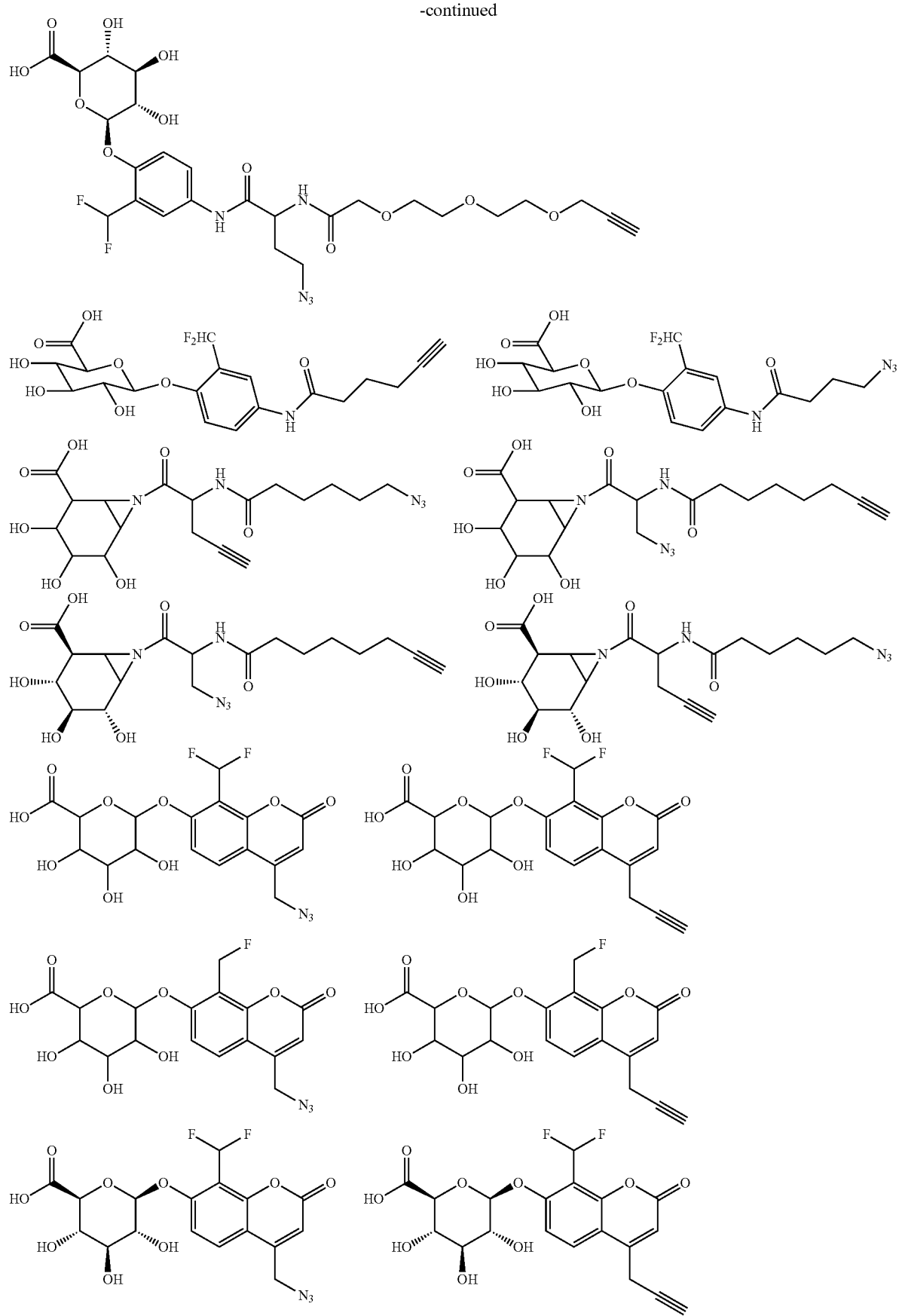

111

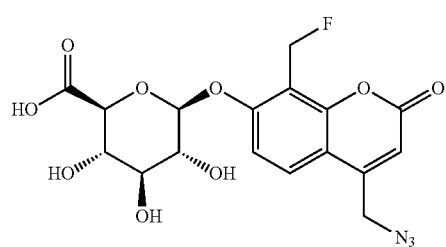

112

-continued

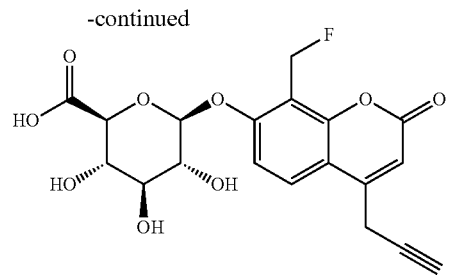

According to some embodiments, the enzyme of xenobiotic metabolism is a glucuronosyl transferase (e.g., a UDP-glucuronosyl transferase), and the probe is a glucuronosyl transferase-specific probe of Formula II, Formula IIIB, Formula VA, VB, or VC Formula II

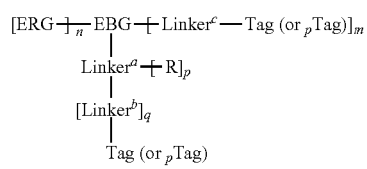

Formula IIIB

Formula VA

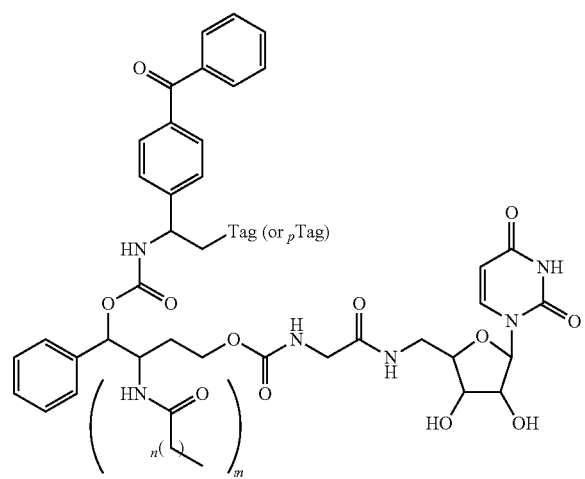

-continued

Formula VB

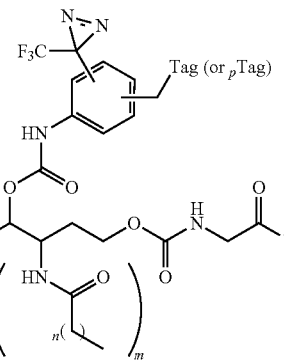

Formula VC

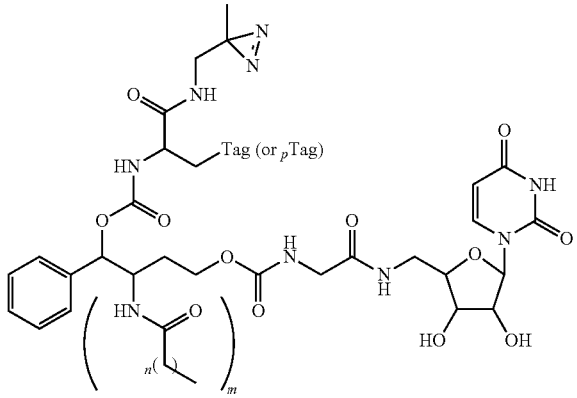

According to some embodiments, the glucuronosyl transferase-specific probe is selected from:

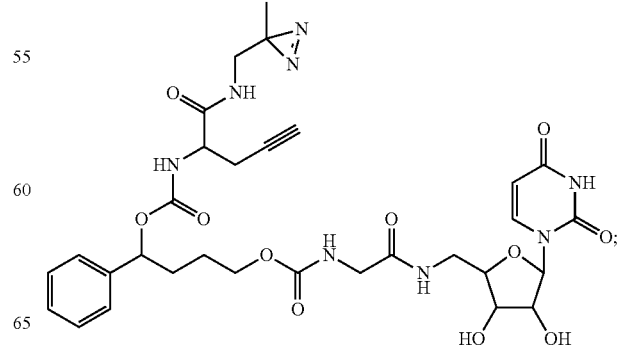

113
-continued
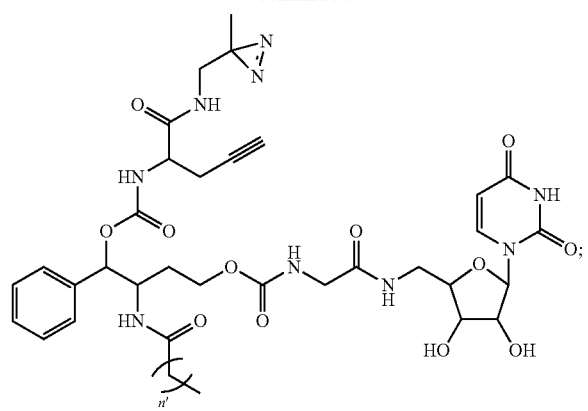
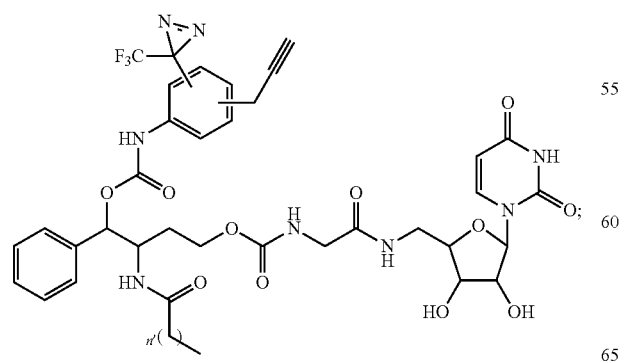
114
-continued
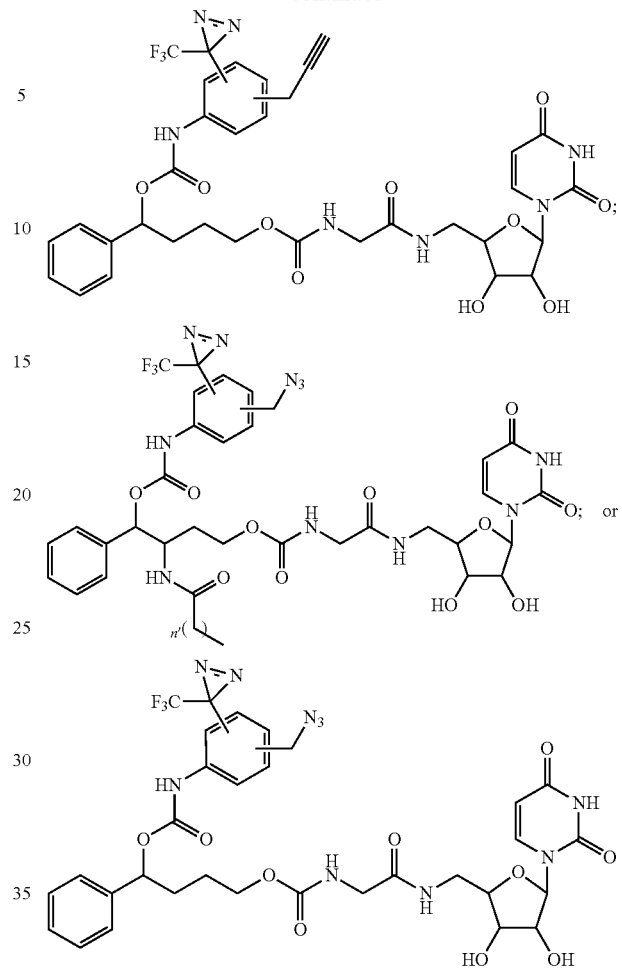
wherein each n' independently ranges from zero to 50, or 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50;
According to some embodiments, the enzyme of xenobiotic metabolism is a glutathione S transferase and the probe is a glutathione S-transferase specific probe of Formula VIA, Formula VIB, or Formula VIC:
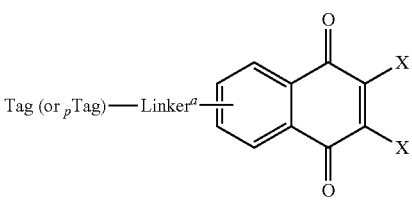
Formula VIA
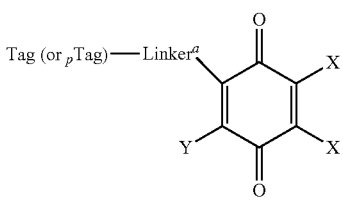
Formula VIB

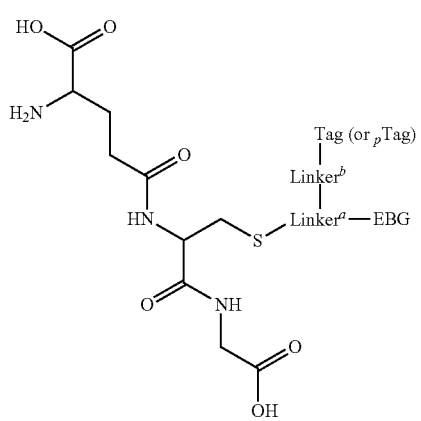
According to some embodiments, the glutathione S-transferase specific probe is selected from:
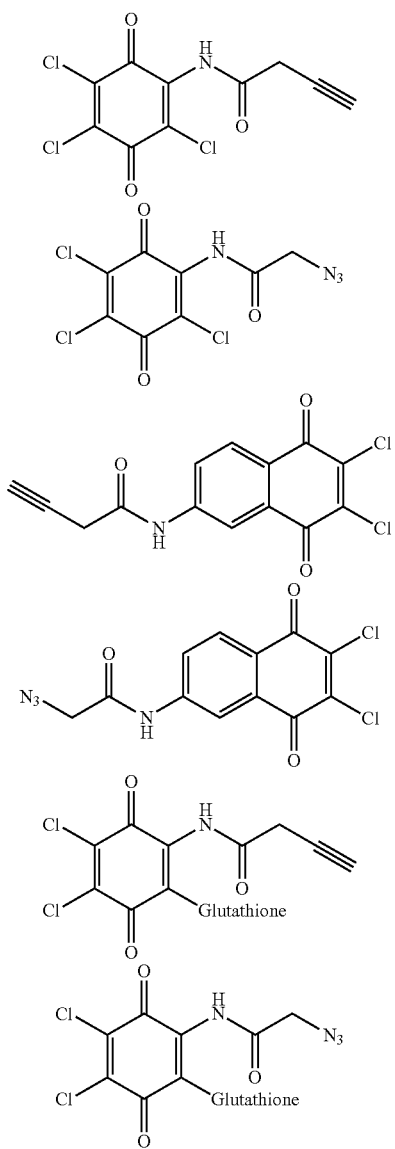
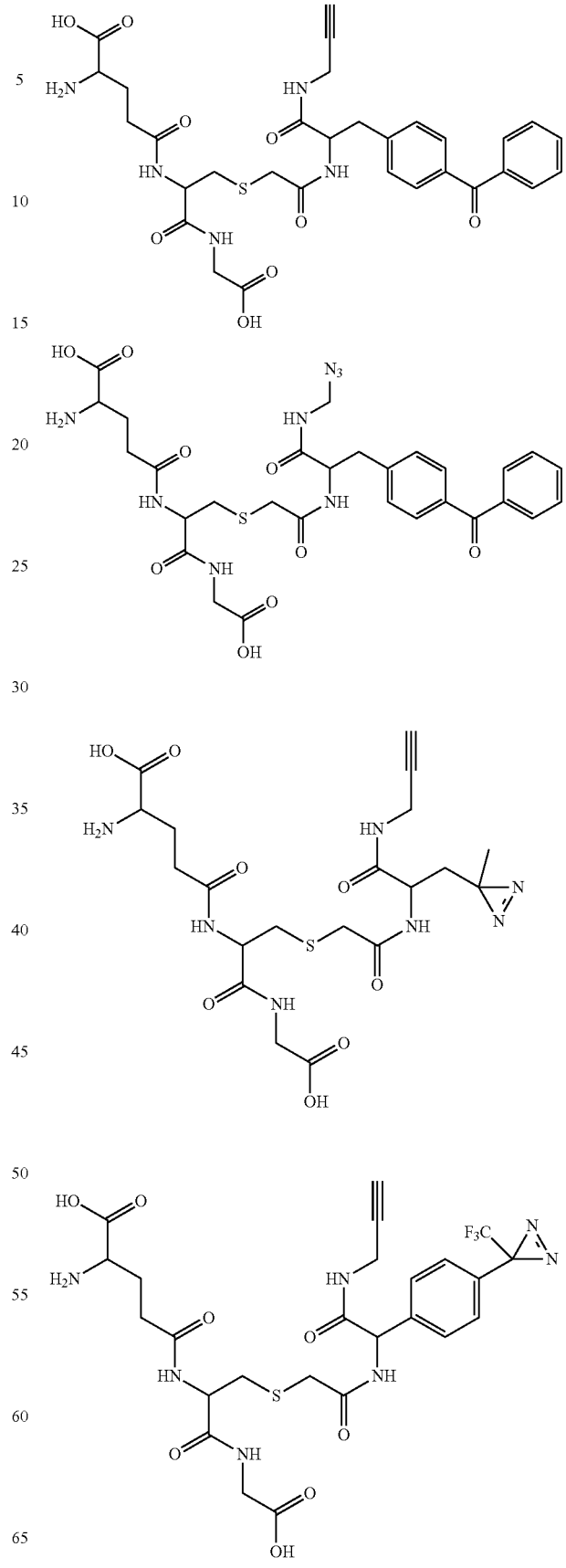

-continued

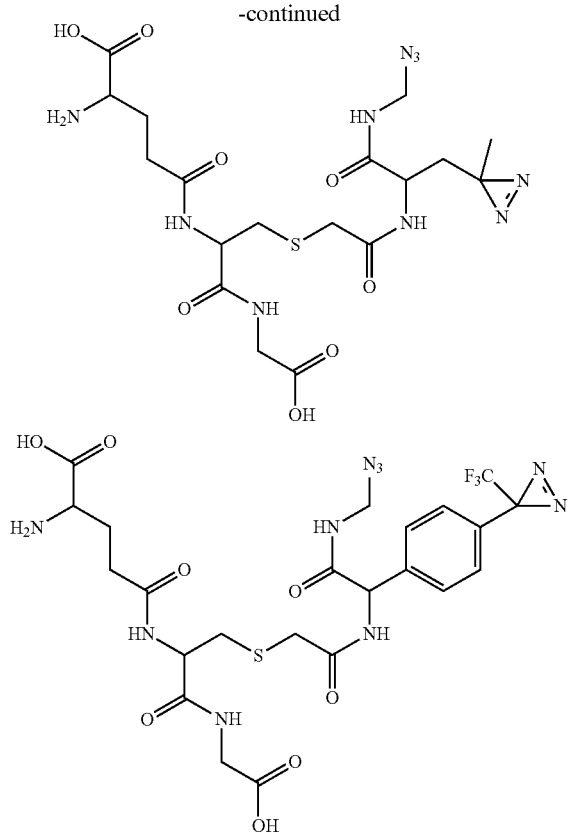

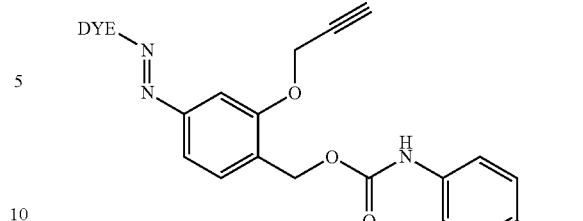

According to some embodiments, the enzyme of xenobiotic metabolism is a reductase enzyme, e.g., an azoreductase, a nitroreductase, an NAD(P)H quinone oxidoreductase, or an aldoketoreductase (AKR), and the probe is a reductase specific probe. According to some embodiments, the probe is a reductase-specific probe of Formula II or Formula IIIA.

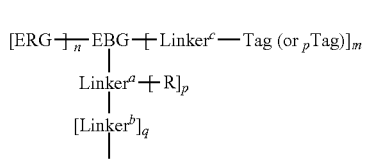
Formula II

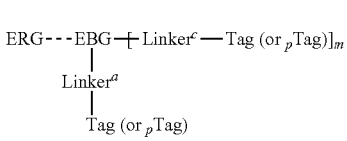
Formula IIIA

According to some embodiments, where the enzyme is an azoreductase, the probe comprises an azo group that is first chemically modified by the azoreductase to form an amine, which activates the enzyme binding group to form an activated quinone methide so that the azoreductase can bind to the probe.

According to some embodiments the azoreductase-specific probe is selected from:

According to some embodiments, where the enzyme is a nitroreductase, the probe comprises a nitro group that can be reduce by the nitroreductase to an amine, which activates the enzyme binding group to form an activated quinone methide so that the nitroreductase can bind to the probe.

According to some embodiments, the nitroreductase-specific probe is selected from:

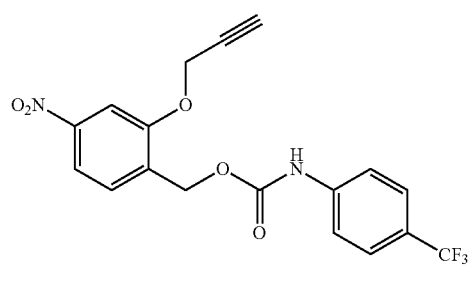

119

-continued

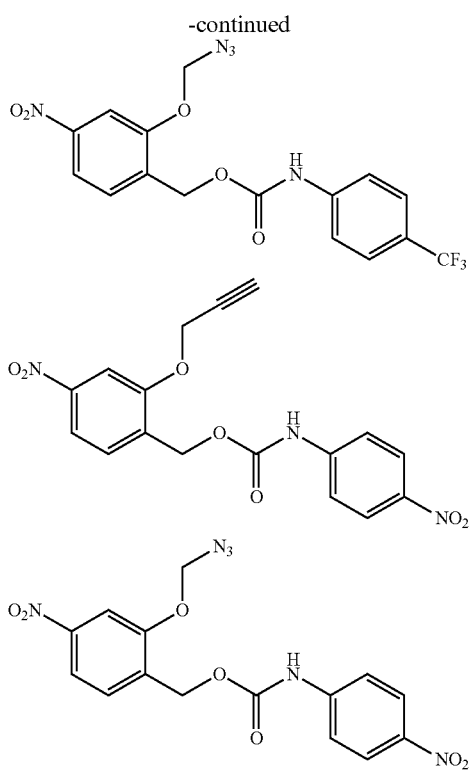

According to some embodiments, the enzyme is an NAD(P)H quione oxidoreductase, and the probe comprises an EBG that selectively binds to the NAD(P)H quione oxidoreductase and an phenolic ERG group that can be displaced by the NAD(P)H quione oxidoreductase.

According to some embodiments, the NAD(P)H quione oxidoreductase specific probe is selected from the group consisting of:

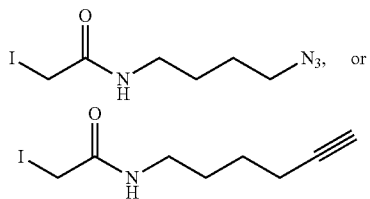

According to some embodiments, the enzyme is an aldoketoreductase, and the aldoketoreductase-specific probe comprises an EBG that selectively binds the active site cysteine residues of the aldoketoreductase.

According to some embodiments the aldoketoreductase specific probe is selected from:

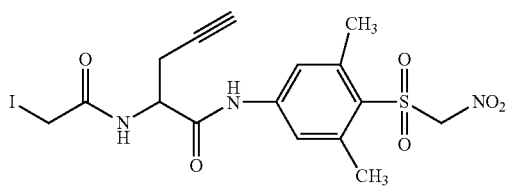

120

-continued

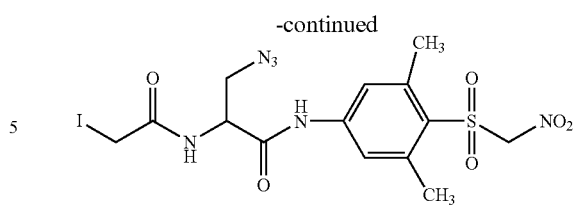

According to some embodiments, the enzyme of xenobiotic metabolism is a sulfatase and sulfotransferase enzyme and the probe is a sulfatase and sulfotransferase specific probe. According to some embodiments, the probe is a sulfatase and sulfotransferase specific probe comprising an ERG that is first cleaved from an EBG of the probe by the sulfatase.

According to some embodiments, the sulfatase and sulfotransferase-specific probe is selected from:

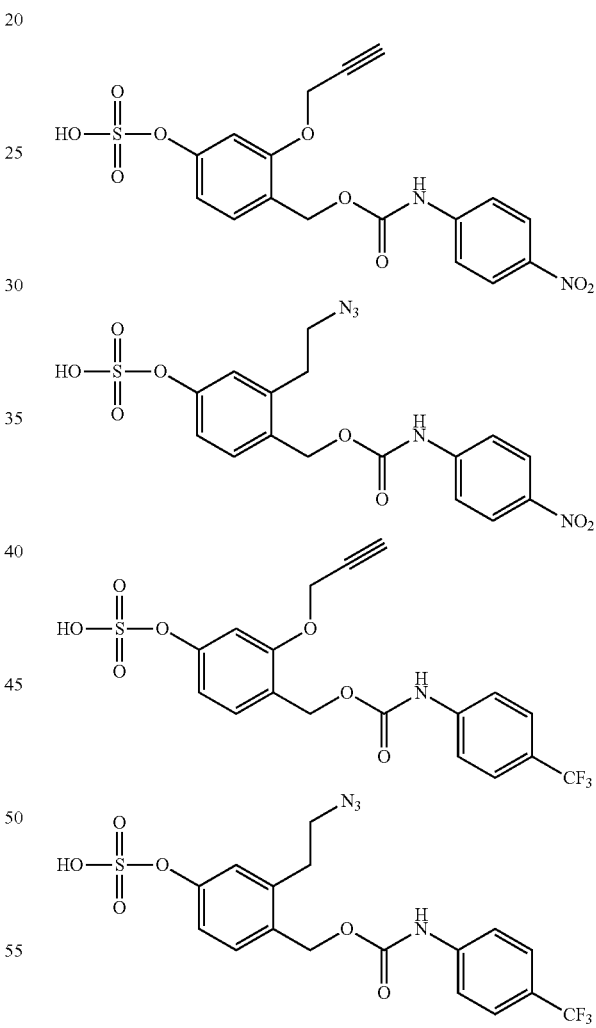

According to some embodiments, the enzyme of xenobiotic metabolism is a cysteine lyase of microbiome origin and the probe is a cysteine lyase-specific probe. According to some embodiments, cysteine lyase-specific probe comprises an olefin-containing enzyme binding group that forms a covalent bond with a cysteine moiety of the cysteine lyase. According to some embodiments, the cysteine lyase-specific probe is of Formula II or Formula IIIA.

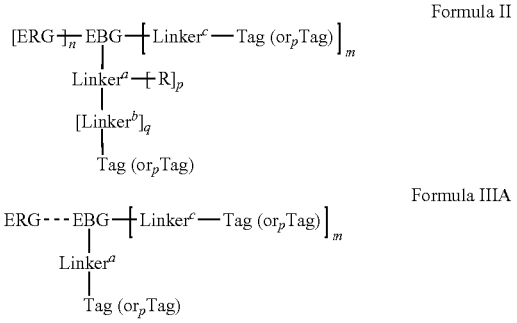

Formula II

Formula IIIA

According to some embodiments, the cysteine lyase-specific probe is selected from:

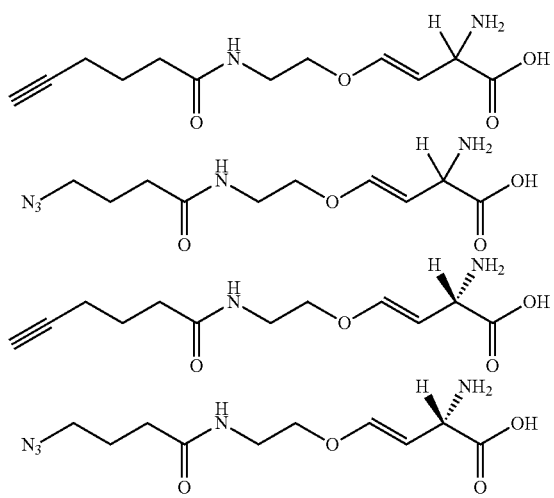

According to some embodiments, the enzyme is a prostaglandin H synthase and the probe is a prostaglandin H synthase specific probe. According to some embodiments, the prostaglandin H synthase-specific probe comprises an ERG that is displaced by a prostaglandin H Synthase enzyme, thereby coupling the probe to the enzyme through the EBG. According to some embodiments, the prostaglandin H synthase probe is selected from:

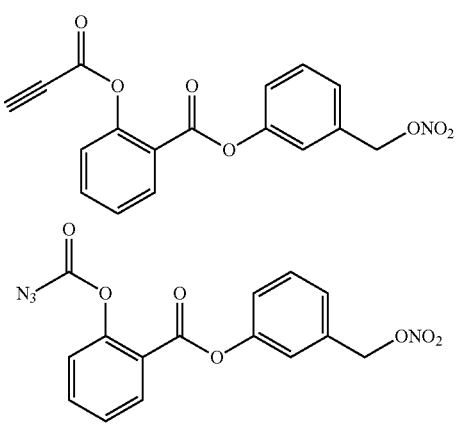

According to some embodiments, the subject is a mammalian subject. According to some embodiments, the mammalian subject is a mouse. According to some embodiments, the mammalian subject is a human. According to some embodiments, the mammalian subject is a non-human primate.

According to some embodiments, a sample can be obtained from a subject following exposure of the subject to a xenobiotic and any enzyme contribution to xenobiotic metabolism can then compared to a nonexposed control. According to some embodiments, the sample can be a biological sample, such as a cell sample (or an extract thereof, such as one containing proteins), an organ sample (or an extract thereof), or a bacterial sample (or an extract thereof). According to some embodiments, the contacting is in vitro, e.g., human hepatic microsomes. According to some embodiments, the sample is derived from one or more of a body tissue, a body fluid, or a body waste product.

According to some embodiments, the xenobiotic is a food, a dietary supplement, a carcinogen, a toxicant or a drug. According to some embodiments, the xenobiotic is a toxicant. Exemplary toxicants include, without limitation, cigarette smoke (active or passive), which can include nitrosamines, aldehydes, and carbon monoxide; bromobenzene; chloroform; acetaminophen; pesticides (e.g., 2,3,7,8-Tetrachlorodibenzodioxin (TCDD); polycyclic aromatic hydrocarbons (PAHs), meaning a widespread environmental contaminant formed during incomplete combustion or pyrolysis of organic material, e.g., benzo[a]pyrene, the prototypical carcinogenic PAH, and dibenzo[def,p]chrysene (DBC), a less prevalent, but highly potent transplacental carcinogenic PAH, both of which are metabolically activated by isoforms of the cytochrome P450 enzyme superfamily to form reactive carcinogenic and cytotoxic metabolites.

According to some embodiments, incubation time of the sample with the activity based probe is that period of time or a period of time sufficient to allow the probe to chemically interact with its target enzyme such that the probe becomes specifically bound to the target enzyme thereby forming a probe-enzyme conjugate, e.g., at least 2 minutes, at least 3 minutes, at least 4 minutes, at least 5 minutes, at least 6 minutes, at least 7 minutes, at least 8 minutes, at least 9 minutes, at least 10 minutes, at least 11 minutes, at least 12 minutes, at least 13 minutes, at least 14 minutes, at least 15 minutes, at least 16 minutes, at least 17 minutes, at least 18 minutes, at least 19 minutes, at least 20 minutes, at least 21 minutes, at least 22 minutes, at least 23 minutes, at least 24 minutes, at least 25 minutes, at least 26 minutes, at least 27 minutes, at least 28 minutes, at least 29 minutes, at least 30 minutes, such as 2 to 60 minutes, 2 to 30 minutes, 2 to 10 minutes, 5 to 10 minutes, or 5 to 15 minutes.

According to some embodiments the binding of the activity-based probe to the target enzyme is photo-activated by light. According to some embodiments, the light source provides UV light, such as light having a wavelength ranging from 10 nm to 400 nm, or from 10 nm to 370 nm, or from 10 nm to 365 nm.

Figure 5:
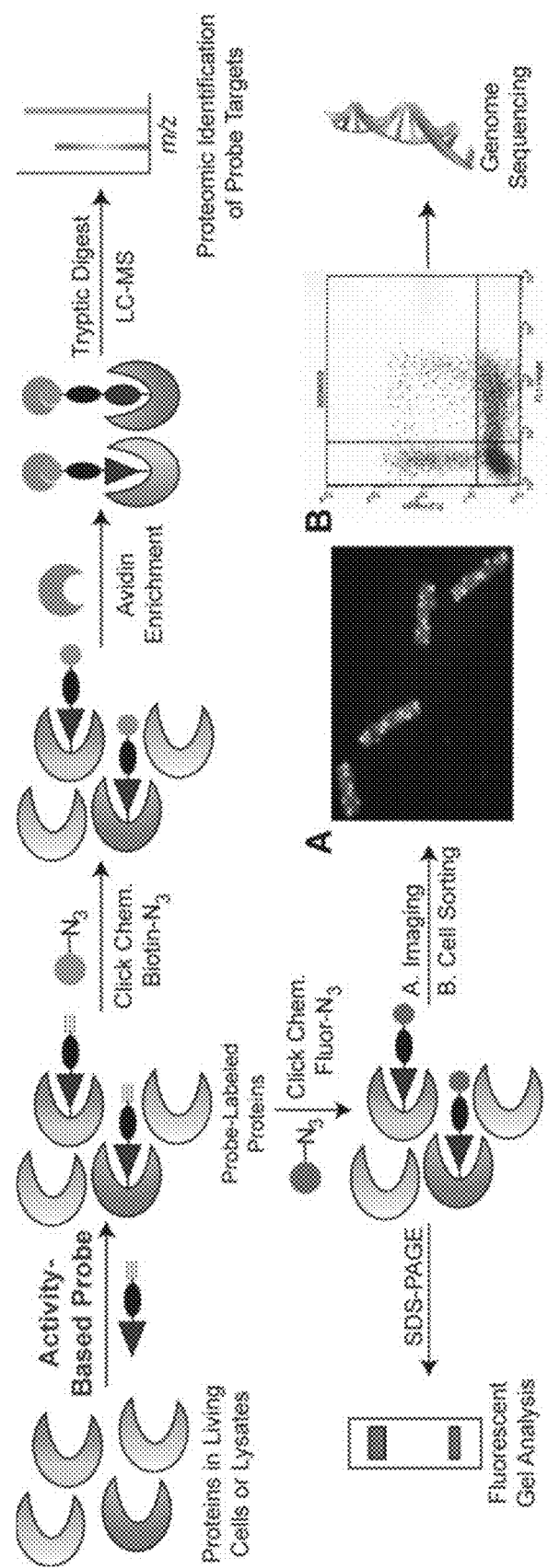
FIG. 5 is a schematic diagram of method embodiments described herein utilizing ABP embodiments.

According to some embodiments, the detecting, measuring or both is via a signal emitted by the probe bound to the enzyme. According to some embodiments, the signal is increased or amplified, e.g., by binding of a biotin-avidin or an enzyme reporter group (alkaline phosphatase or horseradish peroxidase) to the enzyme-specific probe. According to some embodiments, the detecting of the probe bound to the enzyme is by one or more of fluorescence (e.g., fluorescent gel analysis, fluorescence-activated cell sorting, flow cytometry, quantum dot analysis); colorimetry; genome sequencing; or mass spectrometry. According to some embodiments, the methods described herein can be combined with detection techniques typically used in the art as illustrated schematically in FIG. 5.

Figure 6:
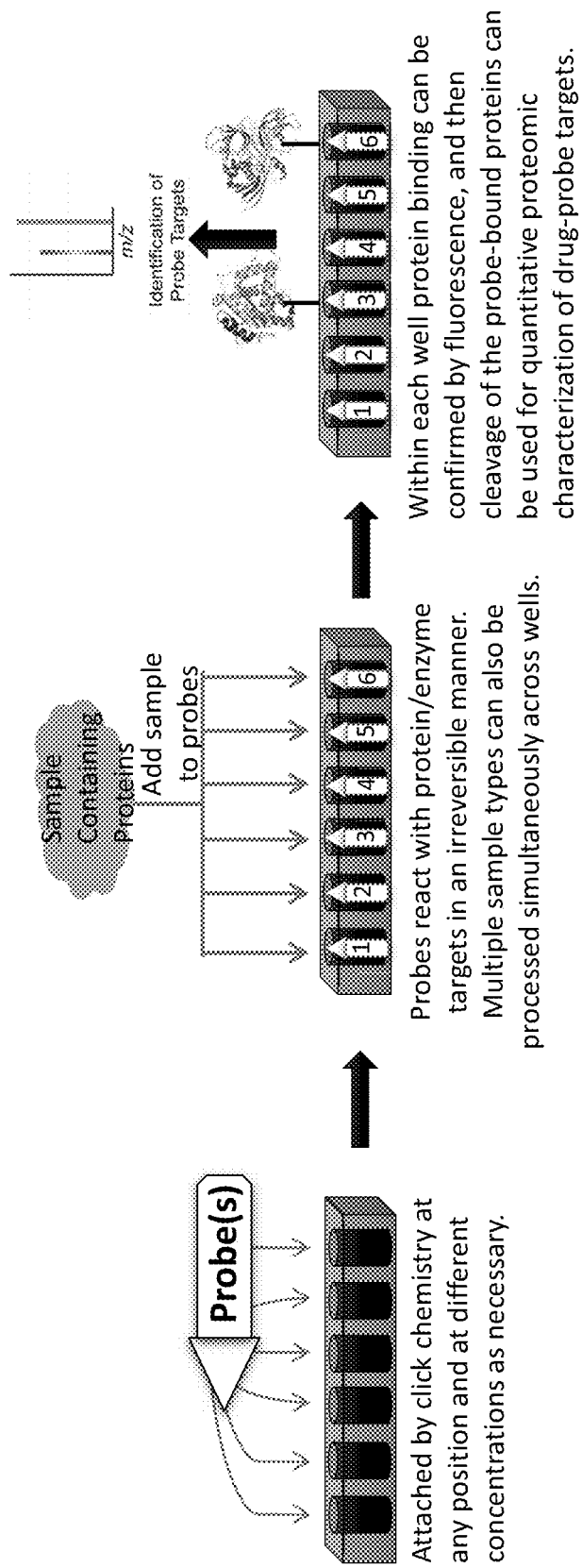
FIG. 6 is a schematic diagram of a representative assay embodiment that uses ABP embodiments described herein to identify different enzymes targeted by the different probes.

According to some embodiments, an activity-based probe further comprises a Tag-containing compound. According to some embodiments, the $_p$Tag moiety of a probe is effective to attach the probe to a support or a resin. According to some such embodiments, the support or resin can comprise, or can be modified to comprise, clickable functional groups. Accordingly, the method to attach an activity-based probe to a support or resin can comprise binding the clickable functional group of the support or resin to a $_p$Tag moiety. In alternate embodiments, the support or resin can be coupled to the probe prior to reacting the probe with its target enzyme. According to some embodiments, a method for high throughput screening of one or more samples using the activity-based probes of the present disclosure can comprise attaching each probe separately to a discrete region of a support or resin (e.g., a well or wells of a multi-well plate), or attaching multiple probes to the same region or well of a multi-well plate. An exemplary method for assaying a sample or samples is illustrated schematically in FIG. 6.

According to some embodiments, a method to verify that labeling is occurring in the microbiome samples is as follows. Bacteria are freshly collected from the small and large intestine of a subject under anaerobic conditions. Microbial content also can be extracted from feces or fecal pellets. Live cells from the gut or feces are exposed to a probe (or to a control for comparison purposes), washed, lysed via bead beating, and then combined with a Tag-containing compound (e.g., azidotetramethylrhodamine) using the click chemistry reagents described herein. Optimal live cell ABP labeling conditions is determined by the highest signal-to-noise ratio obtained through SDS-PAGE of fluorescently labeled proteins for each ABP embodiment. An enzyme activity assay is used before and after ABP labeling to confirm that the ABP targets functionally active enzymes in the microbiome, and that labeling results in enzyme inactivation.

According to some embodiments, the method comprises targeting xenometabolizing activities of the microbiome in a hierarchical manner by using ABP-dependent labeling and sorting studies to identify taxa that make up functional sub-populations of the gut microbiome. Such embodiments comprise the steps of labeling microbiomes from small and large intestine samples and a control; using isolated DNA as a template for 16S rRNA (V4) sequencing; identifying taxa that are more abundant in the ABP-treated, probe-positive sample, and evaluating statistical significance thereof. According to some embodiments, confirming the presence of xenometabolizing enzymes in the genomes of isolated taxa is by a PSI-BLAST analysis of gut microbiome isolates and a database of the gut metagenome. According to some embodiments resolving the distribution of phyla and taxa involved in various xenometabolizing activities is by cell sorting, which provides information about the functional sub-populations of gut microbes performing specific activities and illuminates the levels of functional redundancy in specific activity across different taxa.

To complete a hierarchical analysis, quantitative proteomics is used to characterize the enzymes involved in xenometabolism. The method can include lysing the same ABP-labeled microbiome samples by bead beating, attaching a Tag-containing compound, such as an azido-biotin compound, to probe-labeled enzymes using click chemistry; enriching the biotinylated-ABP-labeled enzymes on streptavidin agarose, digesting the proteins with trypsin, and analyzing the tryptic peptides on a Velos or QExactive HF LC-MS platform using a tandem MS measurement. Searching the resulting peptide spectra against a gut metagenome and quantifying the labeled enzymes using an AMT tag approach, are effective to enable a quantitative readout of the relative activity level of various xenometabolizing enzymes. This provides a functional characterization and annotation of the enzymes, and facilitates mapping of the enzymes back to the species/taxa from which the enzymes are expressed.

Figure 7:
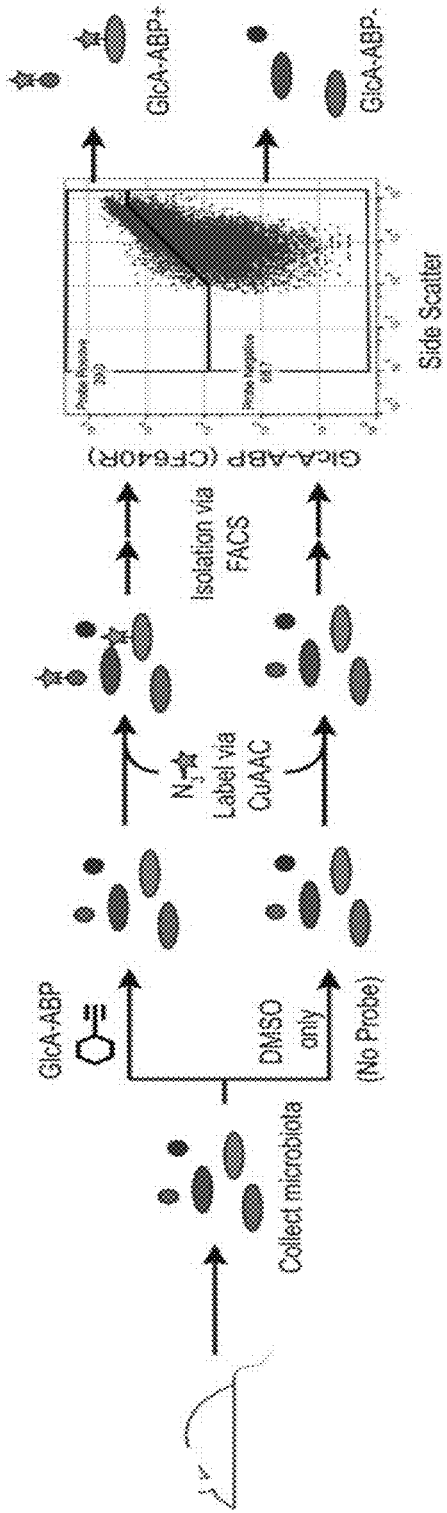
FIG. 7 is a schematic diagram of a representative method embodiment using FACS analysis.
Figure 8C:
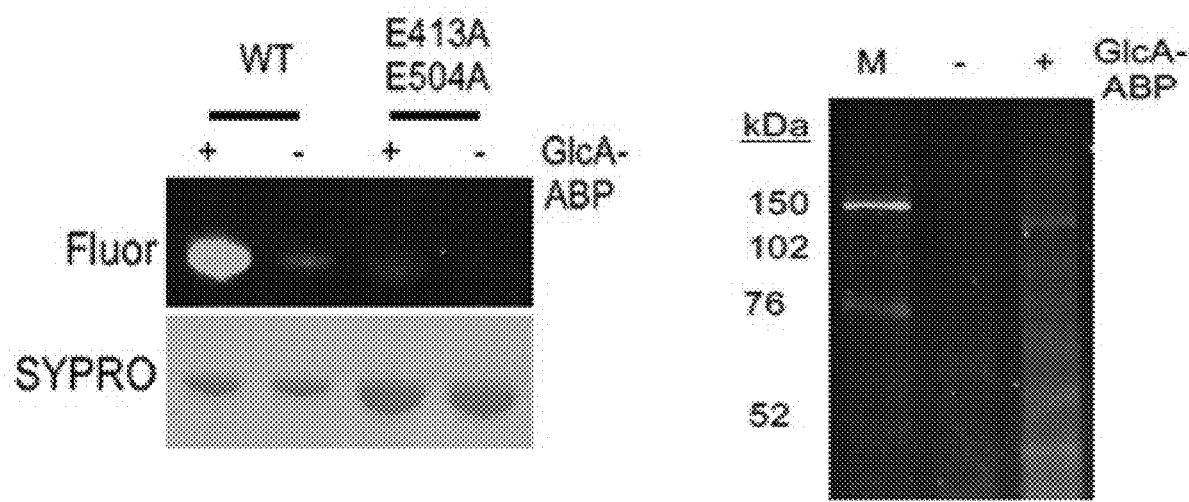
FIG. 8C is a map of 'Probe Positive' and 'Probe Negative' populations collected by FACS.
Figure 8C:
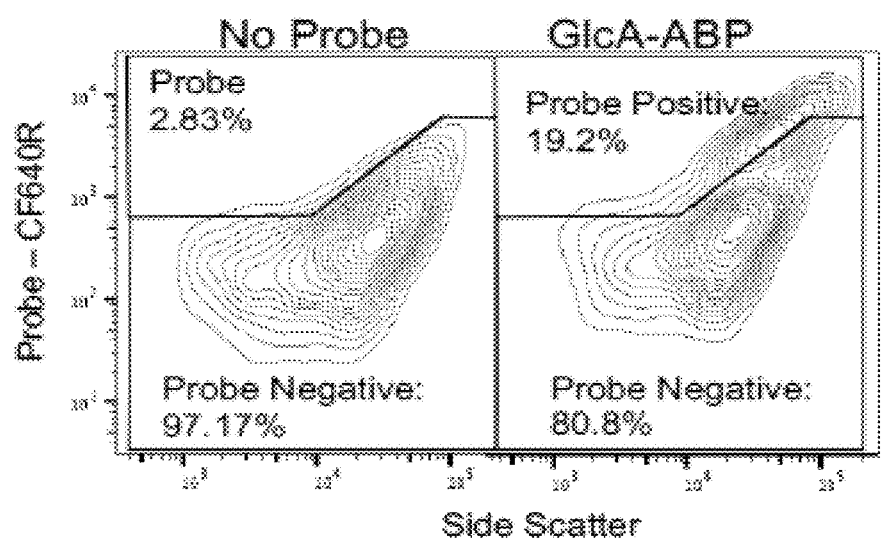
Figure 8D:
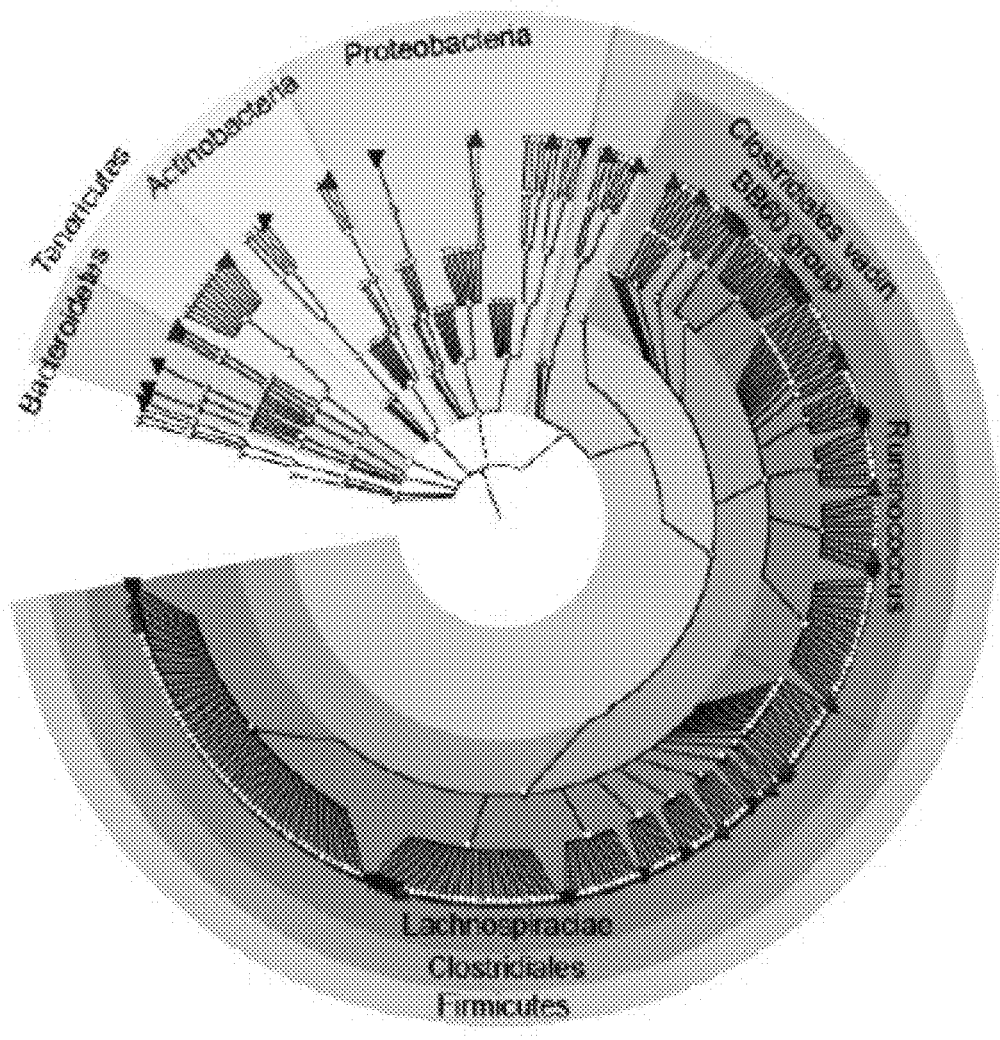
FIG. 8D shows that taxa are significantly enriched (adjusted p value 0.05) in the GlcA-ABP Probe Positive (red triangles) population compared to Probe Negative (blue triangles).

An exemplary method for identifying and quantifying enzymes, which is illustrated schematically in FIG. 7, comprises: exposing a sample comprising a glucuronidase (e.g., a recombinantly expressed and purified β-glucuronidase obtained from *Escherichia coli, Streptococcus agalactiae*, and *Clostridium perfringens*) to a solution comprising one or more probe embodiments designed for targeting glucuronidases. The exemplary probes covalently bind only to active glucuronidases (FIGS. 8A-8D). The method can further include treating live cells with the probe and then lysing the cells; then, adding to the lysed cell mixture a Tag-containing compound, such as a rhodamine-containing azide (or a rhodamine-containing alkyne, depending on the functional group with which the Tag group will react), along with suitable click chemistry reagents, such as those described above; and then, after attaching the Tag to the probe, visualizing labeled enzymes that have been covalently bound to the probe by SDS-PAGE and/or flow cytometry. According to some embodiments, combining FACS with the method to label and sort cells possessing active β-glucuronidases from a mixed population of microbes is useful for studying activity in the context of microbial communities. Genomic sequencing can be used to identify the community members, thereby revealing specific taxa based on true activity rather than potential activity in the form of genes or transcripts, and addressing a major hurdle to understanding host-microbe-xenobiotic interactions.

VI. Kits and Devices

Probe embodiments described herein can be configured for use in a device and/or a kit that can be used to analyze samples, such as biological samples. The device and kit can be used to assess and identify different species present in a sample and also to assess the functions/processes involving such species within the sample. In particular disclosed embodiments, the device can comprise one or more probe embodiments and a substrate, wherein the probe is (or a plurality of probes are) coupled to the substrate prior to exposure to a sample, or wherein the substrate and the probe are capable of being combined after exposure to a sample. The device and kit embodiments are capable of multiple uses such that many samples can be analyzed with a single device or kit.

In particular embodiments, the substrate component of the device is any suitable substrate that be exposed to sample, such as a cellular sample. Representative substrates include, but are not limited to, glass-based substrates that can be functionalized with probe embodiments described herein such that the probe is coupled to functional groups present on the surface of the glass-based substrate. In some embodiments, glass plates and/or glass microspheres are used as the substrate component.

The probes used in the device and/or kit can be selected from any probe embodiments disclosed herein. In some embodiments, the probes comprise or are modified to comprise a $_p$Tag group that is capable of anchoring the probe to a substrate component of the device. In particular disclosed embodiments, the $_p$Tag group is a clickable functional group that can be reacted with a clickable functional group present on the substrate surface using a click chemistry reaction to thereby covalently anchor the probe to the substrate. In some embodiments, the probe can be pre-coupled to the substrate prior to sample exposure using such techniques. In some additional embodiments, the probe can be post-coupled to the substrate using such techniques after the probe has been exposed to a sample.

In some embodiments, the device is pre-assembled such that the probe embodiments are pre-coupled to the substrate and any additional reagents used in analyzing the sample are pre-contained within the device. In some other embodiments, the device may be provided as part of a kit that comprises a pre-assembled device and any additional reagents used to analyze the sample are provided as separate components of the kit (for example, such as in reagent bottles). These components of the kit can then be combined by the user prior to use. In yet some additional embodiments, the kit can comprise a substrate that can be treated with probe embodiments, which are provided by separate reagent bottles within the kit, using suitable coupling conditions to thereby couple any desired probe embodiments to the substrate to ready the apparatus for use.

Methods of making the device embodiments of the present disclosure are also disclosed. In some embodiments, the device can be made by exposing the substrate to a probe embodiment comprising a $_p$Tag group, such as a clickable functional group. In yet additional embodiments, the $_p$Tag can be a different functional group capable of chemically binding to functional groups of the substrate. In embodiments where the probe comprises a clickable functional group, the substrate typically also comprise a clickable functional group on its surface that can react with the clickable functional group of the probe. In some embodiments, the substrate is a glass substrate comprising a surface having hydroxyl groups that can be modified with alkoxysilane molecules to provide a silanized substrate surface. In some embodiments, the silanized substrate surface can further be reacted with a reagent comprising a clickable functional group. In particular disclosed embodiments, the $_p$Tag group of the probe forms a covalent bond with functional groups of the substrate surface (for example, hydroxyl groups, alkoxysilane groups, clickable functional groups, or the like). Exemplary alkoxysilane molecules include, but are not limited to, aminosilanes (for example, (3-aminopropyl)-triethoxysilane, (3-aminopropyl)-diethoxy-methylsilane, (3-aminopropyl)-dimethyl-ethoxysilane, (3-aminopropyl)-trimethoxysilane, and the like), glycidoxysilanes (for example, 3-glycidoxypropyl)-dimethyl-ethoxysilane and the like), and mercaptosilanes (for example, (3-mercaptopropyl)-trimethoxysilane, (3-mercaptopropyl)-methyl-dimethoxysilane, and the like). In some embodiments, these representative groups can be further chemically modified to convert one or more functional groups of the alkoxysilane to a functional group capable of coupling with the functional group of the probe. Solely by way of example, an amine group of an aminosilane can be converted to an azide or can be coupled to an azide-containing reagent to provide a clickable group capable of undergoing a click chemistry reaction with a $_p$Tag group present on a probe (such as a clickable alkyne). In particular disclosed embodiments, the $_p$Tag group of the probe can be selected from a functional group capable of coupling with one or more functional groups present on the silanized substrate surface. For example, the probe can comprise one or more alkyne (or azide) moieties, which can react with any azides (or alkynes) present on the silanized substrate surface; or one or more carboxylic acid groups, which can react with any amines present on the silanized substrate surfaces; or one or more nucleophilic functional groups that can react with any epoxides present on the silanized substrate surface; or one or more alkene moieties that can react with any thiols present on the silanized substrate surface. Additional probe $_p$Tag groups that can be coupled to hydroxyl groups present on the substrate surface and/or a silanized substrate surface will be recognized by those of ordinary skill in the art with the benefit of the present disclosure.

In a representative embodiment, a glass plate device is made by functionalizing a glass slide with an alkoxysilane reagent, such as triethoxysilaneamine. Then, a solution of a reagent comprising a clickable functional group, such as NHS-ester-PEG-azide, is added to the glass slide to functionalize the surface of the substrate with azide moieties. The functionalized glass slide is then either exposed to a probe embodiment prior to sample exposure or is exposed to a probe embodiment that has first been exposed to a sample. The probe comprises a $_p$Tag group, such as a clickable alkyne, that can react with the azide of the substrate. The glass slide and the probe are exposed to reaction conditions that facilitate covalent coupling of the probe to the glass slide through a triazole formed between the alkyne group of the probe and the azide group of the substrate. In this embodiment, the reaction conditions include using DMSO as a solvent, CuI as a catalyst, and trimethylamine (or diisopropylethylamine) as a base.

Figure 30:
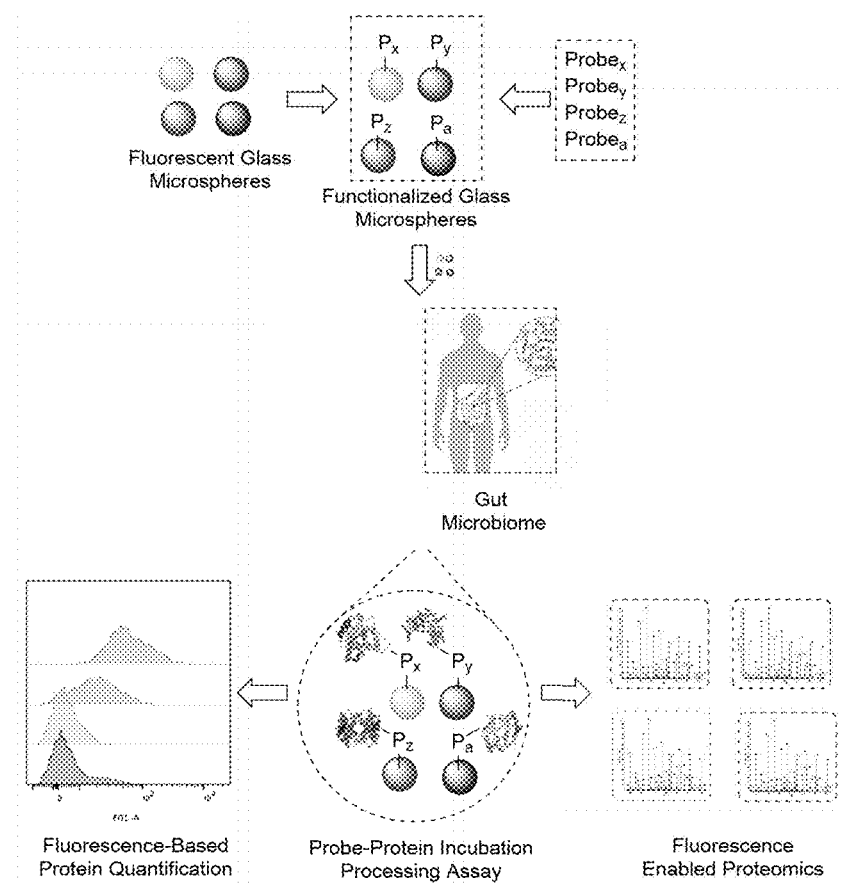
FIG. 30 shows an exemplary method using microspheres for multiplexed probing embodiments, wherein function-based probes ("P") are functionalized on fluorescent glass microspheres to enable flow cytometry, where each fluorophore is matched to a particular probe; the microspheres can be mixed and added to samples for multifunctional characterization of complex biological samples, such as biological samples and after labeling, protein-probe-microspheres can be sorted further analysis (for example, determining the overall functional activity quantified based on their fluorescence emission and/or proteomics analysis of each sorted sample to yield identification of functionally active enzymes and their relative contribution to the overall functional activity).

In another example, probe embodiments can be coupled to fluorescent glass microspheres to provide a device for use in methods described herein. In such embodiments, a single probe embodiment can be coupled to a single microsphere. A plurality of microspheres can be made wherein each microsphere of the plurality is coupled to the same type of probe embodiment or wherein each microsphere of the plurality is coupled to different types of probe embodiments. Similar chemistry as described above can be used to couple the probe to the microsphere. Device embodiments comprising probes coupled to fluorescent glass microspheres enables the using various probes for several different enzyme targets in a single limited-size sample. Additionally, these device embodiments facilitate tandem direct quantification of target enzymes using Fluorescence-Activated Cell Sorting (FACS) and proteomics as depicted schematically in FIG. 30. In particular embodiments, the protein-probe-fluorescent microspheres are sorted and quantified by FACS. Then flow cytometry instruments can be used to provide quantitative fluorescence profiles, or full FACS systems can be used to sort by probe type and make subsequent proteomics measurements to enhance the measurement resolution. Such embodiments also provide the ability to multiplex the probe-functionalized microspheres in limited size samples to label target enzymes, and the ability to first quantify the amount of enzyme targets in a given sample using FACS, and subsequently identifying the specific targets and quantifying these targets using mass spectrometry-based proteomics.

In another representative example, a device comprising a well-plate having wells that are surface-modified with clickable functional groups (for example, azides) are exposed to probe embodiments that each comprise at least one $_p$Tag group (for example, an alkyne) that can react with the clickable functional group of the surface-modified wells to covalently attach the probe to an individual well. In some embodiments, a single well can comprise a plurality of probes covalently bound thereto. In some embodiments, different wells of the well-plate can be functionalized with different probe embodiments.

VII. Overview of Several Embodiments

Disclosed herein are embodiments of a probe having a structure satisfying Formula II

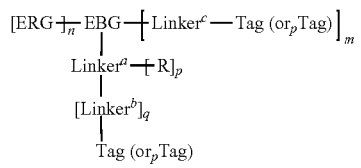

Formula II wherein
ERG, if present, is

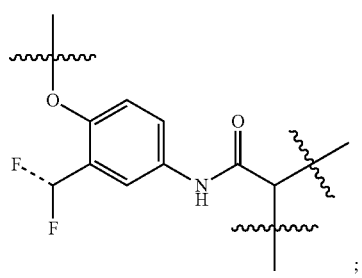

$S(O)_2OH$, or an anionic form thereof; $P(O(OH)_2$, or an anionic form thereof; a halogen; or —OPh-CH$_2$—ONO$_2$;

EBG has a structure satisfying one or more of Formulas IIA$_{EBG}$-IIJ$_{EBG}$

Formula IIA$_{EBG}$

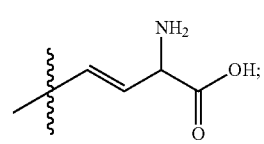

Formula IIB$_{EBG}$

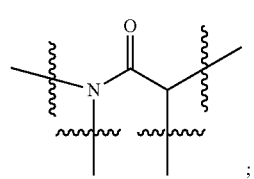

Formula IIC$_{EBG}$

Formula IID$_{EBG}$

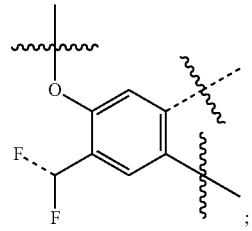

Formula IIE$_{EBG}$

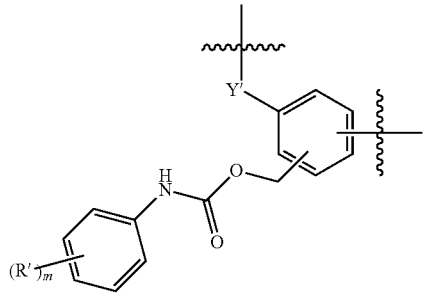

Formula IIF$_{EBG}$

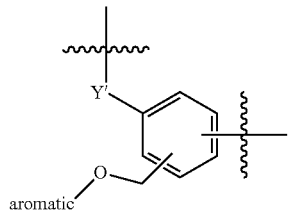

Formula IIG$_{EBG}$

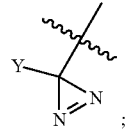

Formula IIH$_{EBG}$

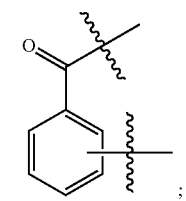

Formula III$_{EBG}$

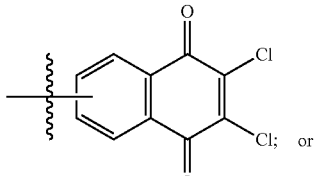

Formula IIJ$_{EBG}$

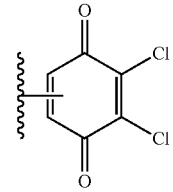

wherein Y is CH$_3$ or CF$_3$; Y' is O, NO$_2$, or —N=NR''', wherein R''' is a dye or other reporting moiety; and m is an integer selected from 0 to 5; and R' is selected from aldehyde, ketone, ester, carboxylic acid, acyl halide, cyano, sulfonate, nitro, nitroso, quaternary amine, $CF_3$, alkyl halide, or combinations thereof;

Linker$^a$ comprises an aliphatic group, a heteroaliphatic group, an aromatic group, an aliphatic-aromatic group, a heteroaliphatic-aromatic group, a heteroaromatic group, an aliphatic-heteroaromatic group, or a heteroaliphatic-heteroaromatic group;

each of Linker$^b$, and Linker, if present, independently comprises an aliphatic group, a heteroaliphatic group, an aromatic group, an aliphatic-aromatic group, a heteroaliphatic-aromatic group, a heteroaromatic group, an aliphatic-heteroaromatic group, or a heteroaliphatic-heteroaromatic group;

R, if present, is a group comprising a carbamate or a carbonate;

each Tag, if present, independently comprises a functional group or molecule capable of generating a detectable signal;

each $_p$Tag, which is present if a Tag is not present, independently comprises a clickable functional group; and each of n, m, p, and q independently is 0 or 1.

In some embodiments, Linker$^a$ is a linker group having a structure satisfying one or more of Formulas IIA$_{Linkera}$-IIH$_{Linkera}$

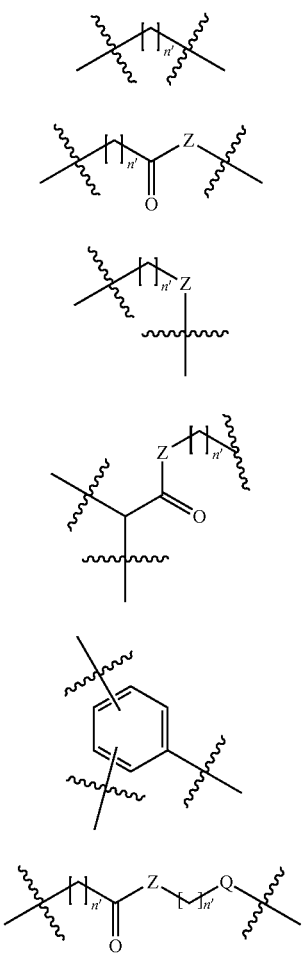

Formula IIA$_{linkera}$

Formula IIB$_{linkera}$

Formula IIC$_{linkera}$

Formula IID$_{linkera}$

Formula IIE$_{linkera}$

Formula IIF$_{linkera}$

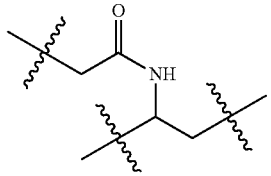

Formula IIG$_{linkera}$

Formula IIH$_{linkera}$ wherein each n' independently is an integer ranging from 1 to 50; Z is oxygen or NR''', wherein R''' is hydrogen, aliphatic, or aromatic; and Q is carbon, oxygen or NR''', wherein R''' is hydrogen, aliphatic, or aromatic.

In any or all of the above embodiments, Linker$^b$ is present and comprises a —(CH$_2$)$_{n'}$— group, wherein n' is an integer ranging from 1 to 50; an amide group; or a combination thereof.

In any or all of the above embodiments, Linker$^c$ is present and has a structure satisfying Formula IIA$_{Linkerc}$ or Formula IIB$_{Linkerc}$

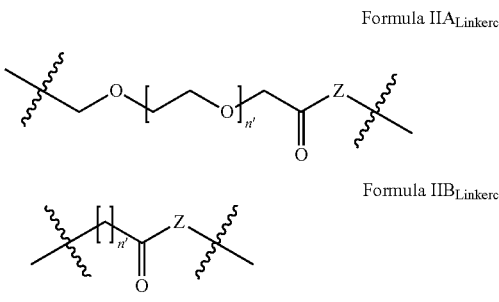

Formula IIA$_{Linkerc}$

Formula IIB$_{Linkerc}$ wherein n' is an integer ranging from 0 to 50; and Z is oxygen or NR''', wherein R''' is hydrogen, aliphatic, or aromatic.

In any or all of the above embodiments, R is present and has a structure satisfying any one or more Formulas IIA$_R$-IIC$_R$

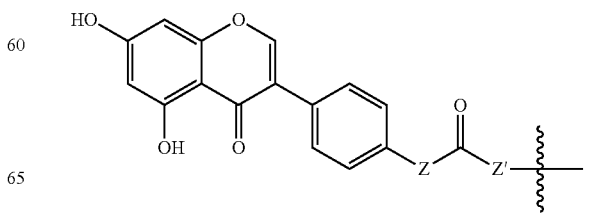

Formula IIA$_R$

131

-continued

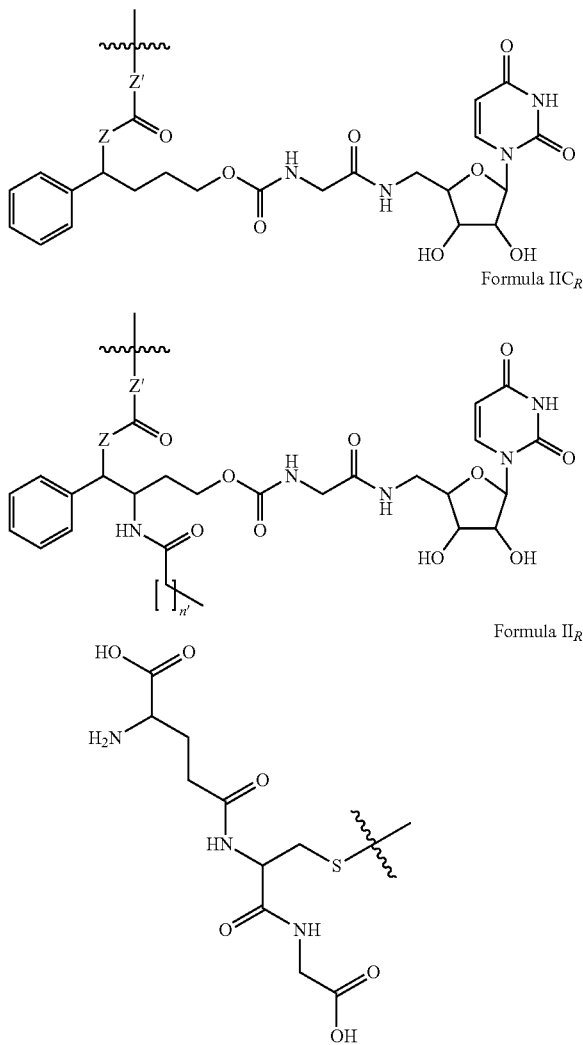

Formula IIB$_R$

Formula IIC$_R$

Formula II$_R$ wherein Z and Z' independently are oxygen or NR''', wherein R''' is hydrogen, aliphatic, or aromatic; and n' is an integer ranging from 0 to 50.

In any or all of the above embodiments, one or more Tags are present and wherein each Tag independently is a fluorophore, a binding partner of an affinity-based binding pair, a quantum dot, or a dye. In some embodiments, the one or more Tags independently are rhodamine, fluorescein, or biotin.

In any or all of the above embodiments, one or more $_p$Tags are present and wherein each $_p$Tag independently is an azide or an alkyne.

In any or all of the above embodiments, the probe has a structure satisfying Formula IIIA

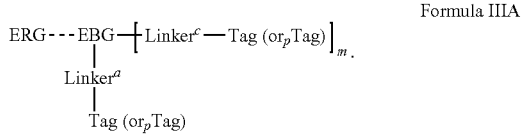

Formula IIIA

132

In any or all of the above embodiments, the ERG is present and is iodo; —OPh-CH$_2$—ONO$_2$; or

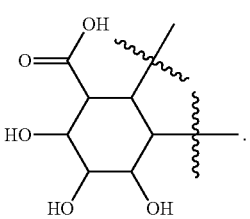 [SMILES: *C1C(*)C(C(=O)O)C(O)C(O)C1O]

In any or all of the above embodiments, Linker$^a$ is an ester group, an —O(CH$_2$)$_n$NR'''C(O)(CH$_2$)$_{n'}$— group, or a —(CH$_2$)$_{n'}$— group, wherein each n' independently is an integer ranging from 1 to 20 and wherein R''' is hydrogen, aliphatic, or aromatic.

In any or all of the above embodiments, m is 1 and Linker is an —NR'''C(O)(CH$_2$)$_{n'}$—group or an —NR'''C(O)CH$_2$[O(CH$_2$)$_2$]$_{n'}$OCH$_2$— group, wherein each n' independently is an integer ranging from 1 to 20 and wherein R''' is hydrogen, aliphatic, or aromatic.

In any or all of the above embodiments, m is 1 and each Tag, if present, independently is a fluorophore, a binding partner of an affinity-based binding pair, a quantum dot, or a dye; or if a $_p$Tag group is present, then each $_p$Tag independently is an alkyne or an azide.

In any or all of the above embodiments, the probe can be selected from any of the probe species disclosed herein.

Also disclosed herein are embodiments of a method, comprising: exposing a subject or a sample to a probe according to any or all of the above embodiments for a time sufficient to allow the probe to bind to an enzyme involved in xenobiotic metabolism such that a probe-enzyme conjugate is formed; and analyzing the probe-enzyme conjugate using a fluorescent detection technique, a colorimetric detection technique, a mass spectrometry technique, or a combination thereof.

In some embodiments, the method comprises exposing the probe-enzyme conjugate to a Tag-containing compound to form a probe-enzyme conjugate comprising a Tag moiety.

In any or all of the above embodiments, the method further comprises exposing the probe to a light source.

In any or all of the above embodiments, the method further comprise extracting a subject sample from the subject and analyzing the subject sample using a fluorescent detection technique, a colorimetric detection technique, a mass spectrometry technique, or a combination thereof.

In any or all of the above embodiments, the probe used in the method can be selected from any of the probe species described herein.

Also disclosed herein are embodiments of an assay platform, comprising a substrate and a probe embodiment according to any or all of the above embodiments, wherein the probe is covalently attached to the substrate.

VIII. Examples

The following examples are put forth so as to provide those of ordinary skill in the art with a complete disclosure and description of how to make and use embodiments of the probes and methods described herein, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Strains, Reagents, and Basic Procedures

Chemicals were purchased from Fisher Scientific or Sigma Aldrich unless otherwise noted. The cloning E. coli strains DH5α and BL21(DE3) were obtained from Life Technologies and cultured at 37° C. with Luria-Bertani medium with 100 µg/mL ampicillin where appropriate. E. coli BW25113 was obtained from an in-house stock. E. coli ΔuidA was obtained from the Coli Genetic Stock Center (strain JW1609-1). Lactobacillus plantarum WCFS1 was purchased from ATCC (BAA-793) and cultured using MRS medium at 37° C. CF640R picolyl azide was purchased from Biotium. Primers were ordered from Integrated DNA Technologies. pET-32c was obtained from a laboratory stock. puidA was constructed using Gibson Assembly (NEB) with the primers uidA_F (5'-AACTTTAAGAAGGAGA-TATAATGTTACGTCCTGTAGAAACCCC-3') [SEQ I NO: 1], uidA_R (5'-TTGTTAGCAGCCGGATCTCAT-TAATGGTGATGGTGATGGTGTTGTTTGCC TCCCTGCTG-3') [SEQ ID NO: 2], pET_F (5'-CACCAT-CACCATCACCATTAATGAGATCCGGCTGCTAAC-3') [SEQ ID NO: 3]' and pET_R (5'-TATATCTCCTTCT-TAAAGTTAAACAAAATTATTTCTAGAGGGGAAT-TGTTATCCGCTC-3') [SEQ ID NO: 4]. Expression of uidA was induced using isopropyl-D-thiogalactopyranoside (IPTG, 10 µM).

Animals

For the glucuronidase studies, female C57BL/6J mice age 6-8 weeks were purchased from Jackson Laboratories and housed with a 12 hour light/12 hour dark light cycle. Food (PMI 5002) and water were provided ad libitum. Mice were acclimated for 7 days prior to the onset of any treatment. During this time, littermates were co-housed. After this time, mice were placed in separate cages for antibiotic treatment. One set of littermates (n=5) were exposed to vancomycin in drinking water (0.1 mg/mL). The other set were given normal water. To monitor for adverse reactions to the antibiotics, researchers could not be blinded to treatment group during exposure, and were not blinded during subsequent analysis.

For the GST studies, three adult male $C_{57}BL/6J$ mice were purchased from Jackson Laboratory (Sacramento, Calif.). Purchased mice were 6 weeks of age and were fed a standard lab diet. Mice were individually housed in a room kept at 23±1° C. and at 55±10% humidity on a 12 hour light/dark cycle with free access to food and water. Mice were fed ad libitum for a period of two weeks on a standard lab diet (SD) (10% calories from fat, 20% calories from protein, 70% calories from carbohydrates, 3.83 kcal/g; Research Diets D12450Bi, New Brunswick, N.J.). All animal experiments were conducted in accordance with institutional guidelines for the care and use of laboratory animals. The Battelle Richland Institutional Animal Care and Use Committee approved protocol #2010-45.

In Vitro Fluorescence Labeling and Gel Imaging

Purified proteins (5 µM) or cell lysate (1 mg/mL) were treated with varying concentrations of GlcA-ABP for 1 hour at 37° C. Rhodamine was attached via copper catalyzed azide-alkyne cycloaddition (CuAAC) and proteins were analyzed via SDS-PAGE. Gels were imaged using a GE Typhoon FLA-9500 and band intensity was quantified using ImageJ.

Fluorescent Labeling of Microbes and Cell Sorting

Figure 9:
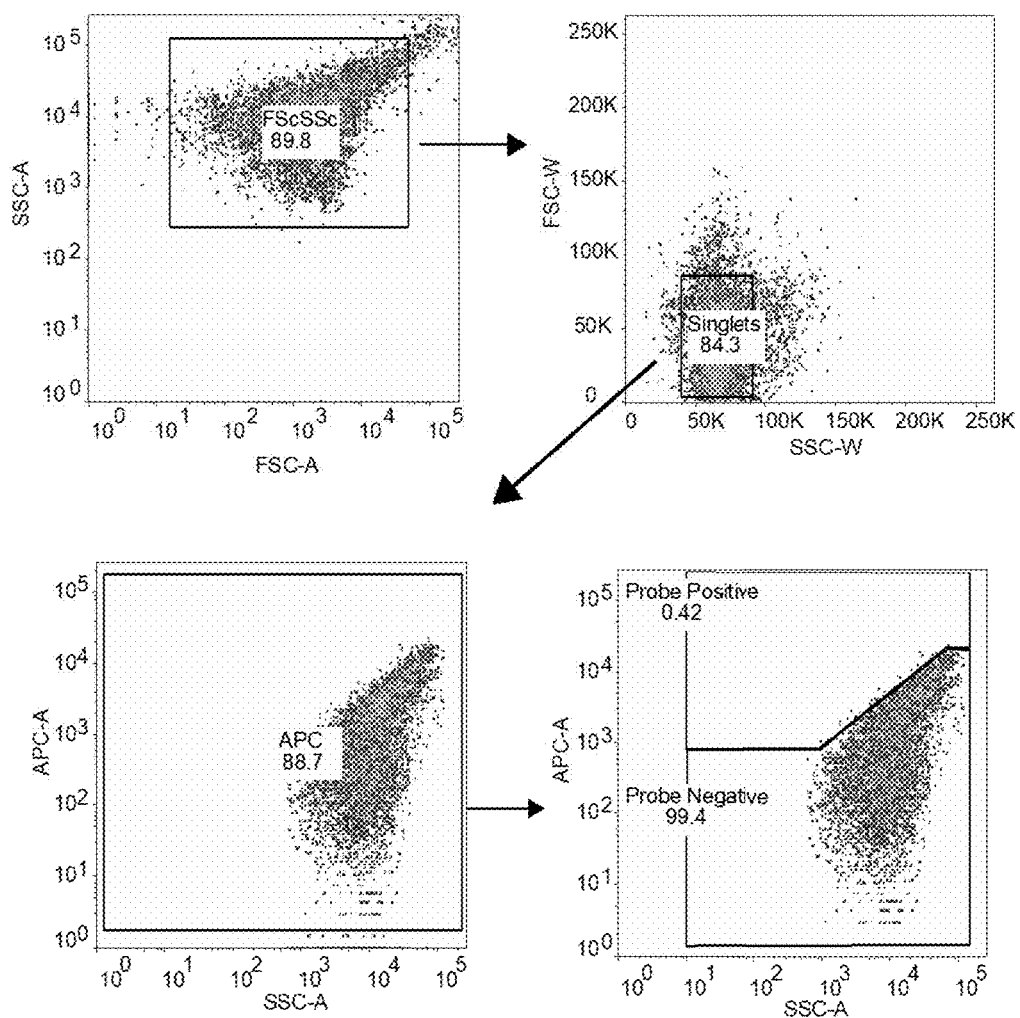
FIG. 9 illustrates the general gating strategy for isolating the ABP+/− populations discussed in FIGS. 8A-8D, wherein using side-scatter and SYBR Gold signal for event threshold, cells are gated on Forward and Side scatter, pulse duration, CF640-R to remove debris, and then CF640-R; gates were drawn such that >95% of events in the No Probe control sample were considered 'Probe Negative'.

Overnight cultures (5 mL) were collected via centrifugation resuspended in 1 mL of PBS and 100 µL was transferred into aliquots. Aliquots were treated with 50 µM GlcA-ABP, 10 µM iodoacetamide alkyne (IAA), or an equal volume of vehicle ('No Probe'; DMSO). Cells were incubated shaking for 1 hour at 37° C. Cells were collected via centrifugation at 10,000 g for 5 minutes and washed 3× with 1 mL deoxygenated PBS. Pellets were resuspended in 100 µL PBS and fixed with 70% ethanol (1 mL) at −20° C. overnight. Cells were washed twice via resuspension in 1 mL PBS and centrifugation at 10,000 g for 5 minutes. Cells were resuspended in 250 µM CuAAC reaction buffer (10 µM CF640R picolyl azide, 8 mM $CuSO_4$, 2 mM THPTA, 10 mM ascorbic acid in PBS:0.5% (w/v) BSA). One-half of the No Probe sample was used as a no fluorescence control (CuAAC reaction buffer without CF640R). Cells were incubated in the dark with rotation at room temperature for 1 hour and collected by centrifugation as above. Cells were washed 4× by resuspension in 1 mL PBS:0.5% BSA, incubating with rotation for 5 minutes in the dark at room temperature, and centrifugation as above. Cells were resuspended in PBS with SYBR Gold (Life Technologies; 1:10,000) and analyzed using a BD FACSAria Ilu with autoclaved sheath fluid. Forward and side scatter (488 nm), SYBR Gold (488 nm excitation; 530/30 nm detection filter) and CF640R (633 nm excitation; 660/20 nm detection filter) parameters were collected. Gates were drawn such that >95% of events in the No Probe sample were classified as Probe Negative (FIG. 9). Flow cytometry data was collected using FACSDiva 8 (BD Biosciences) and analyzed using FlowJo 10.

Fluorescence Labeling and Sorting of Gut Microbes

Microbial cells were collected and sorted as previously described with some modifications. Lower intestinal tract from ileum to rectum was collected and placed into 50 mL conical tubes containing approximately 5 mL sterile glass beads (3 mm diameter) and 20 mL of deoxygenated PBS. Tubes were quickly transferred to an anaerobic chamber, and 1 mM dithiothreitol was added to aid in microbial recovery and incubated for 5 minutes. The suspended intestinal content was then transferred into a new tube, vortexed for 30 seconds, and large debris precipitated for 5 minutes. Supernatant was collected and centrifuged at 700 g for 15 minutes. Supernatant was transferred to a clean 50 mL conical and centrifuged at 8,000 g for 15 minutes to collect bacterial cells. The bacterial cell pellet was washed once via resuspension in 1 mL of deoxygenated PBS and centrifuging at 8,000 g for 15 minutes. Cells were then labeled and sorted as described above.

DNA Isolation and Amplicon Sequencing

Where possible, 2,000,000 events (using side scatter and SYBR Gold as threshold parameters) were collected via 4-way purity sort in UV-irradiated glass tubes. Enrichment was confirmed by re-analyzing a small aliquot of the sorted cells. Enrichment was confirmed by re-analyzing a small aliquot of the sorted cells, where at least 50-60% of the collected cells were probe-positive compared to <20% in the initial sample. Cells were collected via centrifugation at 12,000 g for 10 minutes into 1.5 mL tubes and resuspended in lysis buffer (50 mM NaCl, 10 mM Tris HCl, 5 mM EDTA, 0.5% SDS, and 0.1% β-mercaptoethanol). To control for background DNA contamination, 50,000 beads were collected in a separate tube and one tube of lysis buffer only were prepared with each sort. Tubes were incubated at 4° C. for 30 minutes and then lysed via five freeze/thaw cycles using liquid nitrogen. DNA was then extracted and purified (Zymogen DNA Clean & Concentration-5). PCR amplification of the V4 region of the 16S rRNA gene was performed using the protocol developed by the Earth Microbiome Project as follows: (i) Amplify samples in triplicate, meaning each sample will be amplified in 3 replicate 25-μL PCR reactions; (ii) Pool triplicate PCR reactions for each sample into a single volume (75 μL). Do not combine amplicons from different samples at this point; (iii) Run amplicons from each sample on an agarose gel. Expected band size for 515f-806r is ~300-350 bp. Low-biomass samples may yield faint or no visible bands; alternative methods such as a Bioanalyzer could be used to verify presence of PCR product; (iv) Quantify amplicons with Quant-iT PicoGreen dsDNA Assay Kit (ThermoFisher/Invitrogen cat. no. P11496; follow manufacturer's instructions); (v) Combine an equal amount of amplicon from each sample (240 ng) into a single, sterile tube. Higher amounts can be used if the final pool will be gel-isolated or when working with low-biomass samples. Note: When working with multiple plates of samples, it is typical to produce a single tube of amplicons for each plate of samples; (v) Clean amplicon pool using MoBio UltraClean PCR Clean-Up Kit (cat. no. 12500; follow manufacturer's instructions). If working with more than 96 samples, the pool may need to be split evenly for cleaning and then recombined. Optional: If spurious bands were present on gel (in step 3), one-half of the final pool can be run on a gel and then gel extracted to select only the target bands; (vi) Measure concentration and A260/A280 ratio of final pool that has been cleaned. For best results the A260/A280 ratio should be between 1.8-2.0; (vii) Send an aliquot for sequencing along with sequencing primers. Amplicons were sequenced on an Illumina MiSeq using the 500 cycle MiSeq Reagent Kit v2 per manufacturer's instructions.

Bioinformatics Analysis

Sequences were analyzed using an in-house pipeline. Briefly, raw sequence reads were demultiplexed with using EA-Utils with zero mismatches allowed in the barcode sequence. Reads were quality filtered with BBDuk2 to remove adapter sequences and PhiX with matching kmer length of 31 bp at a hamming distance of 1. Reads shorter than 51 bp were discarded. Reads were merged using USEARCH with a minimum length threshold of 175 bp and maximum error rate of 1%. Sequences were dereplicated (minimum sequence abundance of 2) and clustered using the distance-based, greedy clustering method of USEARCH at blast % pairwise sequence identity among operational taxonomic unit (OTU) member sequences. De novo prediction of chimeric sequences was performed using USEARCH during clustering. Taxonomy was assigned to OTU sequences using BLAST alignments followed by least common ancestor assignments across SILVA database version 123 clustered at 99%. OTU seed sequences were filtered against SILVA database version 123 clustered at 99% to identify chimeric OTUs using USEARCH. OTUs for which read count was higher in the 'Beads' or 'Control' sample compared to samples from sorted cells were excluded from further analysis.

Differential Abundance Analysis

For each OTU and comparison, a differential abundance test was done using a compositional data analysis approach using the ALDEx2 package in R replacing the typical glm in the algorithm with a mixed effects model including a random effect accounting for littermates. Additionally, a qualitative g-test for systematic differences in presence/absence between two groups was run for each OTU and comparison. Differences with adjusted $p<0.05$ were considered significant. Differentially abundant taxa were graphed using GraPhlAn.

β-Glucuronidase Activity Assays

In gut microbiota research, mouse models are a powerful tool, and offer the possibility to perform experiments that would be too invasive for human subjects and with better control over confounding factors. (Nguyen, T L A, et al, Disease Models & Mechanisms (2015) doi: 10.1242/dmm.017400) For example, manipulations that are essential to gut microbiota research include host genetic background manipulation (gene knockouts), gut microbiota composition manipulation (controlled inoculation in germ-free or gnotobiotic mice, i.e. germ-free mice administered with external microbes) and ecosystem interventions including dietary interventions, antibiotic treatment and fecal transplantations. Even though many mouse models do not recapitulate exactly the modeled human disease, with each model having different limitations that need to be taken into account to translate the results to humans, these models have provided valuable insights and unique possibilities to manipulate the human microbiota and potentially assess causality in the role of the gut microbiota in health and disease.

Microbial cells from the mouse gut were suspended in PBS with protease inhibitor (cOmplete EDTA-free Protease Inhibitor, Roche) and lysed via bead beating (Bullet Blender). 4-methylumbelliferyl-β-D-glucuronide (4-MUG; 1 mM) was added to 50 μL lysate (0.9 μg total protein) to achieve a final concentration of 500 μM. At specific time points (0-240 minutes), 10 μL aliquots of each reaction was added to 90 μL of 0.1 M $Na_2HCO_3$ (pH=10) and stored in the dark. Fluorescence was measured using a plate reader (Molecular Biosciences), and amount of hydrolyzed substrate was calculated relative to a standard curve. Rate (mM/s) was determined via linear regression (GraphPad Prism) and activity was calculated as rate per μg protein. Values from three independent replicates were averaged and activity was compared across biological replicates (n=5) using a ratio paired t-test.

Correlation Analysis

Glucuronidase activity was correlated to OTU relative abundance in the total population of control and vancomycin treated samples. The high activity value for one sample (litter set E control) in the water treatment is much larger than all other values drastically affected statistical results, thus these samples were excluded from the analyses. Additionally, OTUs with a large number of zeros (more than ⅔ of samples had observed 0 counts) were excluded as any results from these OTUs would likely be spurious. For the remaining OTUs, the Pearson correlation between the normalized OTU abundance and glucuronidase activity were calculated and a hypothesis test for significance was performed. Correlation was considered significant at a 0.05 level of significance.

Isolation of Tissue Cytosol

Mouse liver, lung, kidney, intestine, spleen, and heart tissue were minced on ice using a tissue tearror, followed by homogenization in 4 mL ice cold 250 mM sucrose in 1×PBS (pH 7.4, 11.9 mM phosphates, 137 mM NaCl, 2.7 mM KCl) buffer using a glass dounce homogenizer with 15 pulses from the loose and tight pestles. Homogenate was spun at 10,000 g (4° C.) for 25 min, followed by collection of the supernatant which was subsequently spun at 100,000 g for 90 minutes at 4° C. The supernatant (cytosolic fraction) was separated from the pellet (microsomal fraction) and protein concentration was determined via BCA assay.

GST Activity Assay

GST activity assays were performed on 1 mg/ml mouse lung, kidney, intestine, spleen, and heart cytosol and 0.5 mg/ml liver cytosol. Four technical replicates per tissue type were measured. The assays were performed in a 96 well plate. Each well consisted of 172 µL PBS Assay Buffer (1×PBS, pH 6.5), 4 µL of GSH (50 mM) in 1×PBS, and 20 µL 1 mg/mL (or 0.5 mg/ml) cytosol. 20 µl additional PBS Assay Buffer was added to the no protein control wells. 4 µL dinitrochlorobenzene (DNCB) (50 mM) in DMSO was added to each well to start the assay. Absorbance at 340 nm was measured every 30 s for 10 minutes. The slope of the absorbance values for each replicate was calculated and the slope of the no protein control was subtracted from each of the calculated sample slopes. In order to determine the GST activity the following equation was applied: (Abs340/minute)/0.00503 µM (DNCB extinction coefficient)*(1 mg/20 µg)=nmol DNCB/min/mg protein.

In Vitro Labeling of GSTs in Mouse Liver and HepG2 Proteome for SDS-PAGE Analysis All probe labeling was conducted on 50 µL 1 mg/mL proteome. If applicable, competitor was added, and the samples were incubated at 37° C. for 30 min, with agitation. 0.5 µL of appropriate probe stock was added to each sample. 0.5 µl DMSO was added to all no probe controls. After incubation, GSH-ABP labeled samples (and controls) were exposed to UV light for 7 minutes on ice. After incubation with the probe, 1.0 µL rhodamine-azide (3 mM) in DMSO, 1.0 µL sodium ascorbate (500 mM), 0.5 µL Tris(3-hydroxypropyltriazolylmethyl)amine (200 mM), and 2.0 µL $CuSO_4$ (100 mM) was added to each sample, vortexed, and quickly spun down. All samples were incubated at room temperature in the dark for 90 minutes. 50 µL 2×SDS Running buffer and 10 µL 10× reducing agent was then added to each sample. Samples were vortexed and heated at 95° C. for 10 minutes, with shaking. 7.5 µg protein was then loaded into each well of a 10-20% Tris-Gly or 4-12% Bis-Tris gel and run at 150 V, 35 mA for 90 minutes. Gels were then imaged on Typhoon FLA 9500 (General Electric) or FluorChemQ (Alpha-Innotech), followed by an incubation with GelCode Blue stain and subsequent imaging using GelDocEZ (Biorad Laboratories). Gel image analyses were done using ImageQuant software.

Probe-Mediated Streptavidin Enrichment

All mouse liver cytosol samples were normalized to 500 µL 1 mg/mL proteome in sucrose (250 mM) in PBS buffer. Samples were then incubated with competitor (if applicable) for 30 minutes at 37° C. GST-ABP, GSH-ABP, or an equal volume of DMSO control was incubated with proteome for 30 minutes at 37° C. GSH-ABP samples were then exposed to UV light (wavelength:365 nm; 115V, 15 W—Fisher UVP95) for 7 minutes on ice. The click chemistry mixture contained final concentrations of biotin-azide (60 µM) in DMSO, sodium ascorbate (5 mM), tetrahydrophthalic anhydride (THPTA) (2 mM), and $CuSO_4$ (4 mM). Each reagent was added individually in that sequence, vortexed, spun down, and incubated at room temperature in the dark for 90 minutes. 800 µL of pre-chilled MeOH was added to each sample. Samples were placed in the −80° C. freezer for 30 minutes to induce protein precipitation. Samples were centrifuged at 14,000 g at 4° C. for 4 minutes. The supernatant was discarded, and the pellet was allowed to air-dry for 5 minutes. Samples were resuspended and sonicated in 520 µL SDS (1.2%) in PBS; followed by incubation at 95° C. for 2 minutes. Samples were centrifuged at 14,000 g for 4 minutes at room temperature. Supernatant was transferred to new eppies, leaving any residual pellet behind. After the samples cooled to room temperature (rt), their protein concentration was determined via BCA assay and samples were normalized to a volume of 500 µL at 0.6 mg/mL. 100 µL Streptavidin-agarose beads were washed twice with 1 mL SDS (0.5%) in PBS, twice with 1 mL urea (6 M) in $NH_4HCO_3$ (25 mM), and 4× using 1 mL 1×PBS. Washes were done via vacuum filtration using BioSpin Disposable Chromatography Columns (Bio-Rad Laboratories). Beads were transferred to 4 mL cryovials using 2, 1 mL aliquots of PBS, protein samples were added, and the bead/protein mixture was incubated at 37° C. for 1 h with inversion. Samples were then added back to the columns and washed with 2, 1 mL aliquots of 0.5% SDS in PBS; 2, 1 mL aliquots of freshly prepared urea (6 M) in $NH_4HCO_3$ (25 mM); 2, 1 mL aliquots of MilliQ water; 8, 1 mL aliquots of PBS; 4, 1 mL aliquots of $NH_4HCO_3$ (25 mM, pH 8). Samples were transferred to DNA lo-bind tubes (Eppendorf) using 2 aliquots of 500 µL PBS followed by centrifugation at 10,500×g for 5 minutes at room temperature. The supernatant was discarded and the beads resuspended in 400 µL urea (6 M) in $NH_4HCO_3$ (25 mM). Samples were reduced via incubation for 30 minutes with TCEP (5 mM) at 37° C. Samples were alkylated with iodoacetamide (10 mM) at 50° C. under foil for 45 minutes. Beads were transferred to the columns and washed 8× with 1 mL PBS and 4× with 1 mL $NH_4HCO_3$ (25 mM). Following that, beads were transferred to DNA lo-bind tubes (Eppendorf) with 2 mL $NH_4HCO_3$ (25 mM). Samples were centrifuged at 10,500×g for 5 minutes at room temp, the supernatant discarded, and resuspended in 200 µL $NH_4HCO_3$ (25 mM, pH 8). 0.075 µg trypsin was added to each bead mixture followed by incubation overnight at 37° C., with inversion. The next morning, beads were spun down at 10,500 g for 5 minutes. The supernatant was collected and samples were placed on a speedvac (Savant SC110) until dry. Peptides were reconstituted by adding 40 µL of 25 mM $NH_4HCO_3$ and heating the samples at 37° C. for 5 minutes. Samples were transferred to ultracentrifuge tubes and were spun at 100,000×g to remove any debris. 25 µL was added to glass vials to be stored at −20° C. until analysis.

LC-MS Analysis of Probe Enriched Murine Liver and Lung Cytosol

All proteomics samples prepared for LC-MS were analyzed using a Velos Orbitrap MS. Sadler, N C et al, Applied & Environmental Microbiology (2016) 82 (24): 7227-35. Data was analyzed using an accurate mass and time (AMT) tag approach. Zimmer, J S D, et al, Mass Spectrometry Reviews (2006): 25(3): 450-82. MS/MS spectra were searched against the *Mus musculus* Uniprot protein database. Following this, data was rescored using the $MSGF_+$ approach. Peptides were further filtered on the following criteria: (i) protein count=1, (ii) MT Uniqueness ≥0.5, and (iii) MT FDR≤1%. Peptides were log 2 transformed and normalized via linear regression. Peptides were then rolled up to the protein level using DAntE. (Polpitiya, A. et al, Bioinformatics (2008) 24(13): 1556-58). A minimum of five proteins were used for the Grubb's test, with a P value cutoff of 0.05. Significance between no probe and probe-labeled samples, as well as non-competed and competed probe-labeled samples, was determined using a paired t-test and calculated fold change abundances.

Example 1

Figure 10A:
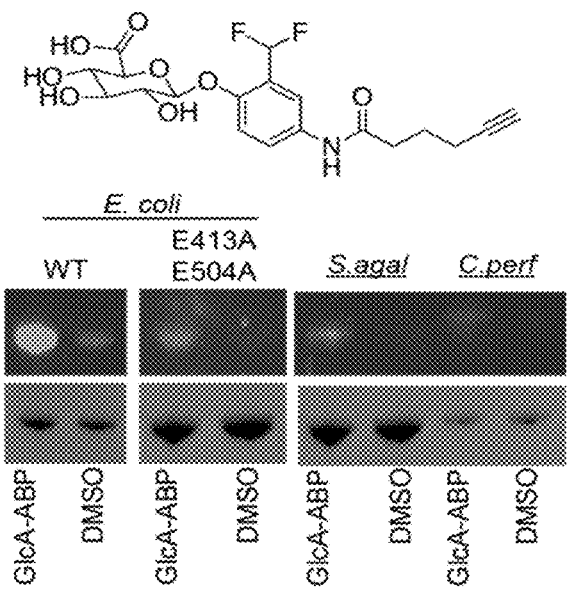
FIG. 10A shows the probe structure and corresponding results from fluorescence (top) and coomassie-stained (bottom) SDS-PAGE analysis of the probe-β-glucuronidase conjugate tagged with tetramethylrhodamine azide via click chemistry.
Figure 10B:
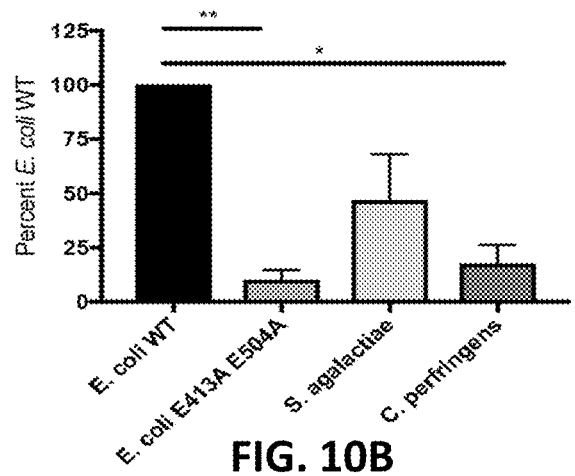
FIG. 10B shows the quantification of labeling intensity using ImageJ, wherein columns indicate mean and error bars indicate standard error of the mean and *=adjusted $p=0.0203$; and **=adjusted $p=0.0047$ by repeated measures one-way ANOVA with Dunnett's multiple comparisons test, n=3.
Figure 10C:
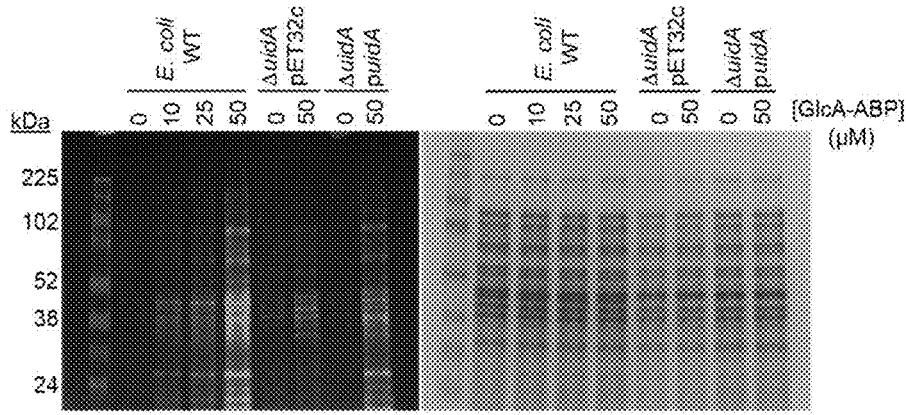
FIG. 10C shows results from a *E. coli* lysate (WT BW25113, ΔuidA pET32c, or the complement ΔuidA puidA), which was labeled with a probe embodiment at various concentrations, wherein the labeled protein is visualized via fluorescence (left) and total protein was imaged via coomassie blue stain (right).
Figure 10D:
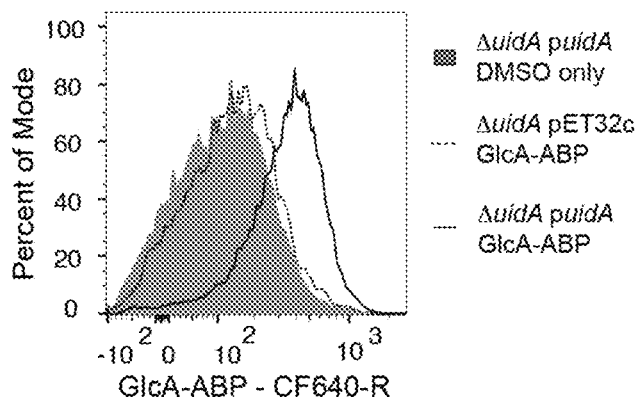
FIG. 10D shows results from embodiments where whole cell *E. coli* were labeled with a probe embodiment, and labeled cells were tagged with CF640-R.
Figure 10E:
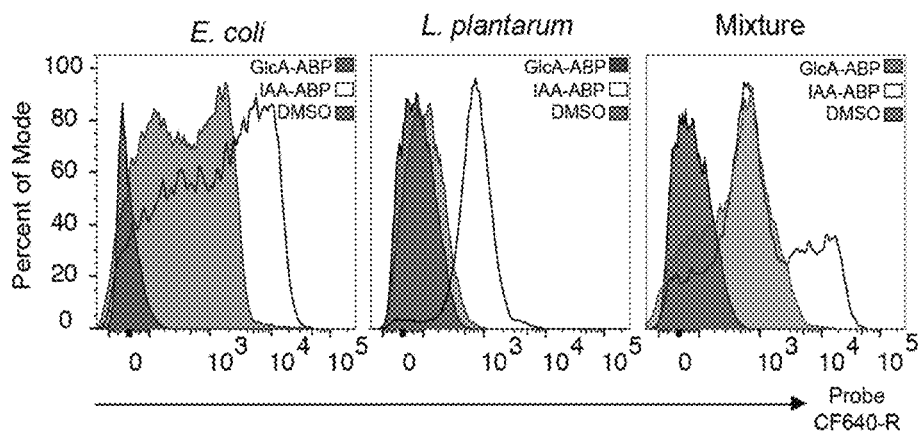
FIG. 10E show histograms of *E. coli* only (top left), *L. plantarum* only (top middle), or a mixture of the two (top right and bottom) labelled with a probe embodiment, a cysteine-reactive IAA probe, or vehicle only (DMSO).
Figure 10E:
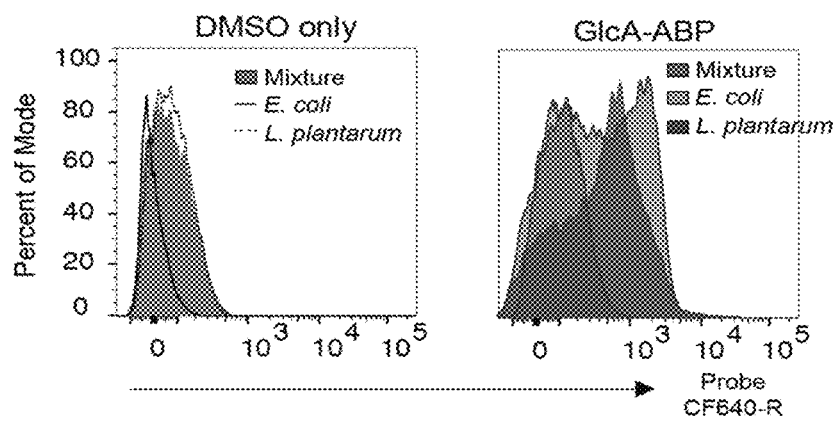

In vitro probe labeling was carried out with recombinantly expressed and purified β-glucuronidases from *Escherichia coli*, *Streptococcus agalactiae*, and *Clostridium perfringens*. Enzymes were treated with a β-Glucuronidase probe embodiment, GlcA-ABP, which was tagged with rhodamine-azide, and analyzed by SDS-PAGE. GlcA-ABP labeling intensity corresponded with the catalytic efficiency of these enzymes reported by Wallace et al. (FIGS. 10A and 10B). Mutation of the catalytic residues from glutamate to alanine abolished probe labeling, confirming that GlcA-ABP probe labels β-glucuronidases in an activity-dependent fashion (FIGS. 10A and 10B). Additional results are shown in FIGS. 10C-10F.

Figure 11:
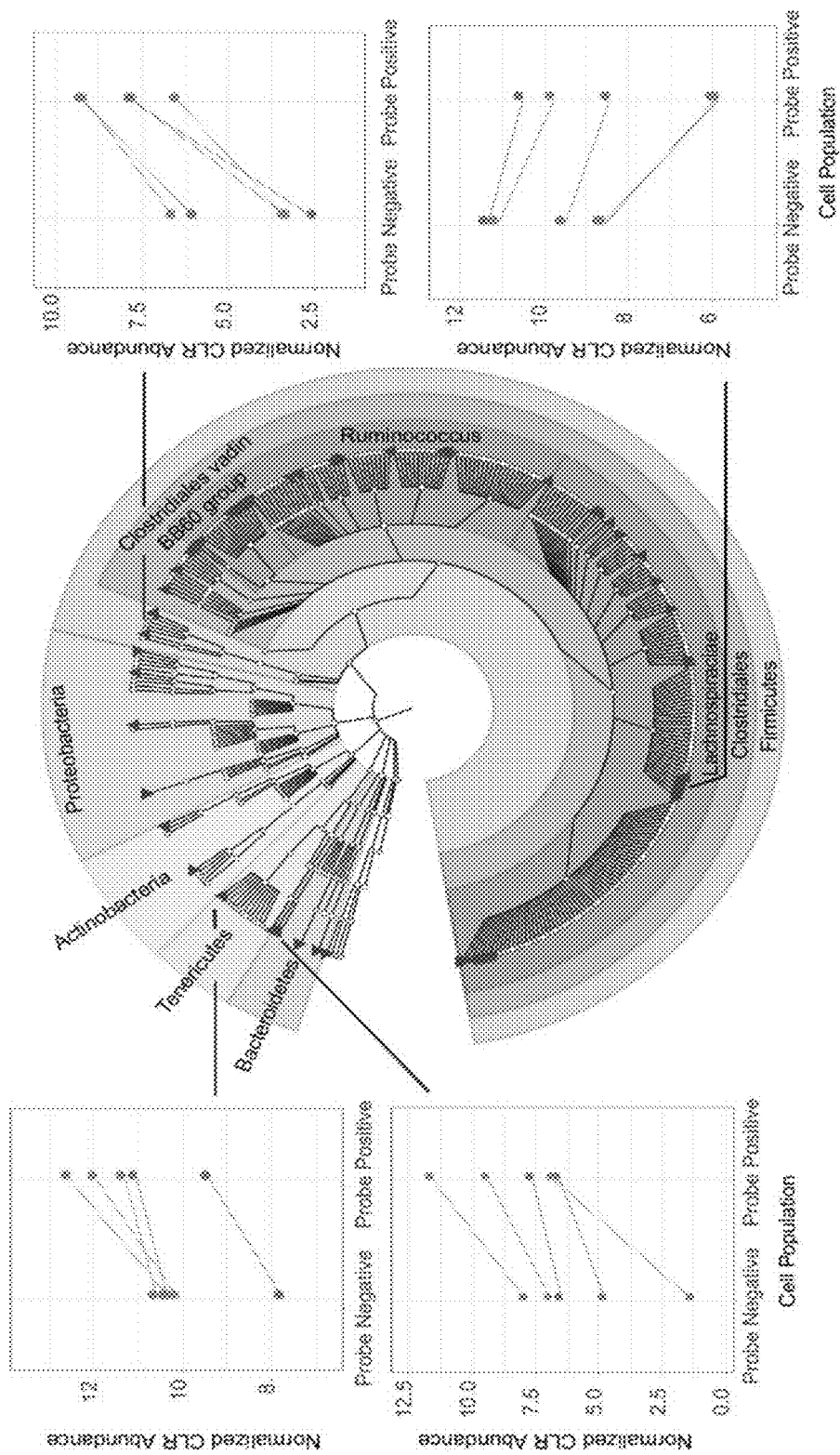
FIG. 11 illustrates the phylogenetic distribution of GlcA-ABP+ and GlcA-ABP− taxa, wherein red triangles indicate taxa with significantly increased abundance in the Probe Positive population; blue triangles indicate taxa with significantly increased abundance in the Probe Negative population; white circles indicate no significant differential abundance was observed; and examples of three GlcA-ABP+ taxa (left and top right) and one GlcA-ABP− taxon (bottom left) are shown (taxa are considered differentially abundant where Benjamini-Hochberg adjusted $p<0.05$ by Welch's t test or by G-test (n=5)).

Next, glucuronidase-active members of the gut microbiota were identified. Microbes were isolated from the mouse gastrointestinal tract and incubated with the GlcA-ABP probe under anaerobic conditions. Cells were fixed, fluorescently tagged, and sorted into populations of probe positive (GlcA-ABP+), probe negative (GlcA-ABP−), and all cells (FIG. 7; FIG. 9). Community composition was then determined for each population by amplicon sequencing of the 16S rRNA gene, and differentially abundant taxa were identified both via paired quantitative analysis and presence/absence analysis. Taxa with statistically increased abundance in the GlcA-ABP+ fraction compared to the GlcA-ABP− fraction were considered glucuronidase-active. Glucuronidase active taxa were found to be taxonomically diverse, including Bacteroidetes, Proteobacteria, and Tenericutes; however, the majority of the taxa (31/37) were Firmicutes (FIG. 11). The three most abundant GlcA-ABP+ operational taxonomic units (OTUs) were also diverse, representing the families Rikkenellaceae, Anaeroplasmaceae, and Erysipelotrichaceae. In contrast, OTUs with significantly increased abundance in the GlcA-ABP− fraction compared to the GlcA-ABP+ fraction were considered to be glucuronidase-inactive. This fraction was also taxonomically diverse, with representative sequences from Bacteroidetes, Proteobacteria, and Firmicutes. The GlcA-ABP-enriched OTU with the highest abundance was a Lachnospiraceae. These results indicate that some taxonomic groups at the level of family or even genus contained both glucuronidase-active and -inactive OTUs, which thus demonstrates that in vivo metabolic activity cannot be ascribed based solely on phylogenetic similarity.

Figure 12:
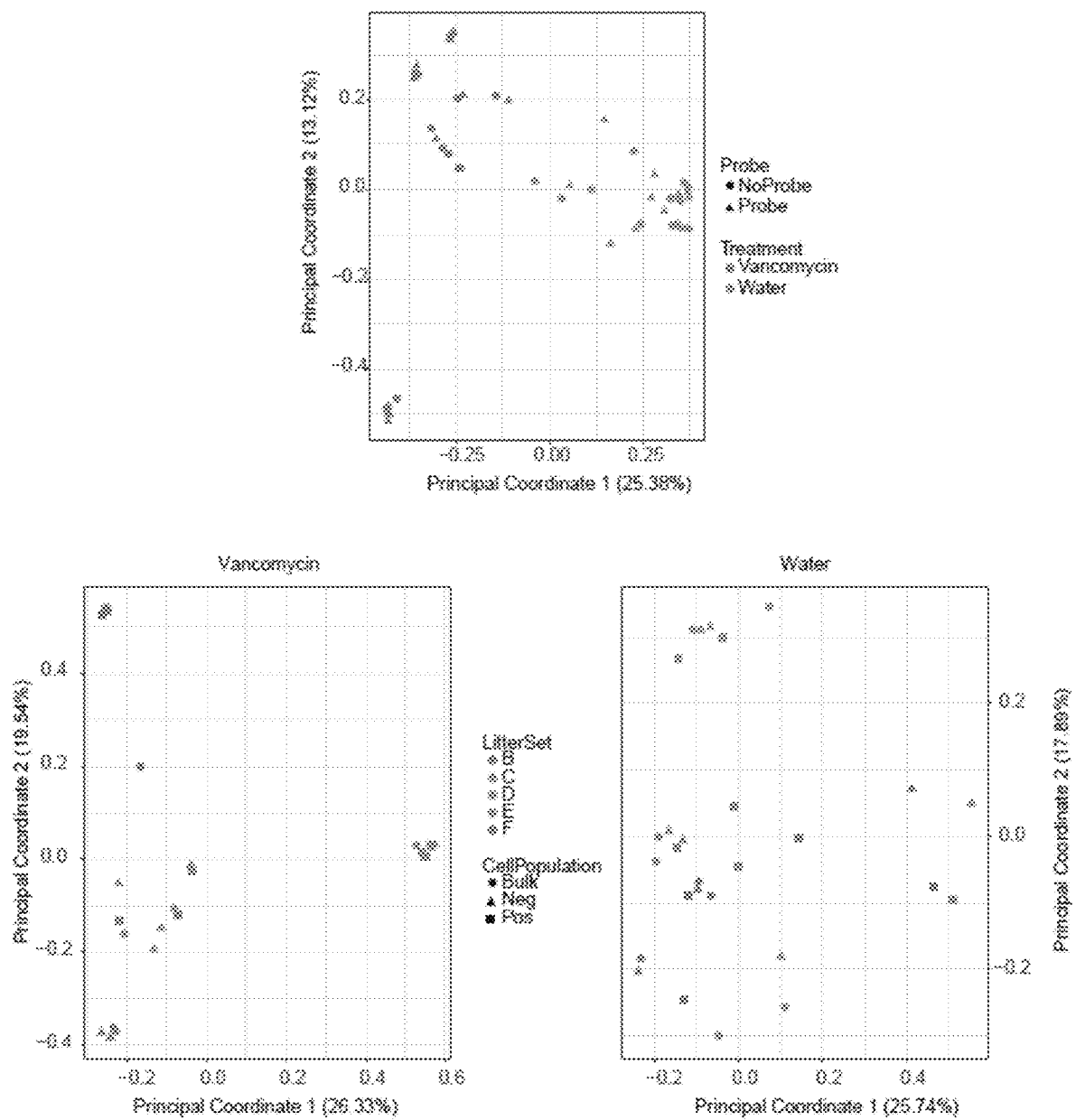
FIG. 12 shows β-diversity among input for GlcA-ABP+ and GlcA-ABP− populations, including Bray-Curtis dissimilarity analysis of sequenced populations from all (top), control (bottom right), or vancomycin treated (bottom left) mice.
Figure 13A:
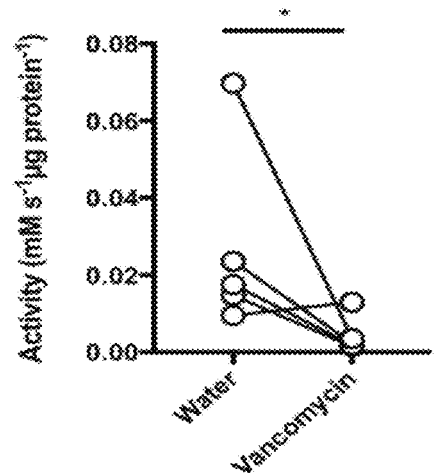
FIG. 13A shows the phylogenetic distribution of GlcA-ABP+ taxa in control (red triangles) compared to vancomycin treated (cyan squares) mice (wherein taxa are considered differentially abundant where Benjamini-Hochberg adjusted $p<0.05$ by Welch's t test or by G-test (n=3 pairs).
Figure 13B:
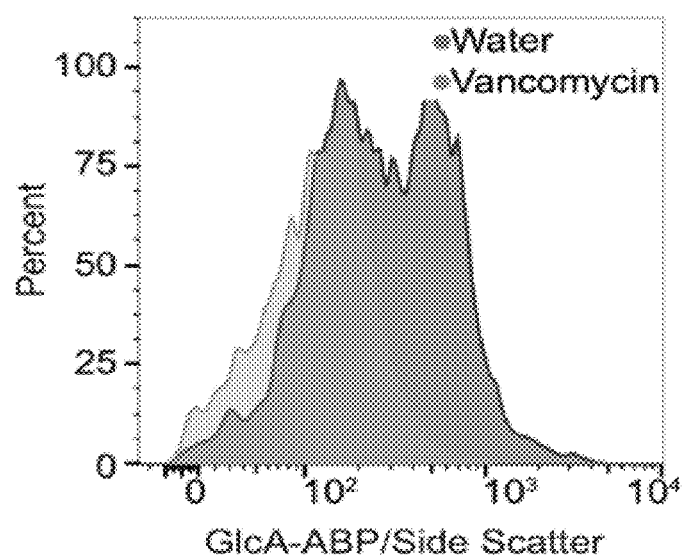
FIG. 13B shows glucuronidase activity in the gut microbiome of control or vancomycin treated mice (wherein paired littermates (n=5) are connected by lines, *: $p<0.05$ by ratio-paired Student's t-test and data are the average of three experimental repeats).
Figure 13C:
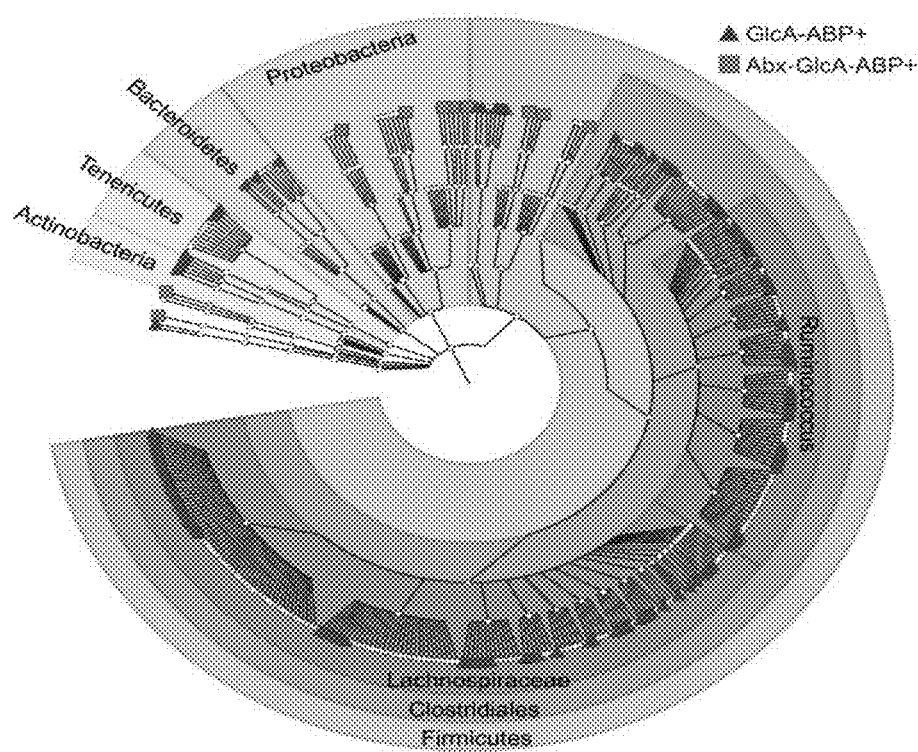
FIG. 13C shows a comparison of GlcA-ABP+ populations in untreated (water) and vancomycin treated mice (wherein data are representative of five pairs of littermates).
Figure 14:
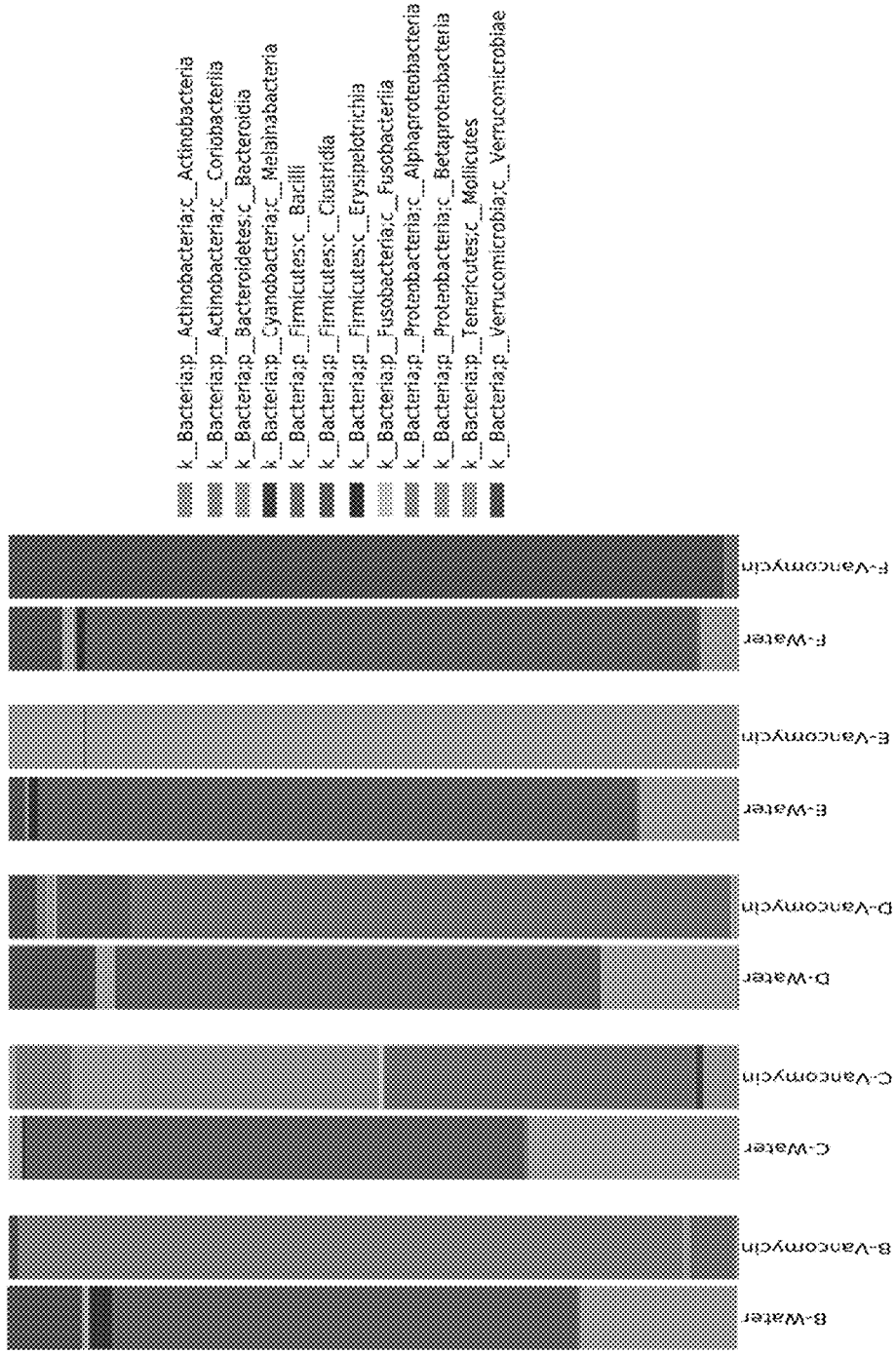
FIG. 14 shows the population shift upon vancomycin treatment for each littermate pair (with normalized relative abundance of taxa at the class level) for the embodiment described by FIGS. 13A-13D.

Given that multiple, phylogenetically distinct taxa contribute to glucuronidase activity in the gut, it was hypothesized that disruption of the gut microbiota would not necessarily aborogate glucuronidase activity, but rather change the taxa responsible for this activity. As such, pairs of litter mates were exposed to water with or without vancomycin, an antibiotic known to target Firmicutes in the gut microbiota (FIG. 12). As Firmicutes made up most the probe positive taxa in the non-treated mice (FIG. 11), it was expected that vancomycin treatment would cause a shift in the GlcA-ABP+ population composition. Vancomycin treatment reduced, but did not eliminate, glucuronidase activity in 4 of 5 sets of litter mates (FIG. 13A). Accordingly, the intensity of GlcA-ABP+ labeling decreased as well (FIG. 13B). To identify the glucuronidase-active taxa that shift following antibiotic treatment, the GlcA-ABP+ populations of vancomycin treated (Abx-GlcA-ABP+) and untreated (GlcA-ABP+) littermates were compared. Vancomycin treatment dramatically decreased the relative abundance of Firmicutes, and with a corresponding increase in the relative abundance of Proteobacteria, Verrucomicrobia, and Bacteroidetes (FIG. 14). Compared to the vancomycin treated GlcA-ABP+ population, the control GlcA-ABP+ population was significantly enriched in OTUs from the Firmicutes (specifically Clostridiales), Bacteroidetes, Tenericutes, and Actinobacteria phyla (FIG. 13C). In contrast, the Abx-GlcA-ABP+ population was significantly enriched in OTUs belonging to the Proteobacteria; additionally, two *Lactobacillus* taxa were also significantly more abundant in the GlcA-ABP+ population following antibiotic treatment. The ability of such disparate taxa to elicit the same function under different conditions (i.e. antibiotic perturbation) highlights the substrate diversity and utility of these enzymes. The binding of glucuronides to β-glucuronidases is primarily mediated by the glucuronic acid rather than the metabolite, allowing microbes to extract carbon and energy in the form of glucuronic acid from multiple parent metabolites. Thus, β-glucuronidases exhibit a high degree of functional redundancy by being both genetically widespread and able to hydrolyze multiple substrates. As a result, perturbation of community structure may change the composition of a functional guild without entirely eliminating the function. This suggests that future therapeutic manipulation of deglucuronidation activity in the gut may not be possible by adding or eliminating specific taxa, but will require inhibitors capable of inhibiting enzymes from multiple gut taxa. While genetic prediction and in vitro analysis of gut microbiota isolates previously suggested this result, the assay described herein, for the first time, confirms biochemical activity at the molecular scale in the microbiome through coupling detection of in situ activity with the ability to identify the responsible, functional taxa.

Figure 13D:
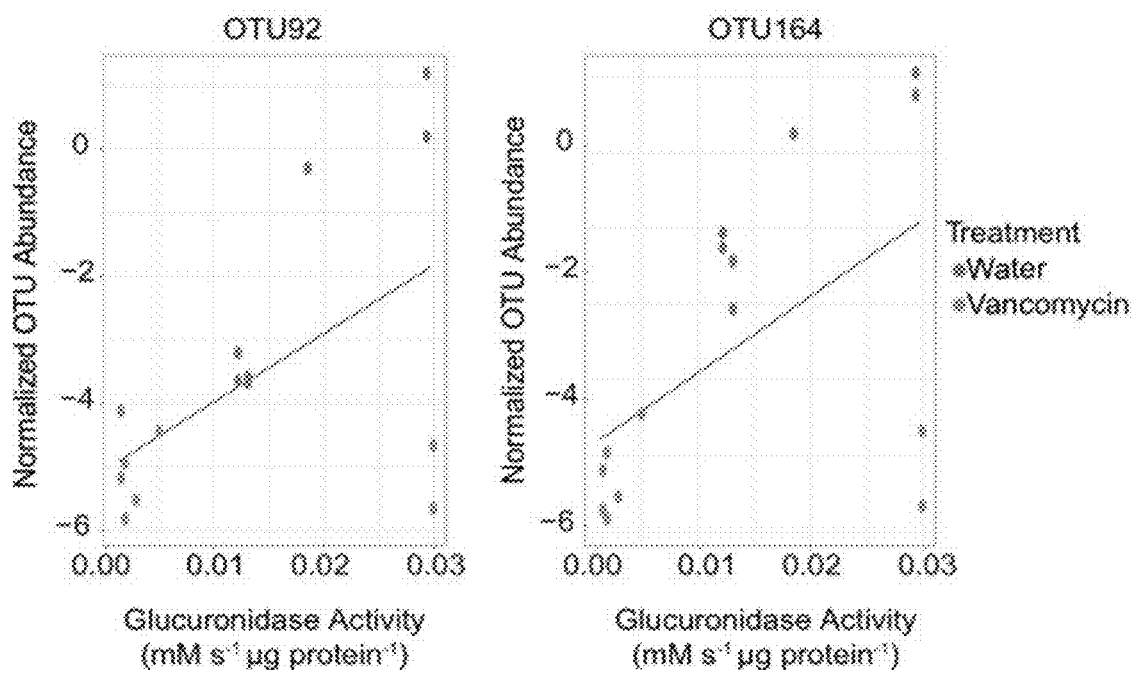
FIG. 13D shows Pearson correlation plots of glucuronidase activity with normalized log abundance for two example OTUs (wherein results were considered significant at a significance level of 0.05).

Additionally, OTUs whose abundance in the total population positively correlated with glucuronidase activity were identified and compared to those that were depleted following vancomycin exposure. 12 OTUs with a significant positive correlation to glucuronidase activity were identified. Two examples, OTU92 corresponding to the Clostridiales and OTU164, corresponding to the Ruminococcus are shown (FIG. 13D). Of these 12 OTUs, 10 were significantly more abundant in the GlcA-ABP+ population than in the Abx-GlcA-ABP+ population (FIG. 13C), suggesting that these taxa were responsible for the glucuronidase activity in the untreated mice, and are reduced upon vancomycin exposure. Of the remaining two OTUs, one was only found in a single sample across the GlcA-ABP+ and Abx-GlcA-ABP+, preventing statistical analysis. The other OTU was an Akkermansia OTU. Interestingly, a dramatic increase in Akkermansia was observed in one of the vancomycin treated mice (Set F), which was also the only litter pair to exhibit increased glucuronidase activity after antibiotic treatment. These results corroborate that there is a functional plasticity or redundancy within the metabolically active-subpopulations of the gut microbiome, and the probe and assay embodiments described herein can be used to access this information.

Example 2

Two probes were developed to enable activity-based protein profiling of GSTs at the GSH-binding G-site and the substrate binding H site, and their ability to target and measure the activity of GSTs in mammalian model systems validated. The first probe, GSH-ABP-G was designed to target the glutathione-binding G site of GSTs by mimicking GSH. A photoreactive benzophenone and a terminal alkyne were appended to the thiol of GSH. This allows for irreversible binding of the probe to GST targets when UV irradiated, and the subsequent enrichment of targeted proteins following click chemistry. GST enzymes recognize and bind the peptidic structure of GSH, whereas the GSH thiol functions as a nucleophile for GST-mediated attachment to xenobiotics. Therefore, to target the G site the thiol was modified with the alkyne and benzophenone containing linker. To complement the G site targeting photoaffinity probe, a mechanism-based probe designed to characterize H site activity was developed. The second probe, GST-ABP-H, is derived from Dichlon (2,3 dichloro-1,4-naphthoquinone), a broad spectrum irreversible inhibitor of human and rodent GST isoenzymes. It was hypothesized that GST-ABP-H would bind H sites due to Dichlon's hydrophobicity and electrophilicity, which are properties of H site binding molecules. In addition, evidence suggests the Dichlon moiety may also have capacity to bind conserved catalytic tyrosines within GST H sites.

Figure 15A:
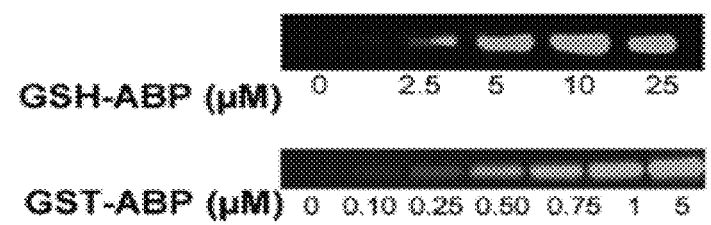
FIG. 15A show results from labeling glutathione transferase (GSH and GST) with probe embodiments described herein using 1 µM recombinant human GSTm1.
Figure 15B:
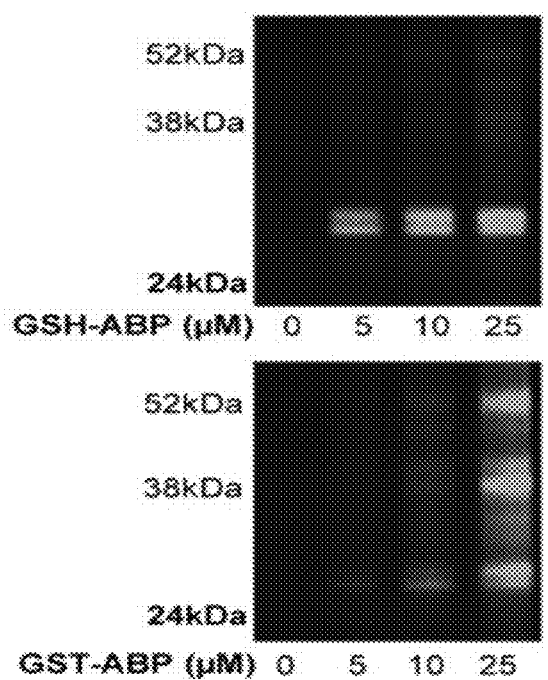
FIG. 15B show results from labeling glutathione transferase (GSH and GST) with probe embodiments described herein using 1 µM mouse liver cytosol.
Figure 16A:
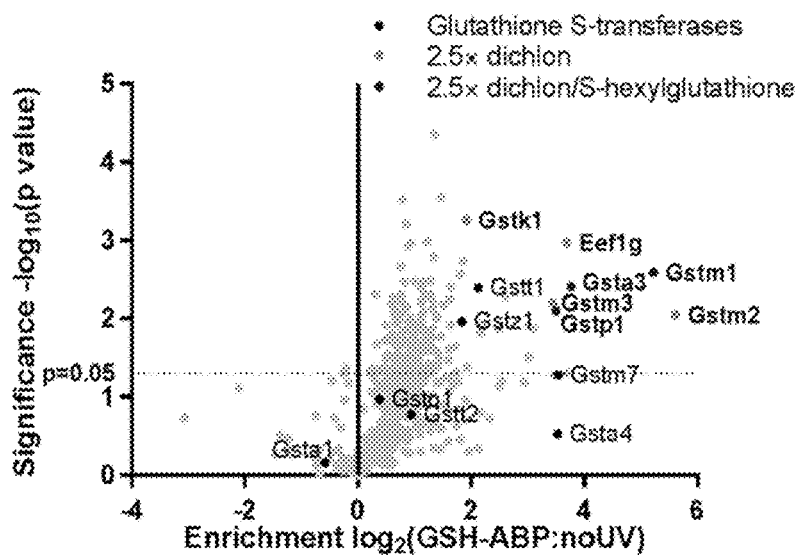
FIG. 16A shows LC-MS/MS chemoproteomics results of probe-enriched and probe competed mouse liver cytosol (n=3), wherein all samples were incubated with 10 µM of a representative probe embodiment or an equal concentration of vehicle control; enrichment was calculated as AMT tag abundances from probe-enriched samples divided by a no UV (for GSH-ABP) or DMSO only (for GST-ABP) control; in particular.
Figure 16B:
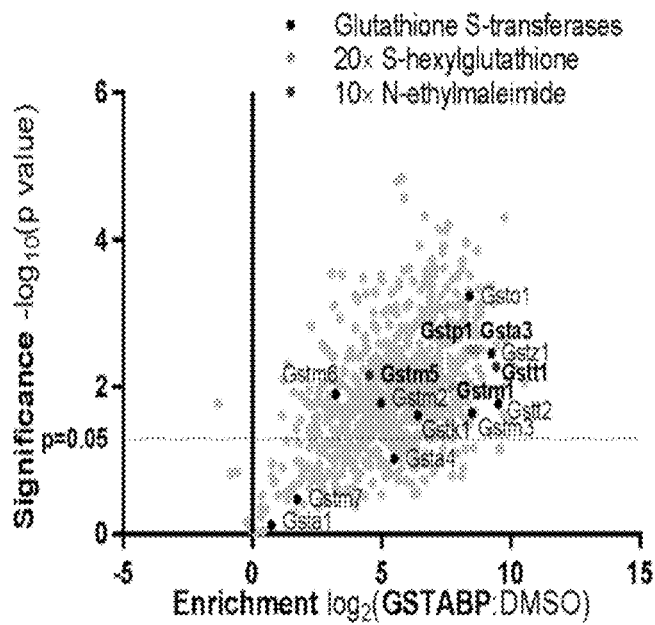
FIG. 16B shows LC-MS/MS chemoproteomics results of probe-enriched and probe-competed mouse liver cytosol (n=3), wherein all samples were incubated with 10 µM of a representative probe embodiment or an equal concentration of vehicle control; enrichment was calculated as AMT tag abundances from probe-enriched samples divided by a no UV (for GSH-ABP) or DMSO only (for GST-ABP) control; in particular.

Concentration dependent labeling of a recombinant GST (FIG. 15A) was evaluated. The two probe embodiments, GSH-ABP-G and GST-ABP-H, were applied with increasing concentrations to the recombinant human GSTM1, a GST isoenzyme that is highly expressed in mammalian liver. After 30 minutes of incubation, a fluorescent rhodamine reporter was added by click chemistry, and SDS-PAGE revealed both probes exhibit concentration-dependent targeting of the recombinant GSTM1 enzyme (FIG. 15A). Both probes were then applied with increasing concentrations to the cytosolic fraction of mouse liver lysate to further test probe targeting (FIG. 15B). Both probes strongly label two distinct bands at 24 kDa. The lower band is likely GSTP1, a 23.6 kDa protein highly abundant in the liver. The upper band shows probable GST targets from the mu and alpha classes, the molecular weights of which are roughly 26 kDa. In addition to these proteins, the GST-ABP-H probe shows concentration-dependent labeling of various higher molecular weight proteins. While the GSH-ABP-G probe embodiment demonstrates high selectivity, the GST-ABP-H probe embodiment seems more susceptible to off-target labeling, likely due to its strong electrophilic nature (FIG. 15B). To determine the specific GST isoforms targeted by each probe, LC-MS based proteomics analyses of mouse liver labeling, and labeling in the presence of specific inhibitors were performed (FIGS. 16A and 16B). Proteomics revealed that the GSH-ABP-G probe embodiment shows high specificity for GSTs (FIG. 16A). 27 probe-targeted proteins were determined to be statistically significant targets of the GSH-ABP-G probe embodiment at a fold-change of 3 over no UV exposure controls. Of these 27 proteins, 8 are known GSTs and include members of mu, alpha, pi, theta, kappa, and zeta classes. The remaining proteins include five proteins with known GSH binding, one with known antioxidant and drug binding activity, and five proteins highly abundant in liver with no known GSH binding activity. The GST-ABP-H probe embodiment also facilitated the enrichment of 12 members of the GST mu, alpha, pi, theta, omega, kappa, and zeta classes (FIG. 16B). However, as with the gel studies, proteomics results for the GST-ABP-H probe indicate considerably more off target labeling than for the GSH-ABP-G probe. An evaluation of the off-targets reveals that many of these proteins have known reactive thiols, akin to the GSTs. Within GSTs, the GSH-ABP-G probe shows selectivity for GSTM2, M1, A3, P1, M4, T1, K1, MAAI (Z) and the GST-ABP-H probe for GSTT2, T1, and Z isoenzymes. These results validate the effectiveness of both probes for isoenzyme-specific targeting of many members of most cytosolic GST classes.

To demonstrate the selectivity of the probes, and the value of an ABP approach over global abundance profiling, ABP labeling results were compared to global proteomics analysis of liver lysate. Only six GSTs were identified by global analysis, but ABP-labeling resulted in the detection of 12 GSTs, including all the GSTs detected in unenriched lysate. The ABPs therefore enable characterization of active and low abundance GSTs.

Figure 17:
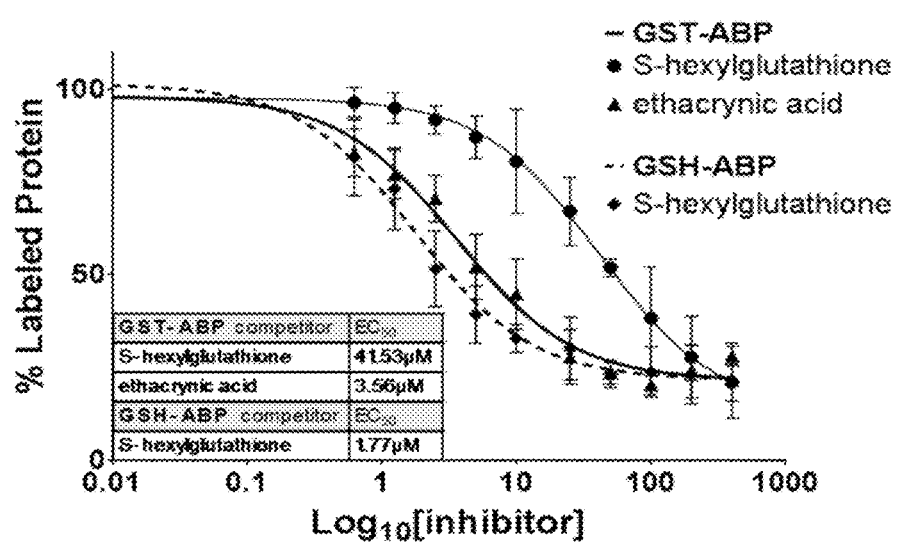
FIG. 17 provides results for competitive inhibition results of GSH-ABP and GST-ABP labeling of mouse liver cytosol to delineate G and H site binding (n=3), wherein 10 µM of the probe was used in all samples and increasing concentrations of S-hexylglutathione or ethacrynic acid was incubated with mouse liver cytosol for 30 minutes before probe labeling for 30 minutes; afterwards, rhodamine was attached to the probe-protein complexes via click chemistry and proteins were resolved via SDS-PAGE followed by fluorescence gel imaging and quantification (arbitrary units) of probe labeled GST bands (all replicates were normalized to a % labeled protein value (probed samples with no inhibitor=100%).

To distinguish between activity-specific binding and general reactivity of the probes, and to characterize their selectivity for G or H site specificity, GST-ABP-H and GSH-ABP-G labeling of mouse liver lysate against several relevant inhibitors were competed. To evaluate G site labeling by the GSH-ABP-G probe, GSH was added in excess to compete G site binding. SDS-PAGE and LC-MS analysis of GSH-competed probe labeling showed no significant inhibition (data not shown). Without being limited to a particular theory, the lack of inhibition can be attributed to the formation of glutathione disulfides (GS-SG) in the in vitro proteome sample. To circumvent the requisite addition of potentially activity-modifying reducing agents to prevent GS-SG formation, probe labeling was competed with S-hexylglutathione, a GSH conjugate incapable of forming disulfide bonds. S-hexylglutathione inhibits GSH-ABP-G labeling of GSTs in a concentration dependent manner, with an effective concentration of 1.77 µM (to 10 µM probe), providing confirmation of the GSH-ABP-G probe's G site specificity (FIG. 17).

To confirm that the GST-ABP-H probe targets the H site of GSTs, competition of GST-ABP inhibition by the G site inhibitor S-hexylglutathione was compared to competition by ethacrynic acid, a known H site inhibitor. Results are summarized in FIG. 17. S-hexylglutathione shows significant inhibition of GST-ABP-H probe labeling with an $EC_{50}$ of 41.5 µM (FIG. 17). It is plausible that this competition is due to a known interaction between S-hexylglutathione's conjugated hexyl moiety and the GST H site. Although the G site inhibitor decreases GST-ABP-H binding, the H site inhibitor, ethacrynic acid, was expected to be much more effective. Ethacrynic acid was nearly 12× more potent in inhibiting GST-ABP-H enzyme labeling compared to S-hexylglutathione, indicating that the GST-ABP-H selectively targets GST H sites (FIG. 17). GST-ABP-G labeling also was competed with ethacrynic acid; it was found to inhibit GST-ABP-G labeling at 0.44 µM (to 10 µM probe). Thus, ethacrynic acid may block both GSTA-ABP-G and GST-ABP-H access to the G site. It is also possible that the presence of ethacrynic acid in the H site interferes with the alkyne and benzophenone moieties of GST-ABP-G that likely reside in the H site.

To determine specific labeling of GSTs and GSH-binding proteins, proteomic analysis of S-hexylglutathione competed liver cytosol (FIGS. 16A and 16B) was performed. GST-ABP-H and GSH-ABP-G labeling of GSTA3, M1, and P1 was significantly inhibited by S-hexylglutathione (fold change>3.0, p≤0.05) and were the top three of all inhibited targets when sorted by fold-change repression, indicating that both probes are labeling the active site of GSTs.

The described subsite complementarity of the probes provide a unique approach to examine each probe's enzyme specificity. Competition with Dichlon selectively inhibits labeling of a 24 kDa protein, the approximate weight of several GSTs. This inhibition may be due to competition between Dichlon and the thiol-appended alkyne/benzophenone moiety for H site occupancy. As such, not only do these results suggest that the GSH-ABP-G is binding within the GST active site, they also provide further evidence that Dichlon, the GST-ABP-H parent molecule, binds within the GST active site. LC-MS was performed on Dichlon (25 µM) competed GSH-ABP-G labeled mouse liver cytosol (FIG. 16A). GSH-ABP-G labeling of GSTP1, M4, A3, M1, K1, and M2 was significantly inhibited when competed with Dichlon (FC>2, p≤0.05), which indicates that the GST-ABP parent molecule selectively inhibits a variety of GST classes near the same binding region as the GSH-ABP-G, further confirming that the GST-ABP-H is binding to the active site of GSTs. To investigate the effects of the addition of the alkyne clickable functional group on the reactivity of the GST-ABP-H's Dichlon moiety, GST-ABP-H labeling of mouse liver cytosol was competed with Dichlon. Inhibition resulted in decreases in all measurable fluorescent bands, indicating that the alkyne-appended clickable functional group does not significantly affect reactivity.

To differentiate between the general reactivity of the GST-ABP-H versus its activity-specific labeling, competitive probe labeling using N-ethylmaleimide (NEM), a reagent commonly used to alkylate cysteine residues of proteins (FIG. 16B), was performed. Proteomic analysis of 100 μM NEM competed GST-ABP-H labeling failed to compete for binding of most GST isoenzymes, indicating that cysteine binding may not be the primary amino acid targeted by GST-ABP-H. In combination with previous studies, these results are suggestive that tyrosine is the primary residue irreversibly bound by GST-ABP-H.

Figure 18A:
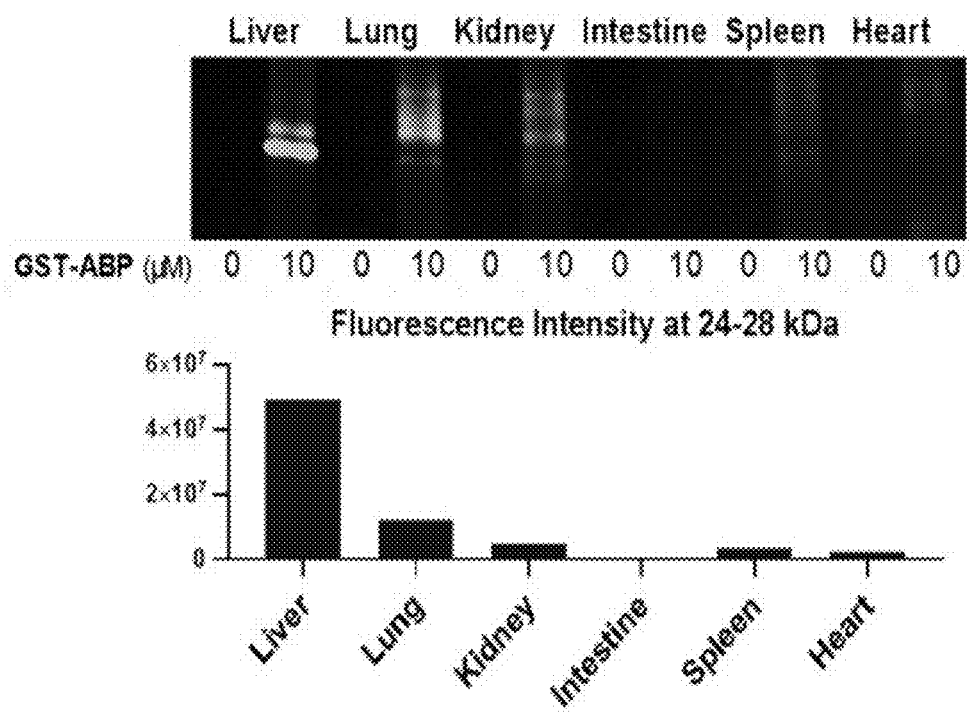
FIG. 18A shows the organ distribution of GST activity using the GSH-ABP and a GST-ABP, and a GST activity assay, wherein the SDS-PAGE fluorescence of GSH-ABP is shown.
Figure 18B:
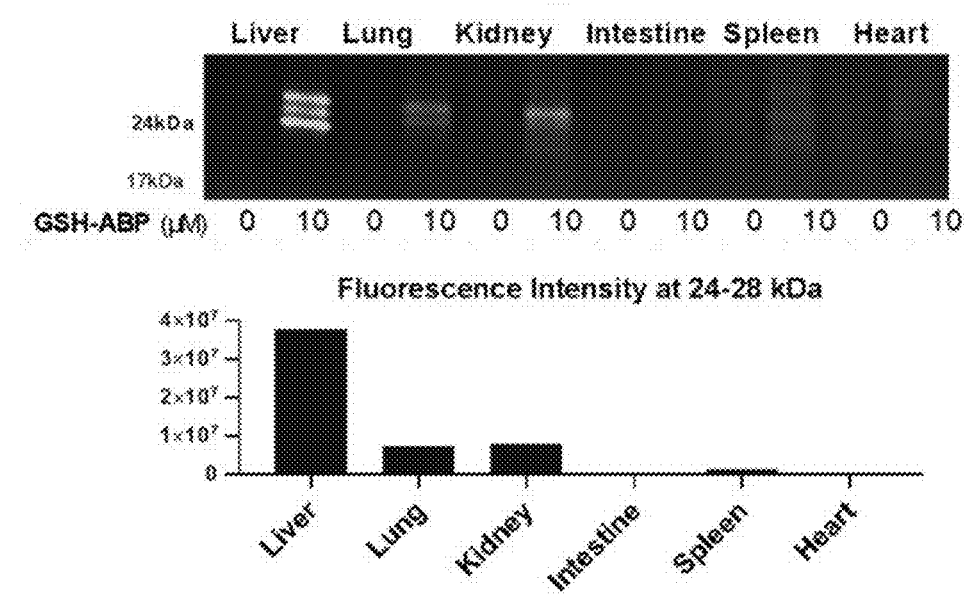
FIG. 18B shows the organ distribution of GST activity using the GSH-ABP and a GST-ABP, and a GST activity assay, wherein the SDS-PAGE fluorescence of GST-ABP is shown.
Figure 18C:
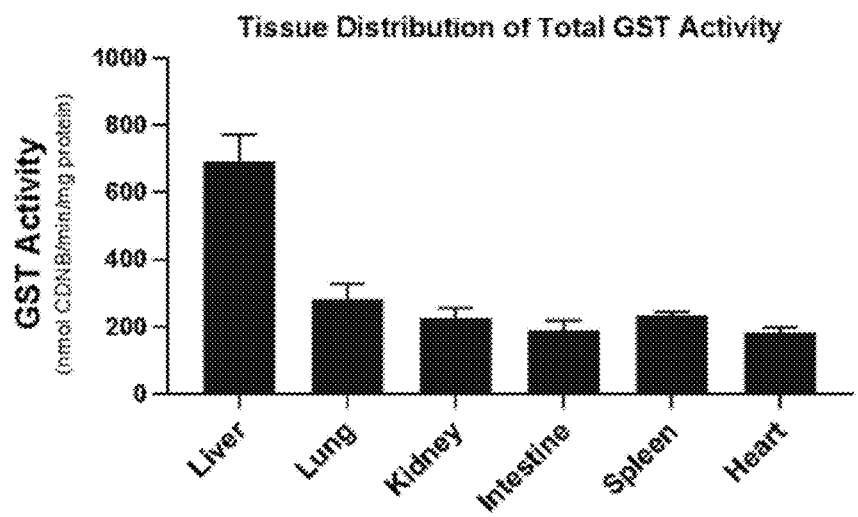
FIG. 18C shows results from labeled mouse liver, lung, kidney, intestine, spleen, and heart cytosol showed total fluorescence intensity of 24-28 kDa bands corresponding with total GST activity.
Figure 18D:
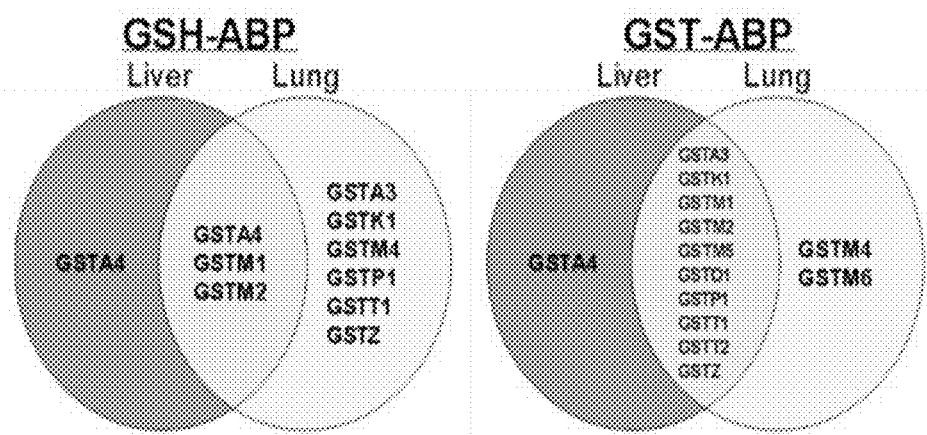
FIG. 18D is a Venn diagram of GSH-ABP and GST-ABP lung and liver GST targets.

Next the ability of the probed to detect changes in site-specific GST activity of organs relevant to xenobiotic metabolism including liver, lung, kidney, intestine, spleen, and heart lysates was evaluated. GST activity determined via probe labeling and fluorescence gel imaging was compared with a colorimetric GST activity assay that measures the total conglomerate of GST activity (FIGS. 18A-18D). Fluorescence intensity of ABP labeling was determined by quantification of the fluorescence signal. Liver GST activity was highest by ABP labeling, followed by lung and kidney. These measurements closely correspond with total GST activity determined by the colorimetric assay. Proteomics studies on lung lysate were then conducted. 11 GST isoenzymes were enriched by GST-ABP-H, and 3 GST enzymes were enriched by GSH-ABP-G (FIG. 18D). Both probes showed high enrichment of lung GSTA4, a protein not significantly enriched by either probe in liver lysate. While GST-ABP-H and GSH-ABP-G show enrichment of GSTM4 in the liver, no activity was detected in lung lysate. GST-ABP-H also enriches GSTM6 in liver lysate, but not lung. This is in agreement with mRNA expression analyses and data showing that these enzymes show decreased expression in mouse lung in comparison to liver. This data demonstrates the effectiveness of these complementary probes to examine the tissue-specific contribution of GSTs in xenobiotic metabolism.

To validate that the probes detect physiologically relevant alterations to GST activity, ABP-determined GST activity in intestines of mice fed standard (10% fat) or high fat, obesogenic, chow (60% fat) over a 20-week period was compared. Statistically significant alterations in several GST isozymes were seen in response to diet-induced obesity, including members of mu and pi GST classes. The activity increases in intestinal GSTs in obese mice is likely a response to oxidative stress resulting from obesity.

Example 3

NMR spectra were recorded on a 499.8 MHz $^1$H, 125.7 MHz $^{13}$C NMR spectrometer at 25° C. Chemical shifts are reported in parts per million (ppm-δ) referenced to the NMR solvent residual peak, and coupling constants (J) are in hertz (Hz) and multiplicities indicated with: singlet (s), doublet (d), triplet (t), doublet of doublets (dd), doublet of triplets (dt), doublet of doublet of doublets (ddd), and multiplet (m) as recorded. Silica gel flash column chromatography was used to purify all compounds using Biotage purification system and prepacked columns for the same were obtained from Luknova. Reagents and solvents were obtained from commercial suppliers and were used as-is without further purification. Wherever necessary, anhydrous solvents were obtained from our in-house solvent purification system. All reactions were monitored using TLC and Thermo Scientific LTQ-MS. Reactions were carried out under nitrogen (N$_2$) atmosphere wherever necessary. For characterization of new compounds, $^1$H, $^{13}$C NMR, $^{19}$F and LTQ-MS data has been included, whereas for known compounds only $^1$H NMR data is reported along with appropriate literature reference.

Process for Synthesizing GST-AB-H Probes:

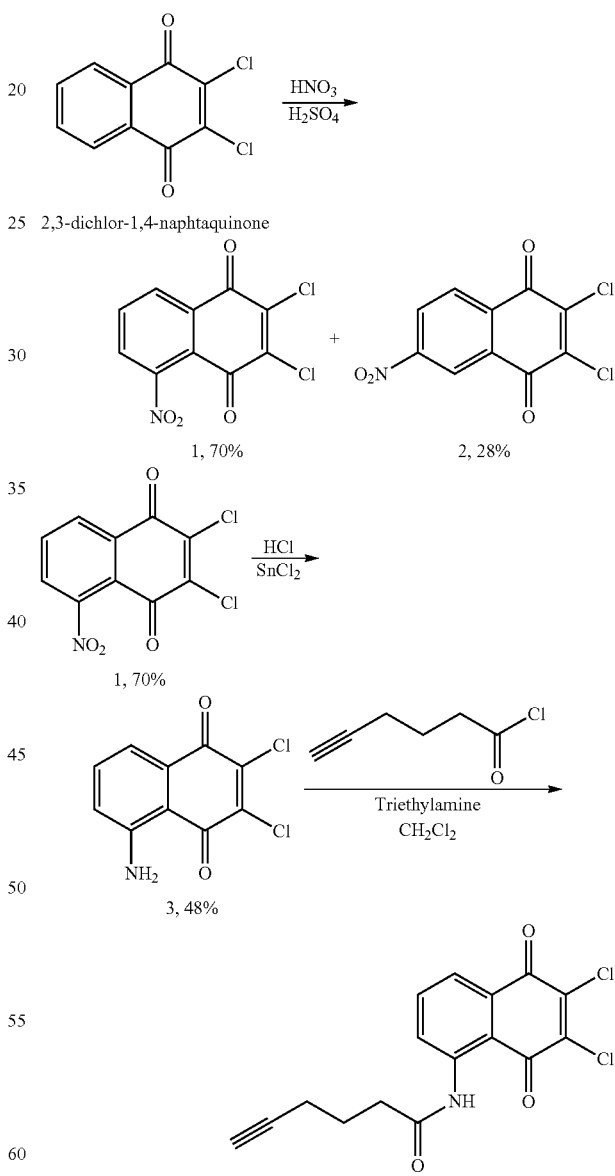

Figure 19:
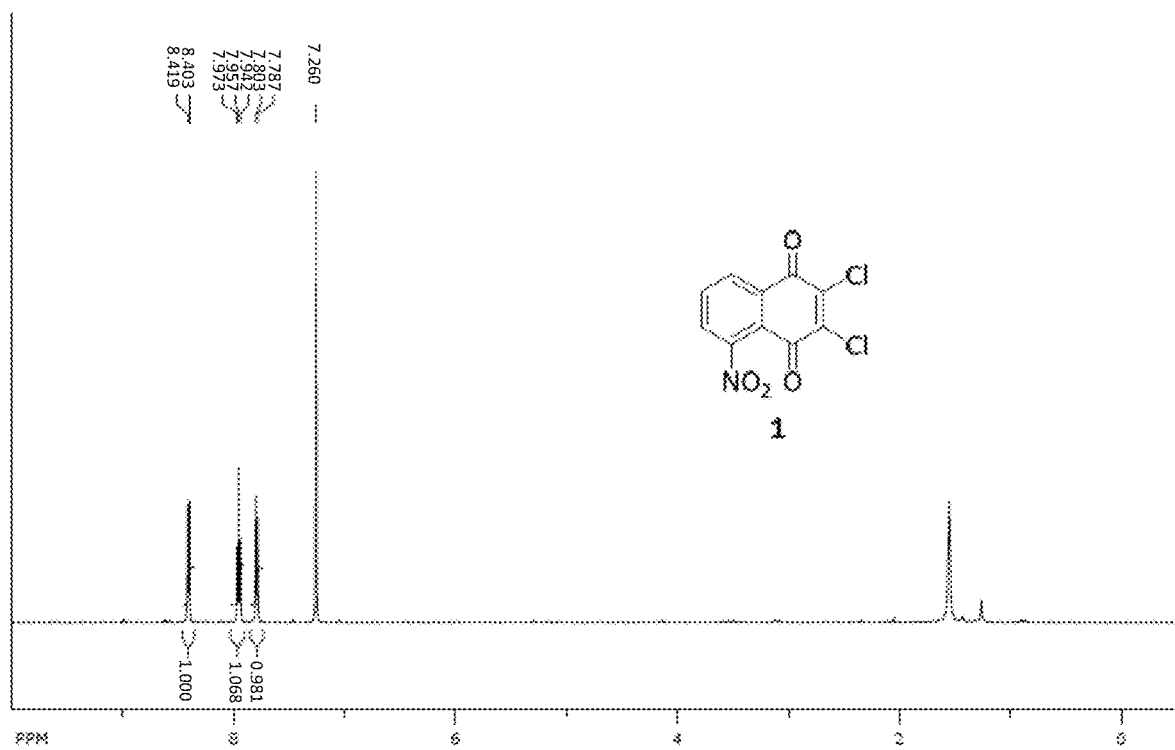
FIG. 19 is a $^1$H-NMR spectrum of a probe embodiment precursor.
Figure 20:
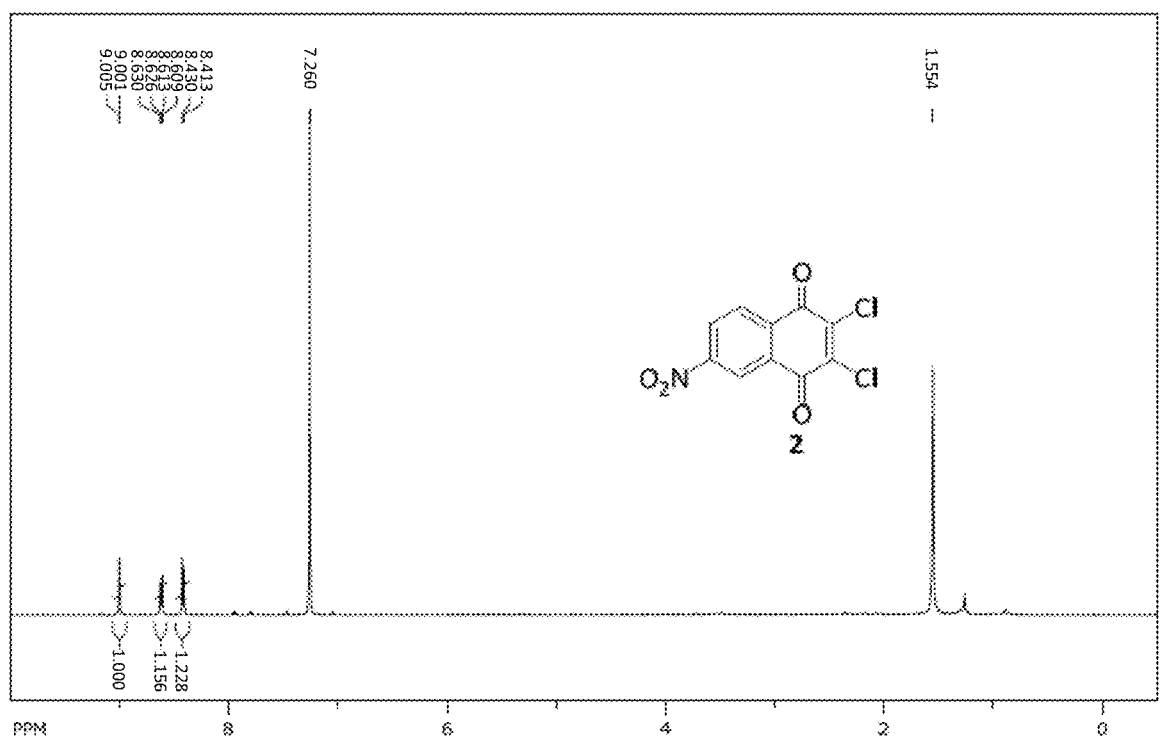
FIG. 20 is a $^1$H-NMR spectrum of a probe embodiment precursor.

2,3-dichloro-5-nitronaphthalene-1,4-dione 2,3-dichloro-1,4-naphthoquinone (5 g, 0.022 mmol) was slowly added to a mixture of fuming HNO$_3$ (15 g) and concentrated H₂SO₄ (50 g) and heated at 70° C. with stirring for 3 hours. The dark brown solution was then poured into ice-water (200 mL) to give bright yellow solid which was collected by filtration and washed with water. Flash chromatography separation with EtOAc/Hexane (20:80) gave two fractions of which were lyophilized after freezing in solution of acetonitrile and water to give a mixture of 2,3-dichloro-5-nitronaphthalene-1,4-dione (1, 3.91 g, 70%) and 2,3-dichloro-6-nitronaphthalene-1,4-dione (2, 1.68 g, 28%) as yellow solids. Compound 1: $^1$H NMR (CDCl₃, 500 MHz): δ 8.40 (d, J=7.9, 1H), 7.95 (t, J=7.7 Hz, 1H), 7.79 (d, J=7.9 Hz, 1H) ppm (FIG. 19); Compound 2: $^1$H NMR (CDCl₃, 500 MHz): δ 9.00 (br s, 1H), 8.64 (dd, J=8.5, 2.0 Hz, 1H), 8.42 (d, J=8.5 Hz, 1H) (FIG. 20).

Figure 21:
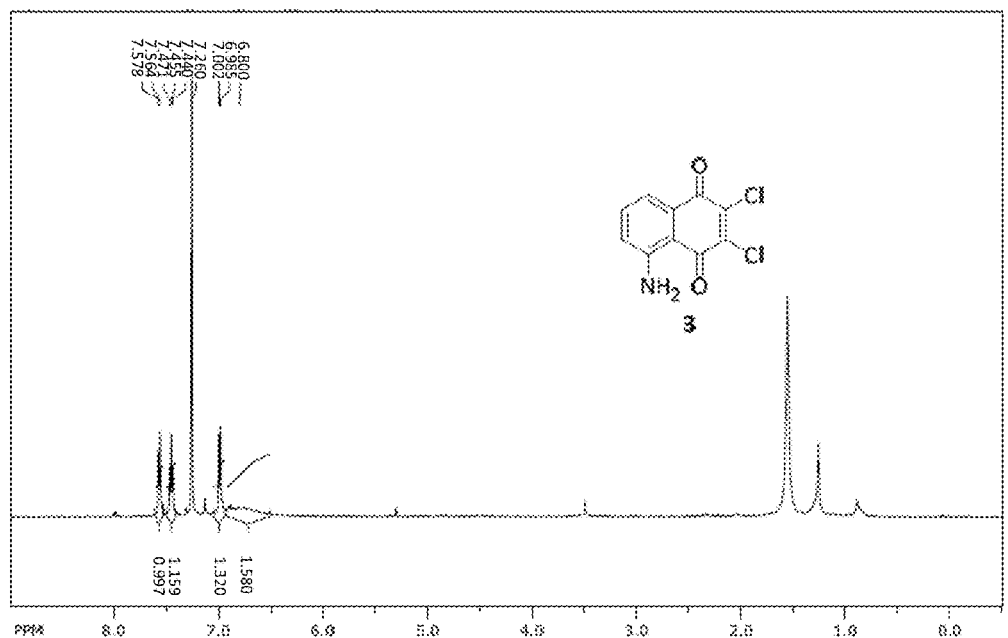
FIG. 21 is a $^1$H-NMR spectrum of a probe embodiment precursor.

5-amino-2,3-dichloronaphthalene-1,4-dione 2,3-dichloro-5-nitronaphthalene-1,4-dione (1) (0.501 g, 1.84 mmol) was suspended in concentrated hydrochloric acid (30 mL). SnCl₂ (2.61 g, 13.78 mmol) was added to this mixture and allowed to stir at 75° C. for 30 minutes. After confirming the disappearance of 1 by TLC, the reaction mixture was cooled to room temperature. The contents were transferred to 500 mL Erlenmeyer flask containing ice and placed in an ice bath. A 10 M solution of NaOH was slowly added under constant stirring until all the effervescence had ceased. After confirming the pH of this solution was above 9, the contents were transferred to a separatory funnel and extracted with CH₂Cl₂. The organic layer was washed with water and brine, dried over sodium sulfate and evaporated solvent on a rotatory evaporator to amine 3 as a purple solid (0.215 g, 48%). $^1$H NMR (CDCl₃, 500 MHz): δ 7.56 (d, J=8.5 Hz, 1H), 7.7 (t, J=7.7 Hz, 1H), 6.95 (d, J=8.6 Hz, 1H), 6.80 (br, 2H) ppm (FIG. 21).

Figure 22:
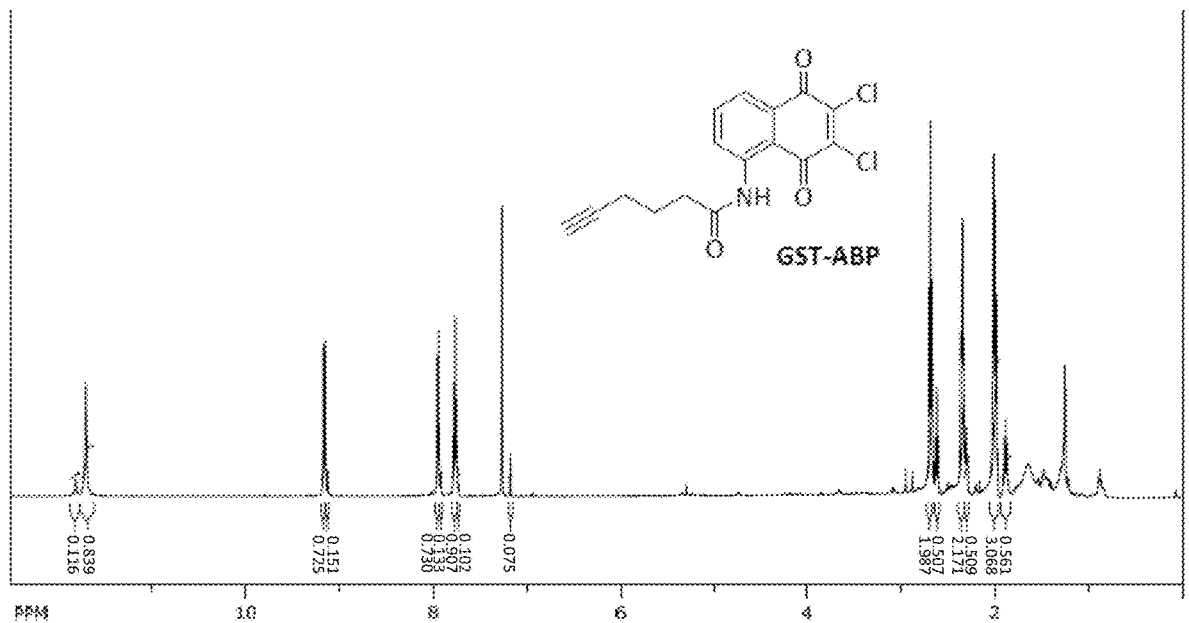
FIG. 22 is a $^1$H-NMR spectrum of a probe embodiment described herein.
Figure 23:
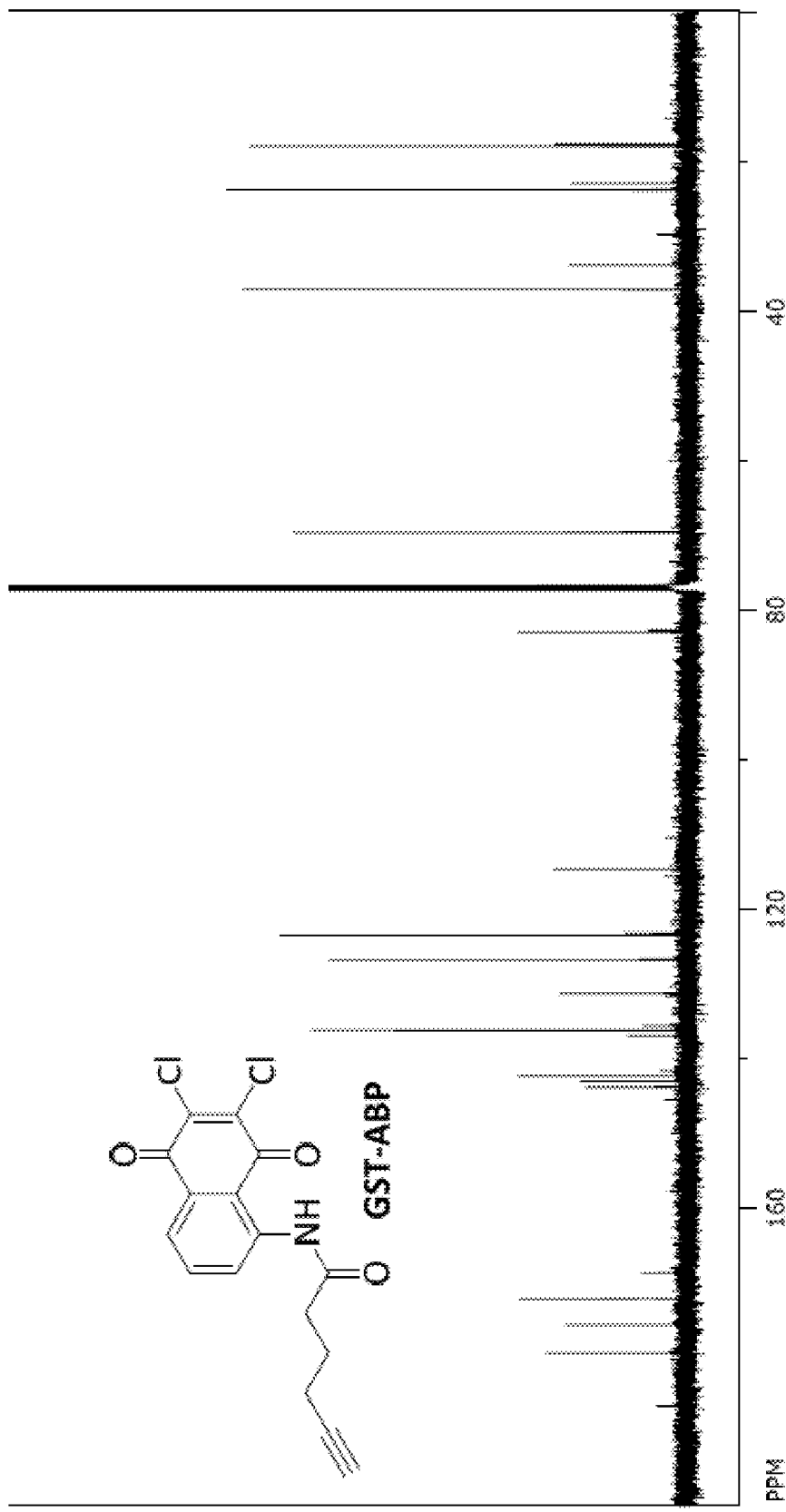
FIG. 23 is a $^{13}$C-NMR spectrum of a probe embodiment described herein.

N-(6,7-dichloro-5,8-dioxo-5,8-dihydronaphthalen-1-yl)hex-5-ynamide 3 (0.025 g, 0.103 mmol) was added to a flask containing methanol (20 mL) and triethylamine (0.030 g, 0.210 mmol) and allowed to stir for 10 minutes. Freshly prepared 5-hexynoyl chloride (0.030 g, 0.211 mmol) was added to the reaction mixture and allowed to stir for 2 hours. After completion of reaction by TLC and LTQ-MS (m/z 336.01-M+H), the reaction was quenched with water and extracted with CH₂Cl₂ using a separatory funnel. The organic layer was washed with water, brine, dried over sodium sulfate and evaporated using a rotatory evaporator to give an orange solid. Final purification using flash chromatography (1:1, Hexane:Ethyl Acetate) yield 4 as an orange solid (23 mg, 65%). $^1$H NMR (CDCl₃, 500 MHz): δ 11.71 (s, 1H), 9.16 (d, J=9.0 Hz, 1H), 7.95 (d, J=7.5 Hz, 1H), 7.76 (t, J=8.0 Hz, 1H), 2.69 (t, J=7.3 Hz), 2H), 2.35 (dt, J=6.5, 2.0 Hz, 2H), 2.01-1.97 (obscured m, 3H), ppm (FIG. 22); $^{13}$C NMR (CDCl₃, 125 MHz) δ 179.5, 175.7, 172.2, 142.3, 136.9, 135.7, 134.1, 131.3, 126.8, 123.5, 114.7, 82.9, 69.5, 37.0, 33.7, 23.7, 22.8, 17.8 ppm (FIG. 23); LTQ-MS Calcd for C₁₆H₁₁Cl₂NO₂—335.011; found 335.011.

Process for Synthesizing GSH-ABP-G Probes:

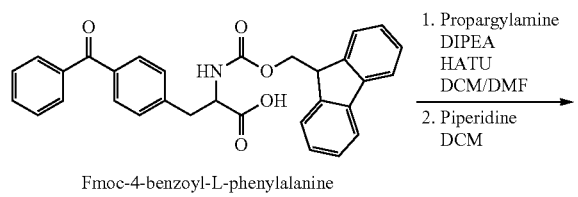

Fmoc-4-benzoyl-L-phenylalanine

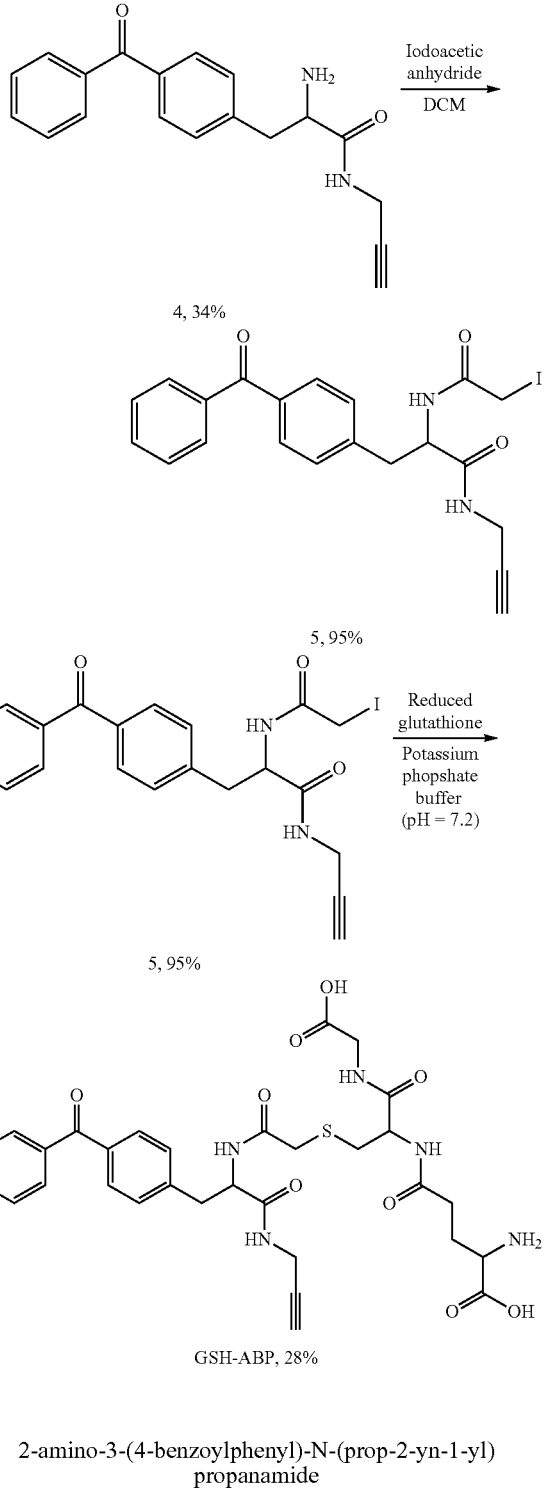

2-amino-3-(4-benzoylphenyl)-N-(prop-2-yn-1-yl) propanamide

Figure 24:
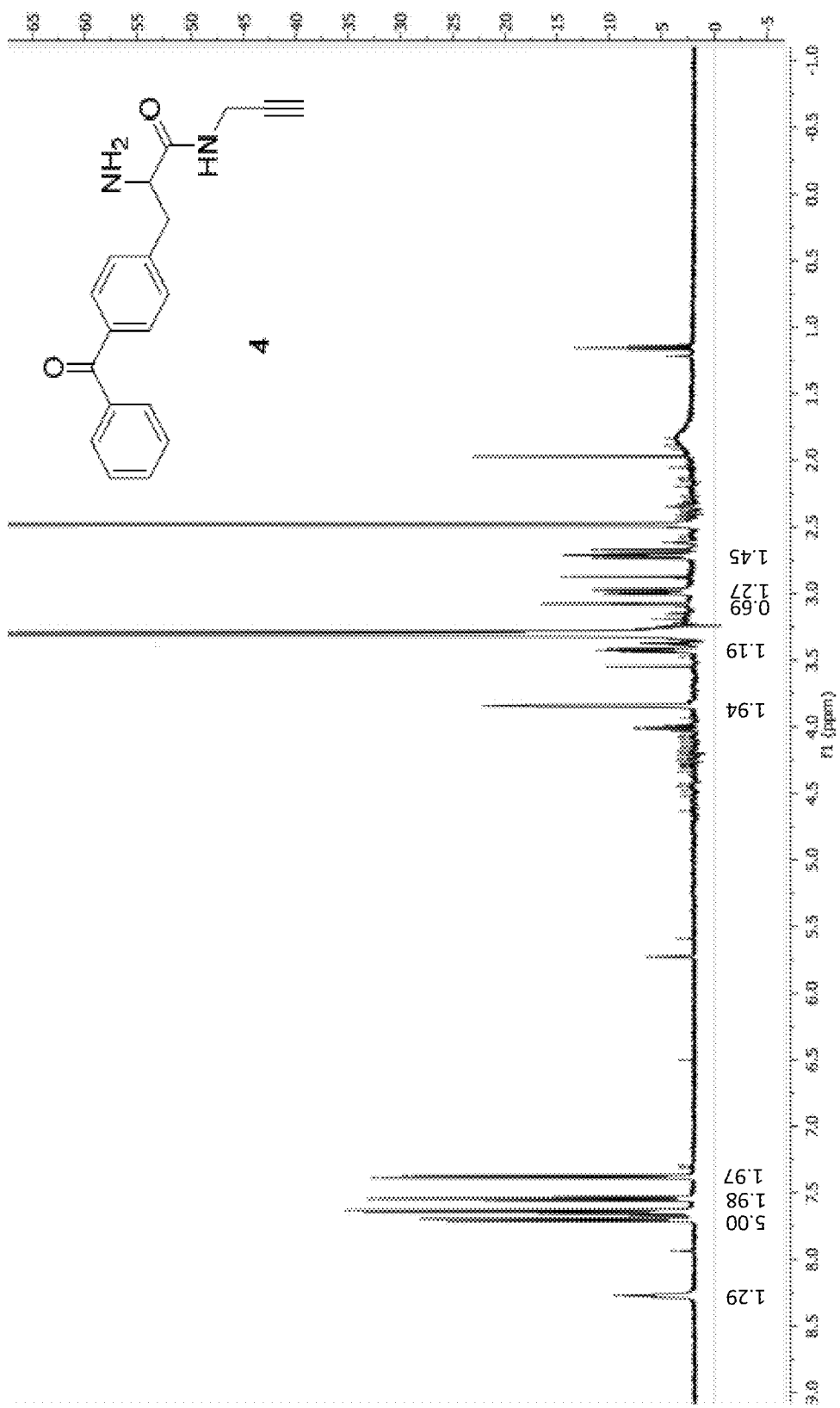
FIG. 24 is a $^1$H-NMR spectrum of a probe embodiment precursor.
Figure 25:
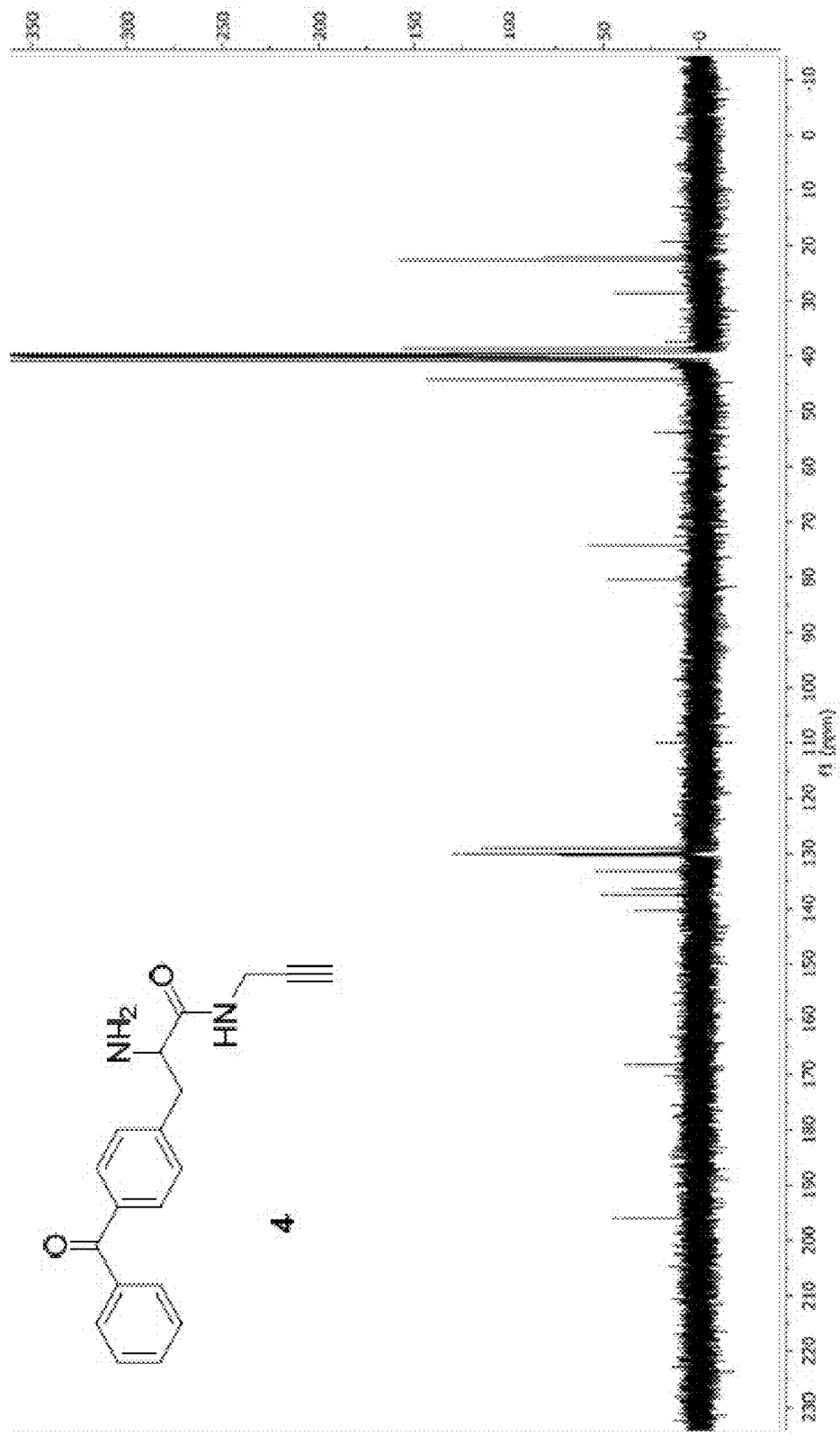
FIG. 25 is a $^{13}$C-NMR spectrum of a probe embodiment precursor.

Fmoc-4-benzoyl-L-phenylalanine (1.00 g, 2.03 mmol) was added to a round bottom flask containing DCM (10 mL). DIPEA (3.54 mL, 20.3 mmol) was added to the flask, followed by HATU (1.08 g, 2.84 mmol). DMF (1.50 mL) was added to fully solubilize the reagents. The reaction mixture was stirred for 30 minutes. Propargylamine (0.156 mL, 2.44 mmol) was added to the reaction mixture and allowed to stir for 6 hours at room temperature. The reaction mixture was added to a brine solution (100 mL) and extracted 3 times with DCM (20 mL) in a separatory funnel. The organic layers were combined, dried over sodium sulfate, and the DCM removed by rotary evaporation to yield a crude yellow oil. DCM (8 mL) was added to the yellow oil, followed by piperidine (2.0 mL, 20.24 mmol) and allowed to stir for 30 minutes. The DCM was removed by rotary evaporation and the product was purified using a linear gradient of DCM to MeOH (0-20% MeOH) to obtain 4 as a yellow oil (0.21 g, 34%). $^1$H NMR (DMSO-d6, 500 MHz): δ 8.27 (t, J=5.4 Hz, 1H), 7.72-7.62 (m, 5H), 7.57-7.52 (m, 2H), 7.40-7.35 (m, 2H), 3.86-3.82 (m, 2H), 3.43 (dd, J=8.2, 5.2 Hz, 1H), 3.09-3.06 (m, 1H), 3.01-2.68 (m, 2H) ppm (FIG. 24); $^{13}$C NMR (DMSO-d6, 125 MHz): δ 195.97, 168.21, 140.27, 137.44, 136.46, 133.22, 130.33, 130.18, 130.01, 129.05, 80.48, 74.27, 53.79, 38.68, 28.65 ppm (FIG. 25); LTQ-MS Calcd for $C_{19}H_{18}N_2O_2$—306.14; found 307.22 (MH+).

Figure 26:
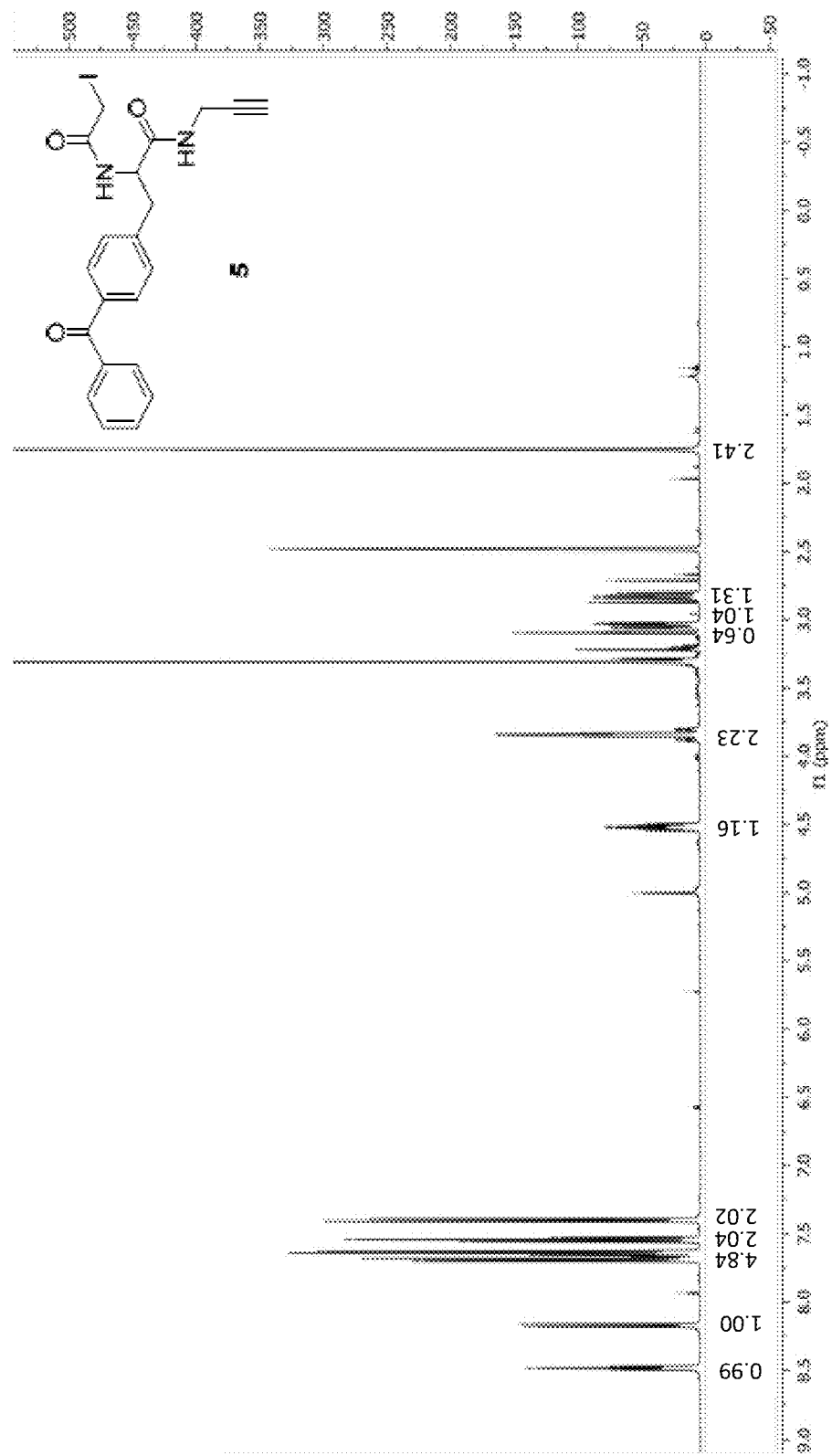
FIG. 26 is a $^1$H-NMR spectrum of a probe embodiment precursor.
Figure 27:
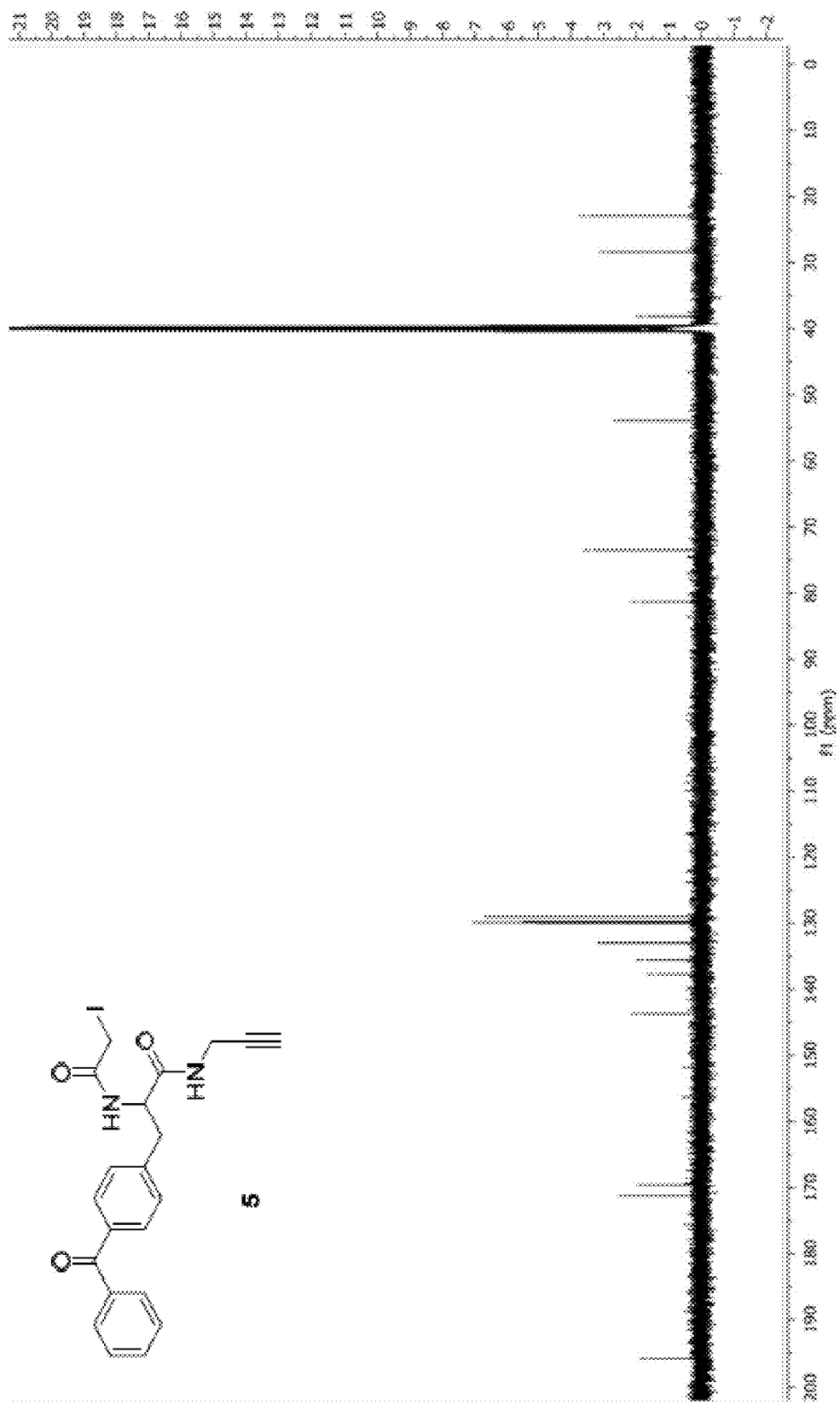
FIG. 27 is a $^{13}$C-NMR spectrum of a probe embodiment precursor.

3-(4-benzoylphenyl)-2-(2-iodoacetamido)-N-(prop-2-yn-1-yl)propanamide 4 (0.036 g, 0.12 mmol) was dissolved in DCM (1 mL) in a round bottom flask. Iodoacetic anhydride (0.10 g, 0.28 mmol) was added to the flask and stirred at room temperature for 15 minutes. The reaction mixture was purified via flash chromatography using a linear gradient of EtOAc to MeOH (0-20% MeOH). Solvents were removed from purified fractions by rotary evaporation to obtain 5 as a white solid (0.053 g, 95%). $^1$H NMR (DMSO-d6, 500 MHz): δ 8.49 (t, J=5.5 Hz, 1H), 8.17 (d, J=8.5 Hz, 1H), 7.72-7.61 (m, 5H), 7.58-7.51 (m, 2H), 7.43-7.37 (m, 2H), 4.52 (td, J=9.2, 4.9 Hz, 1H), 3.84 (td, J=5.0, 2.5 Hz, 2H), 3.11-3.09 (m, 1H), 3.07-2.80 (m, 2H), 1.75 (s, 2H) ppm (FIG. 26); $^{13}$C NMR (DMSO-d6, 125 MHz): δ 195.94, 171.24, 169.60, 143.70, 137.67, 135.52, 132.96, 130.00, 129.92, 129.79, 128.98, 81.35, 73.54, 53.92, 38.14, 28.44, 22.92 ppm (FIG. 27); LTQ-MS Calcd for C21H19IN2O3—474.04; found 475.08 (MH+).

Figure 28:
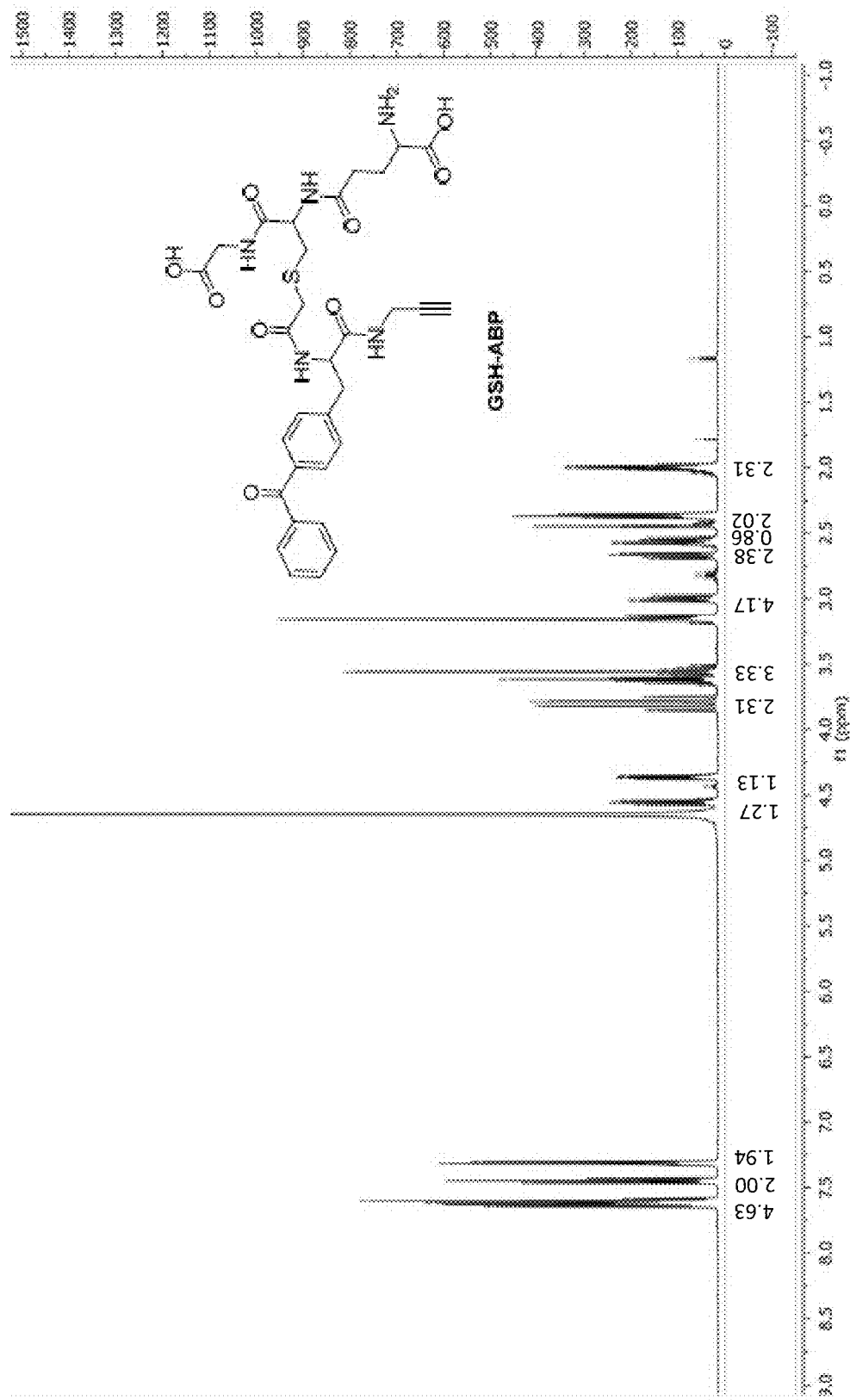
FIG. 28 is a $^1$H-NMR spectrum of a probe embodiment described herein.
Figure 29:
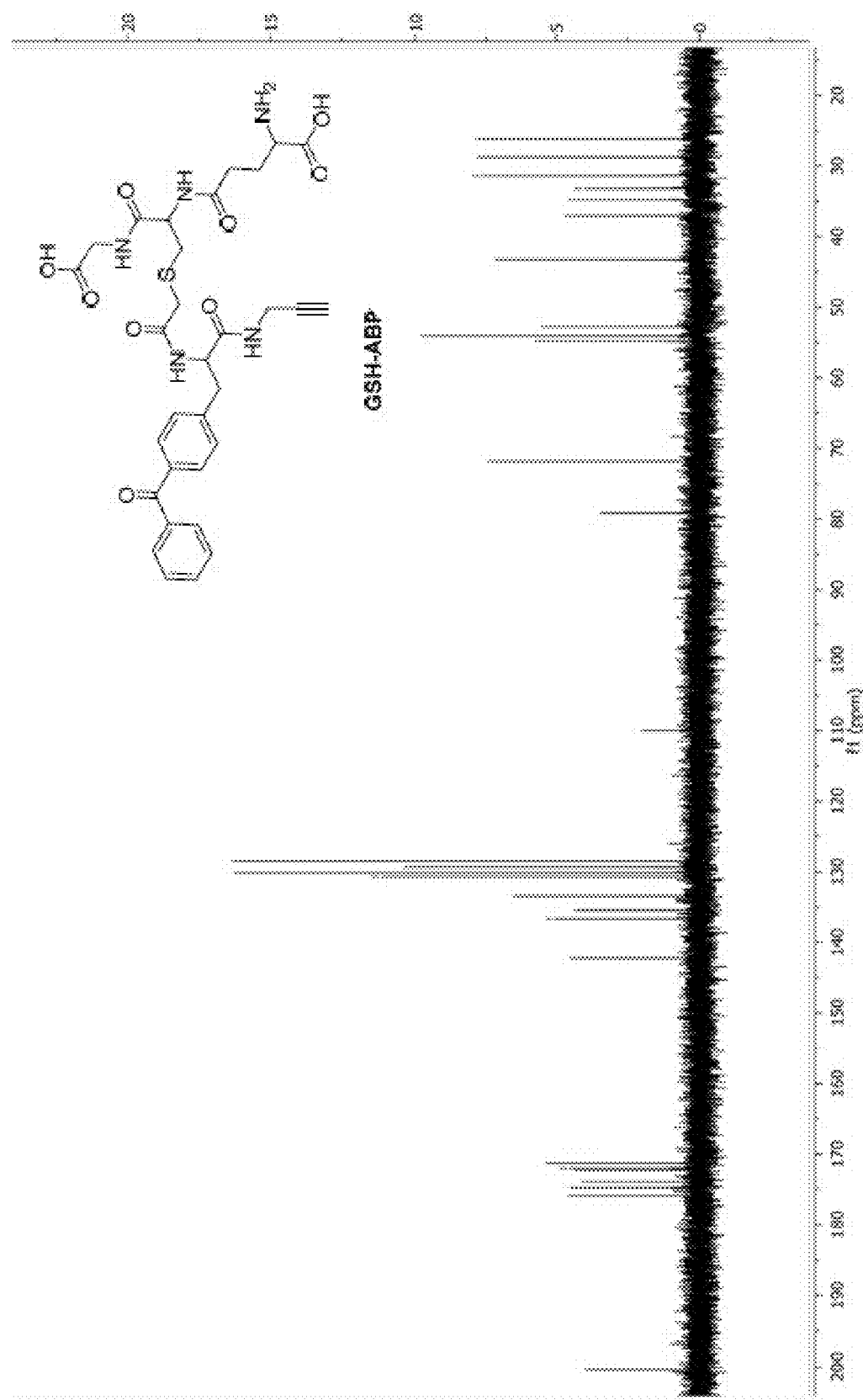
FIG. 29 is a $^{13}$C-NMR spectrum of a probe embodiment described herein.

N5-(3-((2-((3-(4-benzoylphenyl)-1-oxo-1-(prop-2-yn-1-ylamino)propan-2-yl)amino)-2-oxoethyl)thio)-1-((carboxymethyl)amino)-1-oxopropan-2-yl)glutamine 5 (0.048 g, 0.10 mmol) was dissolved in potassium phosphate buffer (10 mL, pH 7.2). Reduced glutathione (0.20 g, 0.65 mmol) was added slowly to the solution and stirred o/n at room temperature. The reaction mixture was then purified using reverse-phase flash chromatography with a linear gradient of H$_2$O to ACN (0-100% ACN). Purified fractions were rotary evaporated and lyophilized to obtain GSH-ABP as a white solid (0.019 g, 28%). +H NMR (D20, 500 MHz): δ 7.67-7.56 (m, 5H), 7.47-7.42 (m, 2H), 7.34-7.28 (m, 2H), 4.55 (dt, J=8.9, 6.8 Hz, 1H), 4.36 (dt, J=10.2, 5.1 Hz, 1H), 3.80 (qd, J=17.6, 2.5 Hz, 2H), 3.65-3.50 (m, 3H), 3.19-2.97 (m, 4H), 2.70-2.52 (m, 2H), 2.46-2.41 (m, 1H), 2.40-2.33 (m, 2H), 2.06-1.95 (m, 2H) ppm (FIG. 28); $^{13}$C NMR (D20, 125 MHz): δ 200.34, 175.94, 174.77, 173.90, 172.28, 171.98, 171.29, 142.21, 136.70, 135.46, 133.44, 130.72, 130.16, 129.31, 128.50, 79.17, 71.83, 54.80, 54.08, 52.76, 43.28, 36.99, 34.76, 33.22, 31.38, 28.69, 26.14 ppm (FIG. 29); LTQ-MS Calcd for C31H35N5O9S—653.22; found 652.28 (MH−).

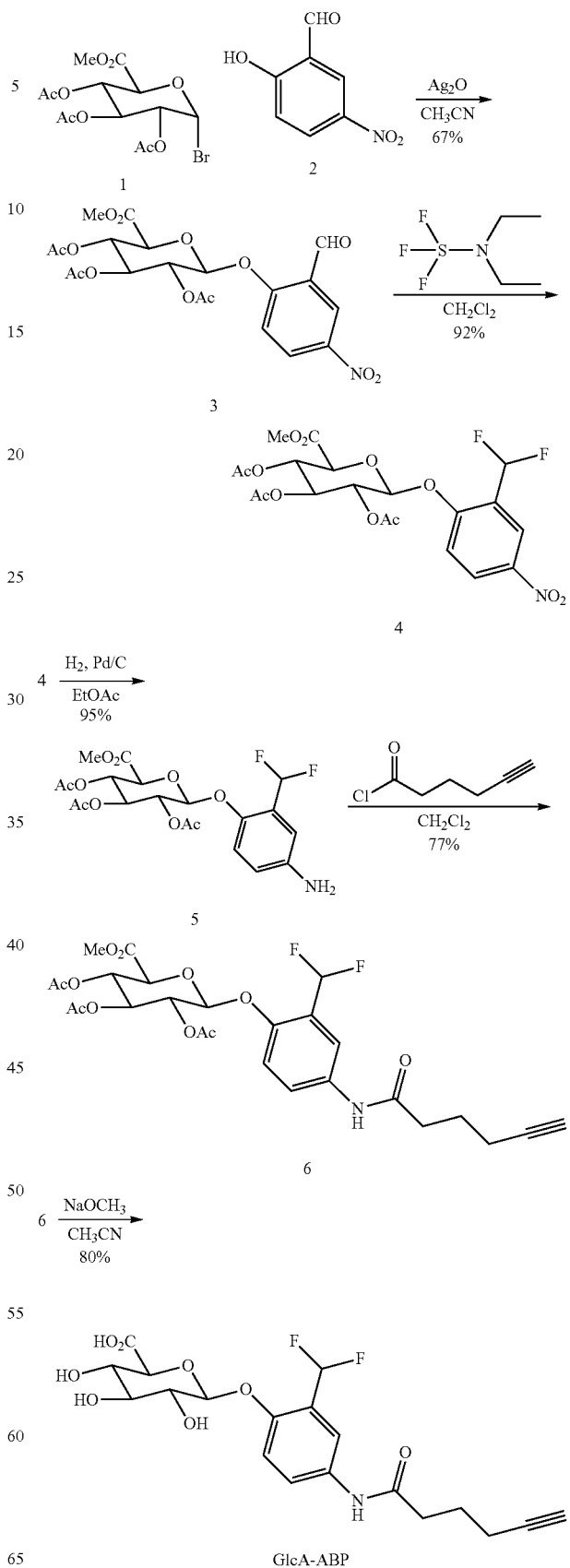

Preparation of 2-(2-formyl-4-nitrophenoxy)-6-(methoxycarbonyl)tetrahydro-2H-pyran-3,4,5-triyl triacetate (3)

A clean and dry 100 mL round bottom flask with stir bar was charged with 1 (0.749 g, 1.89 mmol), 2-hydroxy-5-nitrobenzaldehyde (0.316 g, 1.89 mmol), acetonitrile (50 mL) and allowed to stir for 5 minutes. $Ag_2O$ (0.435 g, 1.89 mmol) was carefully added to the reaction mixture and stirred at room temperature for 4 hours. After confirming completion of reaction by LTQ-MS (m/z 484; M+H) using a filtered aliquot giving desired mass, the reaction was stopped and Ag2O was filtered out over a celite bed. The solvents were removed using a rotary evaporator to give rise to a dark brown crude product, which was further purified using flash chromatography (ethyl acetate:hexanes; 1:2) to give the desired aldehyde 3 as a buff solid (0.62 g; 67%). $^1H$ NMR ($CDCl_3$; 500 MHz) δ 10.32 (s, 1H), 8.70 (br s, 1H), 8.41 (d, J=6.5 Hz, 1H), 7.28 (d, J=9.9 Hz, 1H), 5.46-5.39 (obscured m, 5H), 3.73 (s, 3H), 2.02 (m, 9H) ppm.

Preparation of 2-(2-(difluoromethyl)-4-nitrophenoxy)-6-(methoxycarbonyl)tetrahydro-2H-pyran-3,4,5-triyl triacetate (4)

Compound 3 (0.401 g, 0.83 mmol) was dissolved in anhydrous dichloromethane (50 mL), cooled in an ice bath and allowed to stir for 5 minutes under a constant purge of N2. Diethylaminosulfur trifluoride (DAST) (0.66 g, 4.2 mmol) was dissolved in anhydrous dichloromethane (5 mL) and added drop-wise to the reaction mixture following which the reaction mixture was stirred at 0° C. for 3 hours. After confirming the completion of reaction by TLC and LTQ-MS, the reaction was quenched by aqueous $NaHCO_3$ solution. The contents were transferred to a separatory funnel containing 50 mL dichloromethane and the organic layer was washed with water (3×25 mL) and brine (1×25 mL) following which the dichloromethane layer was separated, dried over anhydrous $MgSO_4$, and filtered. The solvent was evaporated using a rotary evaporator to obtain crude product which was further purified via flash chromatography using ethyl acetate:hexanes (1:2) to give 4 (0.39 g, 92%) as a white solid. $^1H$ NMR ($CD_3OD$; 500 MHz) δ 8.42 (s, 1H), 7.45 (d, J=9.0 Hz, 1H), 7.03-6.81 (br t, J=54.4 Hz, 1H), 5.67 (d, J=7.5 Hz, 1H), 5.50 (t, J=9.5 Hz, 1H), 5.32 (obscured t, 1H), 5.25 (t, J=9.5 Hz, 1H), 4.61 (d, J=9.5 Hz, 1H), 3.72 (s, 3H), 2.07-2.03 (br s, 9H) ppm.

Preparation of 2-(2-(difluoromethyl)-4-(hex-5-ynamido)phenoxy)-6-(methoxycarbonyl)tetrahydro-2H-pyran-3,4,5-triyl triacetate (6)

A clean and dry 50 mL round bottom flask with stir bar was flushed with N2 for 5 minutes, charged with compound 4 (0.201 g, 0.39 mmol) and dissolved in EtOAc (25 mL). To this was added activated (heated in oven at 105° C. overnight) Pd/C (0.4 g) was added and the reaction mixture was purged by bubbling $H_2$ gas (via a balloon) through the reaction mixture for 5 minutes. The reaction was then maintained under a balloon of $H_2$ for 15-20 hours. After confirming the completion of reaction by TLC (2:1 Hex/EtOAc), the $H_2$ balloon was carefully detached and reacting mixture was purged with N2. Under an N2 flow, the contents were filtered over a bed of Celite using dichloromethane as solvent. The filtrate was the concentrated by evaporating solvents using a rotatory evaporator to yield amine 5 (0.180 g, 95%) as a pale yellow solid, mass was confirmed using an LTQ-MS (m/z 476; M+H) and the compound was used in the subsequent step without purification.

To a 100 mL round bottom flask with stir bar was added 5-hexynoic acid (1.00 g), dissolved in dichloromethane (50 mL) and to this was added $SOCl_2$ (10 eq). The reaction mixture was refluxed for 6 hours, then solvents were evaporated using a rotatory evaporator to give hexynoyl chloride as a crude oil which was then reacted with Amine 5.

Amine 5 (0.125 g, 0.26 mmol) was dissolved in anhydrous dichloromethane (25 mL) containing trimethyl amine (0.080 g, 0.78 mmol) and stirred for 5 minutes. Hexynoyl chloride (0.070 g, 0.53 mmol) was dissolved in dichloromethane (2 mL) and slowly added to the reaction mixture dropwise over 5 minutes. The resulting solution was then stirred for 12 hours at room temperature eventually confirming the completion using LTQ-MS (m/z 570, M+H). The reaction mixture was diluted with dichloromethane (50 mL) and contents were transferred to a separatory funnel. The organic layer was washed with saturated $NaHCO_3$ (2×25 mL), $H_2O$ (2×30 mL) and brine (1×50 mL). The organic layer was dried over $Na_2SO_4$, filtered and concentrated by evaporating solvents using a rotary evaporator to give crude product, which was purified by flash column chromatography (1:1 EtOAc/Hex) to give 6 (0.161 g, 77%) as a white solid. $^1H$ NMR ($CD_3OD$, 500 MHz): δ 7.77 (s, 1H), 7.69 (d, J=9.0 Hz, 1H), 7.19 (d, J=9.0 Hz, 1H), 6.96-6.74 (br t, J(H,F)=55.5 Hz, 1H), 5.49-5.44 (obscured d, 1H), 5.40 (d, J=8.0 Hz, 1H), 5.26-5.20 (m, 2H), 4.52 (d, J=10.0 Hz, 1H), 3.73 (s, 3H), 2.50 (t, J=7.5 Hz, 2H), 2.30-2.27 (m, 3H), 2.04-2.03 (m, 9H), 1.91-1.87 (m, 2H); $^{13}C$ NMR ($CD_3OD$, 125 MHz): δ 172.3, 169.9, 169.7, 167.4, 134.3, 123.3, 117.3, 116.0, 98.7, 82.6, 71.6, 71.5, 70.7, 69.3, 68.9, 51.9, 35.0, 24.1, 19.0, 18.9, 17.2; $^{19}F$ NMR ($CD_3OD$, 470 MHz) −111.26, −111.38, −111.90, −112.02, −121.23, −121.34, −121.87, −121.98; HRMS m/z (M+H) calculated for $C_{27}H_{29}F_{29}NO_{11}$: 569.51, observed: 570.49.

Preparation of 6-(2-(difluoromethyl)-4-(hex-5-ynamido)phenoxy)-3,4,5-trihydroxytetrahydro-2H-pyran-2-carboxylic acid (GlcA-ABP)

6 (0.101 g, 0.175 mmol) was dissolved in anhydrous MeOH (20 mL) in a 100 mL round bottom flask and stirred for 5 minutes. $NaOCH_3$ in methanol (25% wt/v; 0.030 g, 0.536 mmol) was dissolved in methanol (5 mL) and added to the reaction mixture slowly by syringe. The reaction mixture stirred at room temperature for 3 hours. After confirming the completion of the reaction by LTQ-MS (m/z 428, M−H), the reaction was stopped and solvents were evaporated using a rotatory evaporator to leave a crude oil. Final purification via flash chromatography using 100% ethyl acetate gave GlcA-ABP as a yellow-brown solid (0.061 g, 80%). $^1H$ NMR ($CD_3OD$, 500 MHz): δ 8.53 (s, 1H), 7.80 (s, 1H), 7.62 (br d, J=7.5 Hz, 1H), 7.29 (obscured s, 1H), 7.27-7.06 (br t, J=55.5 Hz, 1H), 4.58 (br s, 1H), 3.78 (d, J=9.5 Hz, 1H), 3.57-3.55 (m, 1H), 3.54-3.51 (m, 2H), 3.35 (s, 1H), 2.50 (t, J=7.5 Hz, 2H), 2.30-2.27 (m, 3H), 1.93-1.87 (m, 2H); $^{13}C$ NMR ($CD_3OD$, 125 MHz): δ 172.3, 169.8, 168.8, 151.5, 149.3, 135.0, 133.7, 123.3, 117.1, 116.8, 82.7, 76.3, 75.2, 73.2, 72.0, 68.8, 35.0, 24.2, 17.2; $^{19}F$ NMR ($CD_3OD$, 470 MHz) −114.70, −114.81, 115.34, −115.46, −116.98, −117.09, −117.62, −117.74; HRMS m/z (M+) calculated for $C_{19}H_{21}F_2NO_8$: 429.37, observed: 428.11 [M−H].

Example 4

In this example, a representative device embodiment is made using the following steps. Fisherbrand microscope slides are cleaned by submerging the slides in ~100 mL of 20% nitric acid at 85 C for 2 hours. Slides are then removed and placed in a beaker full of milliQ $H_2O$. After soaking for 1 minute, slides are moved to a new beaker of milliQ $H_2O$ and allowed to sit for 5 minutes. Slides are then transferred to a 35% $H_2O_2$ solution at 75 C for 1 hour. Slides are then removed and placed in a beaker full of milliQ $H_2O$. After soaking for 1 minute, slides are moved to a new beaker of milliQ $H_2O$ and allowed to sit for 5 minutes. Slides are moved to a beaker of methanol and allowed to sit for 5 minutes. Slides are dried in 110 C oven for 1 hour (at least). A well cover is wetted with milliQ and attached to the surface of the slide. The well-attached slide is then placed back in the oven for 30 minutes to allow for drying. The device is tested for leaks by adding 1.6 mL milliQ to the surface. If no leaks are present after 10 minutes, discard the milliQ $H_2O$, place back in oven for ~15 minutes, and proceed directly to functionalization. Each slide is functionalized with 32 uL of triethoxysilaneamine in 1.568 mL (1.6 mL total) of a 3:1 milliQ:MeOH solution at pH~=4.5 (with acetic acid) overnight with rocking at room temperature. The slide is washed with DMSO 2×, ethanol 2×, then placed in the oven for 1 hour. A solution of 5 mg NHS-ester-PEG-azide in 1.5 mL DMSO+100 uL TEA is added to the slide and allowed to rock overnight at room temperature. The slide is washed with DMSO 3×. Click chemistry is performed for an individual slide with 1.6 mL total volume with DMSO as the solvent, 100 uM probe, and 20 uM CuI. The reaction is allowed to proceed overnight with rocking at room temperature. The slide is washed with DMSO 3×.

Example 5

In this example, a representative device is used to analyze a sample. In particular, the device (such as the functionalized substrate from Example 4 above) is washed 2× with an aqueous solution containing the biological sample (for example, PBS). The sample is applied to the functionalized device surface for 3 hours with rocking (room temperature or desired temperature). The slide is washed 1× with PBS. Then, the slide is washed 1× with 4% SDS with rocking at room temperature (5 minutes). Then, the slide is washed 2× with DMSO (5 minutes, then 30 minutes with rocking). Next, the slide is washed 1× with PBS, followed by washing 2× with PBS with 0.5% BSA with rocking at room temperature (first wash for 5 minutes, second wash for 30 minutes). Then the slide is washed 2× with 4% SDS with rocking at room temperature (first wash for 5 minutes, second wash o/n). Then the slide is washed 1× with PBS, 1× with milliQ. Then the slide is washed with 6M urea with rocking at room temperature (1 hour). Then the slide is washed 2× with 1M NaCl 2× (1 minute each). Then the slide is washed 2× with milliQ (1 minute each). Then the slide is washed 1× with 2.5 mM $NH_4HCO_3$ (pH 8) (5 minutes with rocking). Next, 1.59 mL 2.5 mM $NH_4HCO_3$ (pH 8) is added to each well. Dilute 20 ug trypsin (in vial) with 100 uL 2.5 mM $NH_4HCO_3$ (pH 8) is prepared and 10 uL trypsin solution (0.2 ug/uL) is added to each well surface (total 2 ug). The device is allowed to rock at room temperature overnight. The sample is collected and put in eppendorf tube. The sample is frozen and lyophilized and then resuspend in 50 uL 2.5 mM $NH_4HCO_3$ (pH 8). 10 uL is used for Quant-IT assay to determine protein concentration. Also, 40 uL of sample is transferred into glass ultracentrifuge tubes, which were spun down at 53,000 rpm in the TLA 120.1 rotor for 20 min. 25 uL of supernatant is collected and transferred into MS vial inserts for analysis.

Example 6

In this example, glass microspheres are used to provide a multiplexing device. To solution of lysate or pure protein (50 uL, typically 1 mg/mL) in Eppendorf tubes (1.5 mL best), is added bifunctional probe (100 uM) and incubated at 37° C. for 1 h with no agitation. To this solution is added DBCO-Rhodamine545 (100 uM) and incubated at 37° C. for 1 h with 500 rpm agitation. Washing with cold (−20° C.) MeOH (500-1000 uL) and centrifugation at 16×g for 2m at 4° C. are performed. Supernatant (will be bright pink, based on fluorophore used) is removed and repeat these three steps are repeated two times. Walls of the Eppendorf may be pink, this is normal. The sample is allowed to dry. Then, 5-10% suspension of functionalized azide microspheres in MeOH are added to protein-containing Eppendorfs. MS is pipetted into the bottom of the tubes and allow to dry completely (~30 m, depending on volume). 100 uL 0.4% BSA in PBS is added back, microspheres are resuspended by sonication, and then vortexing and manual agitation (tapping bottom of tube on the benchtop works well) are performed. After resuspending microspheres, click chemistry conditions (per 50 uL, NaAsc 250 mm, 0.5 uL, THPTA 200 mm, 0.25 uL, $CuSO_4$ 100 mm, 1 uL) are used and the samples are allowed to incubate at 37° C. for 1 h with 1500 rpm agitation. Microspheres at this stage are washed (only really need 0.4% BSA with PBS 2×) and used for fluorescence based readings. Once complete, samples are washed as follows: 1×0.4% BSA in PBS, 4% SDS in PBS, 6M Urea, 2M NaCl, then return to volume (100 uL) 25 mM $NH_4HCO_3$, pH 8. The samples can be prepared for proteomics with fresh trypsin (1 ng/uL), incubate 12-24 h at 37° C. no agitation. BCA can be performed to determine protein amount before preparing mass-spec samples.

In view of the many possible embodiments to which the principles of the present disclosure may be applied, it should be recognized that the illustrated embodiments are only preferred examples and should not be taken as limiting. Rather, the scope is defined by the following claims. We therefore claim as our invention all that comes within the scope and spirit of these claims.

SEQUENCE LISTING

<160> NUMBER OF SEQ ID NOS: 4

<210> SEQ ID NO 1
<211> LENGTH: 43
<212> TYPE: DNA
<213> ORGANISM: Artificial Sequence
<220> FEATURE:
<223> OTHER INFORMATION: uidA_F primer

```
<400> SEQUENCE: 1
aactttaaga aggagatata atgttacgtc ctgtagaaac ccc                43

<210> SEQ ID NO 2
<211> LENGTH: 59
<212> TYPE: DNA
<213> ORGANISM: Artificial Sequence
<220> FEATURE:
<223> OTHER INFORMATION: uidA_R primer

<400> SEQUENCE: 2
ttgttagcag ccggatctca ttaatggtga tggtgatggt gttgtttgcc tccctgctg   59

<210> SEQ ID NO 3
<211> LENGTH: 39
<212> TYPE: DNA
<213> ORGANISM: Artificial Sequence
<220> FEATURE:
<223> OTHER INFORMATION: pET_F primer

<400> SEQUENCE: 3
caccatcacc atcaccatta atgagatccg gctgctaac                     39

<210> SEQ ID NO 4
<211> LENGTH: 58
<212> TYPE: DNA
<213> ORGANISM: Artificial Sequence
<220> FEATURE:
<223> OTHER INFORMATION: pET_R primer

<400> SEQUENCE: 4
tatatctcct tcttaaagtt aaacaaaatt atttctagag gggaattgtt atccgctc    58
```

22. A probe selected from:
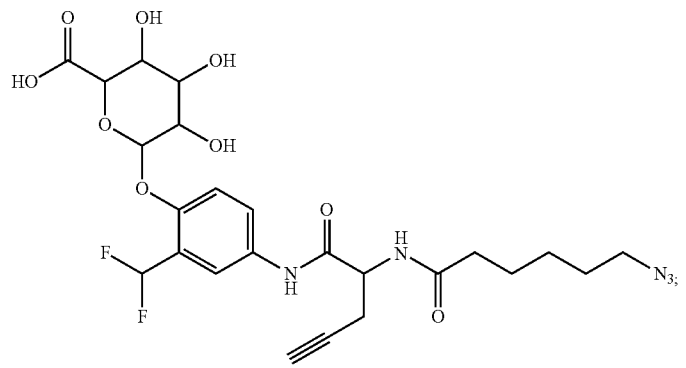
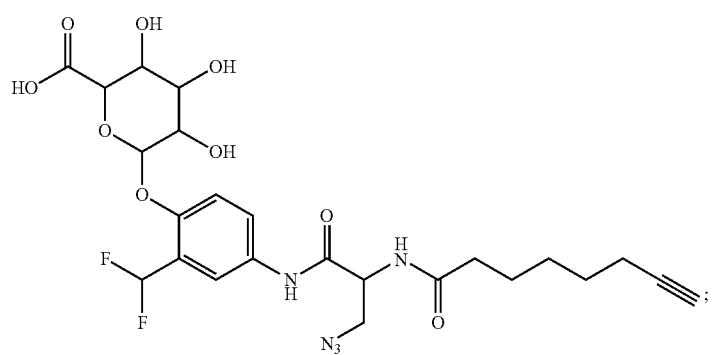
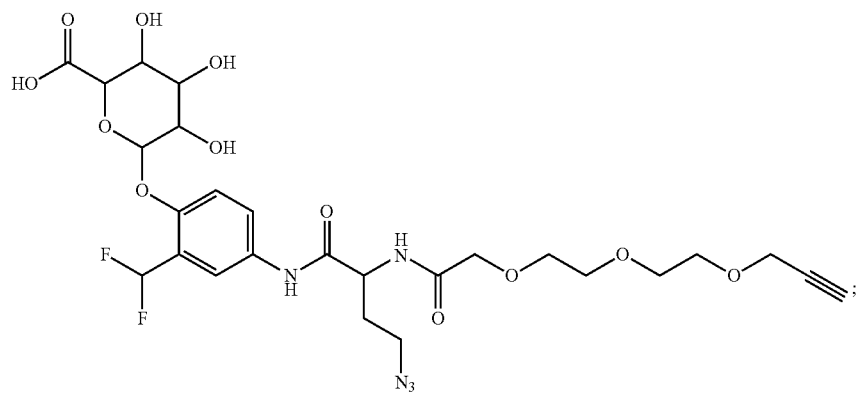
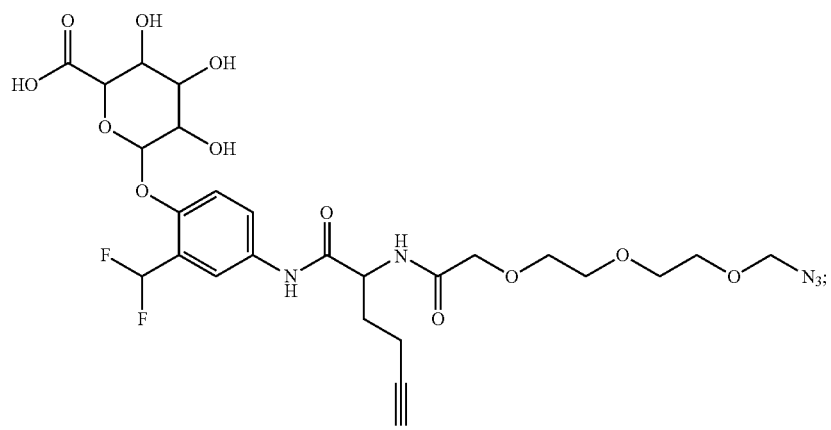

-continued
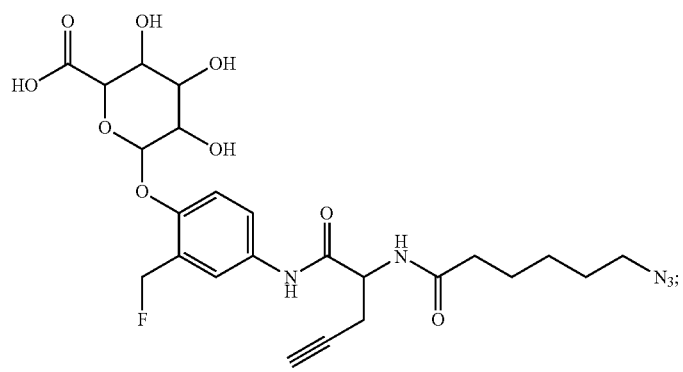
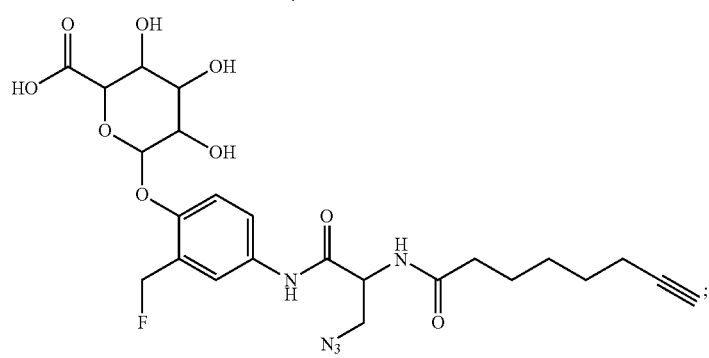
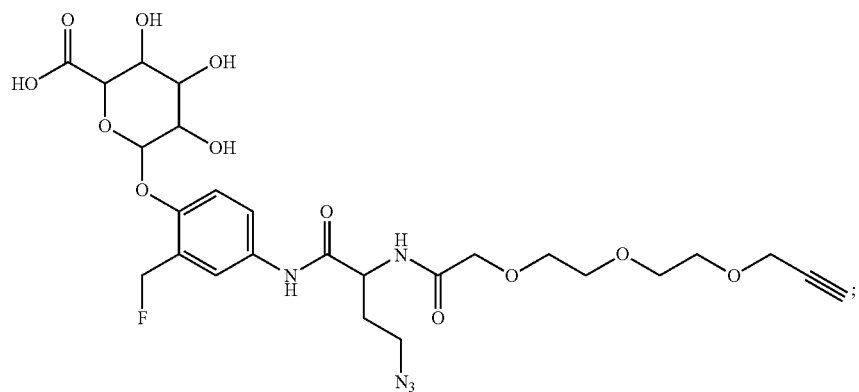
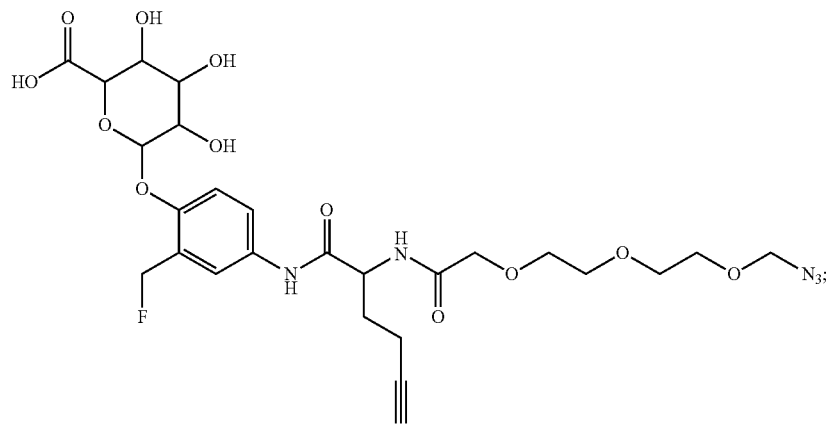

-continued
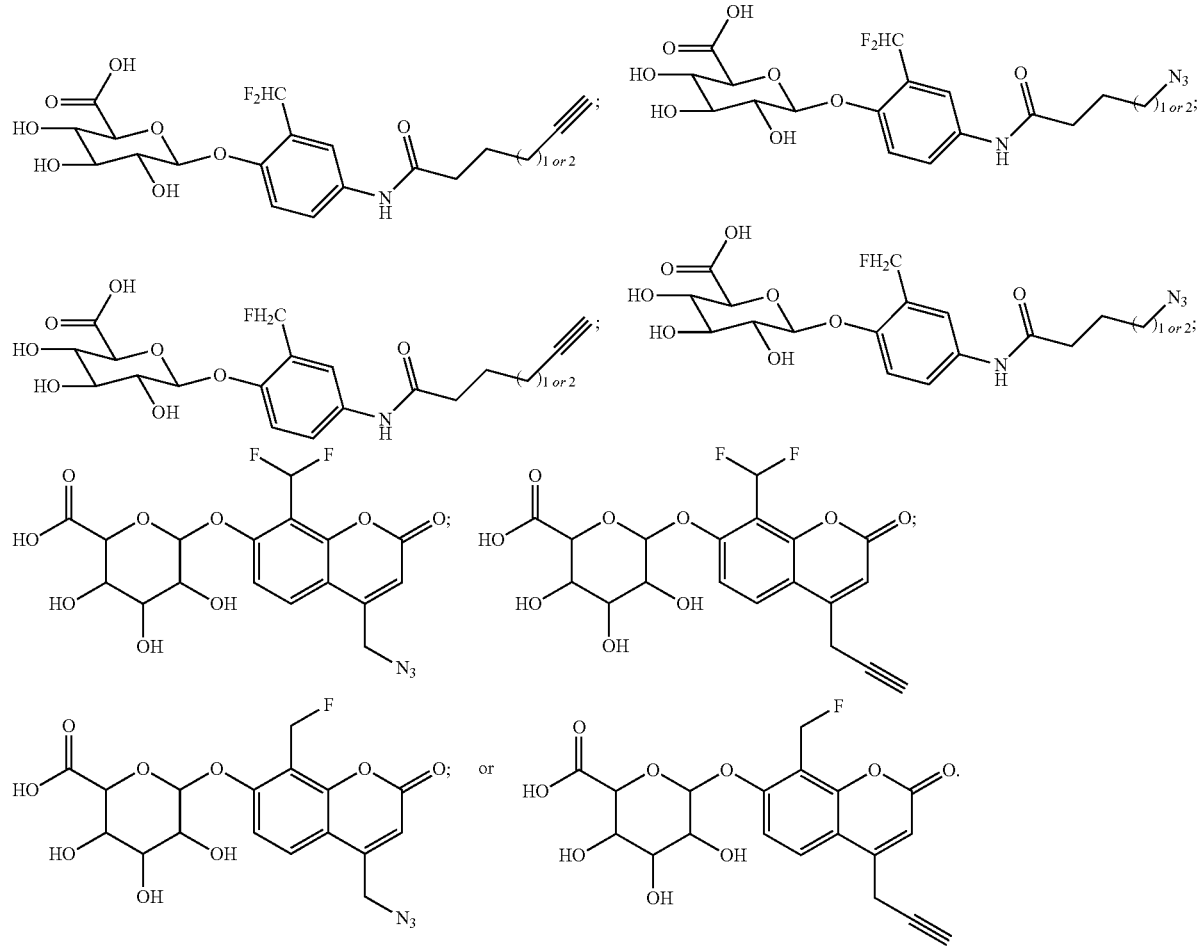

We claim:

1. A probe having a structure satisfying Formula II

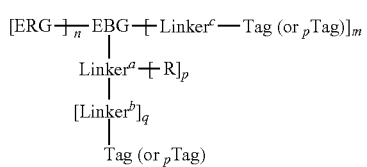

Formula II wherein

ERG, if present, is

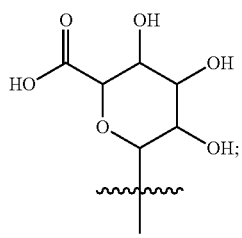

$S(O)_2OH$, or an anionic form thereof; $P(O(OH))_2$, or an anionic form thereof; a halogen; or $-OPh-CH_2-ONO_2$;

EBG has a structure satisfying a formula selected from Formulas $IIA_{EBG}-IIJ_{EBG}$

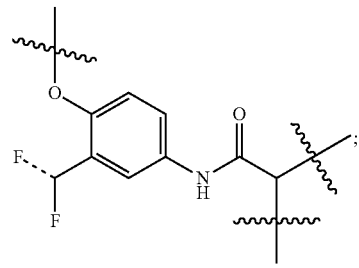

Formula $IIA_{EBG}$

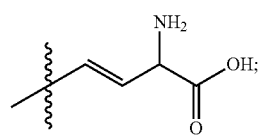

Formula $IIB_{EBG}$

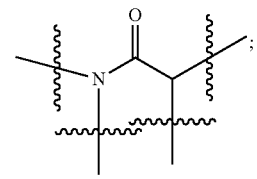

Formula $IIC_{EBG}$

Formula IID_EBG

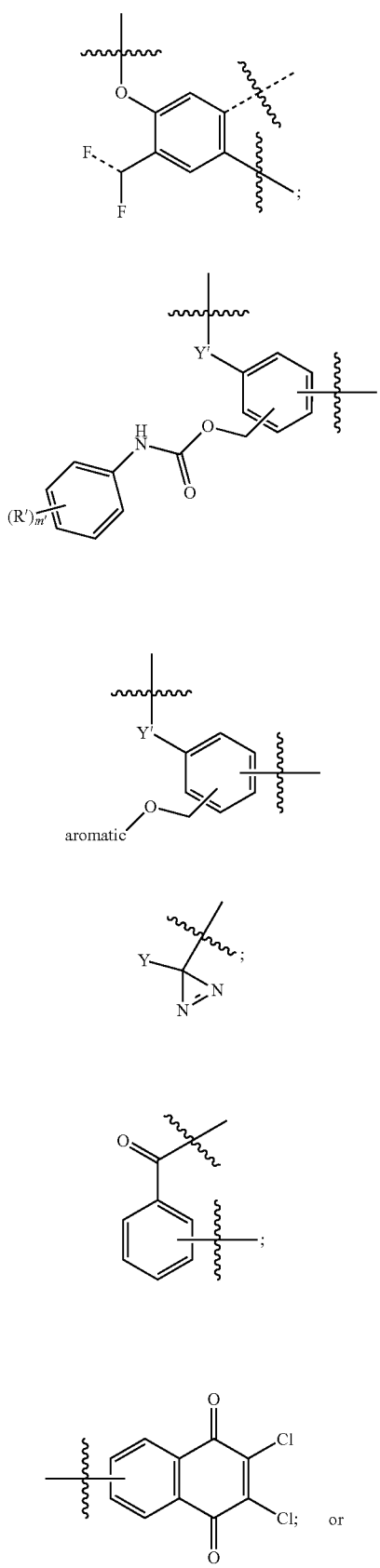

Formula IIE_EBG

Formula IIF_EBG

Formula IIG_EBG

Formula IIH_EBG

Formula III_EBG

Formula IIJ_EBG

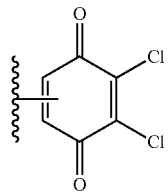

wherein Y is CH$_3$ or CF$_3$; Y' is O, NO$_2$, or —N=NR", wherein R" is a dye or other reporting moiety;

and m' is an integer selected from 0 to 5; and R' is selected from aldehyde, ketone, ester, carboxylic acid, acyl, acyl halide, cyano, sulfonate, nitro, nitroso, quaternary amine, CF$_3$, alkyl halide, or combinations thereof;

Linker$^a$ comprises an aliphatic group, a heteroaliphatic group, an aromatic group, an aliphatic-aromatic group, a heteroaliphatic-aromatic group, a heteroaromatic group, an aliphatic-heteroaromatic group, or a heteroaliphatic-heteroaromatic group;

each of Linker$^b$, and Linker$^c$, if present, independently comprises an aliphatic group, a heteroaliphatic group, an aromatic group, an aliphatic-aromatic group, a heteroaliphatic-aromatic group, a heteroaromatic group, an aliphatic-heteroaromatic group, or a heteroaliphatic-heteroaromatic group;

R, if present, is a group comprising a carbamate or a carbonate; and each of n, m, p, and q independently is 0 or 1;

provided that one of the following applies:
(a) one or more Tags are present, and each Tag is independently a fluorophore, a binding partner of an affinity-based binding pair, a quantum dot, or a dye; or
(b) one or more $_p$Tags are present and each $_p$Tag is independently an azide or an alkyne.

2. The probe of claim 1, wherein Linker$^a$ is a linker group having a structure satisfying a formula selected from Formulas IIA$_{Linkera}$-IIH$_{Linkera}$ Formula IIA$_{linkera}$

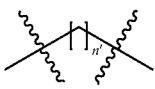

Formula IIB$_{linkera}$

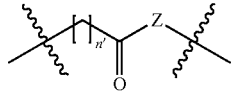

Formula IIC$_{linkera}$

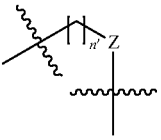

Formula IID$_{linkera}$

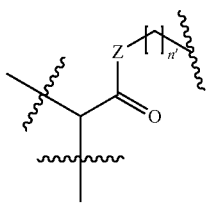

-continued

Formula IIE$_{linkera}$

Formula IIF$_{linkera}$

Formula IIG$_{linkera}$

Formula IIH$_{linkera}$

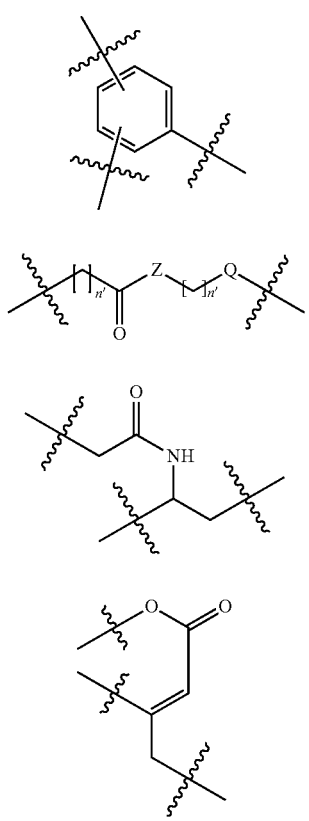

wherein each n' independently is an integer ranging from 1 to 50; Z is oxygen or NR'", wherein R'" is hydrogen, aliphatic, or aromatic; and Q is carbon, oxygen or NR'", wherein R'" is hydrogen, aliphatic, or aromatic.

3. The probe of claim 1, wherein Linker$^b$ is present and comprises a —(CH$_2$)$_{n'}$— group, wherein n' is an integer ranging from 1 to 50; an amide group; or a combination thereof.

4. The probe of claim 1, wherein Linker$^c$ is present and has a structure satisfying Formula IIA$_{Linkerc}$ or Formula IIB$_{Linkerc}$.

Formula IIA$_{Linkerc}$

Formula IIB$_{Linkerc}$

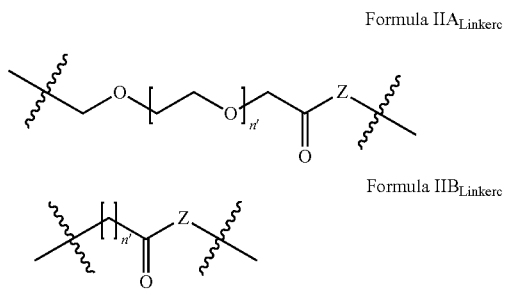

wherein n' is an integer ranging from 0 to 50; and Z is oxygen or NR'", wherein R'" is hydrogen, aliphatic, or aromatic.

5. The probe of claim 1, wherein R is present and has a structure satisfying any one or more Formulas IIA$_R$-IID$_R$.

Formula IIA$_R$

Formula IIB$_R$

Formula IIC$_R$

Formula IID$_R$

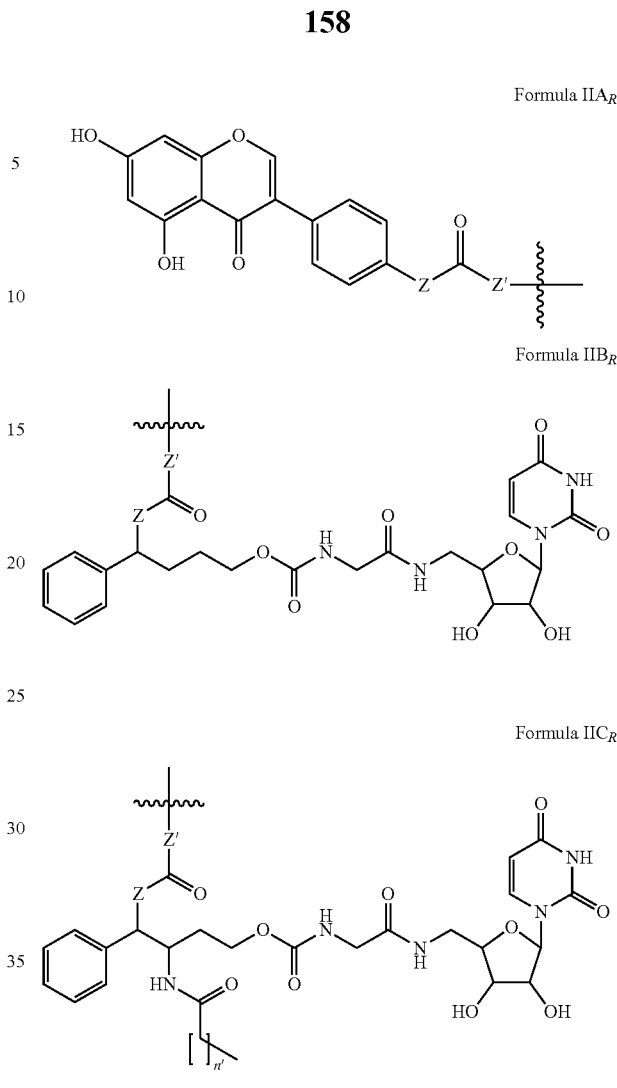
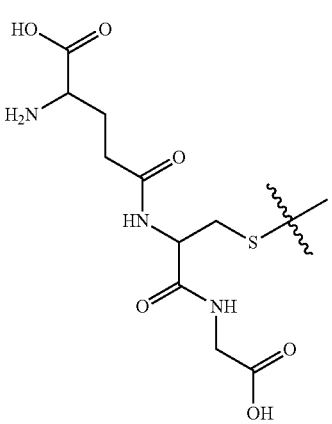

wherein Z and Z' independently are oxygen or NR'", wherein R'" is hydrogen, aliphatic, or aromatic; and n' is an integer ranging from 0 to 50.

6. The probe of claim 1, wherein the one or more Tags independently are rhodamine, fluorescein, or biotin.

7. The probe of claim 1, wherein the compound has a structure satisfying Formula IIIA

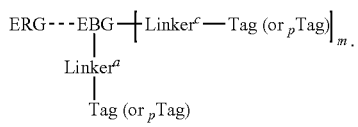

Formula IIIA

8. The probe of claim 7, wherein the ERG is present and is iodo; —OPh-CH$_2$—ONO$_2$;

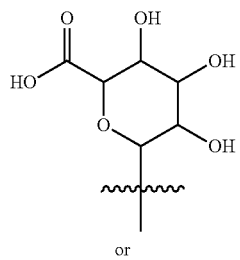

or

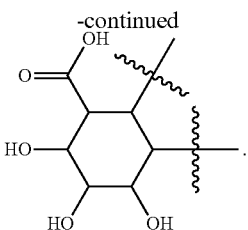

9. The probe of claim 7, wherein Linker$^a$ is an ester group, an —O(CH$_2$)$_{n'}$NR'''C(O)(CH$_2$)$_{n'}$— group, or a —(CH$_2$)$_{n'}$— group, wherein each n' independently is an integer ranging from 1 to 20 and wherein R''' is hydrogen, aliphatic, or aromatic.

10. The probe of claim 7, wherein m is 1 and Linker$^c$ is an —NR'''C(O)(CH$_2$)$_{n'}$— group or an —NR'''C(O)CH$_2$[O(CH$_2$)$_2$]$_{n'}$OCH$_2$— group, wherein each n' independently is an integer ranging from 1 to 20 and wherein R''' is hydrogen, aliphatic, or aromatic.

11. The probe of claim 7, wherein m is 1.

12. A probe selected from:

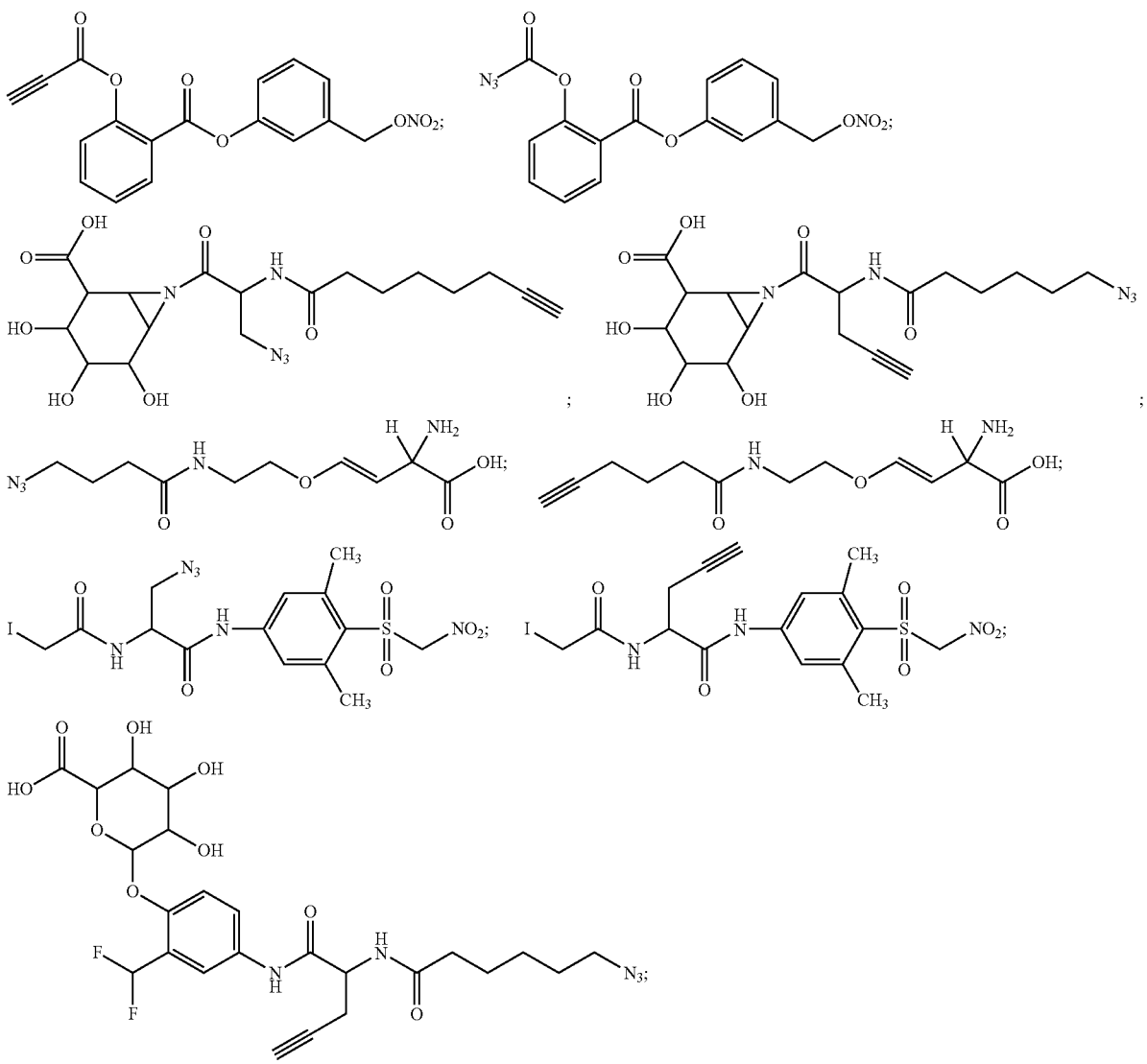

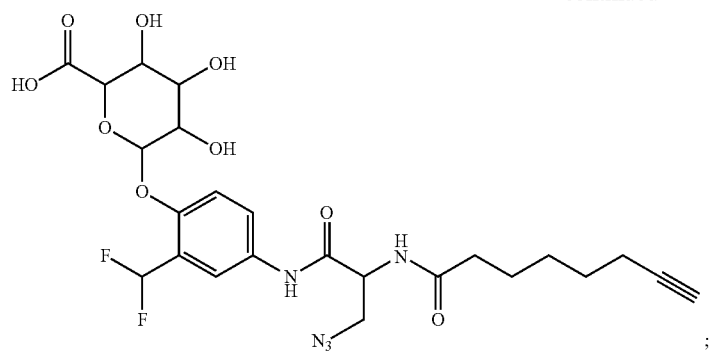
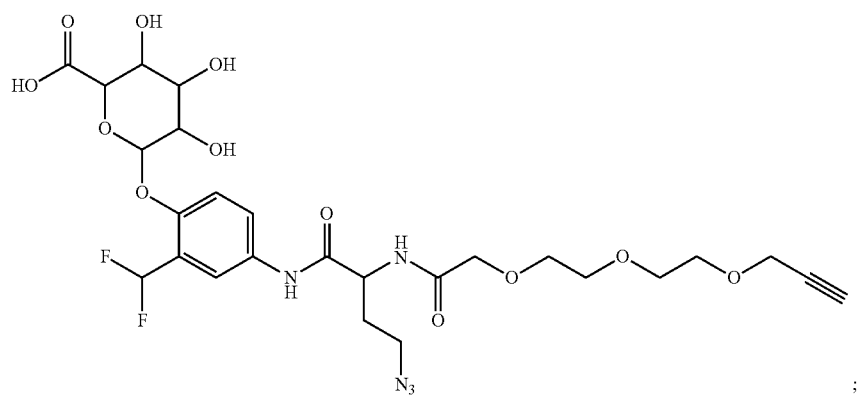
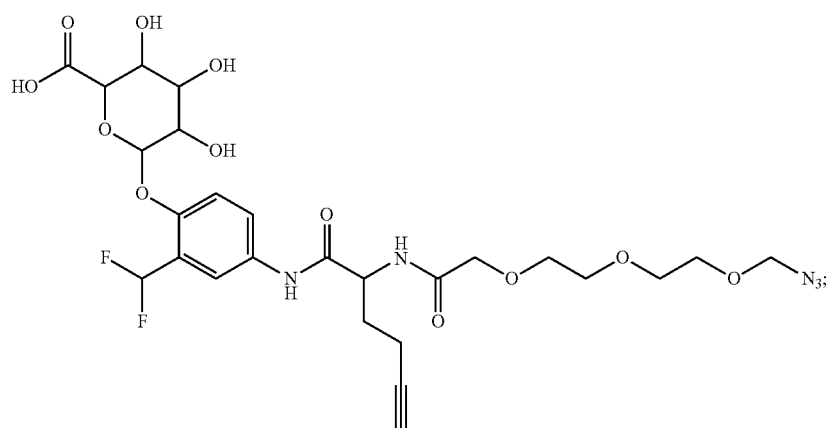
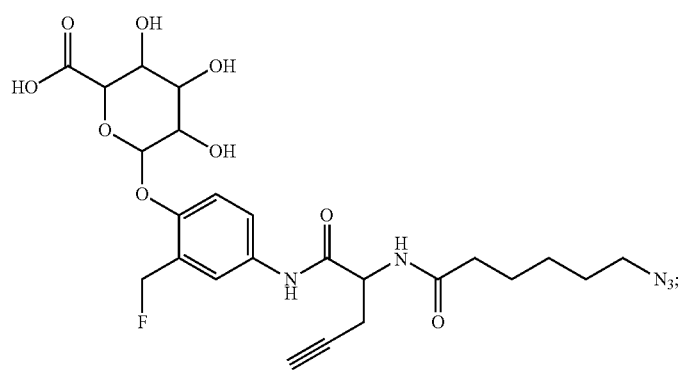

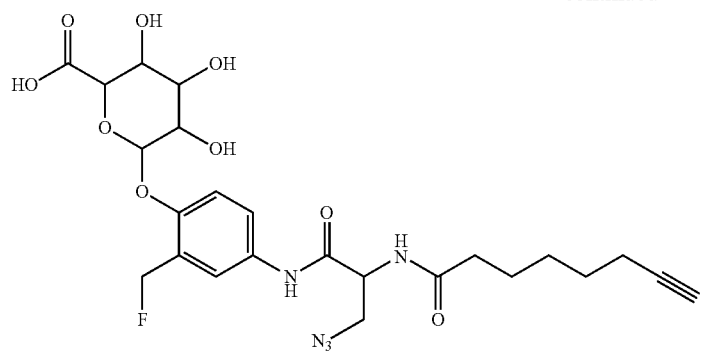
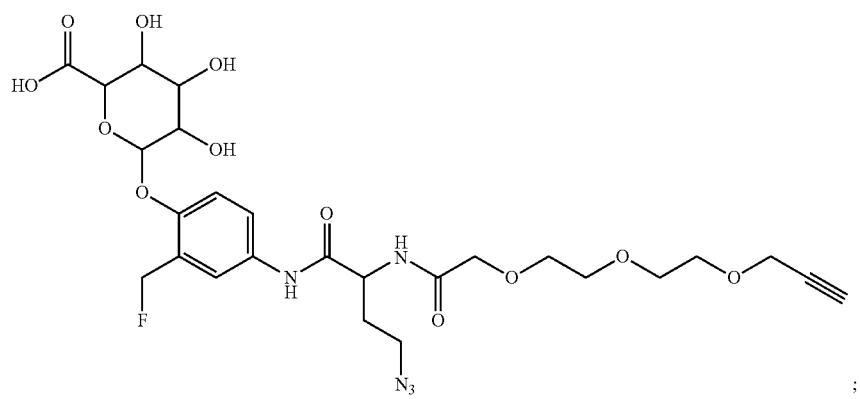
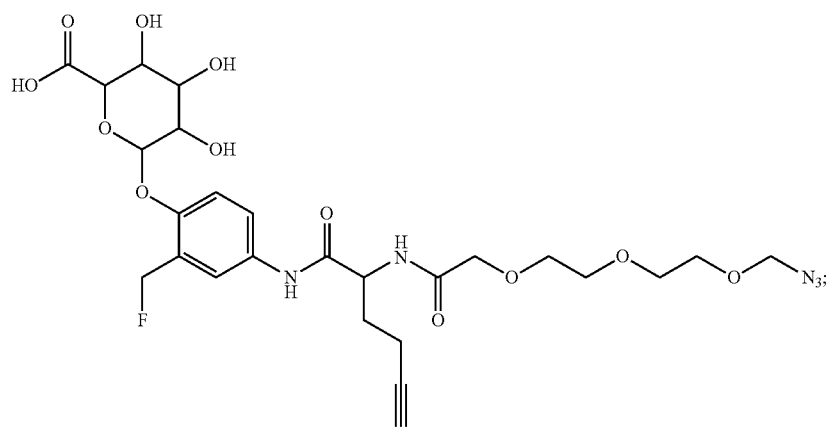
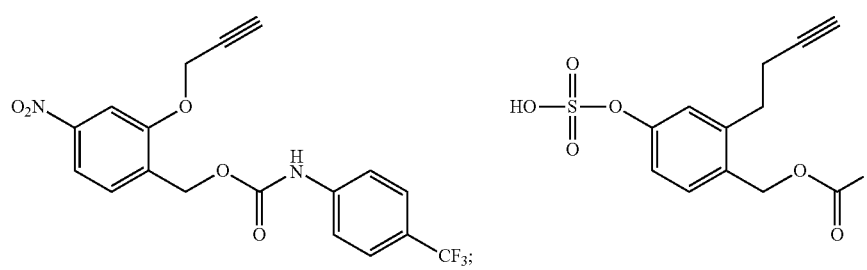
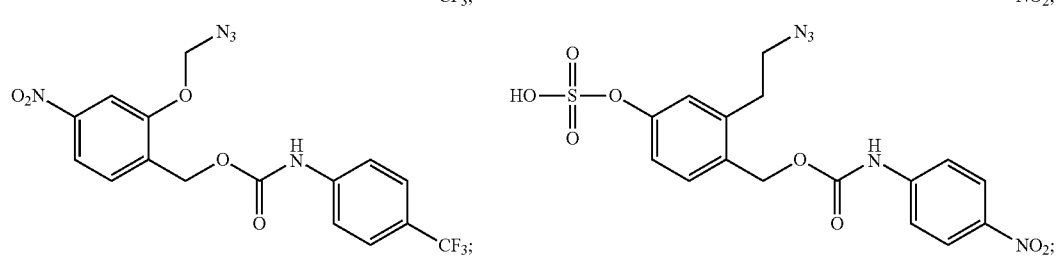
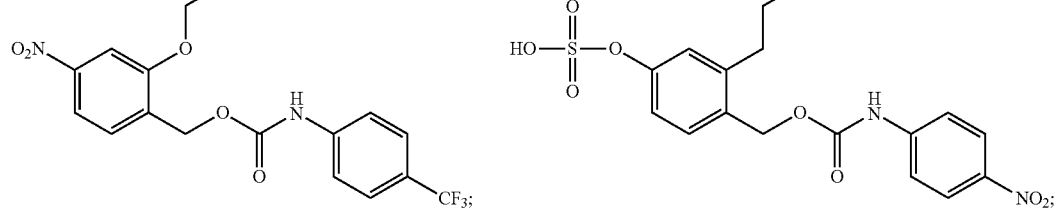

165 166
-continued
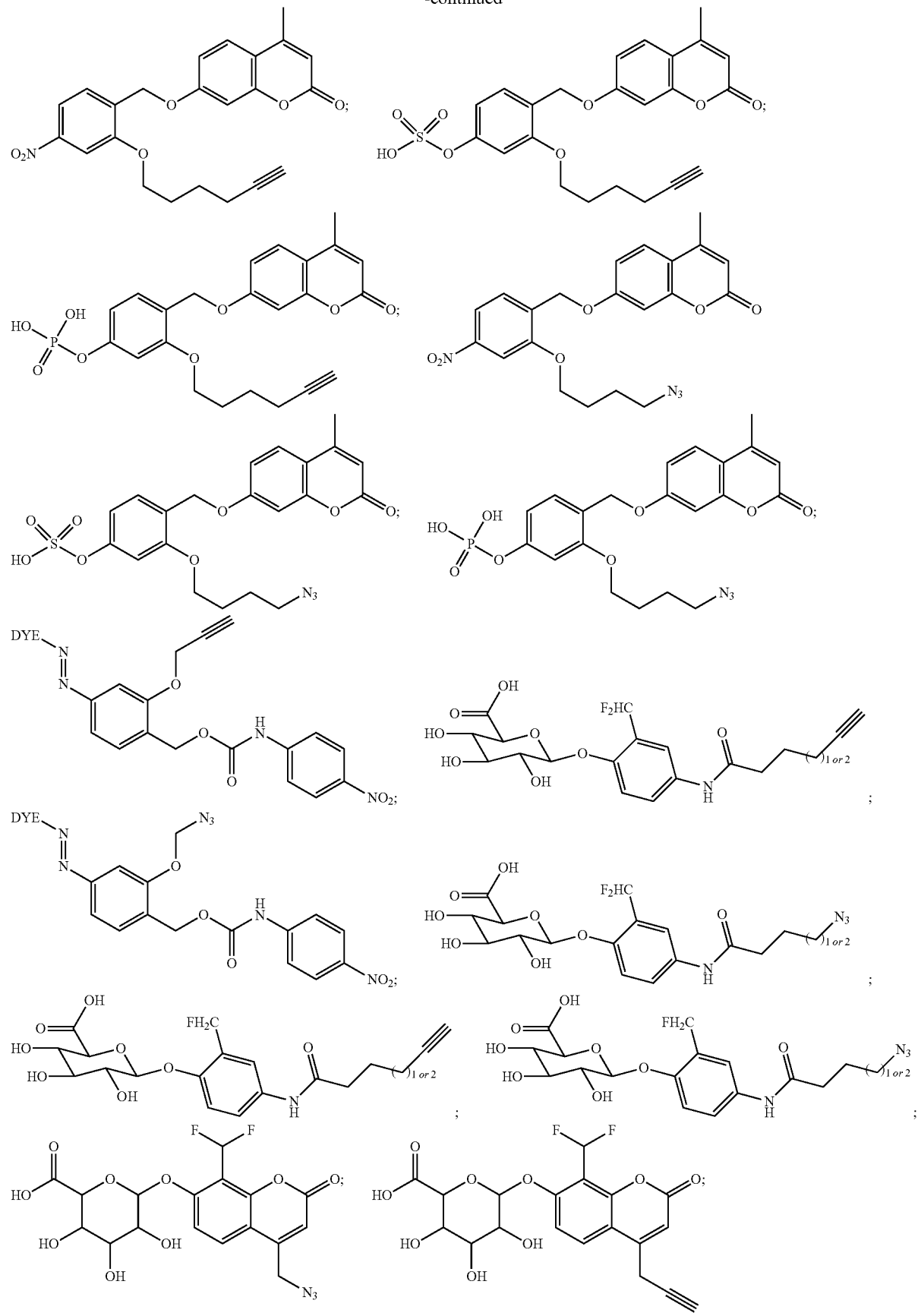

-continued
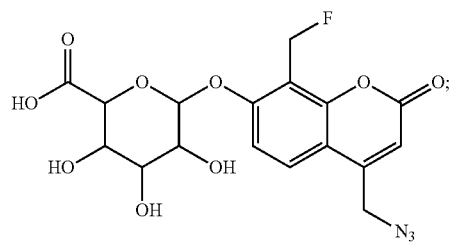
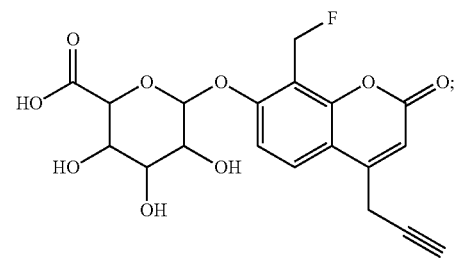
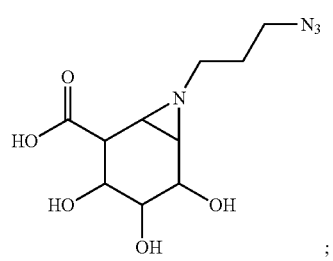
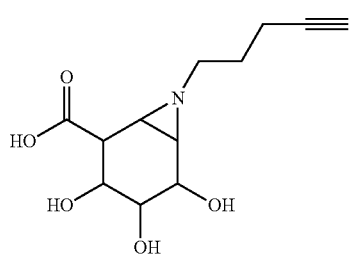
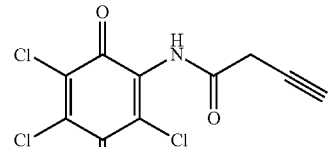
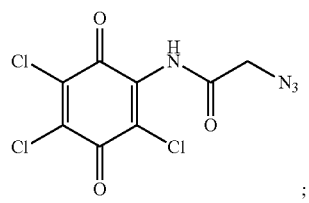
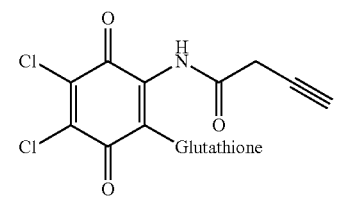
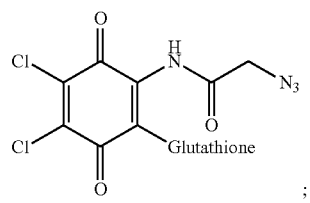
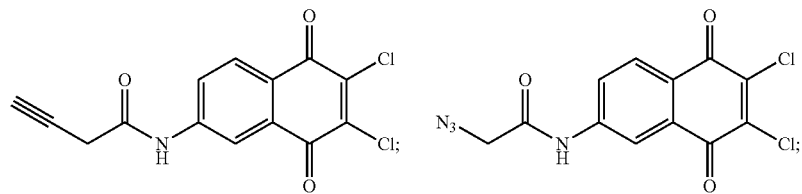
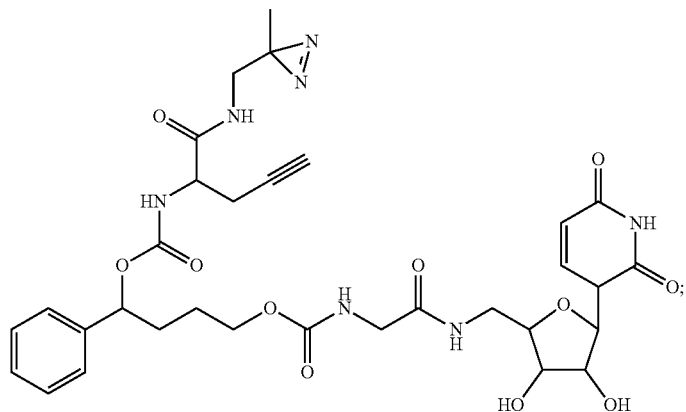

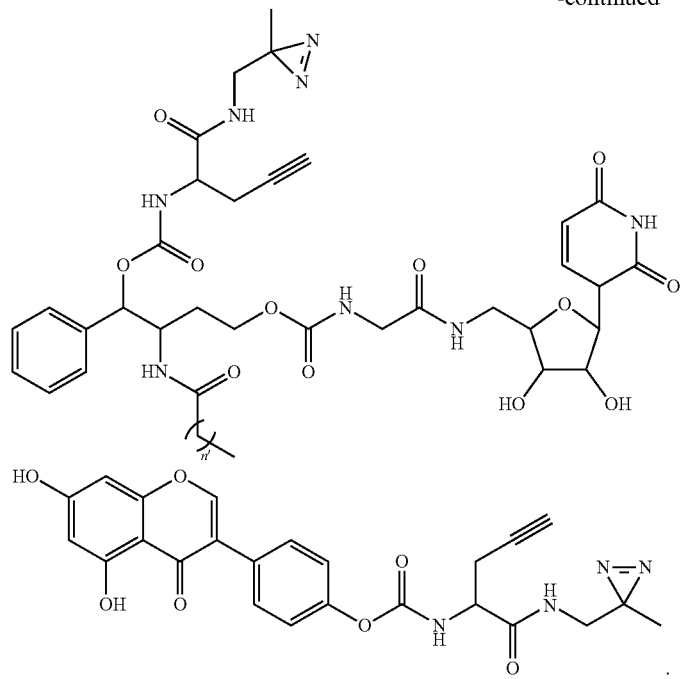
wherein n' is 0 to 50; or
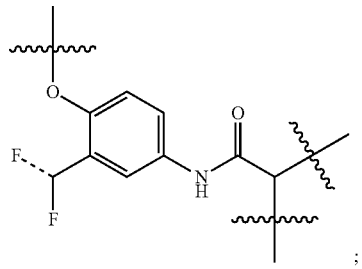
.
13. A probe having a structure satisfying Formula II
$$[ERG]_n - EBG - [Linker^c - Tag\ (or\ _pTag)]_m$$
$$|\ Linker^a - [R]_p$$
$$|\ [Linker^b]_q$$
$$|\ Tag\ (or\ _pTag)$$
Formula II
wherein
ERG is
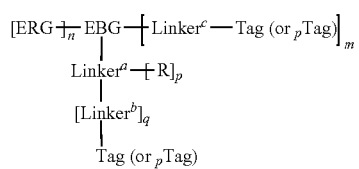
EBG has a structure satisfying a formula selected from
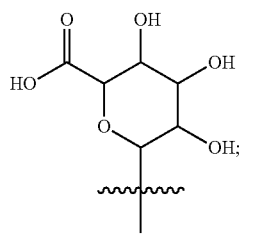 [SMILES: *C1OC(C(=O)O)C(O)C(O)C1O]
Formula IIA$_{EBG}$
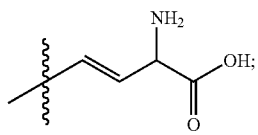
Formula IIB$_{EBG}$
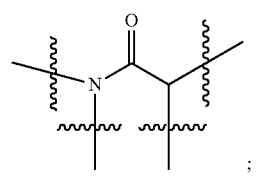
Formula IIC$_{EBG}$
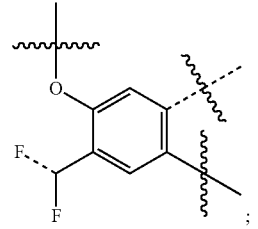
Formula IID$_{EBG}$
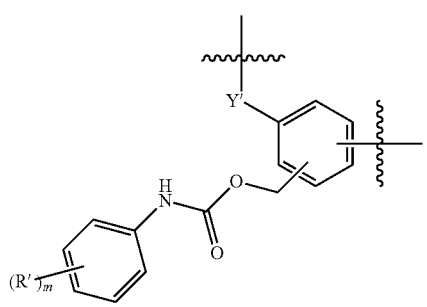
Formula IIE$_{EBG}$ -continued Formula IIF$_{EBG}$

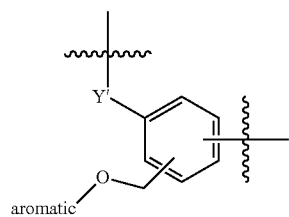

Formula IIG$_{EBG}$

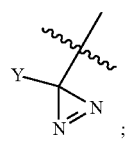

Formula IIH$_{EBG}$

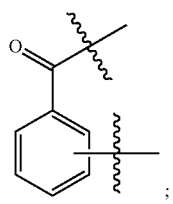

Formula III$_{EBG}$

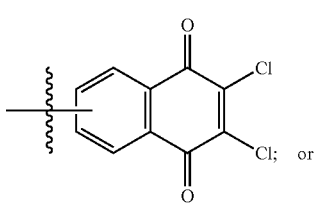

Formula IIJ$_{EBG}$

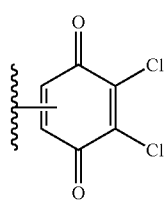

wherein Y' is O; m' is an integer selected from 0 to 5; and
each occurrence of R' is independently selected from
aldehyde, ketone, ester, carboxylic acid, acyl, acyl
halide, cyano, sulfonate, nitro, nitroso, quaternary
amine, CF$_3$, alkyl halide, or combinations thereof;

Linker$^a$ comprises an aliphatic group, a heteroaliphatic
group, an aromatic group, an aliphatic-aromatic group,
a heteroaliphatic-aromatic group, a heteroaromatic
group, an aliphatic-heteroaromatic group, or a heteroaliphatic-heteroaromatic group;

each of Linker$^b$, and Linker$^c$, if present, independently
comprises an aliphatic group, a heteroaliphatic group,
an aromatic group, an aliphatic-aromatic group, a heteroaliphatic-aromatic group, a heteroaromatic group,
an aliphatic-heteroaromatic group, or a heteroaliphatic-heteroaromatic group;

R, if present, is a group comprising a carbamate or a
carbonate;

each of n, m, p, and q independently is 0 or 1; and
provided that one of the following applies:

(a) one or more Tags are present, and each Tag is
independently a fluorophore, a binding partner of an
affinity-based binding pair, a quantum dot, or a dye; or (b) one or more $_p$Tags are present, and each $_p$Tag is
independently an azide or an alkyne.

14. The probe of claim 13, wherein the ERG is

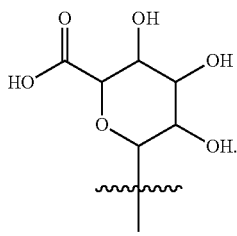

15. The probe of claim 13, wherein the EBG has a structure satisfying a formula selected form Formula IIA$_{EBG}$

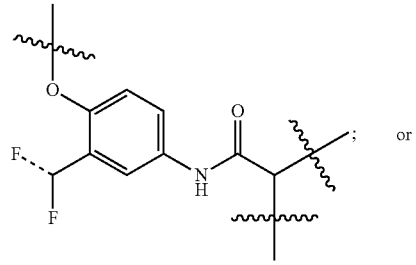

Formula IID$_{EBG}$

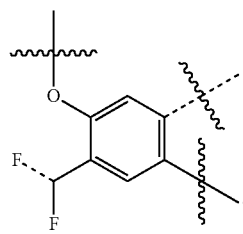

16. The probe of claim 13, wherein the EBG has a structure satisfying a formula of Formula IIA$_{EBG}$

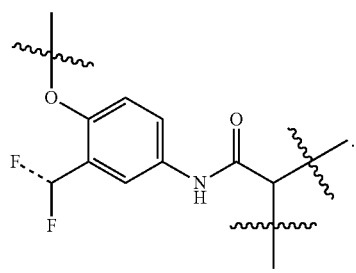

17. The probe of claim 13, wherein Linker$^b$ and R are absent and wherein q and m are 0.

18. The probe of claim 13, wherein Linker$^a$ is an —O(CH$_2$)$_n$·NR'''C(O)(CH$_2$)$_n$·— group, or a —(CH$_2$)$_n$·— group, wherein each n' independently is an integer ranging from 1 to 20 and wherein R''' is hydrogen, aliphatic, or aromatic.

19. The probe of claim 13, wherein the one or more Tags are present.

20. The probe of claim 13, wherein the one or more $_p$Tags are present.

21. The probe of claim 13, wherein n is 1.